United States Patent
Sharma

(10) Patent No.: US 12,279,803 B2
(45) Date of Patent: *Apr. 22, 2025

(54) VAPOR-BASED ABLATION TREATMENT METHODS WITH IMPROVED TREATMENT VOLUME VAPOR MANAGEMENT

(71) Applicant: Aqua Medical, Inc., Santa Ana, CA (US)

(72) Inventor: Virender K. Sharma, Paradise Valley, AZ (US)

(73) Assignee: Aqua Medical, Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/517,488

(22) Filed: Nov. 22, 2023

(65) Prior Publication Data

US 2024/0156506 A1     May 16, 2024

Related U.S. Application Data

(63) Continuation of application No. 17/575,950, filed on Jan. 14, 2022, now Pat. No. 11,864,809, which is a
(Continued)

(51) Int. Cl.
   *A61B 18/04*          (2006.01)
   *A61B 18/00*          (2006.01)

(52) U.S. Cl.
   CPC .... *A61B 18/04* (2013.01); *A61B 2018/00261* (2013.01); *A61B 2018/00345* (2013.01);
(Continued)

(58) Field of Classification Search
CPC .......... A61B 18/04; A61B 2018/00261; A61B 2018/00577; A61B 2018/048; A61B 2018/0072
See application file for complete search history.

(56) References Cited

U.S. PATENT DOCUMENTS

| | | |
|---|---|---|
| 408,899 A | 8/1889 | Small |
| 697,181 A | 4/1902 | Smith |
| (Continued) | | |

FOREIGN PATENT DOCUMENTS

| | | |
|---|---|---|
| CN | 2757751 Y | 2/2006 |
| CN | 1803113 A | 7/2006 |
| (Continued) | | |

OTHER PUBLICATIONS

Kim, J. W., Kim, D. H., Roh, Y. K., Ju, S. Y., Nam, H. Y., Nam, G. E., Kim, D. W., Lee, S. H., Lee, C. W., Han, K., & Park, Y. G. ( 2015). Serum Ferritin Levels Are Positively Associated With Metabolically Obese Normal Weight: A Nationwide Population-Based Study. Medicine, 94(52), e2335 (Year: 2015).
(Continued)

*Primary Examiner* — Daniel W Fowler
*Assistant Examiner* — Annie L Shoulders
(74) *Attorney, Agent, or Firm* — Novel IP

(57) ABSTRACT

Ablation catheters and systems include flexible catheter tips with a distal needle or ports for delivery of an ablative agent to a target tissue. Pressure monitoring during ablation ensure operation is performed within safe limits and with desired efficacy. Positioning elements help maintain the devices in the proper position with respect to the target tissue and also prevent the passage of ablative agent to normal tissues.

18 Claims, 115 Drawing Sheets

Related U.S. Application Data continuation of application No. 16/428,598, filed on May 31, 2019, now Pat. No. 11,806,066.

(60) Provisional application No. 62/679,694, filed on Jun. 1, 2018.

(52) U.S. Cl.
CPC ............... *A61B 2018/00488* (2013.01); *A61B 2018/00494* (2013.01); *A61B 2018/00541* (2013.01); *A61B 2018/00577* (2013.01); *A61B 2018/0072* (2013.01); *A61B 2018/00744* (2013.01); *A61B 2018/00982* (2013.01); *A61B 2018/048* (2013.01)

(56) References Cited

U.S. PATENT DOCUMENTS

| | | |
|---|---|---|
| 1,719,750 A | 7/1929 | Bridge |
| 3,818,913 A | 6/1974 | Wallach |
| 3,880,168 A | 4/1975 | Berman |
| 3,924,628 A | 12/1975 | Droegemueller |
| 3,930,505 A | 1/1976 | Wallach |
| 3,938,502 A | 2/1976 | Bom |
| 4,024,866 A | 5/1977 | Wallach |
| 4,083,077 A | 4/1978 | Knight |
| 4,672,962 A | 6/1987 | Hershenson |
| 4,672,963 A | 6/1987 | Barken |
| 4,682,596 A | 7/1987 | Bales |
| 4,701,587 A | 10/1987 | Carter |
| 4,748,979 A | 6/1988 | Hershenson |
| 4,773,410 A | 9/1988 | Blackmer |
| 4,793,352 A | 12/1988 | Eichenlaub |
| 4,828,544 A | 5/1989 | Lane |
| 4,872,920 A | 10/1989 | Flynn |
| 4,898,574 A | 2/1990 | Uchiyama |
| 4,915,113 A | 4/1990 | Holman |
| 4,950,266 A | 8/1990 | Sinofsky |
| 4,950,267 A | 8/1990 | Ishihara |
| 4,976,711 A | 12/1990 | Parins |
| 4,985,027 A | 1/1991 | Dressel |
| 5,006,119 A | 4/1991 | Acker |
| 5,011,566 A | 4/1991 | Hoffman |
| 5,045,056 A | 9/1991 | Behl |
| 5,084,043 A | 1/1992 | Hertzmann |
| 5,084,044 A | 1/1992 | Quint |
| 5,102,410 A | 4/1992 | Dressel |
| 5,112,328 A | 5/1992 | Taboada |
| 5,122,138 A | 6/1992 | Manwaring |
| 5,158,536 A | 10/1992 | Sekins |
| 5,190,539 A | 3/1993 | Fletcher |
| 5,217,459 A | 6/1993 | Kamerling |
| 5,217,465 A | 6/1993 | Steppe |
| 5,222,938 A | 6/1993 | Behl |
| 5,263,951 A | 11/1993 | Spears |
| 5,277,696 A | 1/1994 | Hagen |
| 5,298,298 A | 3/1994 | Hoffman |
| 5,312,399 A | 5/1994 | Hakky |
| 5,318,014 A | 6/1994 | Carter |
| 5,330,518 A | 7/1994 | Neilson |
| 5,331,947 A | 7/1994 | Shturman |
| 5,334,190 A | 8/1994 | Seiler |
| 5,344,397 A | 9/1994 | Heaven |
| 5,348,551 A | 9/1994 | Spears |
| 5,352,512 A | 10/1994 | Hoffman |
| 5,366,490 A | 11/1994 | Edwards |
| 5,370,609 A | 12/1994 | Drasler |
| 5,370,675 A | 12/1994 | Edwards |
| 5,385,544 A | 1/1995 | Edwards |
| 5,405,376 A | 4/1995 | Mulier |
| 5,409,453 A | 4/1995 | Lundquist |
| 5,417,686 A | 5/1995 | Peterson |
| 5,421,819 A | 6/1995 | Edwards |
| 5,424,620 A | 6/1995 | Cheon |
| 5,425,731 A | 6/1995 | Daniel |
| 5,425,931 A | 6/1995 | Arai |
| 5,433,708 A | 7/1995 | Nichols |
| 5,433,739 A | 7/1995 | Sluijter |
| 5,435,805 A | 7/1995 | Edwards |
| 5,437,629 A | 8/1995 | Goldrath |
| 5,443,470 A | 8/1995 | Stern |
| 5,449,380 A | 9/1995 | Chin |
| 5,451,208 A | 9/1995 | Goldrath |
| 5,462,521 A | 10/1995 | Brucker |
| 5,470,308 A | 11/1995 | Edwards |
| 5,470,309 A | 11/1995 | Edwards |
| 5,484,400 A | 1/1996 | Edwards |
| 5,500,012 A | 3/1996 | Brucker |
| 5,503,638 A | 4/1996 | Cooper |
| 5,524,620 A | 6/1996 | Rosenschein |
| 5,529,076 A | 6/1996 | Schachar |
| 5,531,676 A | 7/1996 | Edwards |
| 5,540,658 A | 7/1996 | Evans |
| 5,542,915 A | 8/1996 | Edwards |
| 5,542,916 A | 8/1996 | Hirsch |
| 5,542,928 A | 8/1996 | Evans |
| 5,545,171 A | 8/1996 | Sharkey |
| 5,549,628 A | 8/1996 | Cooper |
| 5,549,644 A | 8/1996 | Lundquist |
| 5,554,110 A | 9/1996 | Edwards |
| 5,554,172 A | 9/1996 | Horner |
| 5,556,377 A | 9/1996 | Rosen |
| 5,558,673 A | 9/1996 | Edwards |
| 5,562,608 A | 10/1996 | Sekins |
| 5,575,803 A | 11/1996 | Cooper |
| 5,584,872 A | 12/1996 | Lafontaine |
| 5,588,960 A | 12/1996 | Edwards |
| 5,591,125 A | 1/1997 | Edwards |
| 5,591,157 A | 1/1997 | Hennings |
| 5,591,162 A | 1/1997 | Fletcher |
| 5,599,294 A | 2/1997 | Edwards |
| 5,601,591 A | 2/1997 | Edwards |
| 5,609,151 A | 3/1997 | Mulier |
| 5,616,120 A | 4/1997 | Andrew |
| 5,620,440 A | 4/1997 | Heckele |
| 5,624,392 A | 4/1997 | Saab |
| 5,630,794 A | 5/1997 | Lax |
| 5,667,488 A | 9/1997 | Lundquist |
| 5,669,907 A | 9/1997 | Platt, Jr. |
| 5,672,153 A | 9/1997 | Lax |
| 5,672,290 A | 9/1997 | Levy |
| 5,674,191 A | 10/1997 | Edwards |
| 5,681,282 A | 10/1997 | Eggers |
| 5,683,366 A | 11/1997 | Eggers |
| 5,695,507 A | 12/1997 | Auth |
| 5,697,281 A | 12/1997 | Eggers |
| 5,697,536 A | 12/1997 | Eggers |
| 5,697,882 A | 12/1997 | Eggers |
| 5,697,909 A | 12/1997 | Eggers |
| 5,700,262 A | 12/1997 | Acosta |
| 5,707,352 A | 1/1998 | Sekins |
| 5,720,718 A | 2/1998 | Rosen |
| 5,720,719 A | 2/1998 | Edwards |
| 5,730,719 A | 3/1998 | Edwards |
| 5,735,811 A | 4/1998 | Brisken |
| 5,741,247 A | 4/1998 | Rizoiu |
| 5,741,248 A | 4/1998 | Stern |
| 5,743,870 A | 4/1998 | Edwards |
| 5,752,965 A | 5/1998 | Francis |
| 5,755,753 A | 5/1998 | Knowlton |
| 5,769,880 A | 6/1998 | Truckai |
| 5,782,914 A | 7/1998 | Schankereli |
| 5,785,521 A | 7/1998 | Rizoiu |
| 5,797,903 A | 8/1998 | Swanson |
| 5,800,379 A | 9/1998 | Edwards |
| 5,800,482 A | 9/1998 | Pomeranz |
| 5,800,493 A | 9/1998 | Stevens |
| 5,810,764 A | 9/1998 | Eggers |
| 5,820,580 A | 10/1998 | Edwards |
| 5,824,703 A | 10/1998 | Clark, Jr. |
| 5,827,268 A | 10/1998 | Laufer |
| 5,830,179 A | 11/1998 | Mikus |
| 5,836,906 A | 11/1998 | Edwards |
| 5,843,019 A | 12/1998 | Eggers |

(56) References Cited

U.S. PATENT DOCUMENTS

| | | |
|---|---|---|
| 5,843,073 A | 12/1998 | Sinofsky |
| 5,849,011 A | 12/1998 | Jones |
| 5,861,005 A | 1/1999 | Kontos |
| 5,871,469 A | 2/1999 | Eggers |
| 5,871,481 A | 2/1999 | Kannenberg |
| 5,873,855 A | 2/1999 | Eggers |
| 5,873,877 A | 2/1999 | McGaffigan |
| 5,879,329 A | 3/1999 | Ginsburg |
| 5,885,243 A | 3/1999 | Capetan |
| 5,888,198 A | 3/1999 | Eggers |
| 5,891,095 A | 4/1999 | Eggers |
| 5,891,134 A | 4/1999 | Goble |
| 5,891,457 A | 4/1999 | Neuwirth |
| 5,897,553 A | 4/1999 | Mulier |
| 5,902,272 A | 5/1999 | Eggers |
| 5,913,856 A | 6/1999 | Chia |
| 5,938,660 A | 8/1999 | Swartz |
| 5,944,686 A | 8/1999 | Patterson |
| 5,944,715 A | 8/1999 | Goble |
| 5,954,714 A | 9/1999 | Saadat |
| 5,957,919 A | 9/1999 | Laufer |
| 5,957,922 A | 9/1999 | Imran |
| 5,964,752 A | 10/1999 | Stone |
| 5,964,756 A | 10/1999 | McGaffigan |
| 5,968,037 A | 10/1999 | Rizoiu |
| 5,976,123 A | 11/1999 | Baumgardner |
| 5,980,504 A | 11/1999 | Sharkey |
| 5,980,516 A | 11/1999 | Mulier |
| 5,986,662 A | 11/1999 | Argiro |
| 5,989,212 A | 11/1999 | Sussman |
| 5,989,238 A | 11/1999 | Ginsburg |
| 5,989,249 A | 11/1999 | Kirwan, Jr. |
| 5,989,445 A | 11/1999 | Wise |
| 5,997,499 A | 12/1999 | Sussman |
| 6,015,406 A | 1/2000 | Goble |
| 6,016,809 A | 1/2000 | Mulier |
| 6,017,361 A | 1/2000 | Mikus |
| 6,024,733 A | 2/2000 | Eggers |
| 6,027,501 A | 2/2000 | Goble |
| 6,032,077 A | 2/2000 | Pomeranz |
| 6,032,674 A | 3/2000 | Eggers |
| 6,036,713 A | 3/2000 | Kieturakis |
| 6,045,532 A | 4/2000 | Eggers |
| 6,045,549 A | 4/2000 | Smethers |
| 6,047,700 A | 4/2000 | Eggers |
| 6,053,172 A | 4/2000 | Hovda |
| 6,053,909 A | 4/2000 | Shadduck |
| 6,056,746 A | 5/2000 | Goble |
| 6,059,011 A | 5/2000 | Giolo |
| 6,063,079 A | 5/2000 | Hovda |
| 6,063,081 A | 5/2000 | Mulier |
| 6,066,132 A | 5/2000 | Chen |
| 6,066,134 A | 5/2000 | Eggers |
| 6,071,278 A | 6/2000 | Panescu |
| 6,074,358 A | 6/2000 | Andrew |
| 6,077,257 A | 6/2000 | Edwards |
| 6,080,128 A | 6/2000 | Sussman |
| 6,080,151 A | 6/2000 | Swartz |
| 6,083,255 A | 7/2000 | Laufer |
| 6,086,585 A | 7/2000 | Hovda |
| 6,095,149 A | 8/2000 | Sharkey |
| 6,099,251 A | 8/2000 | Lafleur |
| 6,102,046 A | 8/2000 | Weinstein |
| 6,102,885 A | 8/2000 | Bass |
| 6,105,581 A | 8/2000 | Eggers |
| 6,106,516 A | 8/2000 | Massengill |
| 6,109,268 A | 8/2000 | Thapliyal |
| 6,110,162 A | 8/2000 | Sussman |
| 6,112,123 A | 8/2000 | Kelleher |
| 6,113,593 A | 9/2000 | Tu |
| 6,113,597 A | 9/2000 | Eggers |
| 6,113,722 A | 9/2000 | Hoffman |
| 6,117,109 A | 9/2000 | Eggers |
| 6,126,682 A | 10/2000 | Sharkey |
| 6,130,671 A | 10/2000 | Argiro |
| 6,139,538 A | 10/2000 | Houghton |
| 6,139,571 A | 10/2000 | Fuller |
| 6,149,620 A | 11/2000 | Baker |
| 6,156,036 A | 12/2000 | Sussman |
| 6,159,194 A | 12/2000 | Eggers |
| 6,159,208 A | 12/2000 | Hovda |
| 6,162,232 A | 12/2000 | Shadduck |
| 6,168,594 B1 | 1/2001 | Lafontaine |
| 6,174,308 B1 | 1/2001 | Goble |
| 6,176,842 B1 | 1/2001 | Tachibana |
| 6,179,805 B1 | 1/2001 | Sussman |
| 6,179,824 B1 | 1/2001 | Eggers |
| 6,179,836 B1 | 1/2001 | Eggers |
| 6,183,469 B1 | 2/2001 | Thapliyal |
| 6,190,381 B1 | 2/2001 | Olsen |
| 6,194,066 B1 | 2/2001 | Hoffman |
| 6,196,989 B1 | 3/2001 | Padget |
| 6,200,333 B1 | 3/2001 | Laufer |
| 6,203,542 B1 | 3/2001 | Ellsberry |
| 6,206,847 B1 | 3/2001 | Edwards |
| 6,206,848 B1 | 3/2001 | Sussman |
| 6,210,402 B1 | 4/2001 | Olsen |
| 6,210,404 B1 | 4/2001 | Shadduck |
| 6,210,405 B1 | 4/2001 | Goble |
| 6,219,059 B1 | 4/2001 | Argiro |
| 6,224,592 B1 | 5/2001 | Eggers |
| 6,228,078 B1 | 5/2001 | Eggers |
| 6,228,081 B1 | 5/2001 | Goble |
| 6,228,082 B1 | 5/2001 | Baker |
| 6,231,567 B1 | 5/2001 | Rizoiu |
| 6,234,178 B1 | 5/2001 | Goble |
| 6,235,020 B1 | 5/2001 | Cheng |
| 6,235,025 B1 | 5/2001 | Swartz |
| 6,238,389 B1 | 5/2001 | Paddock |
| 6,238,391 B1 | 5/2001 | Olsen |
| 6,241,702 B1 | 6/2001 | Lundquist |
| 6,254,597 B1 | 7/2001 | Rizoiu |
| 6,254,600 B1 | 7/2001 | Willink |
| 6,258,087 B1 | 7/2001 | Edwards |
| 6,261,286 B1 | 7/2001 | Goble |
| 6,261,311 B1 | 7/2001 | Sharkey |
| 6,264,650 B1 | 7/2001 | Hovda |
| 6,264,651 B1 | 7/2001 | Underwood |
| 6,264,652 B1 | 7/2001 | Eggers |
| 6,264,654 B1 | 7/2001 | Swartz |
| 6,277,112 B1 | 8/2001 | Underwood |
| 6,277,114 B1 | 8/2001 | Bullivant |
| 6,277,130 B1 | 8/2001 | Shadduck |
| 6,283,961 B1 | 9/2001 | Underwood |
| 6,283,989 B1 | 9/2001 | Laufer |
| 6,287,274 B1 | 9/2001 | Sussman |
| 6,287,320 B1 | 9/2001 | Slepian |
| 6,290,715 B1 | 9/2001 | Sharkey |
| 6,293,942 B1 | 9/2001 | Goble |
| 6,296,636 B1 | 10/2001 | Cheng |
| 6,296,638 B1 | 10/2001 | Davison |
| 6,299,620 B1 | 10/2001 | Shadduck |
| 6,299,633 B1 | 10/2001 | Laufer |
| 6,300,150 B1 | 10/2001 | Venkatasubramanian |
| 6,306,129 B1 | 10/2001 | Little |
| 6,306,134 B1 | 10/2001 | Goble |
| 6,309,387 B1 | 10/2001 | Eggers |
| 6,312,408 B1 | 11/2001 | Eggers |
| 6,312,474 B1 | 11/2001 | Francis |
| 6,315,755 B1 | 11/2001 | Sussman |
| 6,319,222 B1 | 11/2001 | Andrew |
| 6,322,549 B1 | 11/2001 | Eggers |
| 6,327,505 B1 | 12/2001 | Medhkour |
| 6,331,171 B1 | 12/2001 | Cohen |
| 6,355,032 B1 | 3/2002 | Hovda |
| 6,358,248 B1 | 3/2002 | Mulier |
| 6,363,937 B1 | 4/2002 | Hovda |
| 6,364,877 B1 | 4/2002 | Goble |
| 6,375,635 B1 | 4/2002 | Moutafis |
| 6,379,350 B1 | 4/2002 | Sharkey |
| 6,379,351 B1 | 4/2002 | Thapliyal |
| 6,391,025 B1 | 5/2002 | Weinstein |
| 6,394,949 B1 | 5/2002 | Crowley |
| 6,394,996 B1 | 5/2002 | Lawrence |

(56) References Cited

U.S. PATENT DOCUMENTS

| | | |
|---|---|---|
| 6,398,759 B1 | 6/2002 | Sussman |
| 6,398,775 B1 | 6/2002 | Perkins |
| 6,409,723 B1 | 6/2002 | Edwards |
| 6,416,507 B1 | 7/2002 | Eggers |
| 6,416,508 B1 | 7/2002 | Eggers |
| 6,416,509 B1 | 7/2002 | Goble |
| 6,419,673 B1 | 7/2002 | Edwards |
| 6,423,027 B1 | 7/2002 | Gonon |
| 6,432,103 B1 | 8/2002 | Ellsberry |
| 6,440,127 B2 | 8/2002 | McGovern |
| 6,458,231 B1 | 10/2002 | Wapner |
| 6,461,296 B1 | 10/2002 | Desai |
| 6,461,350 B1 | 10/2002 | Underwood |
| 6,461,354 B1 | 10/2002 | Olsen |
| 6,464,694 B1 | 10/2002 | Massengill |
| 6,464,695 B2 | 10/2002 | Hovda |
| 6,468,270 B1 | 10/2002 | Hovda |
| 6,468,274 B1 | 10/2002 | Alleyne |
| 6,468,313 B1 | 10/2002 | Claeson |
| 6,482,201 B1 | 11/2002 | Olsen |
| 6,482,202 B1 | 11/2002 | Goble |
| 6,488,673 B1 | 12/2002 | Laufer |
| 6,488,680 B1 | 12/2002 | Francischelli |
| 6,491,710 B2 | 12/2002 | Satake |
| 6,493,589 B1 | 12/2002 | Medhkour |
| 6,500,173 B2 | 12/2002 | Underwood |
| 6,508,816 B2 | 1/2003 | Shadduck |
| 6,510,854 B2 | 1/2003 | Goble |
| 6,517,568 B1 | 2/2003 | Sharkey |
| 6,522,930 B1 | 2/2003 | Schaer |
| 6,527,761 B1 | 3/2003 | Soltesz |
| 6,527,766 B1 | 3/2003 | Bair |
| 6,528,771 B1 | 3/2003 | Matsen |
| 6,540,741 B1 | 4/2003 | Underwood |
| 6,544,211 B1 | 4/2003 | Andrew |
| 6,544,248 B1 | 4/2003 | Bass |
| 6,544,261 B2 | 4/2003 | Ellsberry |
| 6,547,810 B1 | 4/2003 | Sharkey |
| 6,551,271 B2 | 4/2003 | Nguyen |
| 6,551,274 B2 | 4/2003 | Heiner |
| 6,551,300 B1 | 4/2003 | McGaffigan |
| 6,551,309 B1 | 4/2003 | LePivert |
| 6,557,559 B1 | 5/2003 | Eggers |
| 6,558,314 B1 | 5/2003 | Adelman |
| 6,558,379 B1 | 5/2003 | Batchelor |
| 6,566,636 B1 | 5/2003 | Bentley |
| 6,569,146 B1 | 5/2003 | Werner |
| 6,575,929 B2 | 6/2003 | Sussman |
| 6,575,932 B1 | 6/2003 | Obrien |
| 6,575,968 B1 | 6/2003 | Eggers |
| 6,579,270 B2 | 6/2003 | Sussman |
| 6,582,423 B1 | 6/2003 | Thapliyal |
| 6,585,639 B1 | 7/2003 | Kotmel |
| 6,585,732 B2 | 7/2003 | Mulier |
| 6,588,613 B1 | 7/2003 | Pechenik |
| 6,589,201 B1 | 7/2003 | Sussman |
| 6,589,204 B1 | 7/2003 | Sussman |
| 6,589,237 B2 | 7/2003 | Woloszko |
| 6,592,594 B2 | 7/2003 | Rimbaugh |
| 6,595,989 B1 | 7/2003 | Schaer |
| 6,595,990 B1 | 7/2003 | Weinstein |
| 6,599,311 B1 | 7/2003 | Biggs |
| 6,602,248 B1 | 8/2003 | Sharps |
| 6,605,087 B2 | 8/2003 | Swartz |
| 6,607,529 B1 | 8/2003 | Jones |
| 6,610,043 B1 | 8/2003 | Ingenito |
| 6,620,130 B1 | 9/2003 | Ginsburg |
| 6,620,155 B2 | 9/2003 | Underwood |
| 6,623,444 B2 | 9/2003 | Babaev |
| 6,629,974 B2 | 10/2003 | Penny |
| 6,632,193 B1 | 10/2003 | Davison |
| 6,632,220 B1 | 10/2003 | Eggers |
| 6,634,363 B1 | 10/2003 | Danek |
| 6,647,300 B1 | 11/2003 | Balasubramanian |
| 6,648,847 B2 | 11/2003 | Sussman |
| 6,652,594 B2 | 11/2003 | Francis |
| 6,653,525 B2 | 11/2003 | Ingenito |
| 6,659,106 B1 | 12/2003 | Hovda |
| 6,669,685 B1 | 12/2003 | Rizoiu |
| 6,669,694 B2 | 12/2003 | Shadduck |
| 6,673,071 B2 | 1/2004 | Vandusseldorp |
| 6,676,628 B2 | 1/2004 | Sussman |
| 6,676,629 B2 | 1/2004 | Andrew |
| 6,679,264 B1 | 1/2004 | Deem |
| 6,679,879 B2 | 1/2004 | Shadduck |
| 6,682,520 B2 | 1/2004 | Ingenito |
| 6,692,494 B1 | 2/2004 | Cooper |
| 6,695,839 B2 | 2/2004 | Sharkey |
| 6,699,244 B2 | 3/2004 | Carranza |
| 6,708,056 B2 | 3/2004 | Duchon |
| 6,712,811 B2 | 3/2004 | Underwood |
| 6,712,812 B2 | 3/2004 | Roschak |
| 6,716,252 B2 | 4/2004 | Lazarovitz |
| 6,719,738 B2 | 4/2004 | Mehier |
| 6,719,754 B2 | 4/2004 | Underwood |
| 6,719,755 B2 | 4/2004 | Sliwa, Jr. |
| 6,723,064 B2 | 4/2004 | Babaev |
| 6,726,684 B1 | 4/2004 | Woloszko |
| 6,726,696 B1 | 4/2004 | Houser |
| 6,726,708 B2 | 4/2004 | Lasheras |
| 6,730,079 B2 | 5/2004 | Lovewell |
| 6,734,405 B2 | 5/2004 | Centanni |
| 6,740,082 B2 | 5/2004 | Shadduck |
| 6,746,447 B2 | 6/2004 | Davison |
| 6,749,604 B1 | 6/2004 | Eggers |
| 6,755,794 B2 | 6/2004 | Soukup |
| 6,758,846 B2 | 7/2004 | Goble |
| 6,760,616 B2 | 7/2004 | Hoey |
| 6,763,836 B2 | 7/2004 | Tasto |
| 6,764,487 B2 | 7/2004 | Mulier |
| 6,766,202 B2 | 7/2004 | Underwood |
| 6,770,070 B1 | 8/2004 | Balbierz |
| 6,770,071 B2 | 8/2004 | Woloszko |
| 6,772,012 B2 | 8/2004 | Ricart |
| 6,773,431 B2 | 8/2004 | Eggers |
| 6,776,765 B2 | 8/2004 | Soukup |
| 6,776,780 B2 | 8/2004 | Mulier |
| 6,780,178 B2 | 8/2004 | Palanker |
| 6,780,180 B1 | 8/2004 | Goble |
| 6,805,130 B2 | 10/2004 | Tasto |
| 6,813,520 B2 | 11/2004 | Truckai |
| 6,827,718 B2 | 12/2004 | Hutchins |
| 6,832,996 B2 | 12/2004 | Woloszko |
| 6,837,884 B2 | 1/2005 | Woloszko |
| 6,837,886 B2 | 1/2005 | Collins |
| 6,837,887 B2 | 1/2005 | Woloszko |
| 6,837,888 B2 | 1/2005 | Ciarrocca |
| 6,852,108 B2 | 2/2005 | Barry |
| 6,860,847 B2 | 3/2005 | Alferness |
| 6,860,868 B1 | 3/2005 | Sussman |
| 6,875,194 B2 | 4/2005 | MacKool |
| 6,893,438 B2 | 5/2005 | Hall |
| 6,896,672 B1 | 5/2005 | Eggers |
| 6,896,674 B1 | 5/2005 | Woloszko |
| 6,896,675 B2 | 5/2005 | Leung |
| 6,901,927 B2 | 6/2005 | Deem |
| 6,904,909 B2 | 6/2005 | Andreas |
| 6,905,475 B2 | 6/2005 | Hauschild |
| 6,905,496 B1 | 6/2005 | Ellman |
| 6,907,881 B2 | 6/2005 | Suki |
| 6,911,028 B2 | 6/2005 | Shadduck |
| 6,915,806 B2 | 7/2005 | Pacek |
| 6,916,318 B2 | 7/2005 | Francischelli |
| 6,918,903 B2 | 7/2005 | Bass |
| 6,921,385 B2 | 7/2005 | Clements |
| 6,929,640 B1 | 8/2005 | Underwood |
| 6,929,642 B2 | 8/2005 | Xiao |
| 6,949,096 B2 | 9/2005 | Davison |
| 6,949,098 B2 | 9/2005 | Mulier |
| 6,952,615 B2 | 10/2005 | Satake |
| 6,955,674 B2 | 10/2005 | Eick |
| 6,955,675 B2 | 10/2005 | Jain |
| 6,960,182 B2 | 11/2005 | Moutafis |
| 6,960,203 B2 | 11/2005 | Xiao |

(56) References Cited

U.S. PATENT DOCUMENTS

| | | |
|---|---|---|
| 6,960,204 B2 | 11/2005 | Eggers |
| 6,969,376 B2 | 11/2005 | Takagi |
| 6,972,014 B2 | 12/2005 | Eum |
| 6,986,769 B2 | 1/2006 | Nelson |
| 6,991,028 B2 | 1/2006 | Comeaux |
| 6,991,631 B2 | 1/2006 | Woloszko |
| 7,004,940 B2 | 2/2006 | Ryan |
| 7,004,941 B2 | 2/2006 | Tvinnereim |
| 7,014,652 B2 | 3/2006 | Cioanta |
| 7,022,088 B2 | 4/2006 | Keast |
| 7,025,762 B2 | 4/2006 | Johnston |
| 7,031,504 B1 | 4/2006 | Argiro |
| 7,083,612 B2 | 8/2006 | Littrup |
| 7,087,040 B2 | 8/2006 | McGuckin, Jr. |
| 7,089,064 B2 | 8/2006 | Manker |
| 7,094,215 B2 | 8/2006 | Davison |
| 7,101,367 B2 | 9/2006 | Xiao |
| 7,104,986 B2 | 9/2006 | Hovda |
| 7,105,007 B2 | 9/2006 | Hibler |
| 7,112,198 B2 | 9/2006 | Satake |
| 7,113,838 B2 | 9/2006 | Funk |
| RE39,358 E | 10/2006 | Goble |
| 7,128,748 B2 | 10/2006 | Mooradian |
| 7,130,697 B2 | 10/2006 | Chornenky |
| 7,131,969 B1 | 11/2006 | Hovda |
| 7,136,064 B2 | 11/2006 | Zuiderveld |
| 7,144,402 B2 | 12/2006 | Kuester, III |
| 7,144,588 B2 | 12/2006 | Oray |
| 7,153,301 B2 | 12/2006 | Swartz |
| 7,166,105 B2 | 1/2007 | Mulier |
| 7,169,143 B2 | 1/2007 | Eggers |
| 7,179,255 B2 | 2/2007 | Lettice |
| 7,186,234 B2 | 3/2007 | Dahla |
| 7,192,400 B2 | 3/2007 | Campbell |
| 7,192,428 B2 | 3/2007 | Eggers |
| 7,201,750 B1 | 4/2007 | Eggers |
| 7,217,268 B2 | 5/2007 | Eggers |
| 7,225,040 B2 | 5/2007 | Eller |
| 7,233,820 B2 | 6/2007 | Gilboa |
| 7,235,070 B2 | 6/2007 | Vanney |
| 7,237,555 B2 | 7/2007 | Kochamba |
| 7,241,293 B2 | 7/2007 | Davison |
| 7,261,709 B2 | 8/2007 | Swoyer |
| 7,261,710 B2 | 8/2007 | Elmouelhi |
| 7,270,658 B2 | 9/2007 | Woloszko |
| 7,270,659 B2 | 9/2007 | Ricart |
| 7,270,661 B2 | 9/2007 | Dahla |
| 7,276,063 B2 | 10/2007 | Davison |
| 7,280,881 B2 | 10/2007 | Eller |
| 7,297,143 B2 | 11/2007 | Woloszko |
| 7,297,145 B2 | 11/2007 | Woloszko |
| 7,320,325 B2 | 1/2008 | Duchon |
| 7,335,195 B2 | 2/2008 | Mehier |
| 7,335,197 B2 | 2/2008 | Sage |
| 7,340,307 B2 | 3/2008 | Maguire |
| 7,347,859 B2 | 3/2008 | Garabedian |
| 7,364,579 B2 | 4/2008 | Mulier |
| 7,410,486 B2 | 8/2008 | Fuimaono |
| 7,419,500 B2 | 9/2008 | Marko |
| 7,422,588 B2 | 9/2008 | Mulier |
| 7,429,262 B2 | 9/2008 | Woloszko |
| 7,435,250 B2 | 10/2008 | Francischelli |
| 7,470,228 B2 | 12/2008 | Connors |
| 7,470,272 B2 | 12/2008 | Mulier |
| 7,503,904 B2 | 3/2009 | Choi |
| 7,512,445 B2 | 3/2009 | Truckai |
| 7,549,987 B2 | 6/2009 | Shadduck |
| 7,559,367 B2 | 7/2009 | Vinegar |
| 7,585,295 B2 | 9/2009 | Ben-Nun |
| 7,597,147 B2 | 10/2009 | Vitek |
| 7,674,259 B2 | 3/2010 | Shadduck |
| 7,678,111 B2 | 3/2010 | Mulier |
| 7,727,228 B2 | 6/2010 | Abboud |
| 7,753,871 B2 | 7/2010 | Mehier |
| 7,794,460 B2 | 9/2010 | Mulier |
| 7,831,133 B2 | 11/2010 | Vinegar |
| 7,892,229 B2 | 2/2011 | Shadduck |
| 7,896,871 B2 | 3/2011 | Bhushan |
| 7,913,698 B2 | 3/2011 | Barry |
| 7,993,323 B2 | 8/2011 | Barry |
| 8,014,711 B2 | 9/2011 | Ito |
| 8,016,823 B2 | 9/2011 | Shadduck |
| 8,145,113 B2 | 3/2012 | Murakami |
| 8,147,532 B2 | 4/2012 | Barry |
| 8,187,269 B2 | 5/2012 | Shadduck |
| 8,216,224 B2 | 7/2012 | Morris |
| 8,224,165 B2 | 7/2012 | Vinegar |
| 8,226,637 B2 | 7/2012 | Satake |
| 8,229,588 B2 | 7/2012 | Tsen |
| 8,231,617 B2 | 7/2012 | Satake |
| 8,251,985 B2 | 8/2012 | Hoey |
| 8,272,383 B2 | 9/2012 | Hoey |
| 8,273,079 B2 | 9/2012 | Hoey |
| 8,313,485 B2 | 11/2012 | Shadduck |
| 8,322,335 B2 | 12/2012 | Barry |
| 8,355,623 B2 | 1/2013 | Vinegar |
| 8,372,065 B2 | 2/2013 | Hoey |
| 8,388,611 B2 | 3/2013 | Shadduck |
| 8,419,723 B2 | 4/2013 | Shadduck |
| 8,437,870 B2 | 5/2013 | Tsai |
| 8,444,636 B2 | 5/2013 | Shadduck |
| 8,512,326 B2 | 8/2013 | Shadduck |
| 8,521,074 B2 | 8/2013 | Murakami |
| 8,574,226 B2 | 11/2013 | Shadduck |
| 8,579,888 B2 | 11/2013 | Hoey |
| 8,579,892 B2 | 11/2013 | Hoey |
| 8,579,893 B2 | 11/2013 | Hoey |
| 8,585,645 B2 | 11/2013 | Barry |
| 8,585,692 B2 | 11/2013 | Shadduck |
| 8,632,530 B2 | 1/2014 | Hoey |
| 8,641,711 B2 | 2/2014 | Kelly |
| 8,647,339 B2 | 2/2014 | Satake |
| 8,721,632 B2 | 5/2014 | Hoey |
| 8,734,380 B2 | 5/2014 | Barry |
| 8,758,341 B2 | 6/2014 | Shadduck |
| 8,761,626 B2 | 6/2014 | Seo |
| 8,801,702 B2 | 8/2014 | Hoey |
| 8,805,466 B2 | 8/2014 | Salahieh |
| 8,858,549 B2 | 10/2014 | Shadduck |
| 8,900,223 B2 | 12/2014 | Shadduck |
| 8,911,430 B2 | 12/2014 | Hoey |
| 9,113,858 B2 | 8/2015 | Barry |
| 9,113,944 B2 | 8/2015 | Shadduck |
| 9,125,667 B2 | 9/2015 | Stone |
| 9,161,801 B2 | 10/2015 | Hoey |
| 9,179,973 B2 | 11/2015 | Nabutovsky |
| 9,198,708 B2 | 12/2015 | Hoey |
| 9,204,889 B2 | 12/2015 | Shadduck |
| 9,345,507 B2 | 5/2016 | Hoey |
| 9,387,310 B2 | 7/2016 | Satake |
| 9,433,457 B2 | 9/2016 | Shadduck |
| 9,468,487 B2 | 10/2016 | Shadduck |
| 9,526,555 B2 | 12/2016 | Hoey |
| 9,615,875 B2 | 4/2017 | Shadduck |
| 9,757,535 B2 | 9/2017 | Rajagopalan |
| 9,844,641 B2 | 12/2017 | Rajagopalan |
| 9,907,599 B2 | 3/2018 | Hoey |
| 9,974,607 B2 | 5/2018 | Stone |
| 10,179,019 B2 | 1/2019 | Chee |
| 10,299,857 B2 | 5/2019 | Rajagopalan |
| 10,864,352 B2 | 12/2020 | Rajagopalan |
| 11,806,066 B2 * | 11/2023 | Sharma .................. A61B 18/04 |
| 11,864,809 B2 * | 1/2024 | Sharma .................. A61B 18/04 |
| 2001/0020167 A1 | 9/2001 | Woloszko |
| 2001/0029370 A1 | 10/2001 | Hodva |
| 2001/0037106 A1 | 11/2001 | Shadduck |
| 2002/0013601 A1 | 1/2002 | Nobles |
| 2002/0019627 A1 | 2/2002 | Maguire |
| 2002/0049438 A1 | 4/2002 | Sharkey |
| 2002/0077516 A1 | 6/2002 | Flanigan |
| 2002/0078956 A1 | 6/2002 | Sharpe |
| 2002/0082667 A1 | 6/2002 | Shadduck |
| 2002/0095152 A1 | 7/2002 | Ciarrocca |
| 2002/0111386 A1 | 8/2002 | Sekins |

(56) References Cited

U.S. PATENT DOCUMENTS

| | | |
|---|---|---|
| 2002/0133147 A1 | 9/2002 | Marchitto |
| 2002/0143325 A1 | 10/2002 | Sampson |
| 2002/0156470 A1 | 10/2002 | Shadduck |
| 2002/0161326 A1 | 10/2002 | Sussman |
| 2002/0177846 A1 | 11/2002 | Mulier |
| 2002/0193789 A1 | 12/2002 | Underwood |
| 2003/0028189 A1 | 2/2003 | Woloszko |
| 2003/0040742 A1 | 2/2003 | Underwood |
| 2003/0069575 A1 | 4/2003 | Chin |
| 2003/0088145 A1 | 5/2003 | Scott |
| 2003/0088246 A1 | 5/2003 | Swartz |
| 2003/0097126 A1 | 5/2003 | Woloszko |
| 2003/0099279 A1 | 5/2003 | Venkatasubramanian |
| 2003/0109869 A1 | 6/2003 | Shadduck |
| 2003/0130655 A1 | 7/2003 | Woloszko |
| 2003/0130738 A1 | 7/2003 | Hovda |
| 2003/0144654 A1 | 7/2003 | Hilal |
| 2003/0158545 A1 | 8/2003 | Hovda |
| 2003/0163178 A1 | 8/2003 | Davison |
| 2003/0181922 A1 | 9/2003 | Alferness |
| 2003/0204138 A1 | 10/2003 | Choi |
| 2003/0212394 A1 | 11/2003 | Pearson |
| 2003/0212395 A1 | 11/2003 | Woloszko |
| 2003/0216729 A1 | 11/2003 | Marchitto |
| 2003/0225364 A1 | 12/2003 | Kraft |
| 2004/0006333 A1 | 1/2004 | Arnold |
| 2004/0024398 A1 | 2/2004 | Hovda |
| 2004/0024399 A1 | 2/2004 | Sharps |
| 2004/0031494 A1 | 2/2004 | Danek |
| 2004/0037986 A1 | 2/2004 | Houston |
| 2004/0038868 A1 | 2/2004 | Ingenito |
| 2004/0047855 A1 | 3/2004 | Ingenito |
| 2004/0049180 A1 | 3/2004 | Sharps |
| 2004/0054366 A1 | 3/2004 | Davison |
| 2004/0055606 A1 | 3/2004 | Hendricksen |
| 2004/0059313 A1 | 3/2004 | Tachibana |
| 2004/0068256 A1 | 4/2004 | Rizoiu |
| 2004/0068306 A1 | 4/2004 | Shadduck |
| 2004/0087937 A1 | 5/2004 | Eggers |
| 2004/0116922 A1 | 6/2004 | Hovda |
| 2004/0193150 A1 | 9/2004 | Sharkey |
| 2004/0199226 A1 | 10/2004 | Shadduck |
| 2004/0230188 A1 | 11/2004 | Cioanta |
| 2004/0230190 A1 | 11/2004 | Dahla |
| 2004/0230316 A1 | 11/2004 | Cioanta |
| 2004/0254532 A1 | 12/2004 | Mehier |
| 2005/0004634 A1 | 1/2005 | Ricart |
| 2005/0010205 A1 | 1/2005 | Hovda |
| 2005/0015047 A1 | 1/2005 | Shah |
| 2005/0095168 A1 | 5/2005 | Centanni |
| 2005/0119650 A1 | 6/2005 | Sanders |
| 2005/0149065 A1 | 7/2005 | Modesitt |
| 2005/0166925 A1 | 8/2005 | Wilson |
| 2005/0171582 A1 | 8/2005 | Matlock |
| 2005/0177147 A1 | 8/2005 | Vancelette |
| 2005/0187543 A1 | 8/2005 | Underwood |
| 2005/0215991 A1 | 9/2005 | Altman |
| 2005/0222485 A1 | 10/2005 | Shaw |
| 2005/0228423 A1 | 10/2005 | Khashayar |
| 2005/0228424 A1 | 10/2005 | Khashayar |
| 2005/0240171 A1 | 10/2005 | Forrest |
| 2005/0267468 A1 | 12/2005 | Truckai |
| 2005/0283143 A1 | 12/2005 | Rizoiu |
| 2006/0004400 A1 | 1/2006 | McGurk |
| 2006/0036237 A1 | 2/2006 | Davison |
| 2006/0041277 A1 | 2/2006 | Deem |
| 2006/0047291 A1 | 3/2006 | Barry |
| 2006/0085054 A1 | 4/2006 | Zikorus |
| 2006/0089636 A1 | 4/2006 | Christopherson |
| 2006/0095032 A1 | 5/2006 | Jackson |
| 2006/0100619 A1 | 5/2006 | McClurken |
| 2006/0130830 A1 | 6/2006 | Barry |
| 2006/0135955 A1 | 6/2006 | Shadduck |
| 2006/0161233 A1 | 7/2006 | Barry |
| 2006/0178670 A1 | 8/2006 | Woloszko |
| 2006/0200076 A1 | 9/2006 | Gonzalez |
| 2006/0200191 A1 | 9/2006 | Zadno-Azizi |
| 2006/0224154 A1 | 10/2006 | Shadduck |
| 2006/0264832 A1 | 11/2006 | Skwarek |
| 2006/0276871 A1 | 12/2006 | Lamson |
| 2007/0032785 A1 | 2/2007 | Diederich |
| 2007/0036417 A1 | 2/2007 | Argiro |
| 2007/0049920 A1 | 3/2007 | McClurken |
| 2007/0083085 A1 | 4/2007 | Birnkrant |
| 2007/0091087 A1 | 4/2007 | Zuiderveld |
| 2007/0142846 A1 | 6/2007 | Catanese |
| 2007/0179496 A1 | 8/2007 | Swoyer |
| 2007/0225744 A1 | 9/2007 | Nobles |
| 2007/0225750 A1 | 9/2007 | Ren |
| 2007/0239197 A1 | 10/2007 | Dubey |
| 2007/0250056 A1 | 10/2007 | Vanney |
| 2007/0265687 A1 | 11/2007 | Deem |
| 2008/0021484 A1 | 1/2008 | Catanese |
| 2008/0021485 A1 | 1/2008 | Catanese |
| 2008/0033232 A1 | 2/2008 | Catanese |
| 2008/0033458 A1 | 2/2008 | McLean |
| 2008/0033488 A1 | 2/2008 | Catanese |
| 2008/0033493 A1 | 2/2008 | Deckman |
| 2008/0039833 A1 | 2/2008 | Catanese |
| 2008/0039872 A1 | 2/2008 | Catanese |
| 2008/0039874 A1 | 2/2008 | Catanese |
| 2008/0039875 A1 | 2/2008 | Catanese |
| 2008/0039876 A1 | 2/2008 | Catanese |
| 2008/0039893 A1 | 2/2008 | McLean |
| 2008/0039894 A1 | 2/2008 | Catanese |
| 2008/0046045 A1 | 2/2008 | Yon |
| 2008/0103566 A1 | 5/2008 | Mehier |
| 2008/0110457 A1 | 5/2008 | Barry |
| 2008/0114297 A1 | 5/2008 | Barry |
| 2008/0132826 A1 | 6/2008 | Shadduck |
| 2008/0167649 A1 | 7/2008 | Edwards |
| 2008/0183036 A1 | 7/2008 | Saadat |
| 2008/0208187 A1 | 8/2008 | Bhushan |
| 2008/0208189 A1 | 8/2008 | Van Wyk |
| 2008/0249399 A1 | 10/2008 | Appling |
| 2008/0275440 A1 | 11/2008 | Kratoska |
| 2008/0281267 A1 | 11/2008 | Mehier |
| 2008/0300571 A1 | 12/2008 | LePivert |
| 2009/0018553 A1 | 1/2009 | McLean |
| 2009/0054868 A1 | 2/2009 | Sharkey |
| 2009/0054869 A1 | 2/2009 | Sharkey |
| 2009/0054870 A1 | 2/2009 | Sharkey |
| 2009/0054871 A1 | 2/2009 | Sharkey |
| 2009/0082837 A1 | 3/2009 | Gellman |
| 2009/0099544 A1 | 4/2009 | Munrow |
| 2009/0105702 A1 | 4/2009 | Shadduck |
| 2009/0105703 A1 | 4/2009 | Shadduck |
| 2009/0125009 A1 | 5/2009 | Zikorus |
| 2009/0125010 A1 | 5/2009 | Sharkey |
| 2009/0149846 A1 | 6/2009 | Hoey |
| 2009/0216220 A1 | 8/2009 | Hoey |
| 2009/0221998 A1 | 9/2009 | Epstein |
| 2009/0227998 A1 | 9/2009 | Aljuri |
| 2009/0277457 A1 | 11/2009 | Hoey |
| 2009/0301483 A1 | 12/2009 | Barry |
| 2009/0306640 A1 | 12/2009 | Glaze |
| 2009/0312753 A1 | 12/2009 | Shadduck |
| 2010/0016757 A1 | 1/2010 | Greenburg |
| 2010/0049031 A1 | 2/2010 | Fruland |
| 2010/0076416 A1 | 3/2010 | Hoey |
| 2010/0094270 A1 | 4/2010 | Sharma |
| 2010/0114082 A1 | 5/2010 | Sharma |
| 2010/0114083 A1 | 5/2010 | Sharma |
| 2010/0145254 A1 | 6/2010 | Shadduck |
| 2010/0145325 A1 | 6/2010 | Hoey |
| 2010/0145326 A1 | 6/2010 | Hoey |
| 2010/0160905 A1 | 6/2010 | Shadduck |
| 2010/0168624 A1 | 7/2010 | Sliwa |
| 2010/0179416 A1 | 7/2010 | Hoey |
| 2010/0179528 A1 | 7/2010 | Shadduck |
| 2010/0204688 A1 | 8/2010 | Hoey |
| 2010/0262133 A1 | 10/2010 | Hoey |
| 2010/0274260 A1 | 10/2010 | Darpiany |
| 2010/0286679 A1 | 11/2010 | Hoey |

(56) References Cited

U.S. PATENT DOCUMENTS

| | | |
|---|---|---|
| 2010/0292767 A1 | 11/2010 | Hoey |
| 2010/0298948 A1 | 11/2010 | Hoey |
| 2011/0077628 A1 | 3/2011 | Hoey |
| 2011/0118717 A1 | 5/2011 | Shadduck |
| 2011/0160648 A1 | 6/2011 | Hoey |
| 2011/0172654 A1 | 7/2011 | Barry |
| 2011/0184400 A1 | 7/2011 | Pageard |
| 2011/0190751 A1 | 8/2011 | Ingle |
| 2011/0238144 A1 | 9/2011 | Hoey |
| 2011/0264090 A1 | 10/2011 | Shadduck |
| 2011/0276046 A1 | 11/2011 | Heimbecher |
| 2012/0065632 A1 | 3/2012 | Shadduck |
| 2012/0078078 A1 | 3/2012 | Macadam |
| 2012/0101413 A1 | 4/2012 | Beetel |
| 2012/0116376 A1 | 5/2012 | Hoey |
| 2012/0197358 A1 | 8/2012 | Prescott |
| 2012/0232409 A1 | 9/2012 | Stahmann |
| 2012/0259271 A1 | 10/2012 | Shadduck |
| 2012/0323167 A1 | 12/2012 | Hoey |
| 2013/0006231 A1 | 1/2013 | Sharma |
| 2013/0030410 A1 | 1/2013 | Drasler |
| 2013/0074847 A1 | 3/2013 | Hoey |
| 2013/0079772 A1 | 3/2013 | Shadduck |
| 2013/0116683 A1 | 5/2013 | Shadduck |
| 2013/0165914 A1 | 6/2013 | Satake |
| 2013/0172867 A1 | 7/2013 | Shadduck |
| 2013/0197555 A1 | 8/2013 | Schaer |
| 2013/0237978 A1 | 9/2013 | Shadduck |
| 2013/0267939 A1 | 10/2013 | Barry |
| 2013/0296837 A1 | 11/2013 | Burnett |
| 2013/0345670 A1 | 12/2013 | Rajagopalan |
| 2014/0025057 A1 | 1/2014 | Hoey |
| 2014/0031805 A1 | 1/2014 | Shadduck |
| 2014/0107637 A1 | 4/2014 | Hoey |
| 2014/0114306 A1 | 4/2014 | Harada |
| 2014/0200569 A1 | 7/2014 | Shadduck |
| 2014/0200570 A1 | 7/2014 | Hoey |
| 2014/0276713 A1 | 9/2014 | Hoey |
| 2014/0288543 A1 | 9/2014 | Hoey |
| 2014/0324037 A1 | 10/2014 | Hoey |
| 2014/0357956 A1 | 12/2014 | Salahieh |
| 2014/0358137 A1 | 12/2014 | Hu |
| 2014/0371736 A1 | 12/2014 | Levin |
| 2015/0025515 A1 | 1/2015 | Hoey |
| 2015/0025516 A1 | 1/2015 | Hoey |
| 2015/0080883 A1 | 3/2015 | Haverkost |
| 2015/0126990 A1 | 5/2015 | Sharma |
| 2015/0148738 A1 | 5/2015 | Caplan |
| 2015/0182740 A1 | 7/2015 | Mickelsen |
| 2015/0265329 A1 | 9/2015 | Lalonde |
| 2016/0220297 A1 | 8/2016 | Kroon |
| 2016/0310200 A1 | 10/2016 | Wang |
| 2016/0354140 A1 | 12/2016 | Sharma |
| 2016/0354144 A1 | 12/2016 | Caplan |
| 2017/0165002 A1 | 6/2017 | Sharma |
| 2017/0231678 A1 | 8/2017 | Sharma |
| 2017/0333122 A1 | 11/2017 | Rajagopalan |
| 2017/0367755 A1 | 12/2017 | Sharma |
| 2019/0110830 A1 | 4/2019 | Hastings |
| 2019/0269449 A1 | 9/2019 | Hastings |
| 2019/0343571 A1 | 11/2019 | Shadduck |
| 2019/0388133 A1 | 12/2019 | Sharma |
| 2021/0007796 A1 | 1/2021 | Panescu |

FOREIGN PATENT DOCUMENTS

| | | |
|---|---|---|
| CN | 102238920 | 9/2011 |
| CN | 102238920 A | 11/2011 |
| CN | 103582463 A | 2/2014 |
| CN | 103619276 A | 3/2014 |
| CN | 104856757 A | 8/2015 |
| CN | 105228547 A | 1/2016 |
| CN | 105726292 A | 7/2016 |
| CN | 107242901 A | 10/2017 |
| EP | 0508942 A2 | 10/1992 |
| EP | 1602338 B1 | 12/2005 |
| EP | 2341859 | 7/2011 |
| EP | 2884928 A1 | 6/2015 |
| FR | 2655548 | 6/1991 |
| WO | 1992010142 | 6/1992 |
| WO | 1995028198 A1 | 10/1995 |
| WO | 9902096 A | 1/1999 |
| WO | 1999053853 | 10/1999 |
| WO | 2000029055 | 5/2000 |
| WO | 2001024715 | 4/2001 |
| WO | 02069821 | 9/2002 |
| WO | 2002069821 | 9/2002 |
| WO | 2003070302 | 8/2003 |
| WO | 2003086498 | 10/2003 |
| WO | 2005025635 | 3/2005 |
| WO | 2005102175 | 11/2005 |
| WO | 2006003665 | 1/2006 |
| WO | 2006004482 | 1/2006 |
| WO | 2006019728 A2 | 2/2006 |
| WO | 2006055695 | 5/2006 |
| WO | 2006108974 | 10/2006 |
| WO | 2009009398 | 1/2009 |
| WO | 2009074844 A1 | 6/2009 |
| WO | 2010042461 | 4/2010 |
| WO | 2010042461 A1 | 4/2010 |
| WO | 2012167213 | 12/2012 |
| WO | 2012167213 A2 | 12/2012 |
| WO | 2013044182 A1 | 3/2013 |
| WO | 2013086461 A1 | 6/2013 |
| WO | 2013152119 A1 | 10/2013 |
| WO | 2014113724 | 7/2014 |
| WO | 2014113724 A2 | 7/2014 |
| WO | 2017201504 A1 | 11/2017 |
| WO | 2018089773 A1 | 5/2018 |

OTHER PUBLICATIONS

Läpădat, A. M., Gheonea, D. I., Florescu, L. M., & Gheonea, I. A. (2019). Before and After Treatment Quantitative Assessment of Hepatic Steatosis in a Romanian Population Using Magnetic Resonance Liver Spectroscopy. Current health sciences journal, 45(3) 258-262 (Year: 2019).

Stål P. (2015). Liver fibrosis in non-alcoholic fatty liver disease—diagnostic challenge with prognostic significance. World journal of gastroenterology, 21(39), 11077-11087 (Year: 2015).

Singh, S., Allen, A. M., Wang, Z., Prokop, L. J., Murad, M. H., & Loomba, R. (2015). Fibrosis progression [ . . . ] and meta-analysis of paired-biopsy studies. Clinical gastroenterology and hepatology : the official clinical practice journal of the American Gastroenterological Association, 13(4), 643-e40 (Year: 2015).

El-Zefzafy, W., Eltokhy, H., Mohamed, N. A., & Abu-Zahab, Z. (2015). Significance of Serum Cytokeratin-18 in Prediction of U Hepatocellular Carcinoma in Chronic Hepatitis C Infected Egyptian Patients. Open access Macedonian journal of medical sciences, 3(1), 117-123 (Year: 2015).

Lee, D. H., Lee, J. M., Yoon, J. H., Kim, Y. J., Lee, J. H., Yu, S. J., & Han, J. K. (2018). Liver Stiffness Measured by Two-Dimensional Shear-Wave Elastography: Prognostic Value after Radiofrequency Ablation for Hepatocellular Carcinoma. Liver cancer, 7(1), 65-75 (Year: 2018).

Microsulis America, Inc.; Instructions for Use, Microsulis Microwave Endometrial Ablation (MEA) System; Microsulis Americas, Inc.—MEA System Instructions for Use; Dec. 2002; 62795/09/038 Issue 1; pp. 16-35; Microsulis Americas.

International Search Report for PCT/US2017/033693, Oct. 2, 2017.

Thibeau; AW-06995-001; Text, Manual, Novasure, V1, EN, US; Aug. 26, 2011; pp. 1-23; Hologic, Inc.

Sharma et al; Barrett's Oesophagus, A randomised controlled trial of ablation of Barrett's oesophagus with multipolar electrocoagulation versus argon plasma coagulation in combination with acid suppression: long term results; Gut; 2006; 55:1233-1239; doi:10.1136/gut.2005.086777.

Sharma et al; Balloon-based, cicrumferential, endoscopic radiofrequency ablation of Barrett's esophagus: 1-year follow-up of 100 patients

(56) References Cited

OTHER PUBLICATIONS (with video); Gastrointestinal Endoscopy; 2007; vol. 65, No. 2; 0016-5/$32.00 doi:10.1016/j.gie.2006.09.033; pp. 185-195.
Sanfilippo et al; Update: Options in Endometrial Ablation; Supplement to OBG Management; Dec. 2009; pp. S1-S24; Dowden Health Media.
United States FDA; Summary of Safety and Effectiveness Data: Cryogen, Inc.: Her Option Uterine Cryoablation Therapy System; PMA P000032; Sep. 14, 2001; pp. 1-22.
American Medical Systems, Inc.; her option office cryoablation therapy Resource Guide; 2007; pp. 1-29; American Medical Systems, Inc . . . 10700 Bren Road West, Minnetonka, MN 55343 USA.
Boston Scientific; HTA System Endometrial Ablation System; 2006; BVU 1090 Rev. A 10M Sep. 2006-Sep. 2008; Boston Scientific Corporation, One Boston Scientific Place, Natick, MA 01760-1537.
Ethicon Women's Health & Urology; Instructions for Use, Gynecare Thermachoice III Uterine Balloon Therapy System, Thermal Balloon Ablation Silicone Catheter and Syringe (Single-Use); Mar. 26, 2008; pp. 1-156; TCIII_389630.R06_Main.indd; Gynecare, a division of Ethicon, Inc. a Johnson & Johnson company, Sommerville, NJ, 08876-0151 USA.
Johnston et al.; Cryoablation of Barrett's esophagus: a pilot study; Gastrointestinal Endoscopy; 2005; pp. 842-848; vol. 62, No. 6, 0016-5107/$30.00 doi:10.1016/j.gie.2005.05.008; American Society for Gastrointestinal Endoscopy.
Carter; Endometrial Ablation: More Choices, More Options; The Female Patient; 2005; pp. 35-40; 30(12).
International Search Report for PCT/US2009/059609, Mar. 5, 2010.
International Search Report for PCT/US2012/040639, Dec. 18, 2012.
International Search Report for PCT/US2014/012131, Jul. 30, 2014.
"Understanding Microprocessors, Advantages of 32-bit CPUs and DSPs." Stevens. Stevens Water Monitoring Systems, Inc., May 12, 2008. Web. Feb. 4, 2013. <http://web.archive.org/web/20080512144927/http://www.stevenswater.com/articles/cpu.aspx>.
Hai; Photoselective Vaporization Prostatectomy: A Palliative Treatment Option for Men with Urinary Obstruction Secondary to Prostate Cancer; PCRI Prost. Cancer Rsrch. Inst. Reprint. from PCRI Insights Nov. 2005, vol. 8(4); pp. 4.
Van De Velde; Vapo-cauterization of the uterus; Amer. J. Med. Sci.; vol. CXVII; 1899.
Blacker; Vaporization of the uterus; J. Obstet. & Gyn.; pp. 488-511; 1901.
Neuwirth et al.; The endometrial ablator: a new instrument; Obst. & Gyn.; vol. 83; No. 5; part 1; pp. 792-796; 1994.
Prior et al.; Treatment of mennorrhagia by radiofrequency heating; Int. J. Hyperthermia; vol. 7; No. 2; pp. 213-220; 1991.
International Search Report for PCT/US2016/012840, Aug. 18, 2016.
International Search Report for PCT/US19/50662, Jan. 7, 2020.
Written Opinion of the International Searching Authority for PCT/US19/50662, Jan. 7, 2020.
International Search Report for PCT/US19/34991, Sep. 20, 2019.
Written Opinion of the International Searching Authority for PCT/US19/34991, Sep. 20, 2019.
International Search Report for PCT/US21/13582, May 13, 2021.
Written Opinion of the International Searching Authority for PCT/US21/13582, May 13, 2021.
International Search Report for PCT/US20/48419, Dec. 18, 2020.
Written Opinion of the International Searching Authority for PCT/US20/48419, Dec. 18, 2020.
International Search Report for PCT/US2021/071778, Feb. 14, 2022.

* cited by examiner

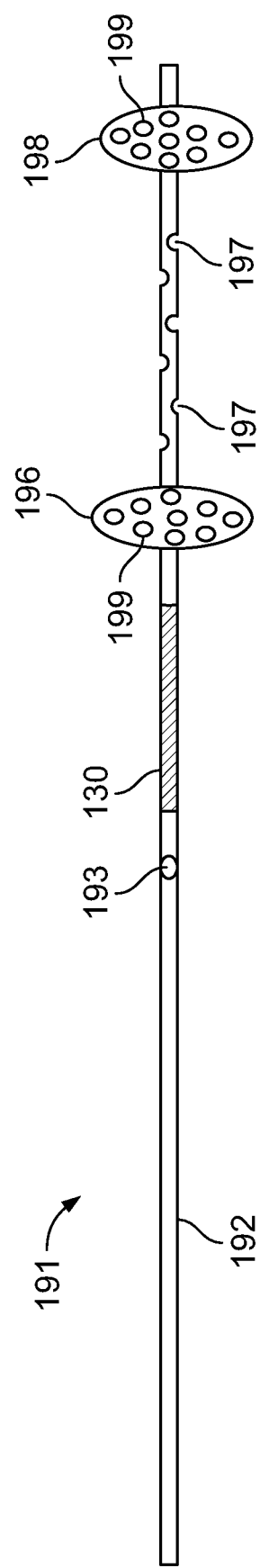

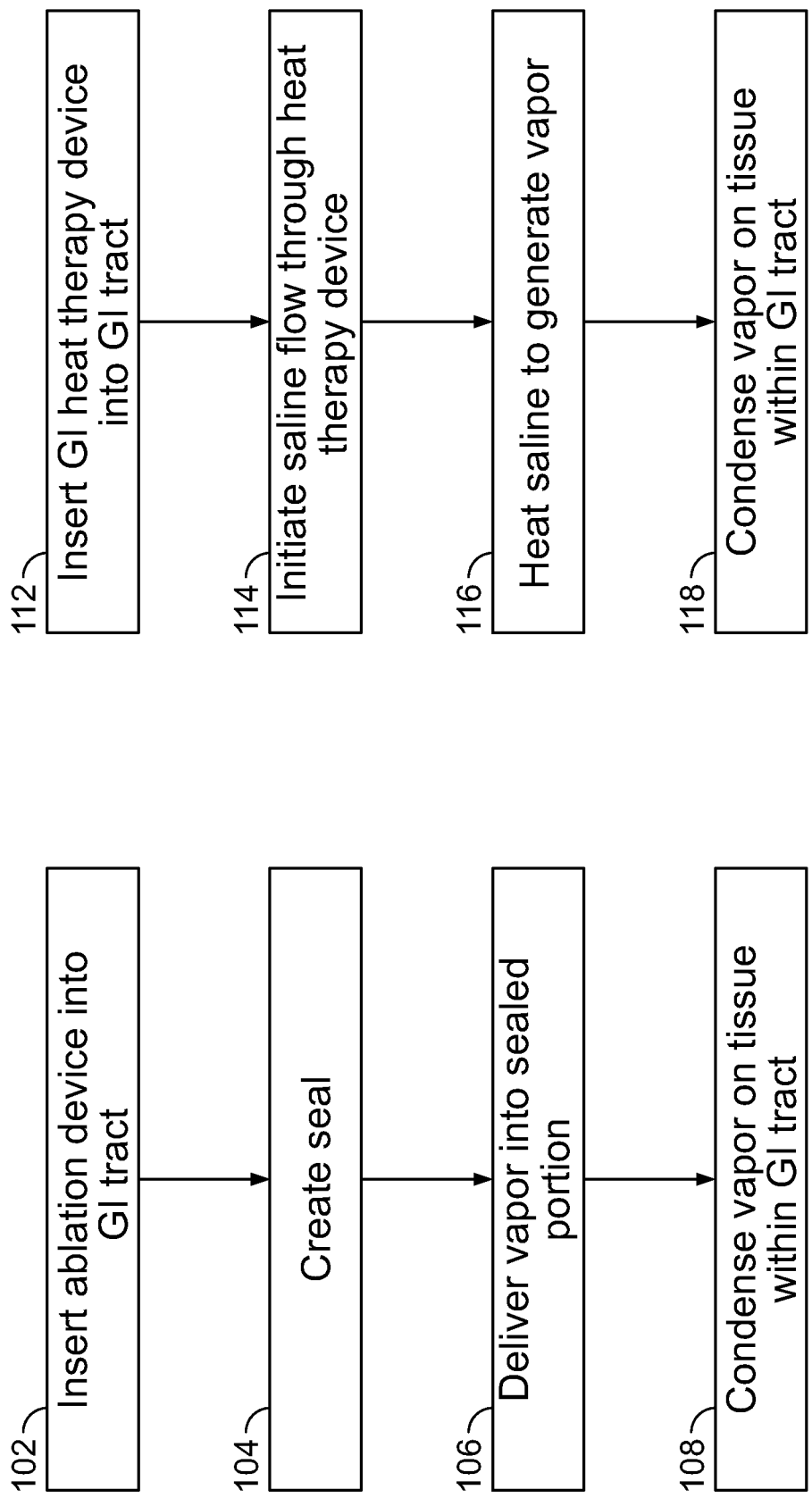

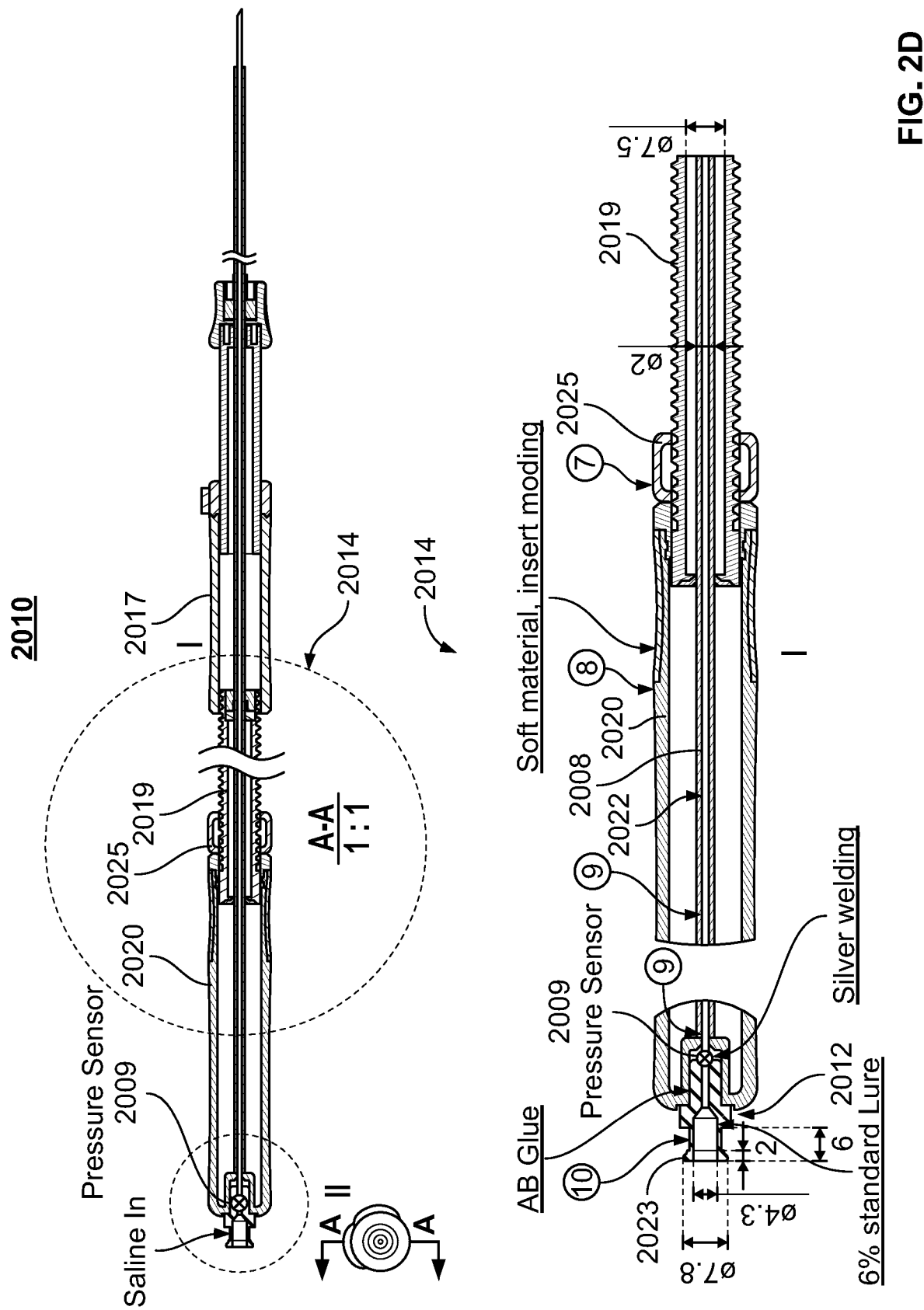

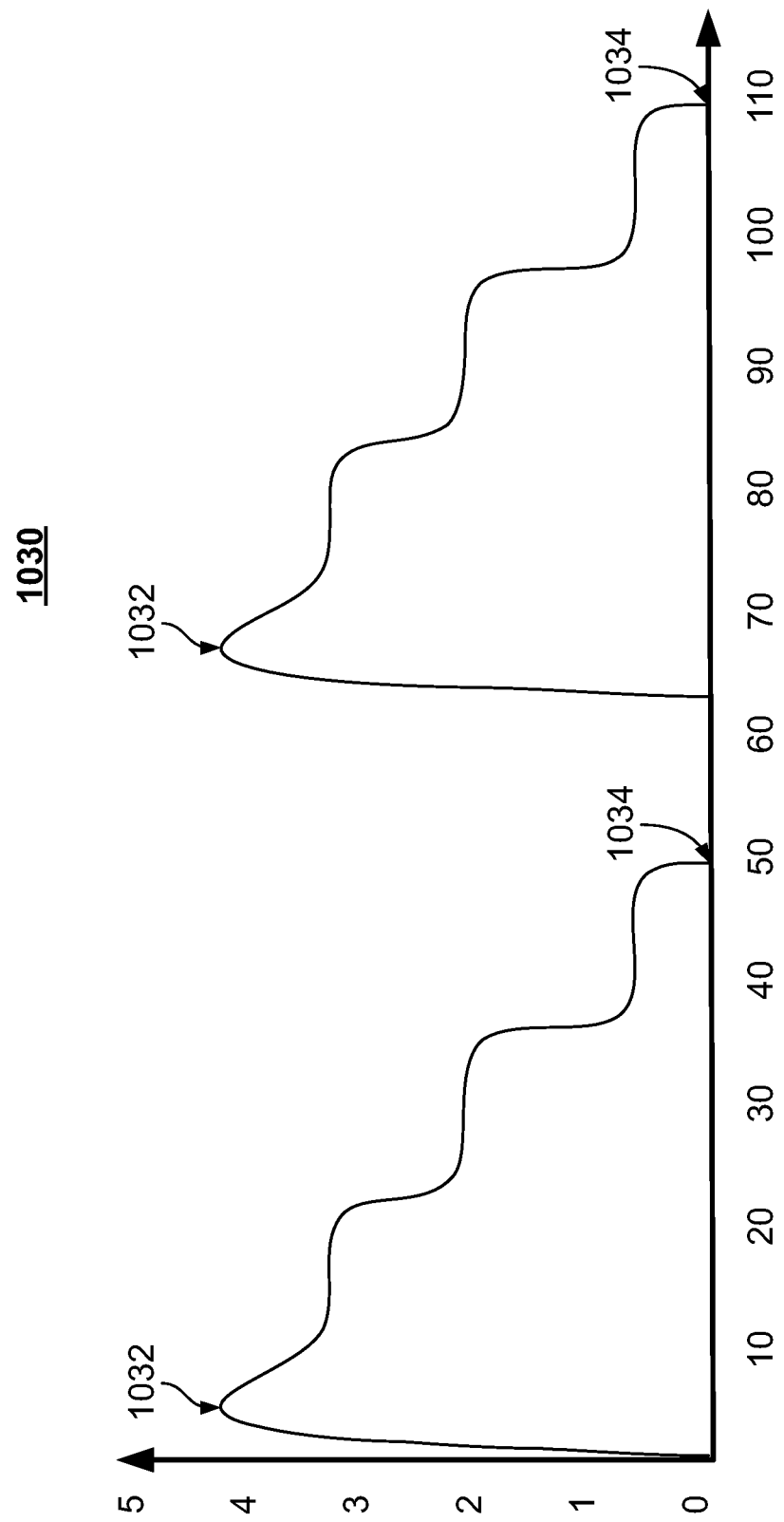

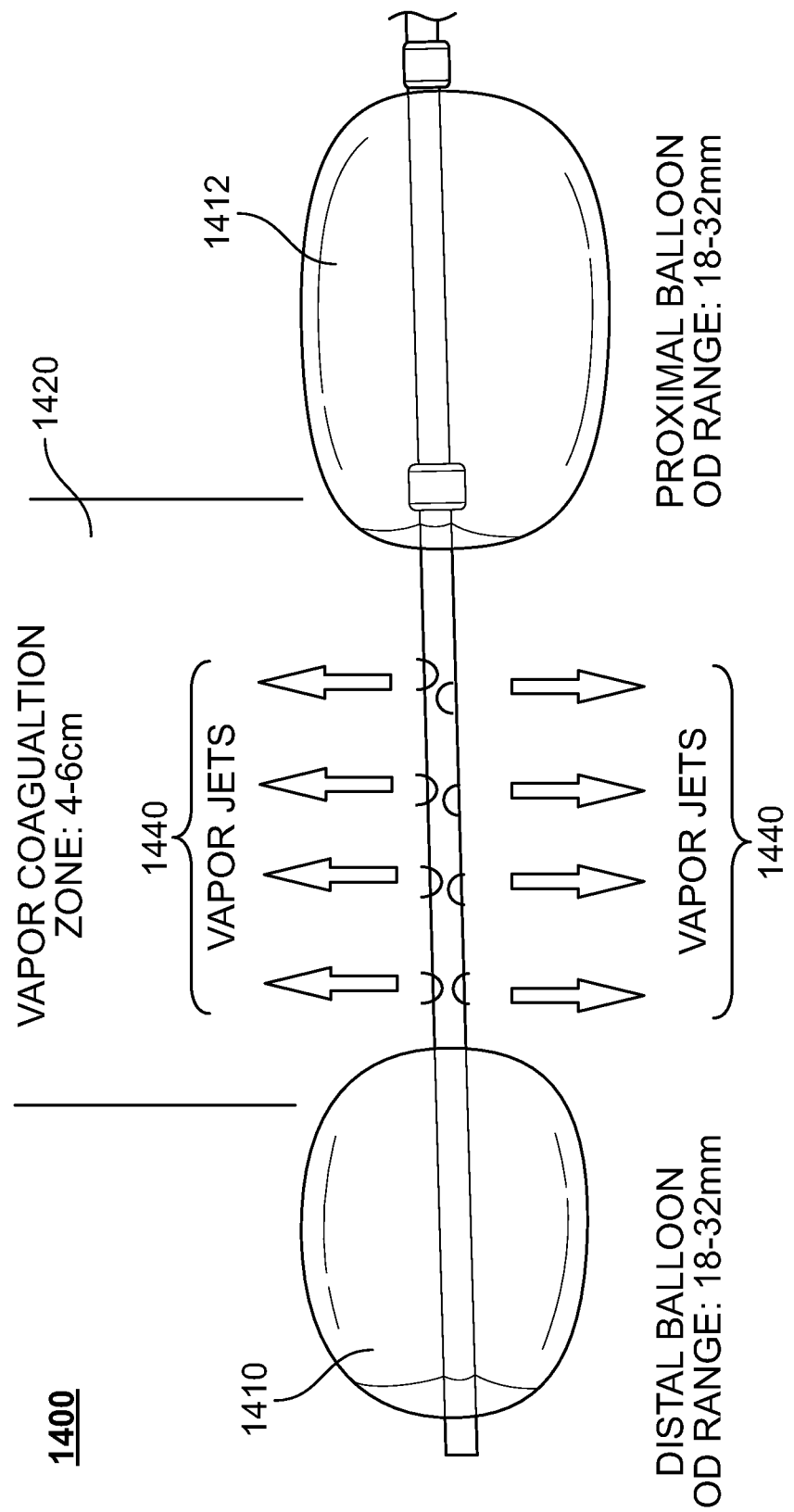

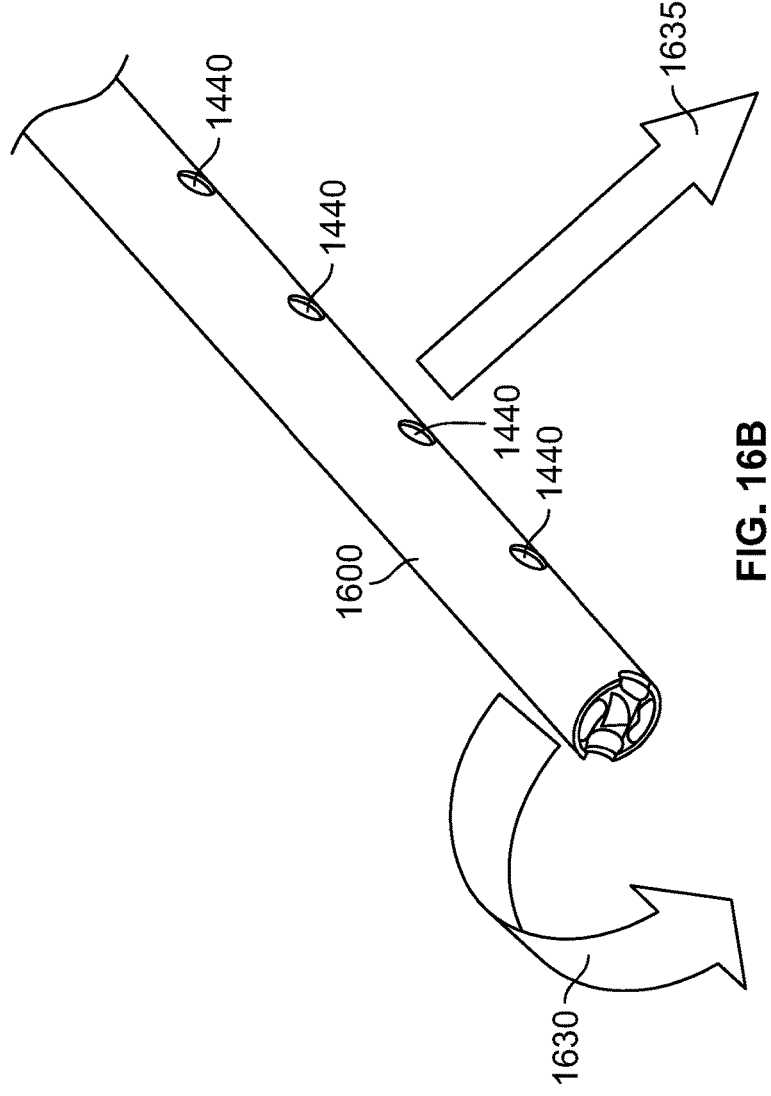
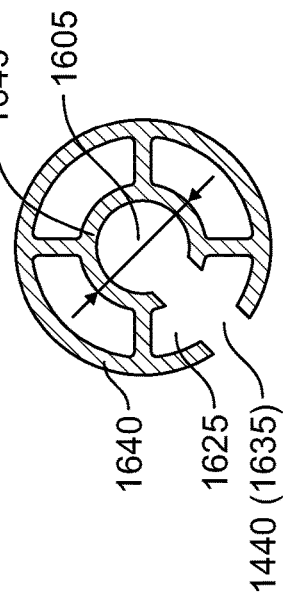
FIG. 16D
FIG. 16B
FIG. 16C

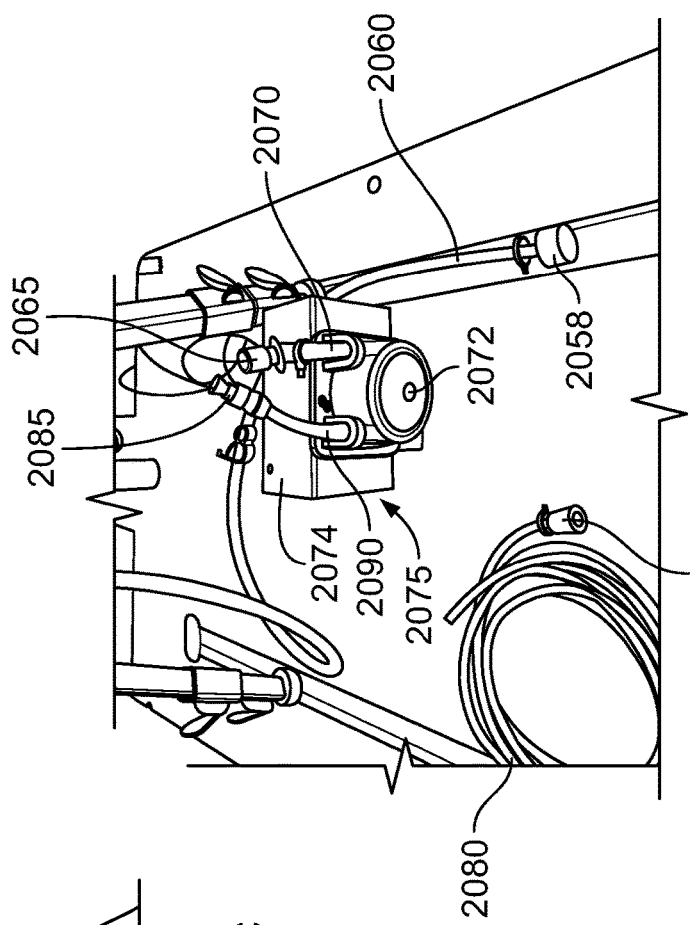
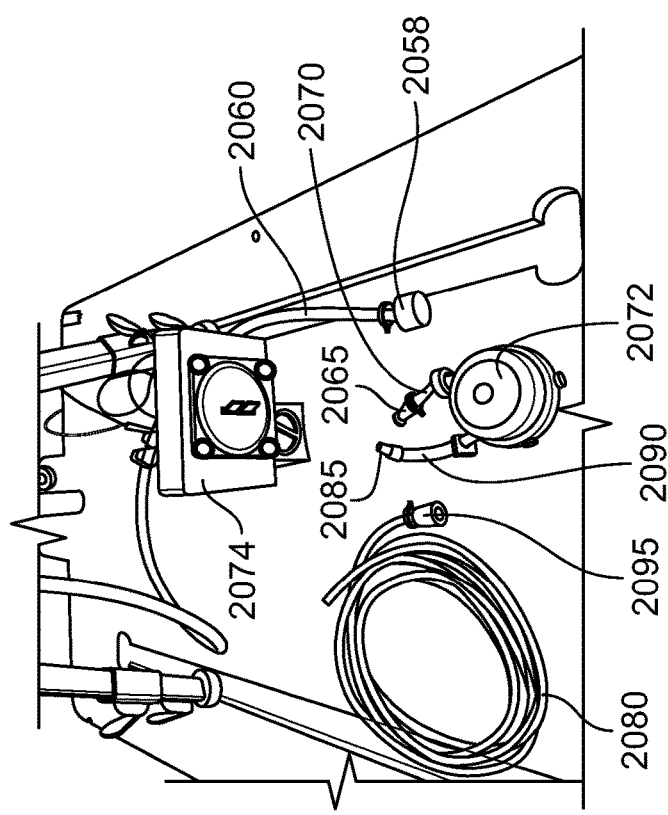
FIG. 20D
FIG. 20C

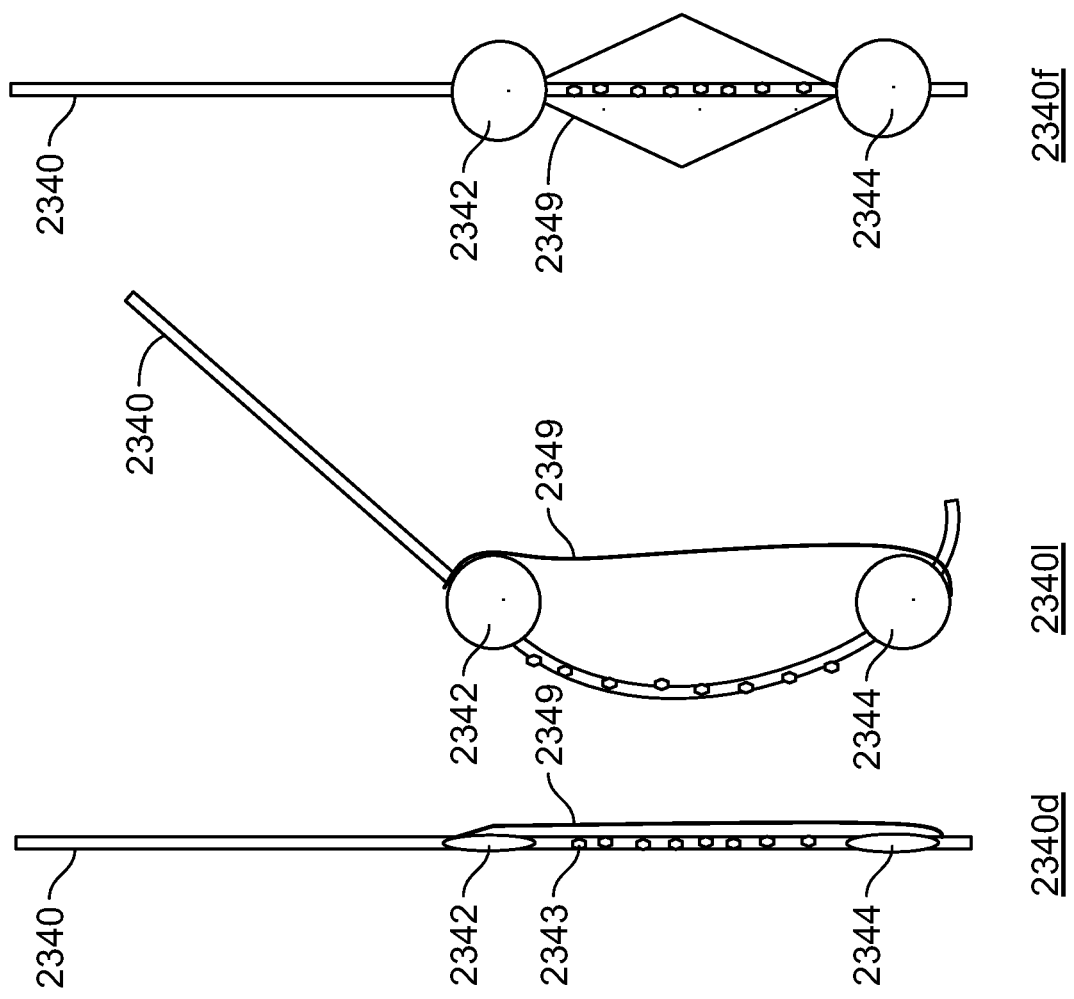

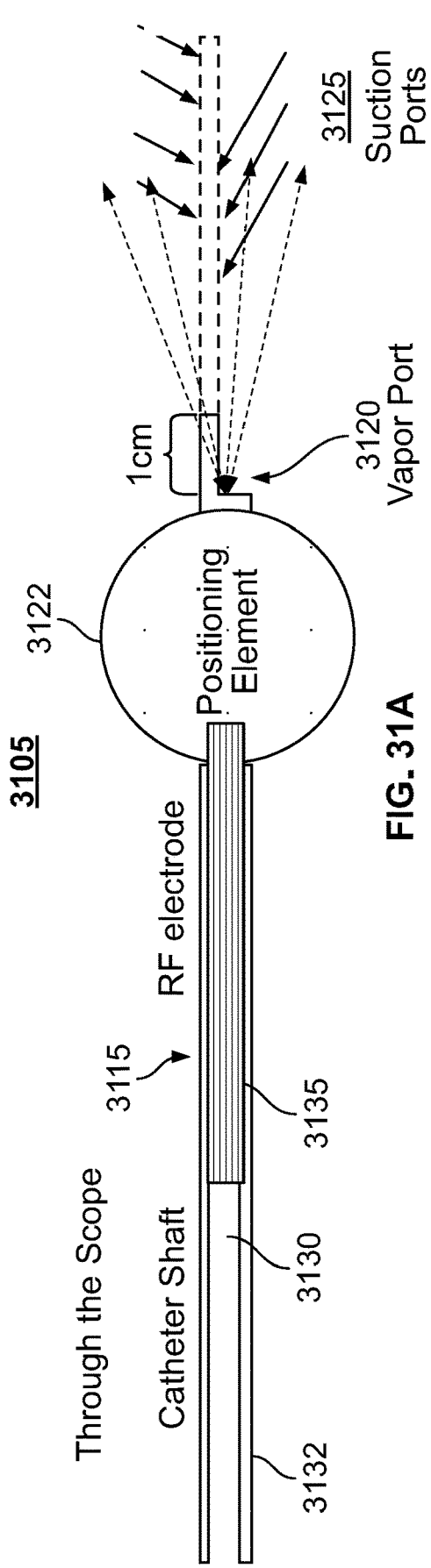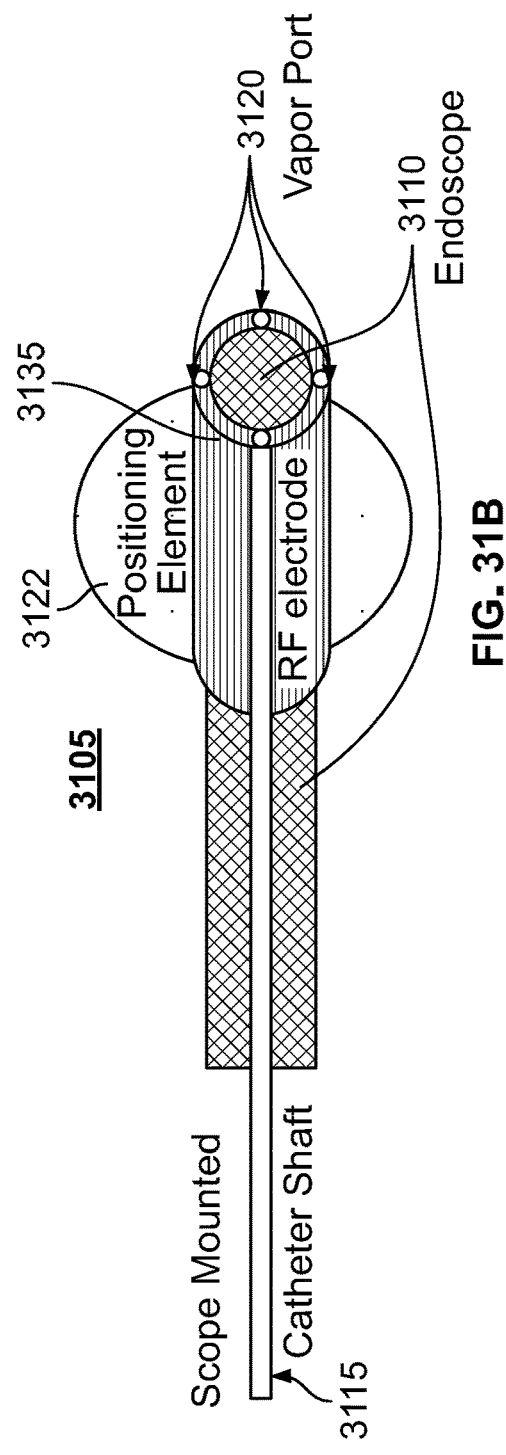
FIG. 31A
FIG. 31B

VAPOR-BASED ABLATION TREATMENT METHODS WITH IMPROVED TREATMENT VOLUME VAPOR MANAGEMENT

CROSS-REFERENCE

The present application is a continuation application of U.S. patent application Ser. No. 17/575,950, titled "Vapor-Based Ablation Treatment Methods with Improved Treatment Volume Vapor Management" and filed on Jan. 14, 2022, which is a continuation application of U.S. patent application Ser. No. 16/428,598, titled "Multi-Stage Vapor-Based Ablation Treatment Methods and Vapor Generation and Delivery Systems", filed on May 31, 2019, and issued as U.S. Pat. No. 11,806,066 on Nov. 7, 2023, which relies on U.S. Patent Provisional Application No. 62/679,694, titled "Ablation Systems and Methods" and filed on Jun. 1, 2018, for priority, all of which are herein incorporated by reference in their entirety.

The present application relates to U.S. patent application Ser. No. 15/600,670, titled "Catheter with a Double Balloon Structure to Generate and Apply a Heated Ablative Zone to Tissue", filed on May 19, 2017, and issued as U.S. Pat. No. 10,695,126 on Jun. 30, 2020, which relies on U.S. Provisional Patent Application No. 62/425,144, titled "Methods and Systems for Ablation" and filed on Nov. 22, 2016, and U.S. Provisional Patent Application No. 62/338,871, titled "Cooled Coaxial Ablation Catheter" and filed on May 19, 2016, for priority.

The present application also relates to U.S. patent application Ser. No. 15/144,768, titled "Vapor based ablation system for treating various indications", filed on May 2, 2016, and issued as U.S. Pat. No. 10,064,697 on Sep. 4, 2018, which is a continuation-in-part application of U.S. patent application Ser. No. 14/594,444, titled "Method and Apparatus for Tissue Ablation", filed on Jan. 12, 2015, and issued as U.S. Pat. No. 9,561,068 on Feb. 7, 2017, which is a continuation-in-part application of U.S. patent application Ser. No. 14/158,687, of the same title, filed on Jan. 17, 2014, and issued as U.S. Pat. No. 9,561,067 on Feb. 7, 2017, which, in turn, relies on U.S. Provisional Patent Application No. 61/753,831, of the same title and filed on Jan. 17, 2013, for priority.

U.S. patent application Ser. No. 14/158,687 is also a continuation-in-part application of U.S. patent application Ser. No. 13/486,980, titled "Method and Apparatus for Tissue Ablation", filed on Jun. 1, 2012, and issued as U.S. Pat. No. 9,561,066 on Feb. 7, 2017, which, in turn, relies on U.S. Provisional Patent Application No. 61/493,344, of the same title and filed on Jun. 3, 2011, for priority.

U.S. patent application Ser. No. 13/486,980 is also a continuation-in-part application of U.S. patent application Ser. No. 12/573,939, titled "Method and Apparatus for Tissue Ablation" and filed on Oct. 6, 2009, which, in turn, relies on U.S. Provisional Patent Application No. 61/102,885, of the same title and filed on Oct. 6, 2008, for priority.

All of the above referenced applications are herein incorporated by reference in their entirety.

FIELD

The present specification relates to systems and methods configured to generate and deliver vapor for ablation therapy. More particularly, the present specification relates to systems and methods comprising flexible catheter positioning elements and/or tips with needles or ports for delivering ablation therapy to specific organ systems.

BACKGROUND

Ablation, as it pertains to the present specification, relates to the removal or destruction of a body tissue, via the introduction of a destructive agent, such as radiofrequency energy, laser energy, ultrasonic energy, cyroagents, or steam. Ablation is commonly used to eliminate diseased or unwanted tissues, such as, but not limited to cysts, polyps, tumors, hemorrhoids, and other similar lesions.

Steam-based ablation systems, such as the ones disclosed in U.S. Pat. Nos. 9,615,875, 9,433,457, 9,376,497, 9,561,068, 9,561,067, and 9,561,066, disclose ablation systems that controllably deliver steam through one or more lumens toward a tissue target. One problem that all such steam-based ablation systems have is the potential overheating or burning of healthy tissue. Steam passing through a channel within a body cavity heats surfaces of the channel and may cause exterior surfaces of the medical tool, other than the operational tool end itself, to become excessively hot. As a result, physicians may unintentionally burn healthy tissue when external portions of the device, other than the distal operational end of the tool, accidentally contacts healthy tissue. U.S. Pat. Nos. 9,561,068, 9,561,067, and 9,561,066 are hereby incorporated herein by reference.

Furthermore, the effective use of steam often requires controllably exposing a volume of tissue to steam. However, prior art approaches to steam ablation either fail to sufficiently enclose a volume being treated, thereby insufficiently exposing the tissue, or excessively enclose a volume being treated, thereby dangerously increasing pressure and/or temperature within the patient's organ. Pressure sensors located on the catheter may help regulate energy delivery, but they are not necessarily reliable and represent a critical point of potential failure in the system.

It is therefore desirable to have steam-based ablation devices that integrate into the device itself safety mechanisms which prevent unwanted burning during use. It is further desirable to be able to provide a way to better control the amount of steam to which a target tissue is exposed. It is also desirable to be able to control a pressure level within an enclosed volume without relying on a pressure sensor in the catheter itself. Finally, it is also desirable to provide steam-based ablation systems and methods used to treat various conditions including pre-cancerous or cancerous tissue in the esophagus, duodenum, bile duct, and pancreas.

SUMMARY

The present specification discloses a multi-stage method for treating at least one of excess weight, obesity, eating disorders, metabolic syndrome, dyslipidemia, diabetes, polycystic ovarian disease, fatty liver disease, non-alcoholic fatty liver disease, or non-alcoholic steatohepatitis disease by ablating duodenal tissue using a vapor ablation system, wherein the vapor ablation system comprises a controller having at least one processor in data communication with at least one pump and a catheter connection port in fluid communication with the at least pump, the multi-stage method comprising: connecting a proximal end of a first catheter to the catheter connection port to place the first catheter in fluid communication with the at least one pump, wherein the first catheter comprises at least two positioning elements separated along a length of the catheter and at least two ports positioned between the at least two positioning elements, wherein each of the at least two positioning elements has a first configuration and a second configuration, and wherein, in the first configuration, each of the at least two positioning elements is compressed within the catheter and in the second configuration, each of the at least two positioning elements is expanded to be at least partially outside the catheter; positioning the first catheter inside a patient such that, upon being expanded into the second configuration, a distal one of the at least two positioning elements is positioned within in the patient's small intestine and a proximal one of the at least two positioning elements is proximally positioned more than 1 cm from the distal one of the at least two positioning elements; expanding each of the at least two positioning elements into their second configurations; activating the controller, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter; delivering vapor through ports positioned in the first catheter between the at least two positioning elements; using the controller, shutting off the delivery of saline and electrical current; removing the first catheter from the patient to complete a first stage of treating; waiting for at least six weeks; determining an efficacy of the first phase of treatment; depending on the determined efficacy, connecting a proximal end of a second catheter to the catheter connection port to place the second catheter in fluid communication with the at least one pump, wherein the second catheter comprises at least two positioning elements separated along a length of the catheter and at least two ports positioned between the at least two positioning elements, wherein each of the at least two positioning elements has a first configuration and a second configuration, and wherein, in the first configuration, each of the at least two positioning elements is compressed within the catheter and in the second configuration, each of the at least two positioning elements is expanded to be at least partially outside the catheter; positioning the second catheter inside a patient such that, upon being expanded into the second configuration, a distal one of the at least two positioning elements is positioned within in the patient's small intestine and a proximal one of the at least two positioning elements is proximally positioned more than 1 cm from the distal one of the at least two positioning elements; expanding each of the at least two positioning elements into their second configurations; activating the controller, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter; delivering vapor through ports positioned in the second catheter between the at least two positioning elements; using the controller, shutting off the delivery of saline and electrical current; and removing the second catheter from the patient to complete a second stage of treatment.

Optionally, in both the first stage of treatment and second stage of treatment, the delivery of saline and electrical current is automatically shut off after no more than 60 seconds.

Optionally, the method further comprises, in both the first stage of treatment and second stage of treatment, repeatedly activating the controller to deliver saline into the lumen and electrical current to the at least one electrode using at least one of a foot pedal in data communication with the controller, a switch on the catheter, or a switch on the controller.

Optionally, in both the first stage of treatment and second stage of treatment, vapor is delivered such that an amount of energy in a range of 5 calories per second to 2500 calories per second is delivered.

Optionally, in both the first stage of treatment and second stage of treatment, vapor is delivered such that an amount of energy in a range of 5 calories to 40 calories per gram of tissue to be ablated is delivered.

Optionally, in both the first stage of treatment and second stage of treatment, vapor is delivered such that at least fifty percent of a circumference of the small intestine is ablated.

Optionally, in the first stage of treatment, the at least two positioning elements, together with the small intestine, define an enclosed volume and wherein at least one of the at least two positioning elements is positioned relative the small intestine to permit a flow of air out of the enclosed volume when the vapor is delivered.

Optionally, in the second stage of treatment, the at least two positioning elements, together with the small intestine, define an enclosed volume and wherein at least one of the at least two positioning elements is positioned relative the small intestine to permit a flow of air out of the enclosed volume when the vapor is delivered.

Optionally, in both the first state of treatment and second stage of treatment, the efficacy is determined by at least one of: a total body weight of the patient decreases by at least 1% relative to a total body weight of the patient before ablation; an excess body weight of the patient decreases by at least 1% relative to an excess body weight of the patient before ablation; a total body weight of the patient decreases by at least 1% relative to a total body weight of the patient before ablation and a well-being level of the patient does not decrease more than 5% relative to a well-being level of the patient before ablation; an excess body weight of the patient decreases by at least 1% relative to an excess body weight of the patient before ablation and a well-being level of the patient does not decrease more than 5% relative to a well-being level of the patient before ablation; a pre-prandial ghrelin level of the patient decreases by at least 1% relative to a pre-prandial ghrelin level of the patient before ablation; a post-prandial ghrelin level of the patient decreases by at least 1% relative to a post-prandial ghrelin level of the patient before ablation; an exercise output of the patient increases by at least 1% relative to an exercise output of the patient before ablation; a glucagon-like peptide-1 level of the patient increases by at least 1% relative to a glucagon-like peptide-1 level of the patient before ablation; a leptin level of the patient increases by at least 1% relative to a leptin level of the patient before ablation; the patient's appetite decreases, over a predefined period of time, relative to the patient's appetite before ablation; a peptide YY level of the patient increases by at least 1% relative to a peptide YY level of the patient before ablation; a lipopolysaccharide level of the patient decreases by at least 1% relative to a lipopolysaccharide level of the patient before ablation; a motilin-related peptide level of the patient decreases by at least 1% relative to a motilin-related peptide level of the patient before ablation; a cholecystokinin level of the patient increases by at least 1% relative to a cholecystokinin level of the patient before ablation; a resting metabolic rate of the patient increases by at least 1% relative to a resting metabolic rate of the patient before ablation; a plasma-beta endorphin level of the patient increases by at least 1% relative to a plasma-beta endorphin level of the patient before ablation; an HbA1c level of the patient decreases by at least 0.3% relative to an HbA1c level of the patient before ablation; a triglyceride level of the patient decreases by at least 1% relative to a triglyceride level of the patient before ablation; a total blood cholesterol level of the patient decreases by at least 1% relative to a total blood cholesterol level of the patient before ablation; a glycemia level of the patient decreases by at least 1% relative to a glycemia level of the patient before ablation; a composition of the person's gut microbiota modulates from a first state before ablation to a second state after ablation, wherein the first state has a first level of bacteroidetes and a first level of firmicutes, wherein the second state has a second level of bacteroidetes and a second level of firmicutes, wherein the second level of bacteroidetes is greater than the first level of bacteroidetes by at least 3%, and wherein the second level of firmicutes is less than the first level of firmicutes by at least 3%; or, a cumulative daily dose of the patient's antidiabetic medications decreases by at least 10% relative to a cumulative daily dose of the patient's antidiabetic medications before ablation.

Optionally, in both the first state of treatment and second stage of treatment, the efficacy is determined by at least one of: a lipid profile of the patient improves by at least 10% relative a lipid profile of the patient before ablation, wherein lipid profile is defined at least by a ratio of LDL cholesterol to HDL cholesterol, and improve is defined as a decrease in the ratio of LDL cholesterol to HDL cholesterol; an LDL-cholesterol level of the patient decreases by at least 10% relative to an LDL-cholesterol level of the patient before ablation; or, a VLDL-cholesterol level of the patient decreases by at least 10% relative to a VLDL-cholesterol level of the patient before ablation.

Optionally, in both the first stage of treatment and second stage of treatment, the efficacy is determined by at least one of: a 10% decrease in either ALT or AST levels relative to ALT or AST levels before ablation; an absolute serum ferritin level of less than 1.5 ULN (upper limit normal) relative to a serum ferritin level before ablation; less than 5% hepatic steatosis (HS) relative to an HS level before ablation, as measured on liver biopsy; less than 5% hepatic steatosis (HS) relative to an HS level before ablation, as measured by magnetic resonance (MR) imaging, either by spectroscopy or proton density fat fraction; at least a 5% improvement in an NAFLD Fibrosis Score (NFS) relative to an NFS before ablation; at least a 5% improvement in an NAFLD Activity Score (NAS) relative to an NAS before ablation; at least a 5% improvement in a Steatosis Activity Fibrosis (SAF) score relative to an SAF score before ablation; at least a 5% decrease in a mean annual fibrosis progression rate relative to a mean annual fibrosis progression rate before ablation, as measured by histology, Fibrosis-4 (FIB-4) index, aspartate aminotransferase (AST) to platelet ratio index (APRI), serum biomarkers (Enhanced Liver Fibrosis (ELF) panel, Fibrometer, FibroTest, or Hepascore), or imaging (transient elastography (TE), MR elastography (MRE), acoustic radiation force impulse imaging, or supersonic shear wave elastography); at least a 5% decrease in circulating levels of cytokeratin-18 fragments relative to circulating levels of cytokeratin-18 fragments before ablation; at least a 5% decrease in liver stiffness relative to liver stiffness before ablation, as measured by vibration controlled transient elastography (VCTE/FibroScan); an improvement in NAS by at least 2 points, with at least 1-point improvement in hepatocellular ballooning and at least 1-point improvement in either lobular inflammation or steatosis score, and no increase in the fibrosis score, relative to NAS, hepatocellular ballooning, lobular inflammation, steatosis, and fibrosis scores before ablation; at least a 5% improvement in NFS scores relative to NFS scores before ablation; or, at least a 5% improvement in any of the above listed NAFLD parameters as compared to a sham intervention or a placebo.

The present specification also discloses a multi-stage method for treating cancerous or precancerous esophageal tissue by ablating the cancerous or precancerous esophageal tissue using a vapor ablation system, wherein the vapor ablation system comprises a controller having at least one processor in data communication with at least one pump and a catheter connection port in fluid communication with the at least pump, the multi-stage method comprising: connecting a proximal end of a first catheter to the catheter connection port to place the first catheter in fluid communication with the at least one pump, wherein the first catheter comprises at least two positioning elements separated along a length of the catheter and at least two ports positioned between the at least two positioning elements, wherein each of the at least two positioning elements has a first configuration and a second configuration, and wherein, in the first configuration, each of the at least two positioning elements is compressed within the catheter and in the second configuration, each of the at least two positioning elements is expanded to be at least partially outside the catheter; positioning the first catheter inside a patient such that, upon being expanded into the second configuration, a distal one of the at least two positioning elements is positioned adjacent the patient's esophagus and a proximal one of the at least two positioning elements is proximally positioned more than 1 cm from the distal one of the at least two positioning elements; expanding each of the at least two positioning elements into their second configurations; activating the controller, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter; delivering vapor through ports positioned in the first catheter between the at least two positioning elements; using the controller, shutting off the delivery of saline and electrical current; removing the first catheter from the patient to complete a first stage of treating; waiting for at least six weeks; determining an efficacy of the first phase of treatment; depending upon the efficacy determination, connecting a proximal end of a second catheter to the catheter connection port to place the second catheter in fluid communication with the at least one pump, wherein the second catheter comprises a distal tip having at least one port and at least one positioning element attached to the distal tip such that, upon being in an operational configuration, the at least one positioning element encircles the at least one port and is configured to direct all vapor exiting from the at least one port; positioning the second catheter inside the patient such that a distal surface of the at least one positioning element is positioned adjacent the patient's esophagus; activating the controller, wherein, upon activation, the controller is configured to cause the at least one pump to deliver saline into at least one lumen in the second catheter and, wherein, upon activation, the controller is configured to cause an electrical current to be delivered to at least one electrode positioned within the at least one lumen of the second catheter; delivering vapor through the at least one port positioned at the distal end of the second catheter; using the controller, shutting off the delivery of saline and electrical current; and removing the second catheter from the patient to complete a second stage of treatment.

Optionally, in both the first stage of treatment and second stage of treatment, the delivery of saline and electrical current is automatically shut off after no more than 60 seconds.

Optionally, the method further comprises, in both the first stage of treatment and second stage of treatment, repeatedly activating the controller to deliver saline into the lumen and electrical current to the at least one electrode using at least one of a foot pedal in data communication with the controller, a switch on the catheter, or a switch on the controller.

Optionally, in both the first stage of treatment and second stage of treatment, vapor is delivered such that an amount of energy in a range of 5 calories per second to 2500 calories per second is delivered.

Optionally, in both the first stage of treatment and second stage of treatment, vapor is delivered such that an amount of energy in a range of 5 calories to 40 calories per gram of tissue to be ablated is delivered.

Optionally, in both the first stage of treatment and second stage of treatment, vapor is delivered such that at least fifty percent of a circumference of the small intestine is ablated.

Optionally, in the first stage of treatment, the at least two positioning elements, together with the esophageal tissue, define an enclosed volume wherein at least one of the at least two positioning elements is positioned relative the esophageal tissue to permit a flow of air out of the enclosed volume when the vapor is delivered.

Optionally, in the second stage of treatment, the at least one positioning element, together with the esophageal tissue, defines an enclosed volume and wherein the at least one positioning element is positioned relative the esophageal tissue to permit a flow of air out of the enclosed volume when the vapor is delivered.

The present specification also discloses a flexible heating chamber configured to be incorporated into a tip of a catheter, the flexible heating chamber comprising: an outer covering; an inner core coaxial to said outer covering; a first array of electrodes disposed between said outer covering and said inner core, wherein said first array of electrodes comprise a first metal ring having a plurality of first fins; and a second array of electrodes disposed between said outer covering and said inner core, wherein said second array of electrodes comprises a second metal ring having a plurality of second fins, and wherein said first and second fins interdigitate with each other such that a segmental space separates each of said first and second fins.

Optionally, said plurality of first and second fins extend radially into a space between said outer covering and said inner core, and wherein said plurality of first and second fins also extend along a longitudinal axis of the heating chamber.

Optionally, each of said plurality of first and second fins has a first dimension along a radius of the heating chamber and a second dimension along a longitudinal axis of the heating chamber.

Optionally, water or saline flows through said segmental spaces and electrical current is provided to said first and second array of electrodes causing said first and second fins to generate heat and vaporize said water or saline into steam.

Optionally, the heating chamber has a width ranging from 1 to 5 mm and a length ranging from 5 to 50 mm.

Optionally, the first array of electrodes has a range of 1 to 50 fins and the second array of electrodes has a range of 1 to 50 fins.

Optionally, said segmental space ranges from 0.01 to 2 mm.

The present specification also discloses a catheter for performing ablation of target tissue and having a body with a proximal end, a distal end, a first lumen and a second lumen, said catheter comprising: a proximal balloon and a distal balloon positioned proximate the distal end of the body; a plurality of ports located on the body between said proximal and distal balloons; and a first flexible heating chamber incorporated in the second lumen and placed proximate to the proximal balloon, said first flexible heating chamber comprising: an outer covering; an inner core coaxial to said outer covering; a first array of electrodes disposed between said outer covering and the inner core, wherein said first array of electrodes comprise a first metal ring having a plurality of first fins; and a second array of electrodes disposed between said outer covering and said inner core, wherein said second array of electrodes comprises a second metal ring having a plurality of second fins, and wherein said first and second fins interdigitate with each other such that a first segmental space separates each of said first and second fins.

Optionally, a first pump coupled to the proximal end of the body propels air through the first lumen to inflate the proximate and distal balloons, a second pump coupled to the proximal end of the body propels water or saline through the second lumen to supply said water or saline to a proximal end of the first heating chamber, and an RF generator coupled to the proximal end of the body supplies electrical current to said first and second array of electrodes causing said first and second fins to generate heat and vaporize said water or saline into steam for delivery to the target tissue through said ports.

Optionally, said plurality of first and second fins extend radially into a space between said outer covering and said inner core of the first heating chamber, and wherein said plurality of first and second fins also extend along a longitudinal axis of the first heating chamber.

Optionally, each of said plurality of first and second fins has a first dimension along a radius of the first heating chamber and a second dimension along a longitudinal axis of the first heating chamber.

Optionally, the catheter further comprises a second flexible heating chamber arranged in series with said flexible heating chamber, wherein the second flexible heating chamber comprises: an outer covering; an inner core coaxial to the outer covering; a third array of electrodes disposed between the outer covering and the inner core, wherein the third array of electrodes comprise a third metal ring having a plurality of third fins; and a fourth array of electrodes disposed between the outer covering and the inner core, wherein said fourth array of electrodes comprises a fourth metal ring having a plurality of fourth fins, and wherein the third and fourth fins interdigitate with each other such that a second segmental space separates each of said third and fourth fins.

Optionally, the plurality of third and fourth fins extend radially into a space between said outer covering and the inner core of the second heating chamber and said plurality of third and fourth fins also extend along a longitudinal axis of the second heating chamber.

Optionally, each of said plurality of third and fourth fins has a first dimension along a radius of the second heating chamber and a second dimension along a longitudinal axis of the second heating chamber.

Optionally, each of said first and second heating chambers has a width ranging from 1 to 5 mm and a length ranging from 5 to 50 mm.

Optionally, the first and third array of electrodes have a range of 1 to 50 fins and the second and fourth array of electrodes have a range of 1 to 50 fins.

Optionally, said first and second segmental spaces range from 0.01 to 2 mm.

The present specification also discloses a method of performing ablation of Barrett's esophagus tissue, comprising: inserting a catheter into an esophagus of a patient, said catheter having a body with a proximal end, a distal end, a first lumen and a second lumen, wherein the catheter comprises: a proximal balloon and a distal balloon positioned proximate the distal end of the body; a plurality of ports located on the body between said proximal and distal balloons; and at least one flexible heating chamber incorporated in the second lumen and placed proximate to the proximal balloon, said at least one flexible heating chamber comprising: an outer covering; an inner core coaxial to said outer covering; a first array of electrodes disposed between said outer covering and said inner core, wherein said first array of electrodes comprise a first metal ring having a plurality of first fins; and a second array of electrodes disposed between said outer covering and said inner core, wherein said second array of electrodes comprises a second metal ring having a plurality of second fins, and wherein said first and second fins interdigitate with each other such that a first segmental space separates each of said first and second fins; positioning the distal balloon distal to a portion of Barrett's esophagus and the proximal balloon proximal to a portion of Barrett's esophagus such that the ports are positioned in said portion of Barrett's esophagus; inflating the proximal and distal balloons to position the catheter in the esophagus; providing water or saline to the catheter; and providing electric current to said first and second array of electrodes causing said first and second fins to generate heat and vaporize said water or saline into steam, wherein said steam is delivered through said ports to ablate the Barrett's esophagus tissue.

Optionally, a first pump coupled to the proximal end of the body propels air through the first lumen to inflate the proximate and distal balloons, a second pump coupled to the proximal end of the body propels water or saline through the second lumen to supply said water or saline to a proximal end of the heating chamber, and an RF generator coupled to the proximal end of the body supplies electrical current to said first and second array of electrodes.

Optionally, each of said plurality of first and second fins has a first dimension along a radius of the heating chamber and a second dimension along a longitudinal axis of the heating chamber.

The present specification also discloses a method of ablating a pancreatic tissue, comprising: providing an ablation device comprising: an echoendoscope; a catheter having a needle at a distal end and configured pass within a channel of said echoendoscope to deliver vapor to said pancreatic tissue; a controller programmed to determine an amount of thermal energy needed to ablate said pancreatic tissue, programmed to limit a maximum dose of said ablative agent based on a type of disorder being treated, and programmed to limit the amount of thermal energy delivered such that a pressure within the patient's pancreas does not exceed 5 atm; advancing said echoendoscope into a gastrointestinal tract of a patient and proximate said pancreatic tissue; localizing said pancreatic tissue using said echoendoscope; advancing said catheter through said channel of said echoendoscope such that said needle passes through a gastrointestinal wall at a puncture site and enters into said pancreatic tissue; and delivering vapor through said needle into said pancreatic tissue for ablation.

Optionally, the method further comprises the steps of: measuring at least one dimension of said pancreatic tissue using said echoendoscope; and said controller using said at least one measured dimension to calculate an amount of vapor to deliver.

Optionally, the method further comprises applying suction to said needle prior to delivering vapor to aspirate fluid and/or cells from said prostatic tissue.

Optionally, said needle comprises an outer sheath and said method further comprises circulating water through said outer sheath as vapor is delivered to cool said puncture site.

Optionally, the method further comprises using said echoendoscope to observe said pancreatic tissue as ablation is performed and stopping said ablation once adequate ablation has been achieved as per visual observation.

Optionally, ablation is terminated after a pressure measured in said pancreas remains in a range of 0.1 to 5 atm for a time period of at least 1 second. Optionally, the method further comprises delivering vapor again after ablation has been terminated for at least a time period of 1 second.

Optionally, ablation is stopped when a pressure measured in said ablation device exceeds 5 atm.

Optionally, a temperature of said pancreatic tissue is in a range of 100° C. to 110° C. for at least a portion of the ablation procedure.

Optionally, said ablation device further comprises a pressure sensor.

Optionally, said ablation device further comprises a temperature sensor.

The present specification also discloses a method of ablating pancreatic tissue comprising the steps of: providing an ablation device comprising: a catheter having a hollow shaft and a retractable needle through which an ablative agent can travel; at least one infusion port on said needle for the delivery of said ablative agent to said upper gastrointestinal tract tissue; at least one sensor for measuring at least one parameter of said catheter; and a controller comprising a microprocessor for controlling the delivery of said ablative agent; inserting an echoendoscope into an upper gastrointestinal tract of a patient; identifying the pancreatic tissue to be ablated using said echoendoscope; passing said catheter through said echoendoscope such that said at least one distal positioning element is positioned proximal to said pancreatic tissue to be ablated in the gastrointestinal tract; extending said needle through the catheter in the upper gastrointestinal tract lumen of said patient such that said infusion port is positioned within said pancreatic tissue of said patient; operating said at least one sensor to measure at least one parameter of said catheter; using said at least one parameter measurement to control the flow of ablative agent to deliver to said pancreatic tissue; and delivering said ablative agent through said at least one infusion port to ablate said pancreatic tissue.

The present specification also discloses a device for use with an endoscope for hot fluid ablation comprising: an elongate tubular member having a length and a lumen for conveying the hot fluid from a proximal end to a distal end, the distal end being open and adapted to spray vapor at a temperature and low pressure at a target tissue; and an insulating element covering at least a portion of the device; wherein an outer diameter of the device is configured to allow passage of the device through the endoscope.

Optionally, the hot fluid is steam or vapor. Optionally, the temperature ranges from 65C to 150C. Optionally, the pressure is <5 atm. Optionally, the insulating element is heat resistant polymer.

The present specification also discloses a catheter for use in an ablation procedure comprising: a tubular member having an inner surface defining a channel for ablative fluid flow, a proximal end for receiving ablative fluid from a source, and a distal end being adapted to spray low pressure ablative agent at a target tissue; and an insulating element disposed longitudinally along at least a portion of the length of the tubular member.

The present specification also discloses a catheter for use with an endoscope in a thermal ablation procedure, the catheter comprising: a tubular member having a proximal end for receiving an ablative agent, an open distal end adapted to spray low pressure ablative agent at a target tissue, an inside surface comprising a heat resistant polymer defining a channel and configured to contact ablative agent flowing from the proximal end to the distal end; and a cooling element disposed longitudinally along at least a portion of an outer surface.

The present specification also discloses a vapor ablation apparatus for vapor spray ablation, comprising: an endoscope; a catheter having a distal end, wherein the catheter is disposed within the endoscope; and a source of vapor attached to the catheter by a conduit, wherein the apparatus is configured such that, in use, high temperature, low pressure vapor exits the catheter distal end, and wherein the distal end of the catheter is adapted to spray vapor in a radial direction substantially perpendicular to the axis of the catheter.

The present specification also discloses a vapor spray apparatus for vapor spray ablation, comprising: an endoscope having a distal end provided with a lens, such that the endoscope is used to locate the target tissue; a catheter having a distal end, said catheter being connected to the endoscope and carried thereby; a source of vapor connected to the catheter by a conduit and disposed externally of the patient; wherein the apparatus is configured such that, in use, high temperature, low pressure vapors exits the catheter distal end.

The present specification also discloses a method of ablating a hollow tissue or a hollow organ comprising the steps of: replacing the natural contents of the hollow tissue or the organ with a conductive medium; and delivering an ablative agent to the conductive medium to ablate the tissue or organ.

The present specification also discloses a device for ablation comprising a port for delivering a conductive medium and a source of ablative agent.

Optionally, said ablation comprises one of cryoablation or thermal ablation.

Optionally, the device comprises ports to remove the content of the hollow organ or the conductive medium.

The present specification also discloses a method of ablating a blood vessel comprising the steps of: replacing a blood in a targeted vessel with a conductive medium; and delivering an ablative agent to the conductive medium to ablate the desired blood vessel.

Optionally, the method further comprises stopping a flow of blood into the target blood vessel. Optionally, the blood flow is occluded by application of a tourniquet. Optionally, the blood flow is occluded by application of an intraluminal occlusive element. Optionally, the intraluminal occlusive element comprises unidirectional valves.

Optionally, sensors are used to control a flow of the ablative agent.

Optionally, the conductive medium is one of water or saline.

The present specification also discloses a device for ablating a blood vessel comprising a catheter with a proximal end and a distal end, wherein the proximal end is operably connected to the distal end, a port at the distal end for infusion of a conductive medium for replacing a blood in a target vessel with a conductive medium, and a source at the distal end for delivering an ablative agent to said conductive medium.

Optionally, the device further comprises an occlusive element to restrict a flow of blood or the conductive medium. Optionally, the occlusive element comprises unidirectional valves.

Optionally, the occlusive element is used to position the source of the ablative agent in the blood vessel.

Optionally, the device further comprises suction ports for removal of blood or the conductive medium.

Optionally, the device further comprises a sensor to measure a delivery of ablative agent, flow of blood or an ablation parameter.

The present specification also discloses a method of ablating a blood vessel wall comprising the steps of placing a catheter in a segment of the blood vessel, occluding a flow of blood to the segment of the blood vessel, replacing a portion of a blood in the segment with a conductive medium, adding an ablative agent into the conductive medium, and conducting ablative energy to the blood vessel wall through the conductive medium to cause ablation of said blood vessel wall.

The present specification also discloses a device for ablating a blood vessel comprising a coaxial catheter with a proximal end and a distal end, an outer sheath, an inner tubular member, at least one port for infusing a conductive medium, a source for delivery of an ablative agent, and at least one occlusive element configured to restrict a flow of blood and position the source of ablative agent in the blood vessel, wherein at least the outer sheath of the coaxial catheter is made of an insulating material.

The present specification also discloses a method of ablating a cyst comprising the steps of: providing an ablation device comprising a catheter having a handle at a proximal end and needle at a distal end; passing said catheter into a patient and advancing said catheter to said cyst; inserting said needle into said cyst; applying suction to said catheter to remove at least a portion of the contents of said cyst; injecting a conductive medium into said cyst through said needle; delivering an ablative agent through into said conductive medium through said needle; and applying suction to said catheter to remove said conductive medium and said ablative agent.

The present specification also discloses a method of ablating a cyst comprising the steps of placing a catheter in the cyst, replacing a portion of the contents in the cyst with a conductive medium, adding an ablative agent into the conductive medium, and conducting ablative energy to a cyst wall through the conductive medium to cause ablation of said cyst.

The present specification also discloses a device for ablating a cyst comprising a coaxial catheter with a proximal end and a distal end, an outer sheath, an inner tubular member, at least one port for infusing a conductive medium, a source for delivery of an ablative agent, and at least one port for removal of the contents of the cyst, wherein at least the outer sheath of the coaxial catheter is made of an insulating material.

Optionally, the device further comprises a sensor to control the delivery of the ablative agent or for measurement of an ablation effect.

Optionally, the catheter comprises echogenic elements to assist with the placement of the catheter into the cyst under ultrasound guidance.

Optionally, the catheter comprises radio-opaque elements to assist with the placement of the catheter into the cyst under radiological guidance.

The present specification also discloses a method of ablating a solid tumor comprising the steps of placing a catheter in the tumor, instilling a conductive medium into the tumor, adding an ablative agent into the conductive medium, and conducting ablative energy to the tumor through the conductive medium to cause ablation of the tumor.

The present specification also discloses a device for ablating a tumor comprising an insulated catheter with a proximal end and a distal end, at least one port for infusing a conductive medium, and a source for delivery of an ablative agent.

Optionally, the device further comprises a sensor to control the delivery of the ablative agent or for measurement of an ablation effect.

Optionally, the catheter comprises echogenic elements to assist with the placement of the catheter into the cyst under ultrasound guidance.

Optionally, the catheter comprises radio-opaque elements to assist with the placement of the catheter into the cyst under radiological guidance.

The present specification also discloses a method of ablating tissue comprising the steps of: providing an ablation device comprising: a thermally insulating catheter having a hollow shaft and a retractable needle through which an ablative agent can travel; at least one infusion port on said needle for the delivery of said ablative agent to said tissue; and a controller comprising a microprocessor for controlling the delivery of said ablative agent; passing said catheter and extending the said needle with the said at least one infusion port so the needle and the infusion port are positioned within said tissue of said patient; and delivering said ablative agent through said at least one infusion port to ablate said tissue.

Optionally, said ablation device further comprises at least one sensor for measuring at least one parameter of said tissue and said method further comprises the steps of: operating said at least one sensor to measure at least one parameter of said tissue; and using said at least one parameter to determine the amount of ablative agent to deliver to said tissue.

Optionally, said ablation device further comprises at least one sensor for measuring at least one parameter of said catheter and said method further comprises the steps of: operating said at least one sensor to measure at least one parameter of said catheter; and using said at least one parameter to turn-off the delivery of ablative agent to said tissue.

Optionally, said at least one sensor comprises a temperature, pressure, infrared, electromagnetic, acoustic, or radiofrequency energy emitter and sensor.

Optionally, said catheter comprises at least one distal positioning element configured such that, once said positioning element is deployed, said catheter is positioned proximate said tissue for ablation. Optionally, said at least one positioning element is any one of an inflatable balloon, a wire mesh disc, a cone shaped attachment, a ring shaped attachment, or a freeform attachment. Optionally, said positioning element is covered by an insulated material to prevent the escape of thermal energy beyond said tissue to be ablated.

Optionally, said at least one distal positioning element is separated from tissue to be ablated by a distance of greater than 0.1 mm.

Optionally, said delivery of said ablative agent is guided by predetermined programmatic instructions.

Optionally, said ablation device further comprises at least one sensor for measuring a parameter of said tissue and said method further comprises the steps of: operating said at least one sensor to measure a parameter of said tissue; and using said parameter measurement to control a flow of said ablative agent to said tissue.

Optionally, said sensor is any one of a temperature, pressure, photo, or chemical sensor.

Optionally, said ablation device further comprises a coaxial member configured to restrain said at least one positioning element and said step of deploying said at least one distal positioning element further comprises removing said coaxial member from said ablation device.

Optionally, said catheter further comprises at least one suction port and said method further comprises operating said at least one suction port to remove ablated tissue from the body.

Optionally, said ablation device further comprises an input device and said method further comprises the step of an operator using said input device to control the delivery of said ablative agent.

Optionally, said tissue is a cyst.

The present specification also discloses a method of ablating tissue comprising the steps of: providing an ablation device comprising: a catheter having a hollow shaft and a retractable needle through which an ablative agent can travel; at least one distal positioning element attached to a distal tip of said catheter; at least one infusion port on said needle for the delivery of said ablative agent to said tissue, said at least one infusion port configured to deliver said ablative agent into a space defined by said distal positioning element; and a controller comprising a microprocessor for controlling the delivery of said ablative agent; inserting said catheter such that said at least one positioning element is positioned proximate said tissue to be ablated; extending the needle through the catheter such that the infusion port is positioned proximate to the tissue; and delivering said ablative agent through said at least one infusion port to ablate said tissue.

Optionally, said ablation device further comprises at least one input port on said catheter for receiving said ablative agent.

Optionally, said tissue is a pancreatic cyst.

The present specification also discloses a method for providing ablation therapy to a patient's gastrointestinal tract comprising: inserting ablation catheter into the gastrointestinal tract, wherein the ablation catheter comprises at least one positioning element and a port for the delivery of vapor; creating a seal between an exterior surface of the at least one positioning element and a wall of the gastrointestinal tract, forming an enclosed volume in the gastrointestinal tract; delivering vapor through the ablation catheter into the enclosed volume; and condensing the vapor on a tissue within the gastrointestinal tract.

Optionally, the seal is temperature dependent. Optionally, the seal breaks when temperature inside the enclosed volume exceeds 90 degrees centigrade.

Optionally, the seal is pressure dependent. Optionally, the seal breaks when pressure inside the enclosed volume exceeds 5 atm.

The present specification also discloses a method for providing ablation therapy to a patient's gastrointestinal tract comprising: inserting an ablation catheter into the gastrointestinal tract; initiating a flow of saline through the ablation catheter, wherein the flow rate of saline is variable; heating the saline by delivering RF energy to the saline to generate vapor; delivering vapor through the ablation catheter into the gastrointestinal tract; and condensing the vapor on a tissue within the gastrointestinal tract.

Optionally, the flow rate of saline during heat therapy is different from flow rate of saline during the phase where no heat therapy is delivered.

Optionally, the flow rate of saline during heat therapy is higher from flow rate of saline during the phase where no heat therapy is delivered.

Optionally, the flow rate of saline during heat therapy is lower from flow rate of saline during the phase where no heat therapy is delivered.

The present specification also discloses a method for ablating a tissue, comprising: inserting a first ablation catheter into a patient's gastrointestinal (GI) tract, wherein the first ablation catheter comprises a distal positioning element, a proximal positioning element, and a plurality of vapor delivery ports between the distal and proximal positioning elements; expanding the distal positioning element; expanding the proximal positioning element to create a first seal between the peripheries of the distal and proximal positioning elements and the GI tract and form a first enclosed treatment volume between the distal and proximal positioning elements and a surface of the patient's GI tract; delivering vapor via the delivery ports; allowing the vapor to condense on tissue within the first enclosed treatment volume to circumferentially ablate the tissue; removing the first ablation catheter from the GI tract; examining an area of tissue ablated by the first ablation catheter to identify patches of tissue requiring focused ablation; inserting a second ablation catheter into the GI tract through an endoscope, wherein the second ablation catheter comprises a distal attachment or positioning element and at least one delivery port at a distal end of the catheter; expanding the distal attachment or positioning element to create a second seal between the periphery of the distal attachment or positioning element and the GI tract and form a second enclosed treatment volume between the distal attachment or positioning element and the surface of the patient's GI tract; delivering vapor via the at least one port; allowing the vapor to condense on the tissue within the second enclosed treatment volume to focally ablate the tissue; and removing the second ablation catheter from the GI tract.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings, wherein:

FIG. 1K illustrates a catheter with proximal and distal positioning elements and an electrode heating chamber, in accordance with embodiments of the present specification;

FIG. 1L is a flow chart illustrating a method of ablating a tissue inside a gastrointestinal tract of a patient, in accordance with some embodiments of the present specification;

FIG. 1M is a flow chart illustrating a method of ablating a tissue inside a gastrointestinal tract of a patient, in accordance with other embodiments of the present specification;

FIG. 2D shows a second enlarged cross-sectional view of the needle ablation device of FIG. 2A, in accordance with an embodiment of the present specification;

FIG. 10K illustrates a third pressure therapy profile, in accordance with an embodiment of the present specification;

FIG. 14A shows a dual-balloon, multi-lumen catheter system, in accordance with embodiments of the present specification;

FIG. 16B illustrates a pattern of vapor exit ports on a portion of the shaft of FIG. 16A, in accordance with embodiments of the present specification;

FIG. 16C is a first cross-sectional view of the shaft of FIG. 16A, in accordance with embodiments of the present specification;

FIG. 16D is a second cross-sectional view of the shaft of FIG. 16A, in accordance with embodiments of the present specification;

FIG. 20C is a disassembled view of a disposable pump of the vapor generator, in accordance with embodiments of the present specification;

FIG. 20D is an assembled view of the disposable pump, in accordance with embodiments of the present specification;

FIG. 23A illustrates deflated, lateral inflated, and frontal inflated views of an ablation catheter having an insulating membrane for duodenal ablation, in accordance with one embodiment of the present specification;

FIG. 29B is a flowchart illustrating a method of ablation of bronchial tissue in accordance with another embodiment of the present specification;

FIG. 30A illustrates a cross-sectional view of a catheter for performing bronchial thermoplasty, in accordance with an embodiment of the present specification;

FIG. 30B illustrates a plurality of patterns of channels of a balloon of the catheter of FIG. 30A, in accordance with some embodiments of the present specification;

FIG. 30C illustrates a workflow for performing a bronchial thermoplasty procedure using the catheter of FIG. 30A, in accordance with an embodiment of the present specification;

FIG. 31A illustrates a lung volume reduction (LVR) catheter, in accordance with an embodiment of the present specification;

FIG. 31B illustrates the LVR catheter of FIG. 31A deployed through an endoscope/bronchoscope, in accordance with an embodiment of the present specification;

FIG. 31C is a workflow for performing lung volume reduction using the catheter of FIG. 31A, in accordance with an embodiment of the present specification;

FIG. 32A illustrates a needle catheter incorporating one flexible heating chamber of FIG. 1A through 1D, in accordance with an embodiment;

FIG. 32B illustrates the needle catheter of FIG. 32A incorporating two flexible heating chambers, in accordance with an embodiment; and FIG. 32C is a flowchart illustrating one embodiment of a method of ablation of a tissue using the needle catheter of FIG. 32A.

DETAILED DESCRIPTION

Figure 1A:
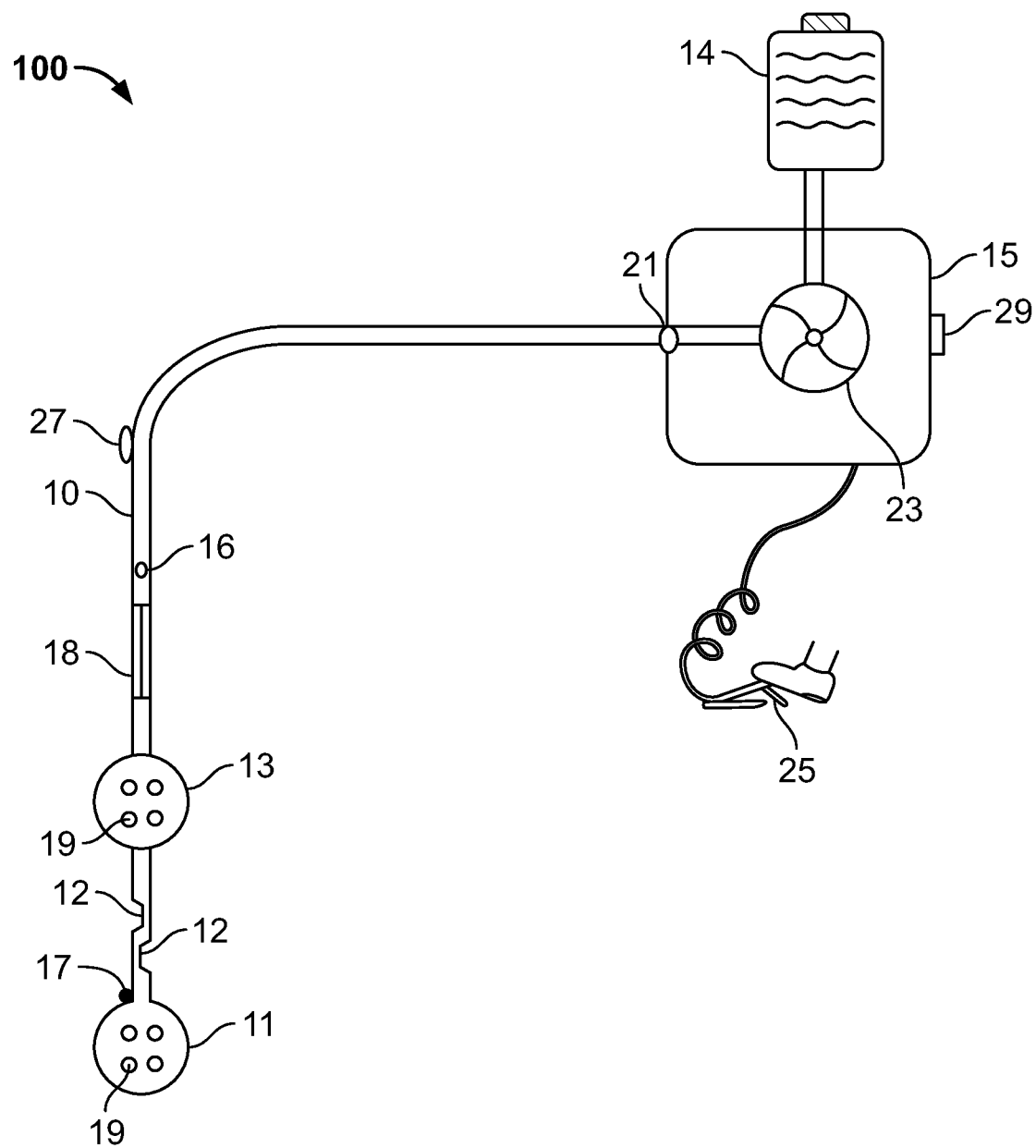
FIG. 1A illustrates an ablation system, in accordance with embodiments of the present specification.

Embodiments of the present specification provide ablation systems and methods for treating various indications including, but not limited to, pre-cancerous or cancerous tissue in the esophagus, duodenum, bile duct, and pancreas. In various embodiments, steam, generated by heating saline, is used as an ablative agent. In various embodiments, the ablation systems include a generator for generating an ablative agent (steam generator), comprising a source for providing a fluid (saline) for conversion to a vapor (steam) and a catheter for converting and delivering said steam, wherein the catheter comprises at least one electrode embedded in a central lumen of the catheter and configured to function as a heating chamber to convert the saline to steam. The ablation systems further include an attachment at a distal end of the catheter, wherein the attachment comprises at least one of a needle, cap, hood, or disc. The attachment is configured to direct the delivery of ablative agent. The catheters may further include positioning elements to position the catheter for optimal steam delivery. The attachments and positioning elements are configured to create seals and form enclosed treatment volumes for the delivery of steam and ablation of target tissues. In embodiments, the ablation systems and methods of the present specification are configured to enclose an area or volume of tissue with at least one positioning attachment, fill that area or volume with vapor, allow the temperature in the area or volume to rise above 100° C., and then let the additional vapor escape, maintaining the temperature above 100° C. for a predetermined duration of time and the pressure in the area or volume less than 5 atm to allow the vapor to condense and ablate the tissue.

Configurations for the various catheters of the ablation systems of the embodiments of the present specification may be different based on the tissue or organ systems being treated. For example, in some embodiments, catheters for esophageal and duodenal ablation are similar, with the exception that the spacing between two positioning elements, positioned at distal and proximal ends of a distal portion of the catheter with vapor delivery ports between the two positioning elements, may be greater for esophageal applications (approximately 1-20 cm) than for duodenal applications (approximately 1-10 cm). Distribution and depth of ablation provided by the systems and methods of the present specification are dependent on the duration of exposure to steam, the ablation size, the temperature of the steam, the contact time with the steam, and the tissue type.

In some embodiments, a patient is treated in a two-step process to ensure complete or near complete ablation of a target tissue. In some embodiments, a patient is first treated with a catheter having two positioning elements—a distal positioning element that is initially deployed followed by a proximal positioning element deployed thereafter, and a tube length with ports positioned between the two positioning elements, thereby enabling wide area circumferential ablation. The positioning elements may be a balloon, a disc, or any other structure. A first seal is created by contact of the periphery of the positioning elements with a patient's tissue at said distal and proximal positioning elements. Creation of the first seal results in the formation of an enclosed first treatment volume, bounded by the distal positioning element at the distal end, the proximal positioning element as the proximal end, and the walls of the patient's tissue, such as the esophagus or duodenum, on the sides. Ablative energy, in the form of steam, is then delivered by the catheter via the ports into the first treatment volume, where it condenses and contacts the patient's tissue for circumferential ablation and cannot escape from the distal or proximal ends as it is blocked by the positioning elements or, alternatively, controllably escapes from the distal or proximal ends based on the configuration of the positioning elements, as further described below.

After ablation is performed using the catheter with two positioning elements, the ablation area is examined by the physician. Upon observing the patient, the physician may identify patches of tissue requiring focused ablation. A second step is then performed, wherein a second catheter with a needle or cap, hood, or disc attachment on the distal end is passed through an endoscope and used for focal ablation. The needle provides for directed, focal ablation and the cap, hood, or disc attachment encloses the focal ablation area, creating a second seal and an enclosed second treatment volume for ablation of the tissue. The seal is created by positioning at least a portion of a periphery of the cap, hood, or disc attachment in contact with a surface of a patient's tissue, such as the esophagus or duodenum, such that a portion of the patient's tissue is positioned within an area circumscribed by the attachment. A second treatment volume, configured to receive steam and bounded by the sides of the attachment and said circumscribed portion of patient tissue, is created when the seal is formed. Ablative energy, in the form of steam, is then delivered via the catheter by at least one port at the distal tip of the catheter into the second treatment volume, where it condenses and contacts the patient's tissue for focal ablation and cannot escape as it is bounded by the attachment or, alternatively, controllably escapes from the attachment based on the configuration of the attachment, as further described below. In one embodiment, the flow rate of vapor out of the enclosed, or partially enclosed, volume is a predefined percentage of the flow rate of vapor into the enclosed, or partially enclosed, volume from the catheter ports, where the predefined percentage is in a range of 1% to 80%, preferably less than 50%, and more preferably less than 30%. The at least one port is positioned at a distal end of the catheter such that it exits into the second treatment volume when the attachment is positioned.

During both the first and second steps, when creating the enclosed first and second treatment volumes, it is preferred to avoid creating a perfect (100%) seal. A perfect seal would trap air in the treatment volume. The trapped air would not be hot, relative to the steam used for ablation, and, therefore, would create 'cold air pockets' which act as a heat sink, sapping a portion of the thermal ablation energy of the steam and resulting in uneven distribution of the ablative energy of the steam. Creating less than a perfect seal allows for the air to be pushed out of the treatment volume, through a gap in the seal, as steam is delivered into the treatment volume.

Additionally, as the temperature in the treatment volume increases, no steam escapes until the temperature is greater than or equal to 100° C., at which point steam condensation stops and the steam is allowed to escape through the gap, preventing excessive pressurization of the treatment volume. In some embodiments, the catheter includes a filter with micro-pores which provides back pressure to the delivered steam, thereby pressurizing the steam as it enters the treatment volume from the catheter. The predetermined size of micro-pores in the filter determine the backpressure and hence the temperature of the steam being generated. During ablation with the attachment with two positioning elements, in various embodiments, a gap, or less than perfect seal, is positioned only at the distal positioning element, only at the proximal positioning element, or at both the distal and proximal positioning elements.

To create the gaps or less than perfect seals and allow air to leak or be pushed out of the treatment volumes, embodiments of the present specification provide positioning elements or attachments that have a range of 40% to 99% of their surface area in contact with the patient tissue. In embodiments, a surface area of a cross-sectional slice along a plane where a positioning element or attachment contacts the tissue is in a range of 20% to 99%. A low value, such as of 20%, represents an extremely porous seal, indicates that spacing exists between the positioning element or attachment and the tissue or that the positioning element or attachment includes voids therein, while a high value, such as 99%, represents a near perfect seal. Additionally, the first and second seals are considered low pressure seals, wherein pressure within the first and second treatment volumes formed by the seals is less than 5 atm and usually close to 1 atm. Therefore, as the pressure rises above a predetermined pressure level, the seal breaks and the heated air or vapor is allowed to escape, thereby obviating the need for a pressure sensor in the catheter itself.

In embodiments, one or more of the positioning elements or attachments are configured such that they permit a range of flow out of the treatment volumes enclosed by the two positioning elements or attachment. The permissible flow out is a function of steam flow into the enclosed volume, thereby acting as a relief valve and allowing for the maintenance of a desired pressure range (less than 5 atm) without regulation from the steam generator itself. In some embodiments, the positioning element or attachment comprises a plurality of spaces within the surface area of the positioning element or attachment and/or between the periphery of the positioning element or attachment and the tissue sufficient to permit a flow of fluid out of the enclosed volume in a range of 1 to 80% of the steam input flowrate to maintain the pressure level within the enclosed volume at less than 5 atm without regulation from the steam generator.

In some embodiments, the enclosed volume ranges from 3 cubic centimeters (cc) to 450 cc, when a surface area of mucosa to be ablated ranges from 5 square centimeter ($cm^2$) to 200 $cm^2$.

In embodiments, one or more of the positioning elements or attachment are deformable over the course of treatment. Positioning elements and attachments in accordance with the embodiments of the present specification are designed to physically modify or deform when a pressure in the treatment volume increases above 10% of a baseline pressure, therefore effectively acting as a pressure relief valve. As a result of the ability to deform, the flow out of the volume enclosed by the two positioning elements or attachment is variable. In an exemplary embodiment, only a small portion, if any, of flow out of the enclosed volume is blocked at the beginning of therapy. The percentage of flow that is blocked decreases over the course of the therapy, thereby increasing leakiness, due to pressure changes. In some embodiments, assuming a positioning element or attachment blocks flow out of an enclosed volume (or has the cross-sectional area covered) in a range of 100% (total flow blockage or total cross section covered) to 20% (only 20% of flow blocked or only 20% of cross sectional area covered) at the start of treatment, the percentage changes during treatment where the amount of blockage/cross sectional area is decreased by 1% to 25% relative to the starting percentage. In various embodiments, as previously stated, it is preferred that pressure sensors are not included in the catheter itself to reduce costs and possible sensor failure. Therefore, the deformable positioning elements naturally act as relief valves, without requiring active pressure sensing.

In various embodiments, the ablation devices and catheters described in the present specification are used in conjunction with any one or more of the heating systems described in U.S. patent application Ser. No. 14/594,444, entitled "Method and Apparatus for Tissue Ablation", filed on Jan. 12, 2015 and issued as U.S. Pat. No. 9,561,068 on Feb. 7, 2017, which is herein incorporated by reference in its entirety.

"Treat," "treatment," and variations thereof refer to any reduction in the extent, frequency, or severity of one or more symptoms or signs associated with a condition.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribed treatment plan.

The term "and/or" means one or all of the listed elements or a combination of any two or more of the listed elements.

In the description and claims of the application, each of the words "comprise" "include" and "have", and forms thereof, are not necessarily limited to members in a list with which the words may be associated. The terms "comprises" and variations thereof do not have a limiting meaning where these terms appear in the description and claims.

Unless otherwise specified, "a," "an," "the," "one or more," and "at least one" are used interchangeably and mean one or more than one.

The term "controller" refers to an integrated hardware and software system defined by a plurality of processing elements, such as integrated circuits, application specific integrated circuits, and/or field programmable gate arrays, in data communication with memory elements, such as random access memory or read only memory where one or more processing elements are configured to execute programmatic instructions stored in one or more memory elements.

The term "vapor generation system" refers to any or all of the heater or induction-based approaches to generating steam from water described in this application.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present specification. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the specification are approximations, the numerical values set forth in the specific examples are reported as precisely as possible. All numerical values, however, inherently contain a range necessarily resulting from the standard deviation found in their respective testing measurements.

The devices and methods of the present specification can be used to cause controlled focal or circumferential ablation of targeted tissue to varying depth in a manner in which complete healing with re-epithelialization can occur. Additionally, the vapor could be used to treat/ablate benign and malignant tissue growths resulting in destruction, liquefaction and absorption of the ablated tissue. The dose and manner of treatment can be adjusted based on the type of tissue and the depth of ablation needed. The ablation device can be used not only for the treatment of cardiac arrhythmias, Barrett's esophagus and esophageal dysplasia, flat colon polyps, gastrointestinal bleeding lesions, endometrial ablation, pulmonary ablation, but also for the treatment of any mucosal, submucosal or circumferential lesion, such as inflammatory lesions, tumors, polyps and vascular lesions. The ablation device can also be used for the treatment of focal or circumferential mucosal or submucosal lesions of any hollow organ or hollow body passage in the body. The hollow organ can be one of gastrointestinal tract, pancreaticobiliary tract, genitourinary tract, respiratory tract or a vascular structure such as blood vessels. The ablation device can be placed endoscopically, radiologically, surgically or under direct visualization. In various embodiments, wireless endoscopes or single fiber endoscopes can be incorporated as a part of the device. In another embodiment, magnetic or stereotactic navigation can be used to navigate the catheter to the desired location. Radio-opaque or sonolucent material can be incorporated into the body of the catheter for radiological localization. Ferro- or ferromagnetic materials can be incorporated into the catheter to help with magnetic navigation.

Ablative agents such as steam, heated gas or cryogens, such as, but not limited to, liquid nitrogen are inexpensive and readily available and are directed via the infusion port onto the tissue, held at a fixed and consistent distance, targeted for ablation. This allows for uniform distribution of the ablative agent on the targeted tissue. The flow of the ablative agent is controlled by a microprocessor according to a predetermined method based on the characteristic of the tissue to be ablated, required depth of ablation, and distance of the port from the tissue. The microprocessor may use temperature, pressure or other sensing data to control the flow of the ablative agent. In addition, one or more suction ports are provided to suction the ablation agent from the vicinity of the targeted tissue. The targeted segment can be treated by a continuous infusion of the ablative agent or via cycles of infusion and removal of the ablative agent as determined and controlled by the microprocessor.

It should be appreciated that the devices and embodiments described herein are implemented in concert with a controller that comprises a microprocessor executing control instructions. The controller can be in the form of any computing device, including desktop, laptop, and mobile device, and can communicate control signals to the ablation devices in wired or wireless form.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

FIG. 1A illustrates an ablation system 100, in accordance with embodiments of the present specification. The ablation system comprises a catheter 10 having at least one first distal attachment or positioning element 11 and an internal heating chamber 18, disposed within a lumen of the catheter 10 and configured to heat a fluid provided to the catheter 10 to change said fluid to a vapor for ablation therapy. In some embodiments, the catheter 10 is made of or covered with an insulated material to prevent the escape of ablative energy from the catheter body. The catheter 10 comprises one or more infusion ports 12 for the infusion of ablative agent, such as steam. In some embodiments, the one or more infusion ports 12 comprises a single infusion port at the distal end of a needle. In some embodiments, the catheter includes a second positioning element 13 proximal to the infusion ports 12. In various embodiments, the first distal attachment or positioning element 11 and second positioning element 13 may be any one of a disc, hood, cap, or inflatable balloon. In some embodiments, the first distal attachment or positioning element 11 and second positioning element 13 include pores 19 for the escape of air or ablative agent. A fluid, such as saline, is stored in a reservoir, such as a saline pump 14, connected to the catheter 10. Delivery of the ablative agent is controlled by a controller 15 and treatment is controlled by a treating physician via the controller 15. The controller 15 includes at least one processor 23 in data communication with the saline pump 14 and a catheter connection port 21 in fluid communication with the saline pump 14. In some embodiments, at least one optional sensor 17 monitors changes in an ablation area to guide flow of ablative agent. In some embodiments, optional sensor 17 comprises at least one of a temperature sensor or pressure sensor. In some embodiments, the catheter 10 includes a filter 16 with micro-pores which provides back pressure to the delivered steam, thereby pressurizing the steam. The predetermined size of micro-pores in the filter determine the backpressure and hence the temperature of the steam being generated. In some embodiments, the system further comprises a foot pedal 25 in data communication with the controller 15, a switch 27 on the catheter 10, or a switch 29 on the controller 15, for controlling vapor flow.

In one embodiment, a user interface included with the microprocessor 15 allows a physician to define device, organ, and condition which in turn creates default settings for temperature, cycling, volume (sounds), and standard RF settings. In one embodiment, these defaults can be further modified by the physician. The user interface also includes standard displays of all key variables, along with warnings if values exceed or go below certain levels.

The ablation device also includes safety mechanisms to prevent users from being burned while manipulating the catheter, including insulation, and optionally, cool air flush, cool water flush, and alarms/tones to indicate start and stop of treatment.

Figure 1B:
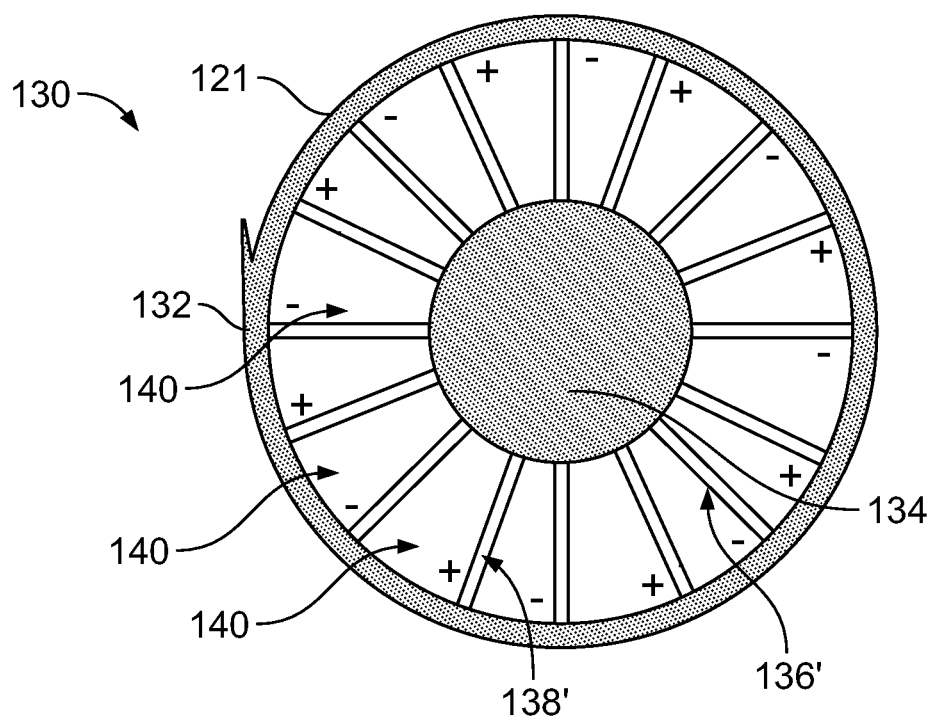
FIG. 1B is a transverse cross-section view of a flexible heating chamber, in accordance with an embodiment of the present specification.
Figure 1C:
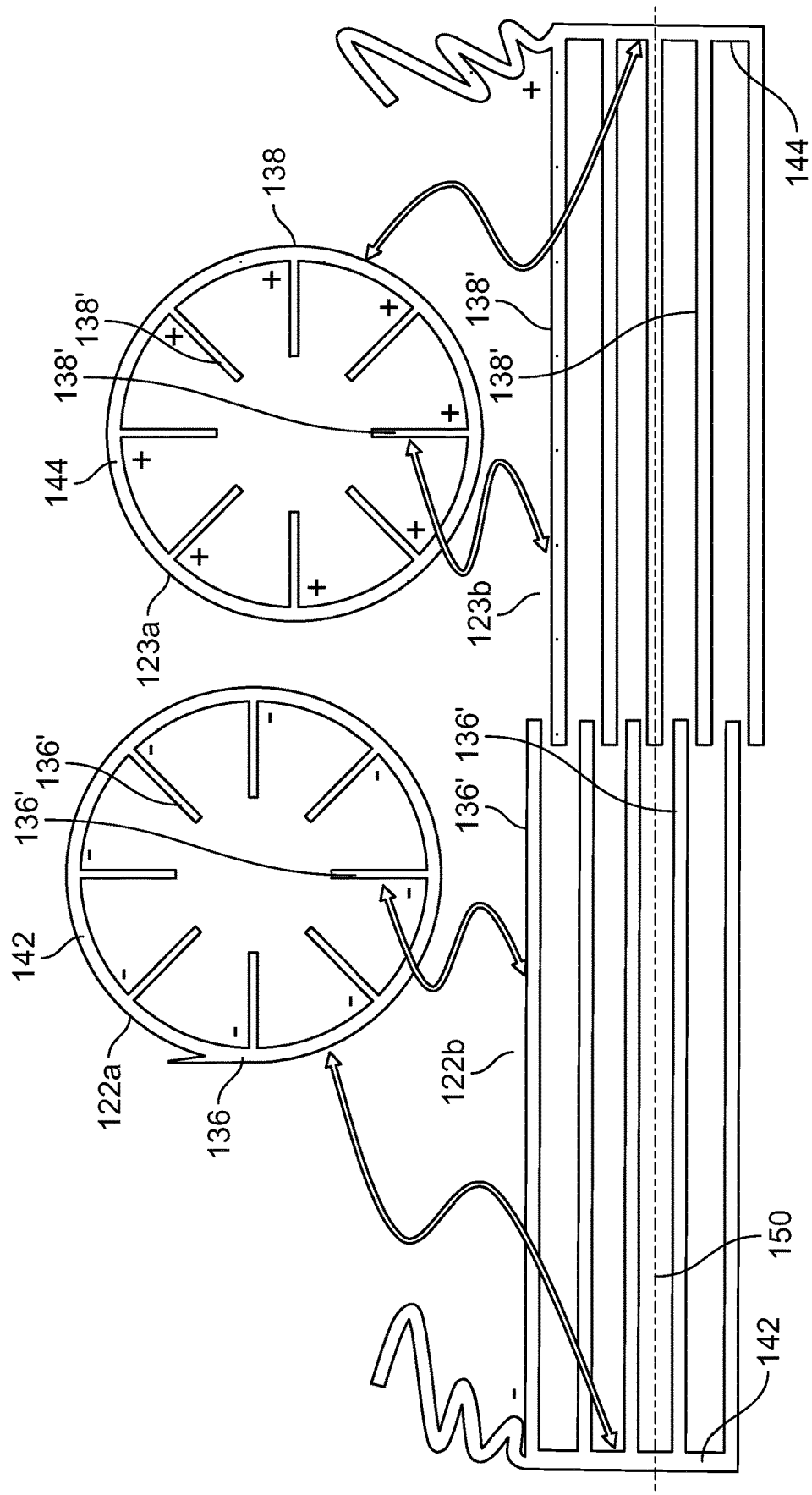
FIG. 1C illustrates transverse and longitudinal cross-section views of first and second arrays of electrodes of a flexible heating chamber, in accordance with an embodiment of the present specification.
Figure 1D:
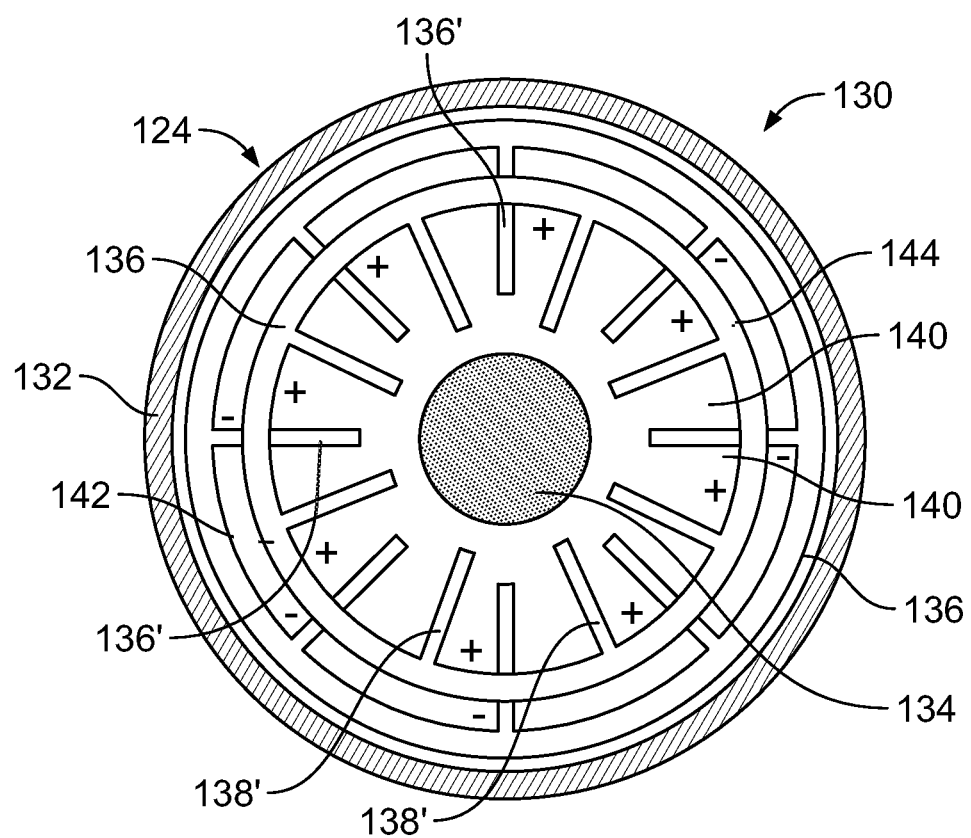
FIG. 1D is a transverse cross-section view of the heating chamber of FIG. 1B, including assembled first and second arrays of electrodes, in accordance with an embodiment of the present specification.
Figure 1E:
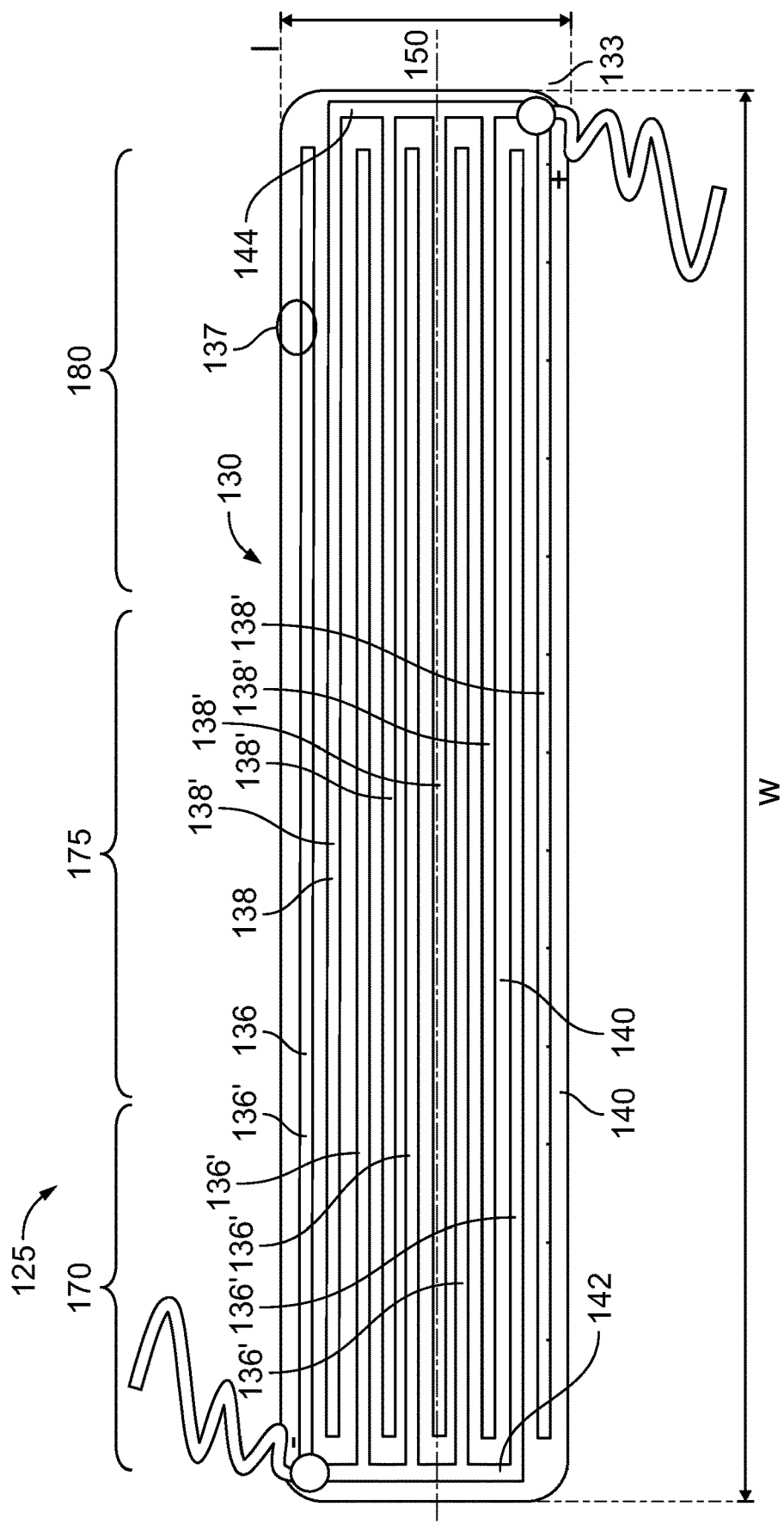
FIG. 1E is a longitudinal cross-section view of the heating chamber of FIG. 1B, including assembled first and second arrays of electrodes, in accordance with an embodiment of the present specification.

FIG. 1B is a transverse cross-section view 121 of a flexible heating chamber 130 configured to be incorporated at or into a distal portion or tip of a catheter, in accordance with an embodiment of the present specification. FIG. 1C illustrates a transverse cross-section view 122a and a longitudinal cross-section view 122b of a first array of electrodes 136 along with a transverse cross-section view 123a and a longitudinal cross-section view 123b of a second array of electrodes 138 of a flexible heating chamber for a catheter, in accordance with an embodiment of the present specification. FIGS. 1D and 1E are, respectively, transverse and longitudinal cross-section views 124, 125 of the heating chamber 130 including assembled first and second electrodes 136, 138.

Referring now to FIGS. 1B, 1C, 1E, and 1E simultaneously, the heating chamber 130 comprises an outer covering 132 and a coaxial inner core, channel, or lumen 134. A plurality of electrodes, configured as first and second arrays of electrodes 136, 138, is disposed between the outer covering 132 and the inner lumen 134. In some embodiments, the first and second array of electrodes 136, 138 respectively comprise metal rings 142, 144 from which a plurality of electrode fins or elements 136', 138' extend radially into the space between the outer covering 132 and inner lumen 134 (see 122a, 123a). The electrode fins or elements 136', 138' also extend longitudinally along a longitudinal axis 150 of the heating chamber 130 (see 122b, 123b). In other words, each of the electrode fins 136', 138' have a first dimension along a radius of the heating chamber 130 and a second dimension along a longitudinal axis 150 of the heating chamber 130. The electrode fins or elements 136', 138' define a plurality of segmental spaces 140 there-between through which saline/water flows and is vaporized into steam. Electrical current is directed from the controller, into the catheter, through a lumen, and to the electrodes 136, 138 which causes the fins or elements 136', 138' to generate heat which is then transferred to the saline in order to convert the saline to steam. The first and second dimensions enable the electrodes 136, 138 to have increased surface area for heating the saline/water flowing in the spaces 140. In accordance with an embodiment, the first electrodes 136 have a first polarity and the second electrodes 138 have a second polarity opposite said first polarity. In an embodiment, the first polarity is negative (cathode) while the second polarity is positive (anode).

In embodiments, the outer covering 132 and the inner lumen 134 are comprised of silicone, Teflon, ceramic or any other suitable thermoplastic elastomer known to those of ordinary skill in the art. The inner lumen 134, outer covering 132, electrodes 136, 138 (including rings 142, 144 and fins or elements 136', 138') are all flexible to allow for bending of the distal portion or tip of the catheter to provide better positioning of the catheter during ablation procedures. In embodiments, the inner lumen 134 stabilizes the electrodes 136, 138 and maintains the separation or spacing 140 between the electrodes 136, 138 while the tip of the catheter flexes or bends during use.

As shown in FIGS. 1D and 1E, when the heating chamber 130 is assembled, the electrode fins or elements 136', 138' interdigitate or interlock with each other (similar to fingers of two clasped hands) such that a cathode element is followed by an anode element which in turn is followed by a cathode element that is again followed by an anode element and so on, with a space 140 separating each cathode and anode element. In various embodiments, each space 140 has a distance from a cathode element to an anode element ranging from 0.01 mm to 2 mm. In some embodiments, the first array of electrodes 136 has a range of 1 to 50 electrode fins 136', with a preferred number of 4 electrode fins 136', while the second array of electrodes 138 has a range of 1 to 50 electrode fins 138', with a preferred number of 4 electrode fins 138'. In various embodiments, the heating chamber 130 has a width w in a range of 1 to 5 mm and a length 1 in a range of 5 to 50 mm.

Figure 1F:
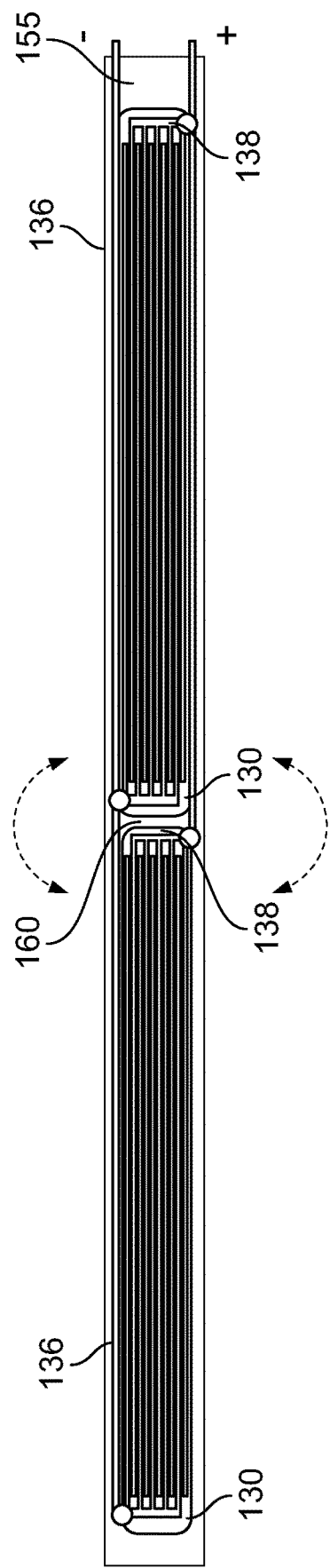
FIG. 1F is a first longitudinal view of two heating chambers of FIG. 1B arranged in series in a catheter tip, in accordance with an embodiment of the present specification.
Figure 1G:
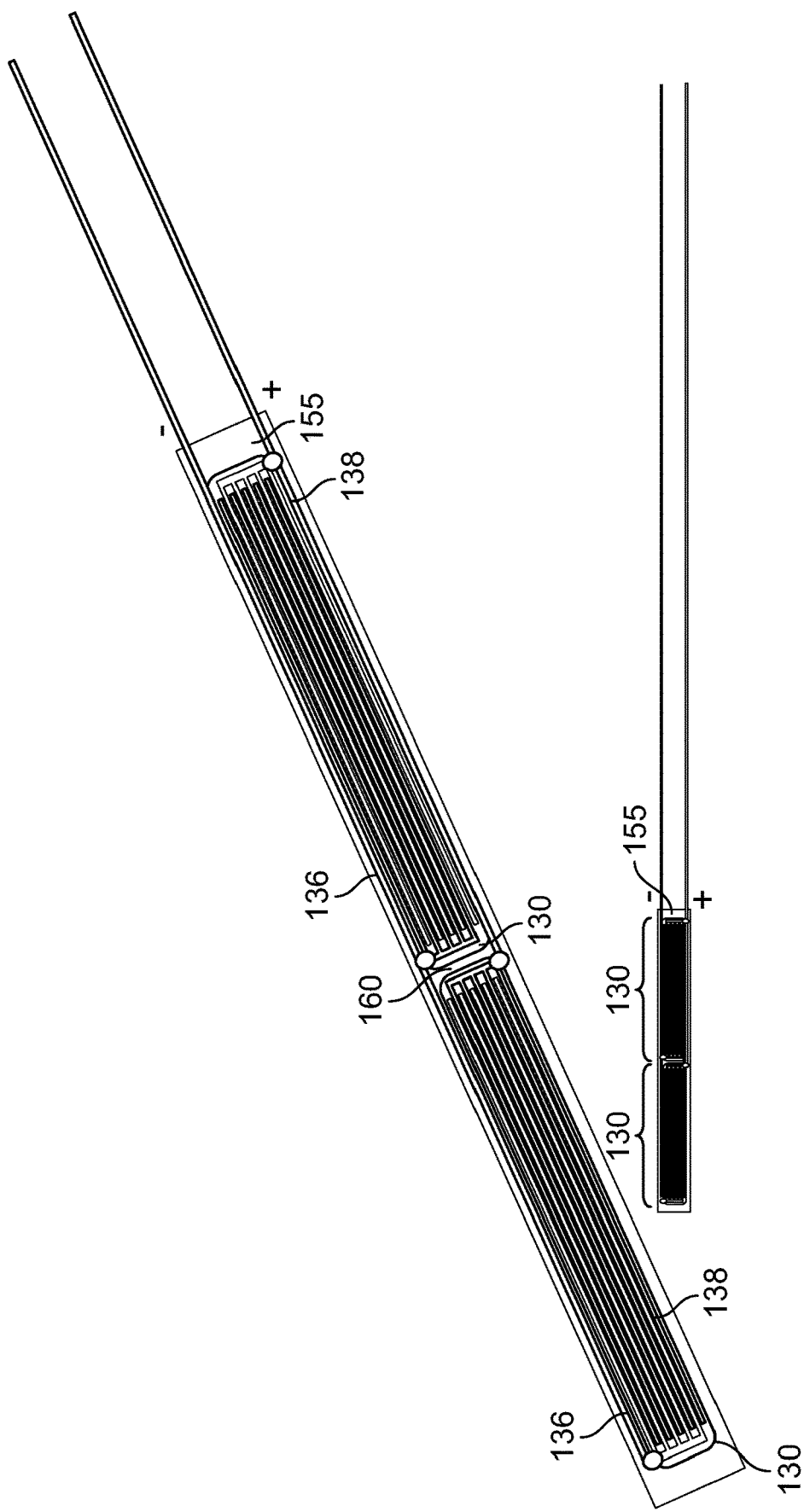
FIG. 1G is a second longitudinal view of two heating chambers of FIG. 1B arranged in series in a catheter tip, in accordance with an embodiment of the present specification.

In accordance with an aspect of the present specification, multiple heating chambers 130 can be arranged in the catheter tip. FIGS. 1F and 1G are longitudinal cross-section views of a catheter tip 155 wherein two heating chambers 130 are arranged in series, in accordance with an embodiment of the present specification. Referring to FIGS. 1F and 1G, the two heating chambers 130 are arranged in series such that a space 160 between the two heating chambers 130 acts as a hinge to impart added flexibility to the catheter tip 155 to allow it to bend. The two heating chambers 130 respectively comprise interdigitated first and second arrays of electrodes 136, 138. Use of multiple, such as two, heating chambers 130 enables a further increase in the surface area of the electrodes 136, 138 while maintaining flexibility of the catheter tip 155.

Referring now to FIGS. 1B through 1G, for generating steam, fluid is delivered from a reservoir, such as a syringe, to the heating chamber 130 by a pump or any other pressurization means. In embodiments, the fluid is sterile saline or water that is delivered at a constant or variable fluid flow rate. An RF generator, connected to the heating chamber 130, provides power to the first and second arrays of electrodes 136, 138. As shown in FIG. 1E, during vapor generation, as the fluid flows through spaces 140 in the heating chamber 130 and power is applied to the electrodes 136, 138 causing the electrodes to heat, the fluid is warmed in a first proximal region 170 of the heating chamber 130. When the fluid is heated to a sufficient temperature, such as 100 degrees Centigrade at atmospheric pressure, the fluid begins to transform into a vapor or steam in a second middle region 175. All of the fluid is transformed into vapor by the time it reaches a third distal region 180, after which it can exit a distal end 133 of the heating chamber 130 and exit the catheter tip 155. If the pressure in the heating chamber is greater than atmospheric pressure, higher temperatures will be required and if it is lower than atmospheric pressure, lower temperatures will generate vapor.

In one embodiment, a sensor probe may be positioned at the distal end of the heating chambers within the catheter. During vapor generation, the sensor probe communicates a signal to the controller. The controller may use the signal to determine if the fluid has fully developed into vapor before exiting the distal end of the heating chamber. Sensing whether the saline has been fully converted into vapor may be particularly useful for many surgical applications, such as in the ablation of various tissues, where delivering high quality (low water content) steam results in more effective treatment. In some embodiments, the heating chamber includes at least one sensor 137. In various embodiments, said at least one sensor 137 comprises an impedance, temperature, pressure or flow sensor, with the pressure sensor being less preferred. In one embodiment, the electrical impedance of the electrode arrays 136, 138 can be sensed. In other embodiments, the temperature of the fluid, temperature of the electrode arrays, fluid flow rate, pressure, or similar parameters can be sensed.

Figure 1H:
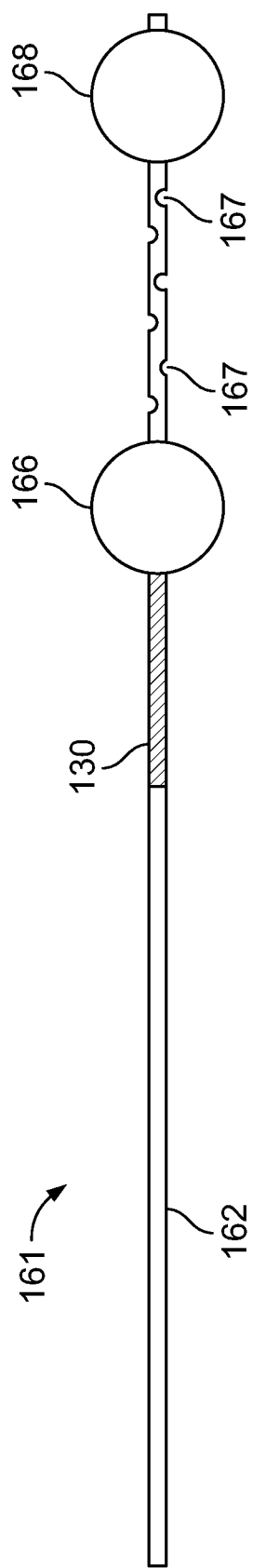
FIG. 1H illustrates a multiple lumen balloon catheter incorporating one heating chamber of FIG. 1B, in accordance with an embodiment of the present specification.
Figure 1I:
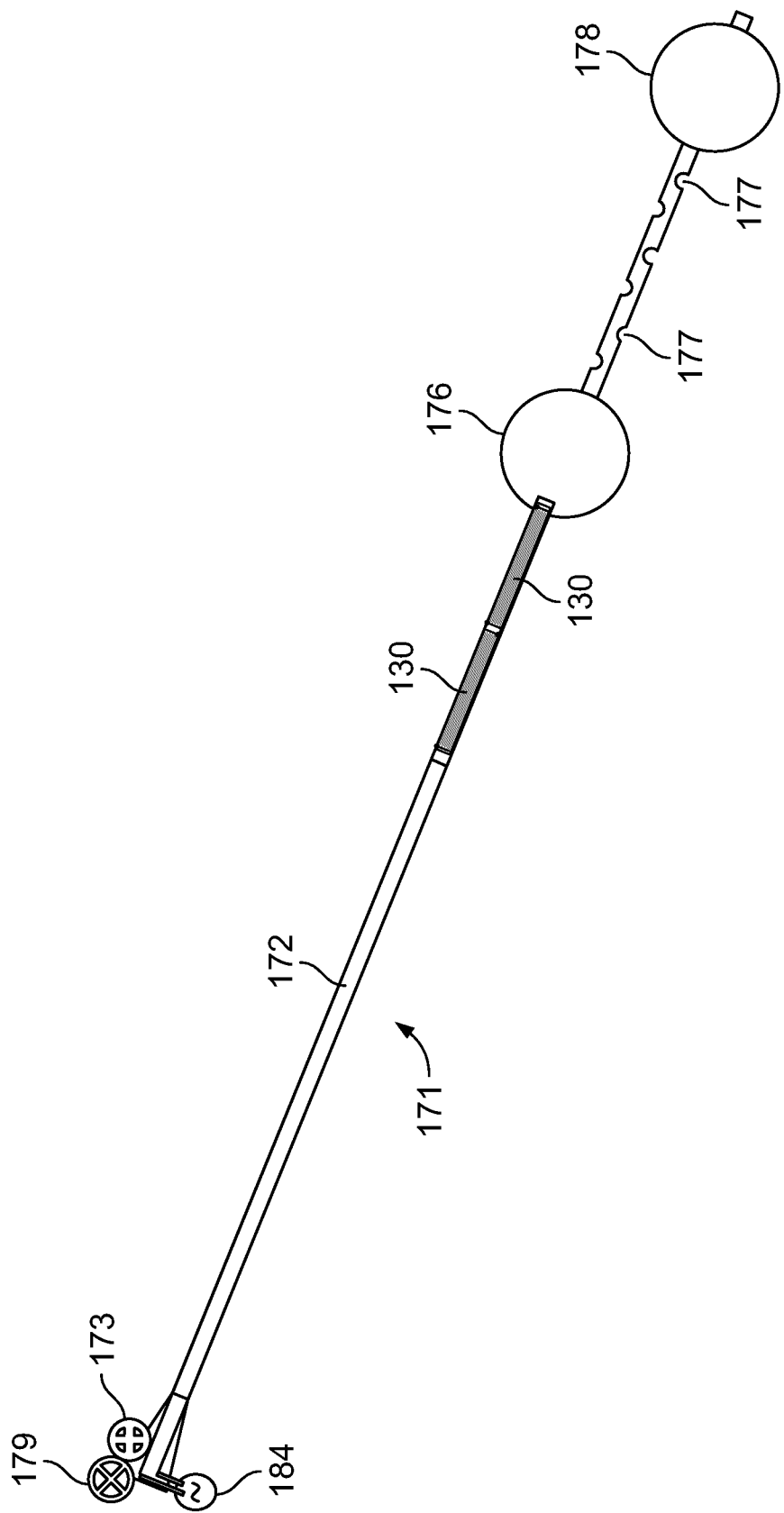
FIG. 1I illustrates a multiple lumen balloon catheter incorporating two heating chambers of FIG. 1B, in accordance with an embodiment of the present specification.

FIG. 1H and FIG. 1I illustrate multiple lumen balloon catheters 161 and 171 respectively, in accordance with embodiments of the present specification. The catheters 161, 171 each include an elongate body 162, 172 with a proximal end and a distal end. The catheters 161, 171 include at least one positioning element proximate their distal ends. In various embodiments, the positioning element is a balloon. In some embodiments, the catheters include more than one positioning element.

In the embodiments depicted in FIGS. 1H and 1I, the catheters 161, 171 each include a proximal balloon 166, 176 and a distal balloon 168, 178 positioned proximate the distal end of the body 162, 172 with a plurality of infusion ports 167, 177 located on the body 162, 172 between the two balloons 166, 176, and 168, 178. The body 162, 172 also includes at least one heating chamber 130 proximate and just proximal to the proximal balloon 166, 176. The embodiment of FIG. 1H illustrates one heating chamber 130 included in the body 165 proximate and just proximal to the proximal balloon 166. In some embodiments, multiple heating chambers are arranged in series in the body of the catheter.

In the embodiment of FIG. 1I, two heating chambers 130 are arranged in the body 172 proximate and just proximal to the proximal balloon 176. Referring to FIG. 1I, for inflating the balloons 176, 178 and providing electrical current and liquid to the catheter 171, a fluid pump 179, an air pump 173 and an RF generator 184 are coupled to the proximal end of the body 172. The air pump 173 pumps air via a first port through a first lumen (extending along a length of the body 172) to inflate the balloons 176, 178 so that the catheter 171 is held in position for an ablation treatment. In another embodiment, the catheter 171 includes an additional air port and an additional air lumen so that the balloons 176, 178 may be inflated individually. The fluid pump 179 pumps the fluid through a second lumen (extending along the length of the body 172) to the heating chambers 130. The RF generator 184 supplies electrical current to the electrodes 136, 138 (FIGS. 1G, 1H), causing the electrodes 136, 138 to generate heat and thereby converting the fluid flowing through the heating chambers 130 into vapor. The generated vapor flows through the second lumen and exits the ports 177. The flexible heating chambers 130 impart improved flexibility and maneuverability to the catheters 161, 171, allowing a physician to better position the catheters 161, 171 when performing ablation procedures, such as ablating Barrett's esophagus tissue in an esophagus of a patient.

Figure 1J:
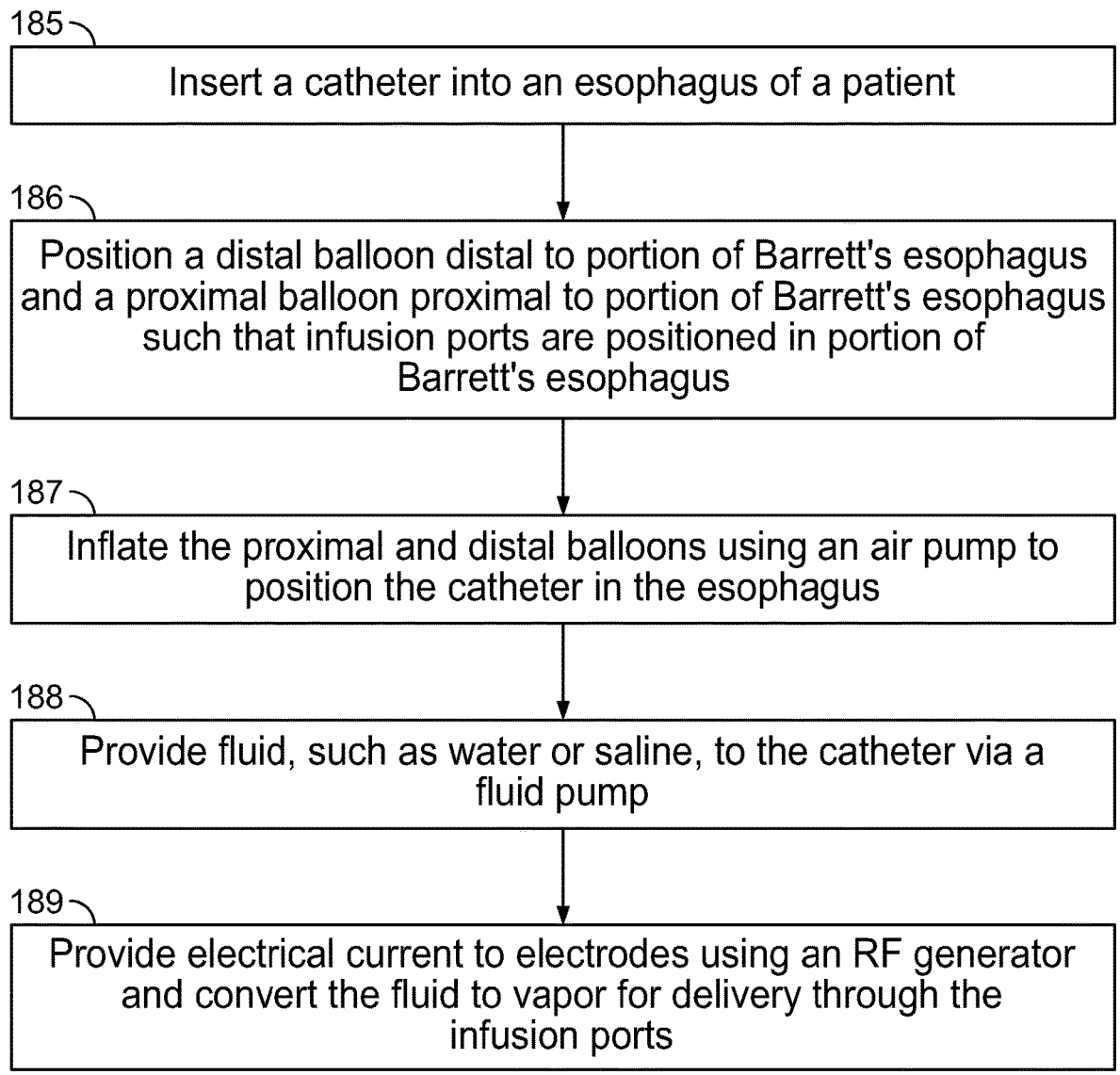
FIG. 1J is a flow chart of a plurality of steps of using the catheter of FIG. 1H or FIG. 1I to perform ablation of Barrett's esophagus tissue in an esophagus of a patient, in accordance with an embodiment of the present specification.

FIG. 1J is a flow chart of a plurality of steps of using the catheters 161, 171 of FIG. 1H or 1I to perform ablation of Barrett's esophagus tissue in an esophagus of a patient, in accordance with embodiments of the present specification. At step 185, insert the catheter 161, 171 into an esophagus of a patient. At step 186, position the distal balloon 168, 178 distal to a portion of Barrett's esophagus and the proximal balloon 166, 176 proximal to a portion of Barrett's esophagus such that infusion ports 167, 177 are positioned in said portion of Barrett's esophagus. At step 187, inflate the balloons 166, 176 and 168, 178 using an air pump to position the catheter 161, 171 in the esophagus. At step 188, provide fluid, such as water or saline, to the catheter 161, 171 via a fluid pump. Finally, at step 189, provide electrical current to electrodes 136, 138 using an RF generator to heat the electrodes and convert the fluid to vapor, wherein the generated vapor is delivered through the infusion ports 167, 177 to ablate the Barrett's esophagus tissue of the patient.

FIG. 1K illustrates a catheter 191 with proximal and distal positioning elements 196, 198 and an electrode heating chamber 130, in accordance with embodiments of the present specification. The catheter 191 includes an elongate body 192 with a proximal end and a distal end. The catheter 191 includes a proximal positioning element 196 and a distal positioning element 198 positioned proximate the distal end of the body 192 with a plurality of infusion ports 197 located on the body 192 between the two positioning elements 196, 198. The body 192 also includes at least one heating chamber 130 within a central lumen. In some embodiments, the proximal positioning element 196 and distal positioning element 198 comprises compressible discs which expand on deployment. In some embodiments, the proximal positioning element 196 and distal positioning element 198 are comprised of a shape memory metal and are transformable from a first, compressed configuration for delivery through a lumen of an endoscope and a second, expanded configuration for treatment. In embodiments, the discs include a plurality of pores 199 to allow for the escape of air at the start of an ablation procedure and for the escape of steam once the pressure and/or temperature within an enclosed treatment volume created between the two positioning elements 196, 198 reaches a predefined limit, as described above. In some embodiments, the catheter 191 includes a filter 193 with micro-pores which provides back pressure to the delivered steam, thereby pressurizing the steam. The predetermined size of micro-pores in the filter determine the backpressure and hence the temperature of the steam being generated.

It should be appreciated that the filter 193 may be any structure that permits the flow of vapor out of a port and restricts the flow of vapor back into, or upstream within, the catheter. Preferably, the filter is a thin porous metal or plastic structure, positioned in the catheter lumen and proximate one or more ports. Alternatively, a one-way valve may be used which permits vapor to flow out of a port but not back into the catheter. In one embodiment, this structure 193, which may be a filter, valve or porous structure, is positioned within 5 cm of a port, preferably in a range of 0.1 cm to 5 cm from a port, and more preferably within less than 1 cm from the port, which is defined as the actual opening through which vapor may flow out of the catheter and into the patient.

FIG. 1L is a flow chart illustrating a method of ablating a tissue inside a gastrointestinal tract of a patient, in accordance with some embodiments of the present specification. In embodiments, the method of FIG. 1L illustrates circumferential vapor ablation that is followed by a focused vapor ablation after observing the patient, to treat a pre-cancerous tissue, cancerous tissue, or otherwise unwanted tissue in the esophagus, duodenum, bile duct, or pancreas. In embodiments, ablation catheters disclosed in the present specification, such as ablation catheter 191 of FIG. 1K, are used to perform the ablation method of FIG. 1L.

At 102, an ablation catheter configured for the gastrointestinal (GI) tract is inserted into the GI tract of the patient. At 104, a seal is created between an exterior surface of the ablation catheter and an interior wall of the GI tract, forming a treatment volume. The seal is created by the expansion of one or more positioning elements of the ablation catheter, as explained in the embodiments of the present specification. In some embodiments, the seal is temperature dependent and it breaks or becomes porous when the temperature or pressure within the sealed portion or treatment volume exceeds a threshold value. In one embodiment, the specific temperature is 90° C. In some embodiments, the seal is pressure dependent and it begins to leak when the pressure within the sealed portion or treatment volume exceeds a specific pressure. In one embodiment, the specific pressure is 5 atm. At 106, vapor is delivered through the ablation catheter into the sealed portion within the GI tract, while the seal is still in place. At 108, the vapor condenses on the tissue under treatment, thereby ablating the tissue.

FIG. 1M is a flow chart illustrating a method of ablating a tissue inside a gastrointestinal tract of a patient, in accordance with other embodiments of the present specification. In embodiments, the method of FIG. 1M illustrates circumferential vapor ablation that is followed by focused vapor ablation after observing the patient, to treat a pre-cancerous tissue, cancerous tissue, or otherwise unwanted tissue in the esophagus, duodenum, bile duct, or pancreas. In embodiments, ablation catheters disclosed in the present specification, such as ablation catheter 191 of FIG. 1K, are used to perform the ablation method of FIG. 1M. At 112, an ablation catheter configured for the gastrointestinal (GI) tract is inserted into the GI tract of the patient. At 114, saline with a variable flow rate is introduced through the ablation catheter into the GI tract. At 116, the saline is heated using RF energy to generate vapor through the ablation catheter into the GI tract. In embodiments, the rate of flow of the saline during vapor delivery is different from flow of the saline during the phase where no therapy is delivered. In some embodiments, the rate of flow of saline during the therapy is lower than that during no therapy. In some embodiments, the rate of flow of saline during the therapy is lower than that during no therapy. At 118, the vapor condenses on the tissue under treatment, thereby ablating the tissue.

Exemplary Treatment—Gastrointestinal System

Figure 1N:
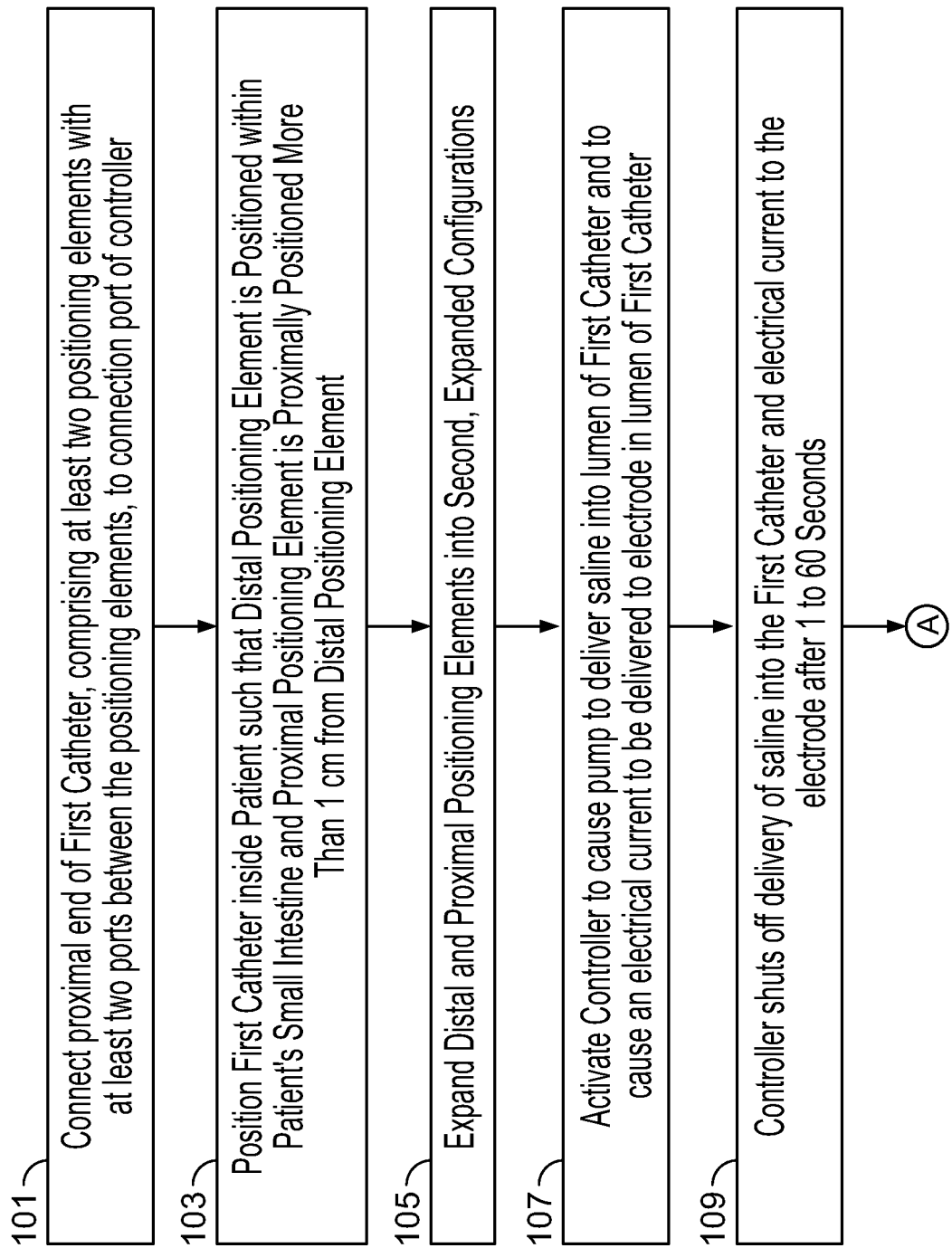
FIG. 1N is a flow chart illustrating a method for treating a gastrointestinal condition in a patient using a vapor ablation system, in accordance with embodiments of the present specification.
Figure 1N:
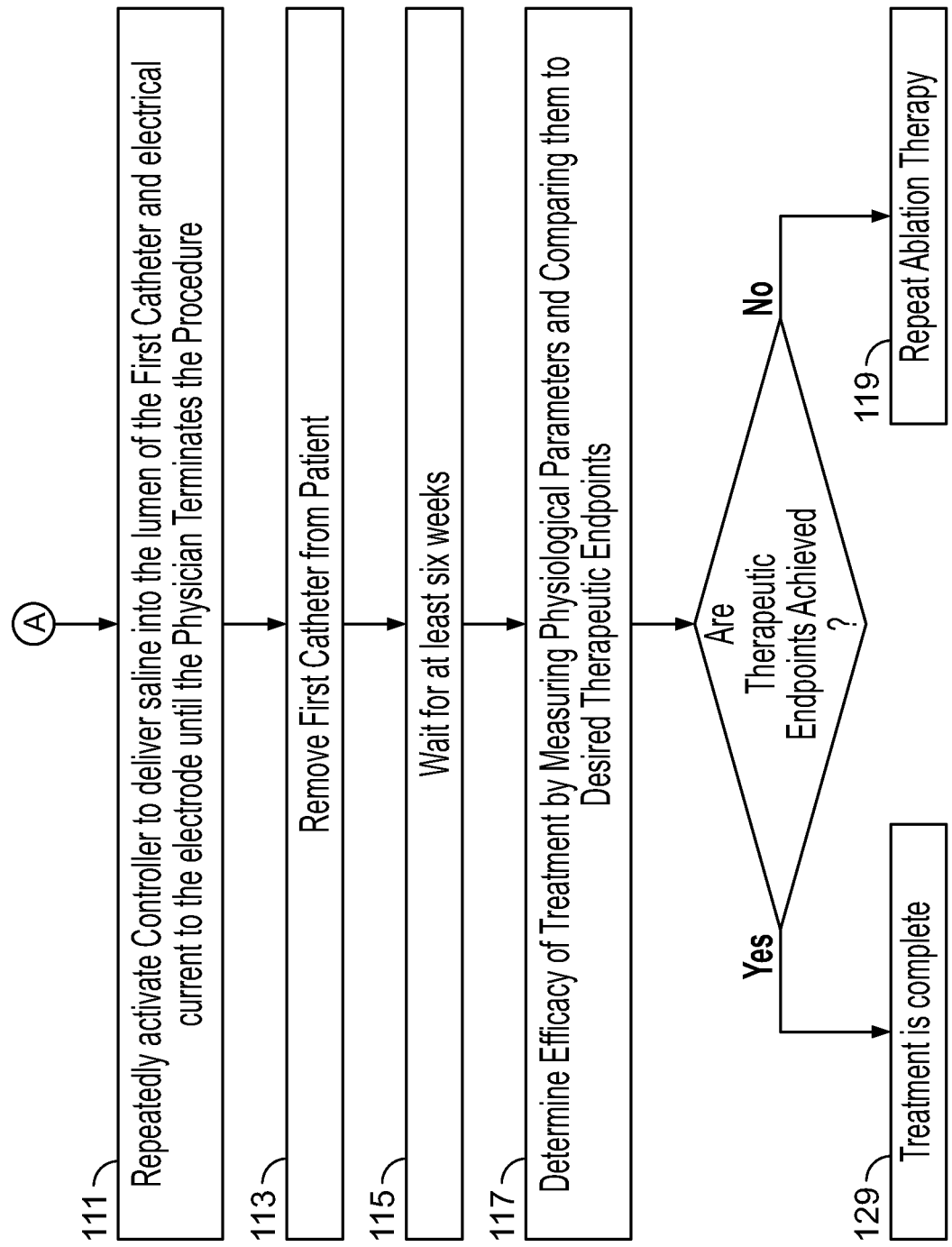

FIG. 1N is a flow chart illustrating a method for treating a gastrointestinal condition in a patient using a vapor ablation system, in accordance with embodiments of the present specification. In various embodiments, the condition may include, but is not limited to, obesity, excess weight, eating disorders, metabolic syndrome, and diabetes, fatty liver, non-alcoholic fatty liver disease (NAFLD), or non-alcoholic steatohepatitis (NASH). The vapor ablation system comprises a controller having at least one processor in data communication with at least one pump and a catheter connection port in fluid communication with the at least one pump. At step 101, a proximal end of a first catheter is connected to the catheter connection port to place the first catheter in fluid communication with the at least one pump. The first catheter comprises at least two positioning elements separated along a length of the catheter and at least two ports positioned between the at least two positioning elements, wherein each of the at least two positioning elements has a first configuration and a second configuration, and wherein, in the first configuration, each of the at least two positioning elements is compressed within the catheter and in the second configuration, each of the at least two positioning elements is expanded to be at least partially outside the catheter. At step 103, the first catheter is positioned inside a patient such that, upon being expanded into the second configuration, a distal one of the at least two positioning elements is positioned within in the patient's small intestine and a proximal one of the at least two positioning elements is proximally positioned more than 1 cm from the distal one of the at least two positioning elements. Then, at step 105 each of the at least two positioning elements is expanded into their second configurations. At step 107, the controller is activated, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter. The electrical current causes the electrode to heat and contact of the saline with the heating electrode converts the saline to steam which is delivered via the at least two ports to ablate gastrointestinal tissue. In various embodiments, each treatment dose delivered to the gastrointestinal tract comprises the following parameters: 1-15 cm of contiguous or non-contiguous small intestine mucosa is treated; at least 50% of a circumference of a small intestine is treated; energy in a range of 5-25 J/cm$^2$; delivery period of 1-60 seconds; delivery rate of 5-2,500 cal/sec; total dose of 5-40 cal/gm of tissue to be ablated; target tissue temperature between 60° C. and 110° C.; vapor temperature between 99° C. and 110° C.; and pressure in the gastrointestinal tract less than 5 atm, and preferably less than 1 atm.

At step 109, the controller shuts off the delivery of saline and electrical current after a time period ranging from 1 to 60 seconds. In embodiments, the controller automatically shuts off the delivery of saline and electrical current. The controller is repeatedly activated at step 111 to deliver saline into the lumen and electrical current to the at least one electrode until the physician terminates the procedure. In some embodiments, the system further comprises a foot pedal in data communication with the controller, a switch on the catheter, or a switch on the controller, for controlling vapor flow and step 111 is achieved using the foot pedal in data communication with the controller, a switch on the catheter, or a switch on the controller. The first catheter is removed from the patient at step 113.

The physician then waits for at least at least six weeks at step 115 before evaluating the efficacy of treatment. In some embodiments, the physician waits a time frame ranging from six weeks to two years before evaluating efficacy of treatment. An efficacy of the treatment is determined at step 117 my measuring at least one physiological parameter relating to the gastrointestinal disorder, as disclosed in the present specification, and comparing the measured parameter to a desired therapeutic endpoint. If the therapeutic endpoint has been achieved, treatment is complete at step 129. If the therapeutic endpoint has not been achieved, ablation therapy is repeated at step 119.

It should be appreciated that, while the above discussion is directed to duodenal ablation, any ablation catheter or system of the present specification, used to ablate tissue in an organ, may be used with a controller, wherein the controller is configured to limit a pressure generated by ablation fluid, such as steam/vapor, within the organ to less than 5 atm or 100 psi. In various embodiments, the organ may be a pancreatic cyst, esophagus, duodenum/small bowel, uterine cavity, prostate, bronchus or alveolar space.

Needle Vapor Delivery Device

Figure 2A:
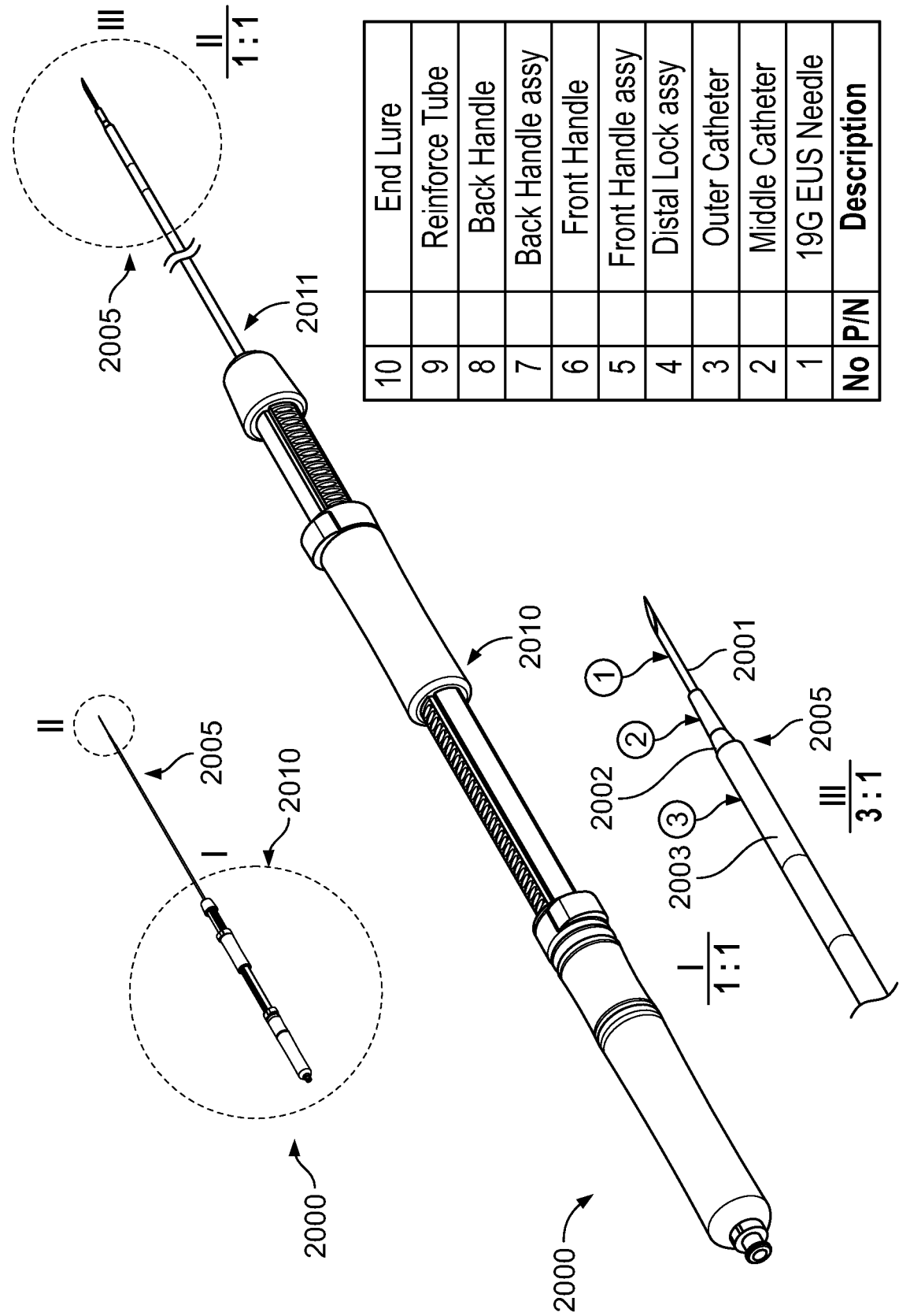
FIG. 2A shows perspective views of a needle ablation device, in accordance with an embodiment of the present specification.

FIG. 2A shows perspective views of a needle-based vapor delivery device 2000, in accordance with an embodiment of the present specification. The device 2000 comprises a needle 2005 protruding from a distal end 2011 of a composite handle 2010. The needle 2005 has a needle tip portion 2001 and is encompassed at its proximal end by an inner or middle catheter 2002 and an outer catheter 2003. In some embodiments, the composite handle 2010 and the needle 2005 are hollow. In some embodiments, the needle 2005 is retractable within the composite handle 2010. In some embodiments, the needle 2005 is of stainless steel, the middle catheter 2002 is of PTFE (Polytetrafluoroethylene) while the outer catheter 2003 is of braided Teflon.

Figure 2B:
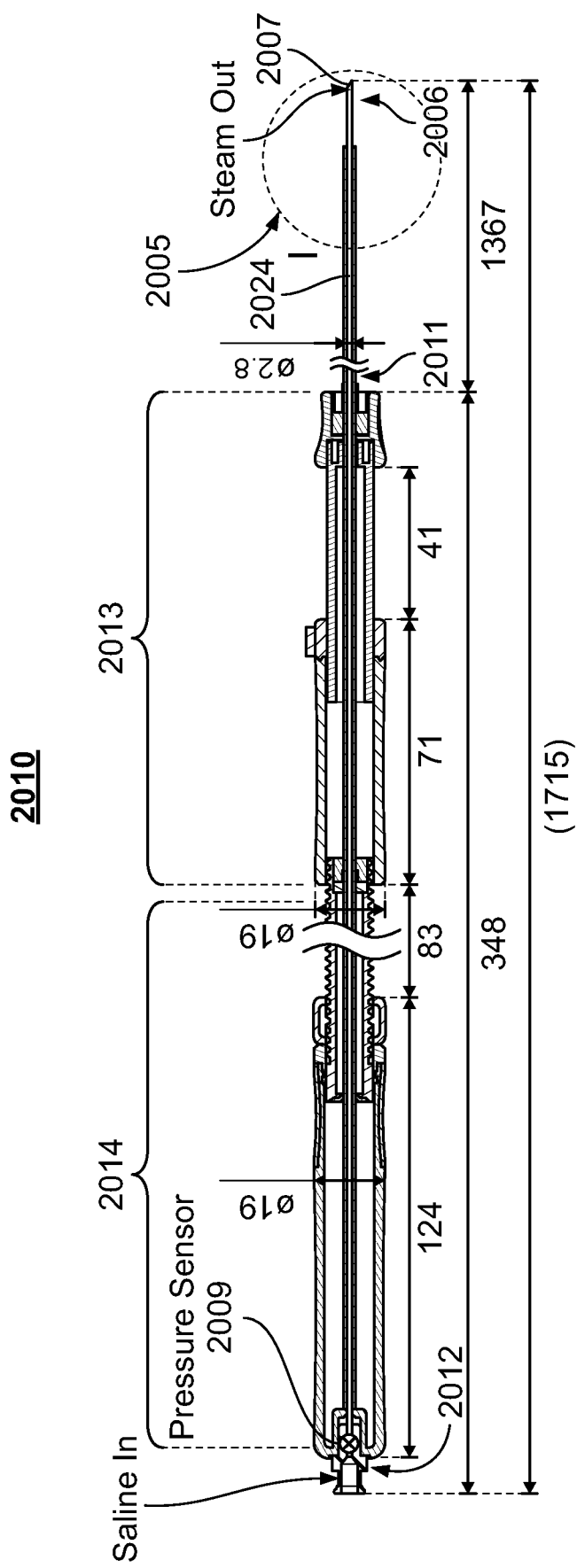
FIG. 2B shows a cross-sectional view of the needle ablation device of FIG. 2A, in accordance with an embodiment of the present specification.

FIG. 2B is a cross-sectional view of the composite handle 2010 illustrating the needle 2005 emanating from the distal end 2011, a front or distal handle portion 2013 and a back or proximal handle portion 2014. A lumen 2008 extends from a proximal end 2012 to the distal end 2011 of the composite handle 2010 and is in fluid communication with a lumen 2024 of the needle 2005. Saline enters the lumen 2008 from the proximal end 2012 and steam exits from at least one port 2007 located at a distal end 2006 of the needle 2005. A pressure sensor 2009 is located proximate the proximal end 2012 of the composite handle 2010.

Figure 2C:
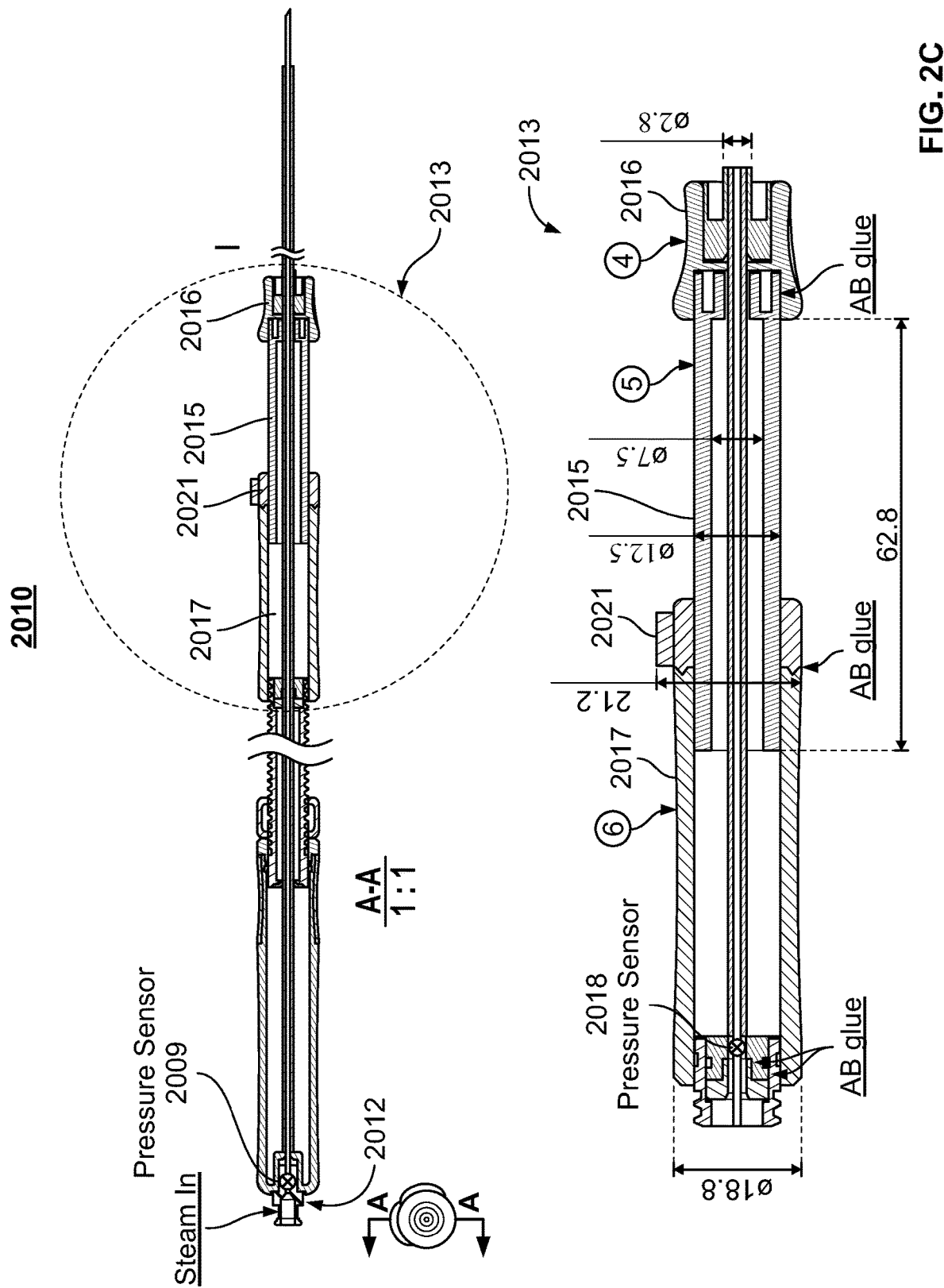
FIG. 2C shows a first enlarged cross-sectional view of the needle ablation device of FIG. 2A, in accordance with an embodiment of the present specification.

FIG. 2C shows an enlarged view of the front or distal handle portion 2013 of the composite handle 2010. Referring now to FIGS. 2B and 2C, the distal handle portion 2013 is an assembly comprising a front tube 2015 coupled, at its distal end, to a distal lock 2016 and, at its proximal end, to a front handle 2017. A lock 2021 secures the front tube 2015 to the front handle 2017. A pressure sensor 2018 is located proximate a proximal end of the front handle 2017 while the pressure sensor 2009 is located proximate the proximal end 2012.

FIG. 2D shows an enlarged view of the back or proximal handle portion 2014 of the composite handle 2010. Referring now to FIGS. 2B, 2C and 2D, the proximal handle portion 2014 is an assembly comprising a back tube 2019 coupled, at its distal end, to the front handle 2017 and, at its proximal end, to a back handle 2020. A lock 2025 secures the back tube 2019 to the back handle 2020. The lumen 2008 is covered or encompassed within a reinforce tube or sheath 2022. The proximal end 2012 of the composite handle 2010 includes a lure connection 2023 defining an opening to enable saline to enter the lumen 2008. The pressure sensor 2009 is visible again in the enlarged view of the back or proximal handle portion 2014 of FIG. 2D.

Referring again to FIGS. 2A, 2B, 2C and 2D, in accordance with an exemplary embodiment, the device 2000 has the following dimensions: a length of 1715 mm from a proximal end of the lure connection 2023 to the distal end 2006 of the needle 2005, a length of 1367 mm from a distal end of the distal lock 2016 to the distal end 2006 of the needle 2005, a length of 41 mm from a proximal end of the distal lock 2016 to a distal end of the lock 2021, a length of 71 mm from the distal end of the lock 2021 to a proximal end of the front handle 2017, a length of 83 mm from the proximal end of the front handle 2017 to a distal end of the lock 2025, a length 124 mm from the distal end of the lock 2025 to the proximal end 2012, a length of 348 mm from the distal end of the distal lock 2016 to the proximal end of the lure connection 2023, a length of 62.8 mm from the proximal end of the distal lock 2016 to a proximal end of the front tube 2015, an outer diameter of 2.8 mm of the sheath 2022, an outer diameters of 19 mm of the front handle 2017 and the back handle 2020, an inner diameters of 7.5 mm of the front and back tubes 2015, 2019, and an outer diameters of 12.5 mm of the front and back tubes 2015, 2019.

Figure 3A:
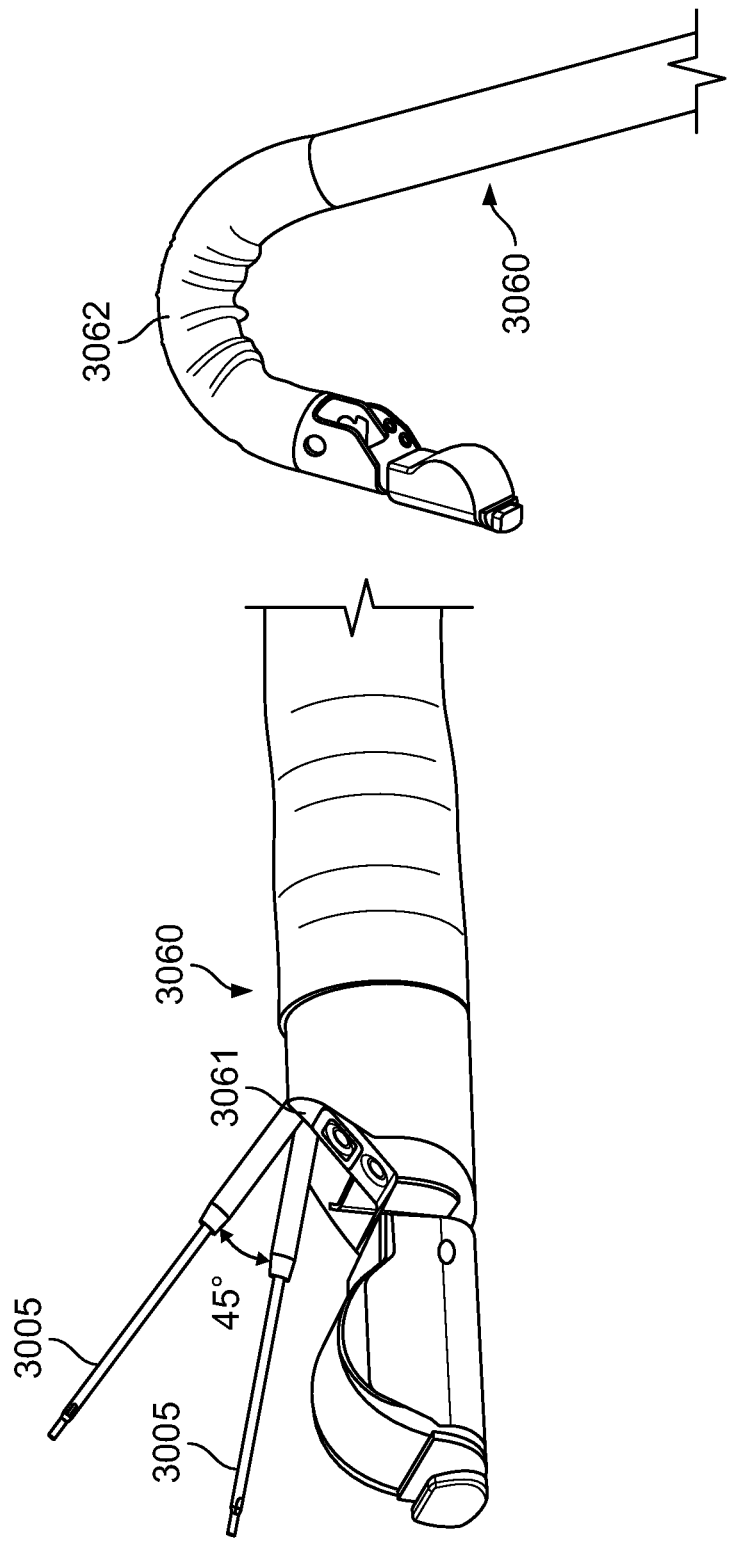
FIG. 3A shows perspective views of an endoscope and of the needle ablation device of FIG. 2A being deployed through the endoscope, in accordance with an embodiment of the present specification.
Figure 3B:
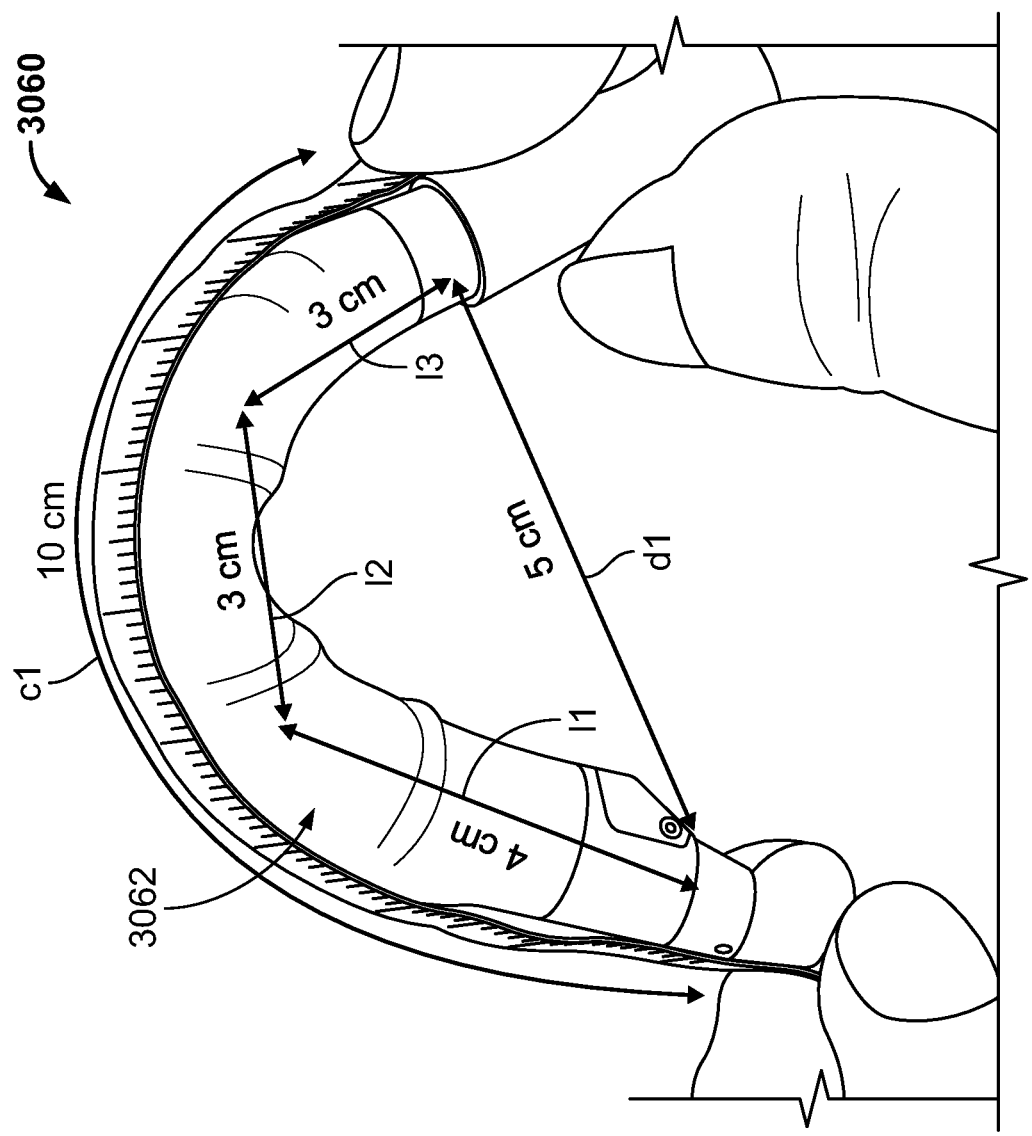
FIG. 3B shows a perspective view of a bending section of the endoscope, in accordance with an embodiment of the present specification.

In accordance with an aspect of the present specification, the needles of the needle ablation catheters and devices have a form factor that enables the needle to be functional with a conventional endoscope—that is, the form factor enables the needle to be slid through a working channel of the endoscope. FIGS. 3A and 3B illustrate a conventional endoscope 3060 with a bending section 3062 and a needle 3005 of a needle ablation catheter protruding from a working channel 3061 of the endoscope 3060. In embodiments, when bent, the bending section 3062 has a curve length $c_1$ of 10 cm comprising a first distal length $l_1$ of 4 cm, a second middle length $l_2$ of 3 cm and a third proximal length $l_3$ of 3 cm. When bent, a distance d1 between a distal end and a proximal end of the bending section 3062 is 5 cm. As shown in FIG. 3A, the needle 3005 is capable of bending or flexing by at least an angle of 45 degrees.

Figure 4A:
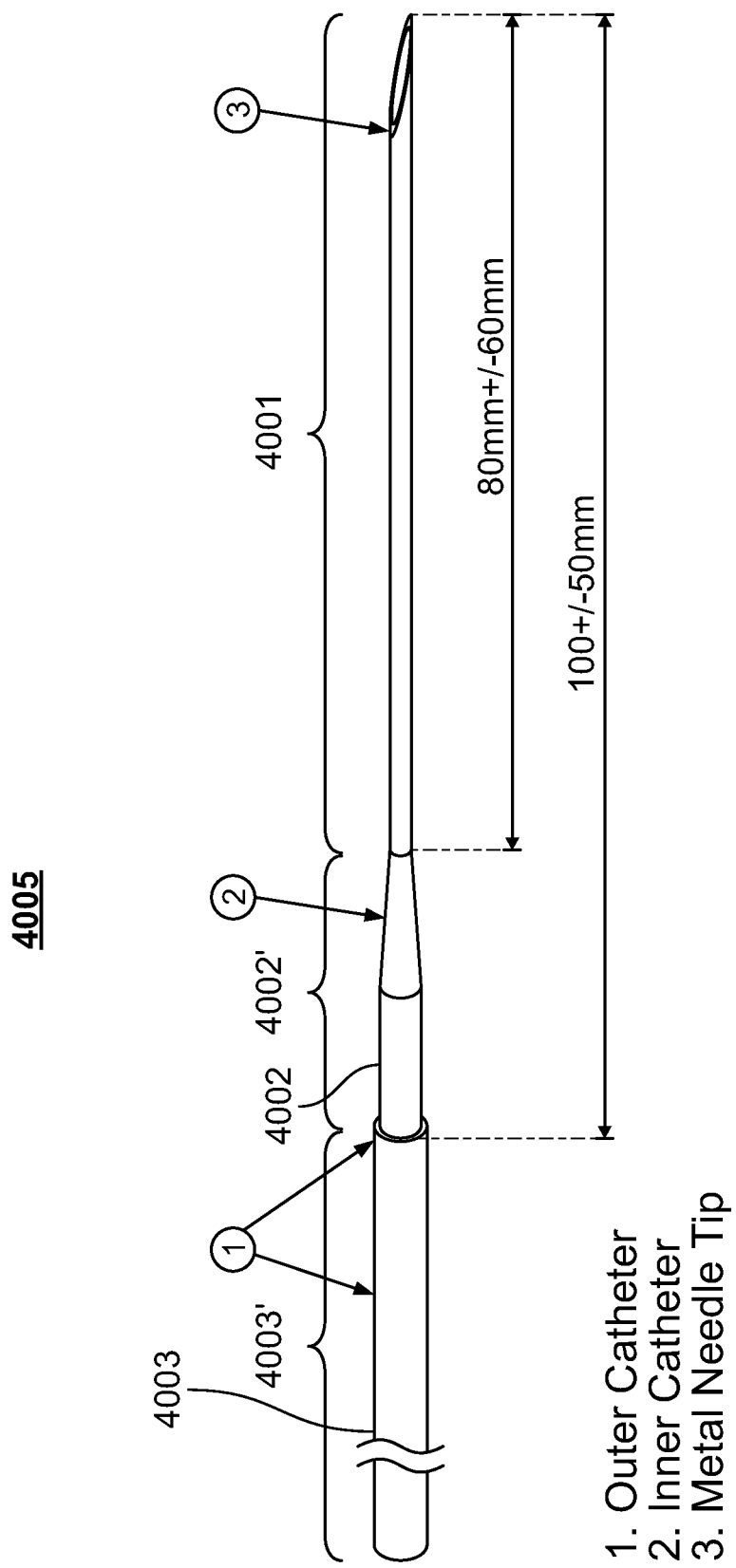
FIG. 4A shows a perspective view of a needle of a needle ablation device, in accordance with an embodiment of the present specification.
Figure 4B:
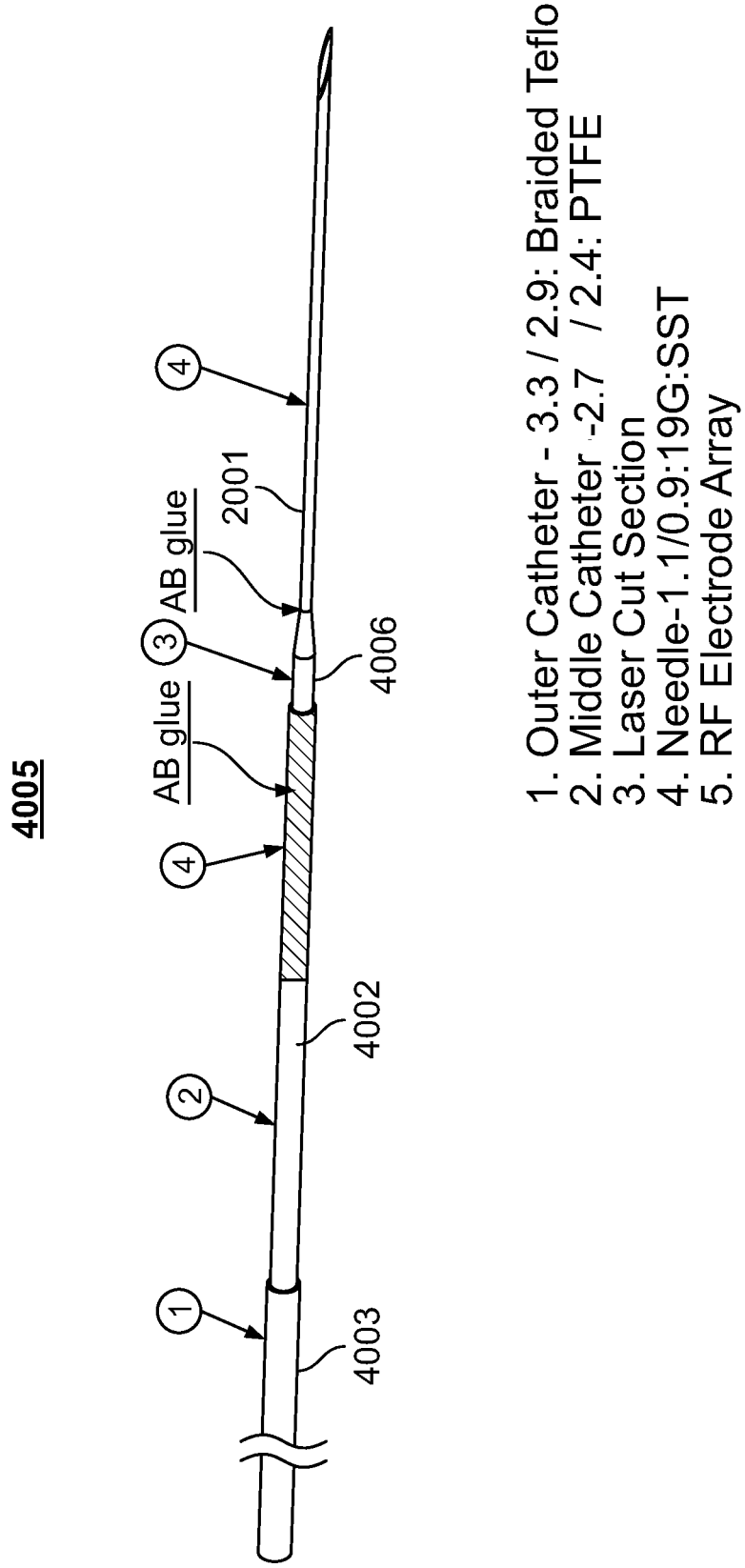
FIG. 4B shows another perspective view of the needle of the needle ablation device of FIG. 4A, in accordance with an embodiment of the present specification.
Figure 4C:
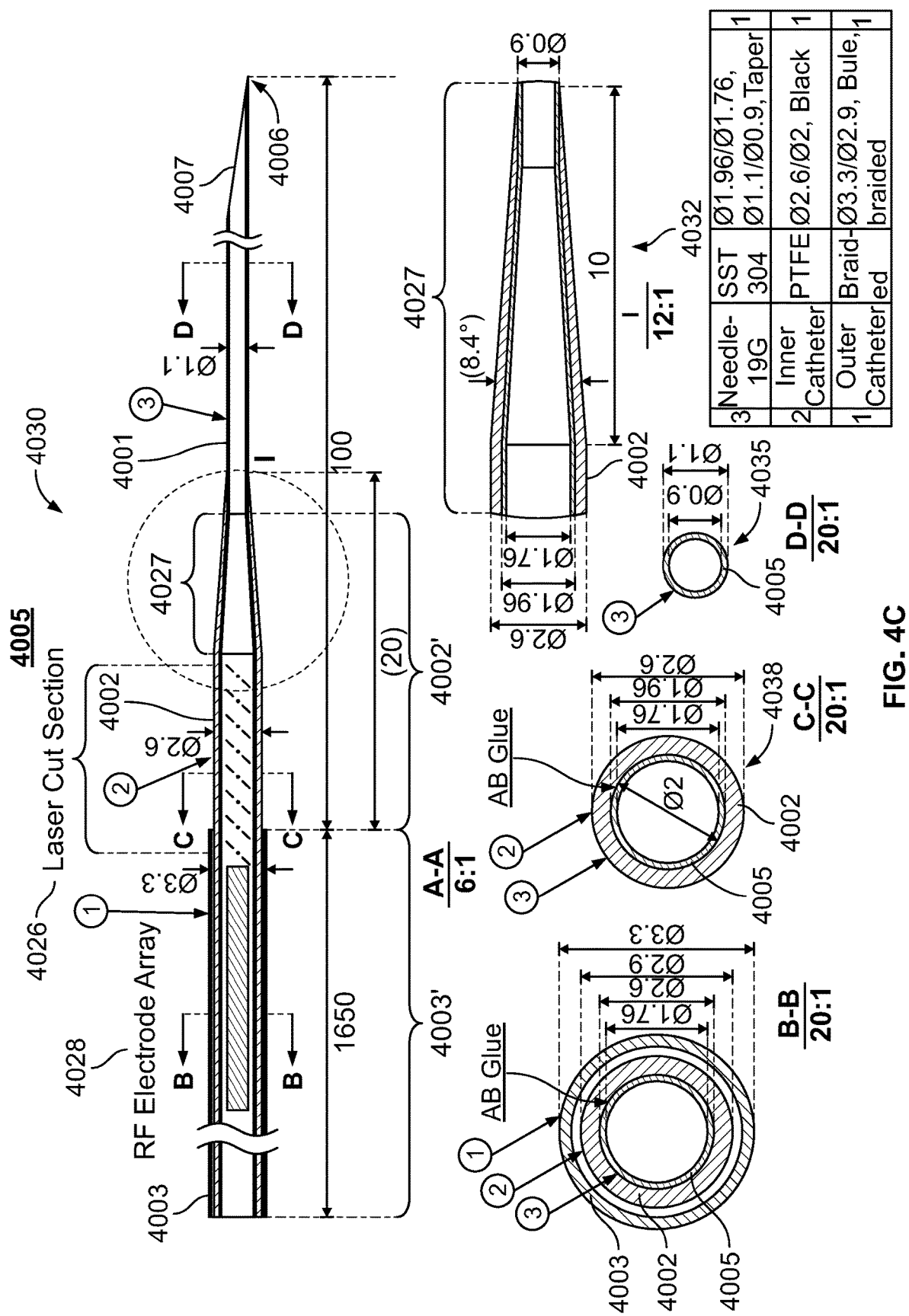
FIG. 4C shows cross-sectional views of the needle of the needle ablation device of FIG. 4A, in accordance with a first embodiment of the present specification.

FIGS. 4A, 4B show perspective views of a needle 4005 while FIG. 4C illustrates cross-sectional views of the needle 4005, in accordance with an embodiment of the present specification. In accordance with an embodiment, the needle 4005 can be distinguished into the distal needle tip portion 4001, a middle portion 4002' and a proximal portion 4003'. FIGS. 4A, 4B and a longitudinal cross-sectional view 4030 of FIG. 4C show the needle tip portion 4001, the inner or middle catheter 4002 and the outer catheter 4003. In accordance with an embodiment, the needle tip portion 4001 has a length of 80 mm (+/−60 mm) from a proximal end to a distal end of the needle tip portion 4001. The needle 4005 has a length of 100 mm (+/−50 mm) from a proximal end of the middle portion 4002' to the distal end of the needle tip portion 4001. The proximal portion 4003' has a length of 1650 mm.

Referring now to the longitudinal cross-sectional view 4030 of FIG. 4C, the middle portion 4002' comprises a proximal laser cut portion 4026 (also shown in FIG. 4B) and a distal tapered portion 4027. In accordance with an embodiment of the present specification, the proximal portion 4003' houses or accommodates at least one flexible heating chamber 4028 (comprising a plurality of RF electrodes) positioned proximate the proximal laser cut portion 4026 (the at least one flexible heating chamber 4028 is also shown in FIG. 4B). During operation, saline enters from the proximal end (2012 of FIG. 2B) to reach the heating chamber 4028 where the saline is converted to steam/vapor that exits through at least one port 4007 located at the distal end 4006 of the needle 4005.

As shown in an enlarged cross-sectional view 4032, in one embodiment, at a proximal end of the tapered portion 4027—the needle 4005 has an inner diameter of 1.76 mm and an outer diameter of 1.96 mm while the inner catheter 4002 has an outer diameter of 2.6 mm and an inner diameter of 2 mm. In another embodiment, the inner catheter 4002 has an outer diameter of 2.7 mm and an inner diameter of 2.4 mm. At a distal end of the tapered portion 4027, the needle 4005 has an inner diameter of 0.9 mm. From the proximal end to the distal end, the portion 4027 has a taper or slope of 8.4 degrees with respect to a horizontal axis. The length of the tapered portion 4027 is 10 mm.

As shown in an enlarged cross-sectional view 4035, at the tip portion 4001, the needle 4005 has an outer diameter of 1.1 mm and an inner diameter of 0.9 mm. As shown in an enlarged cross-sectional view 4038, at the middle portion 4002', the needle 4005 has an inner diameter of 1.76 mm and an outer diameter of 1.96 mm while the inner or middle catheter 4002 has an outer diameter of 2.6 mm. As shown in an enlarged cross-sectional view 4040, at the proximal portion 4003', the needle 4005 still has the inner diameter of 1.76 mm and the outer diameter of 1.96 mm, the inner or middle catheter 4002 still has the outer diameter of 2.6 mm while the outer catheter 4003 has an inner diameter of 2.9 mm and an outer diameter of 3.3 mm.

In some embodiments, the proximal portion 4003' of the needle 4005 has an inner diameter of greater than or equal to 1.5 mm (to accommodate the heating chamber 4028) while the needle tip portion 4001 has an outer diameter of less than or equal to 1.1 mm to minimize leaks and infection. In some embodiments, the needle 4005 is electrically insulated and does not have leaks along its length (see FIG. 4D). In various embodiments, the needle 4005 is sufficiently stiff at the tip and proximal portions 4001, 4003' and has a 10 to 20 cm flexible middle portion 4002' in order to make a bend in the endoscope.

Figure 4D:
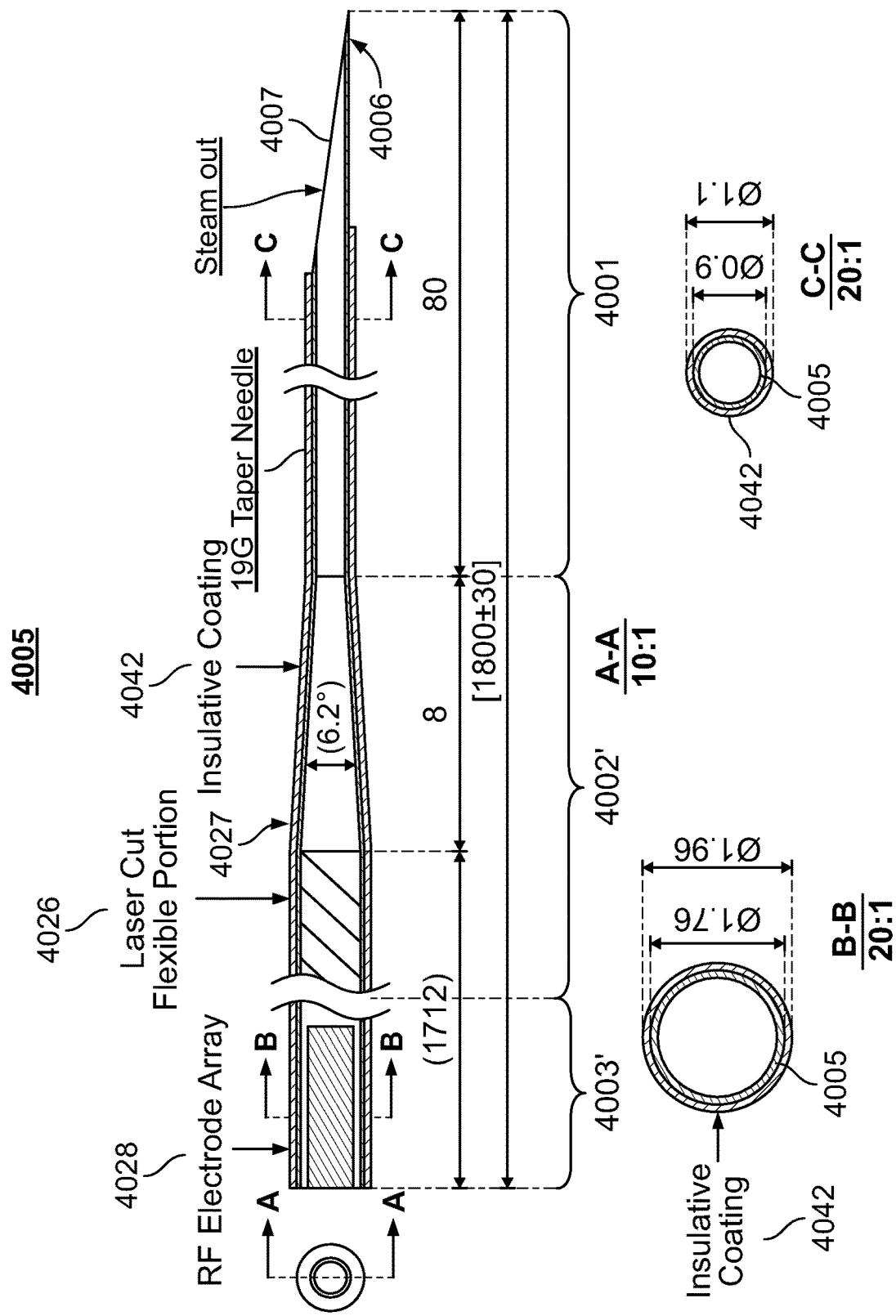
FIG. 4D shows cross-sectional views of the needle of the needle ablation device of FIG. 4A, in accordance with a second embodiment of the present specification.

FIG. 4D illustrates cross-sectional views of the needle 4005, in accordance with another embodiment of the present specification. In this embodiment, the needle 4005 is covered or sheathed in an insulating coating 4042 that covers the proximal portion 4003', the middle portion 4002' and the needle tip portion 4001 to a point proximate the at least one port 4007. In some embodiments, the insulating coating 4042 covers the entirety of the needle 4005, which, in some embodiments, comprises the distal 8 cm of the inner catheter. In some embodiments, needle 4005 diameter is within a range of 12 Birmingham Gauge (G) and 30G and needle 4005 length is in a range of 1 cm to 10 cm. In some embodiments, the slope of the needle taper is defined in a range of 12G/1 cm to 30G/10 cm. The proximal portion 4003' houses or accommodates at least one flexible heating chamber 4028 (comprising a plurality of electrodes) positioned proximate the proximal laser cut portion 4026.

Referring to FIG. 4D, in an embodiment, the needle 4005 has the following dimensions: a length of 80 mm from the distal end 4006 of the needle 4005 to the distal end of the middle portion 4002', a length of 8 mm from the distal end to the proximal end of the tapered portion 4027, a length of 1712 mm from the distal end of the laser cut portion 4026 to a proximal end of the proximal portion 4003', a total length of 1800 mm (+/−30 mm) from the proximal end of the proximal portion 4003' to the distal end 4006 of the needle 4005, and the tapered portion 4027 has a taper or slope in a range of 1 to 20 degrees (or any increment therein), preferably a range of 3 to 10 degrees (or any increment therein), and more preferably 6.2 degrees, with respect to a horizontal axis. At the tip portion 4001, the needle 4005 has an outer diameter of 1.1 mm and an inner diameter of 0.9 mm while at the proximal portion 4003', the needle 4005 has an inner diameter of 1.76 mm and an outer diameter of 1.96 mm.

Figure 4E:
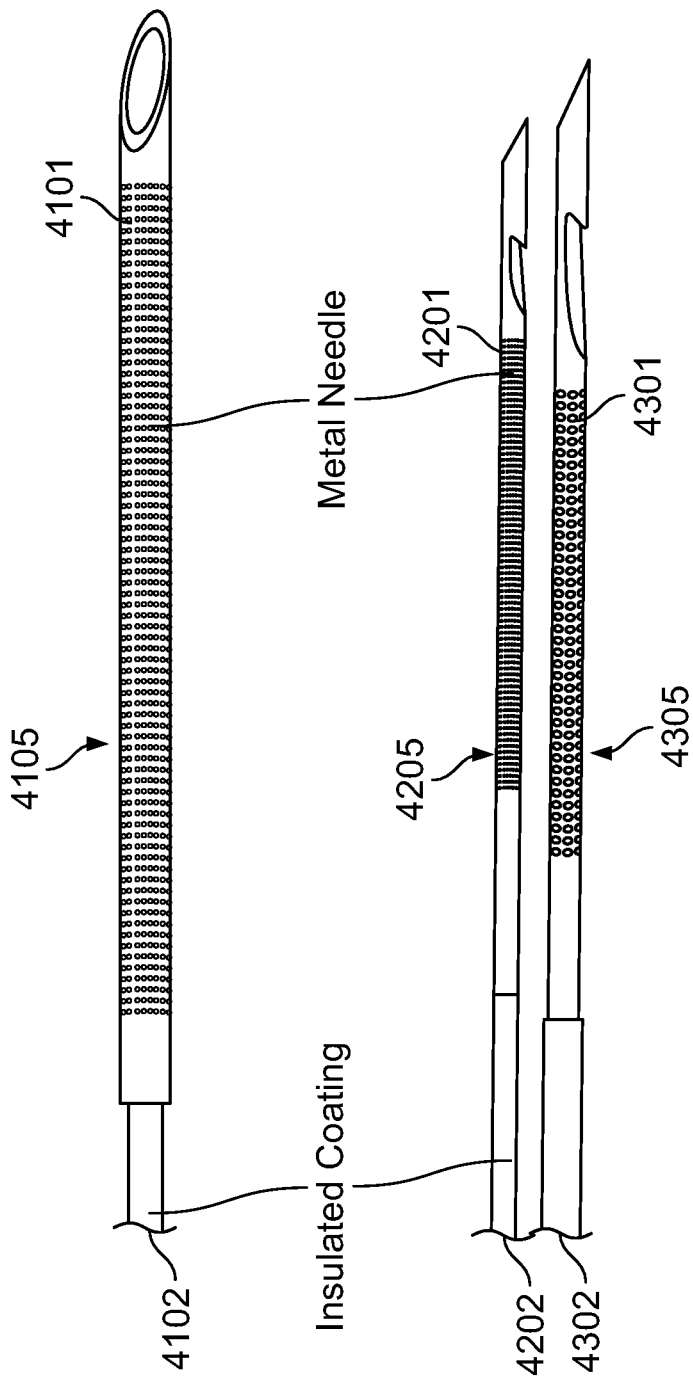
FIG. 4E shows perspective views of various needles illustrating the needle tip portions and insulating coatings, in accordance with embodiments of the present specification.

FIG. 4E shows perspective views of various needles 4105, 4205, 4305 illustrating the needle tip portions 4101, 4201, 4301 and insulating coatings 4102, 4202, 4302, in accordance with embodiments of the present specification. The needles 4105, 4205, 4305 are composed of metal such as, but not limited to, stainless steel while the insulating coatings 4102, 4202, 4302 comprise PTFE, ePTFE or silicone.

Figure 5A:
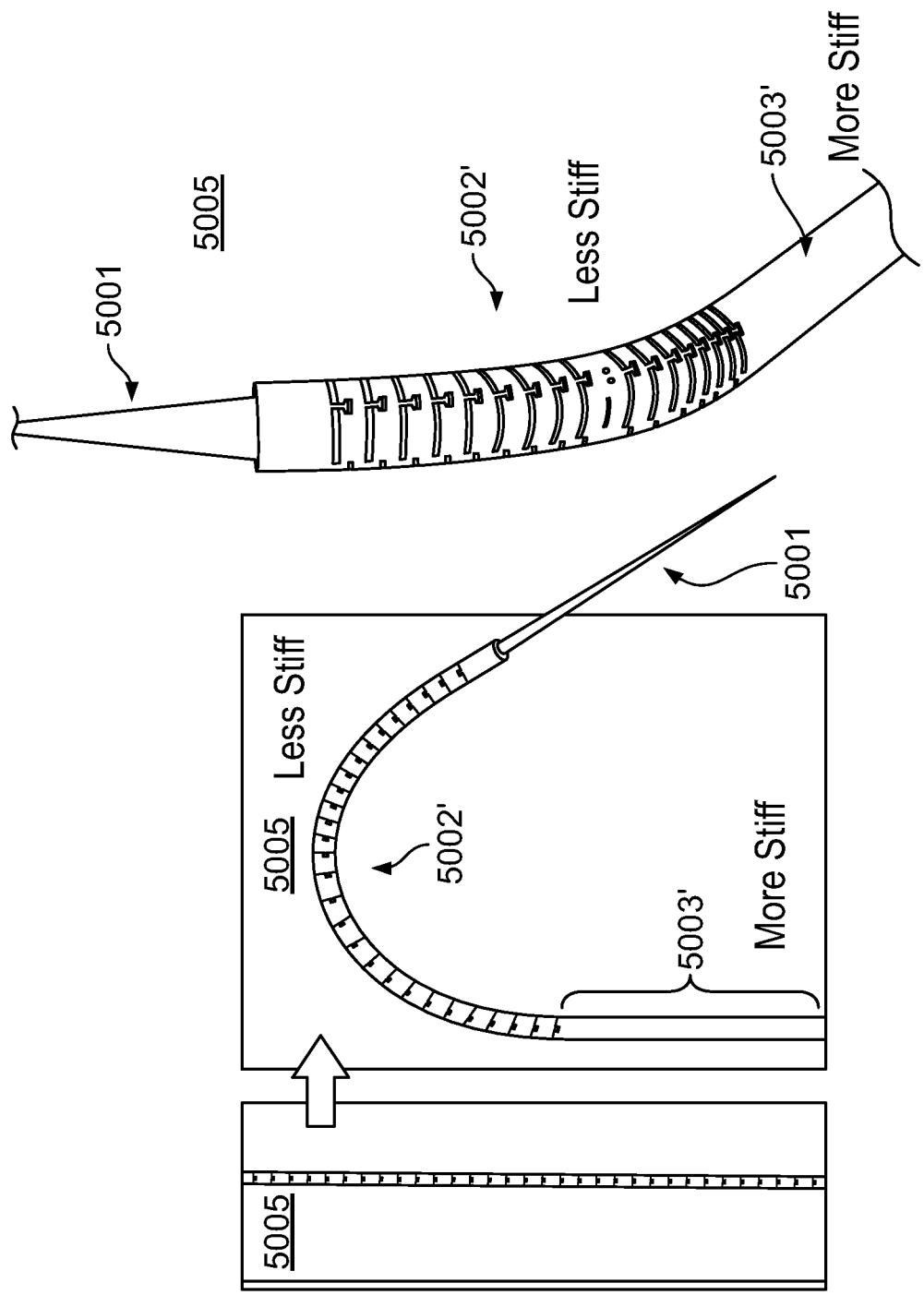
FIG. 5A shows perspective views of a needle of a needle ablation catheter having variable stiffness along its length, in accordance with an embodiment of the present specification.

In accordance with an aspect of the present specification, the needles of the needle ablation catheters are configured to have variable stiffness across their lengths. As shown in FIG. 5A, a proximal portion 5003' of a needle 5005 has a first stiffness, the middle portion 5002' has a second stiffness and a tip portion 5001 has a third stiffness. In some embodiments, the second stiffness is less than the first stiffness and the third stiffness. In some embodiments, the first and third stiffness are substantially same. In some embodiments, the first stiffness is greater than the third stiffness. In some embodiments, the first stiffness is less than the third stiffness.

Figure 5B:
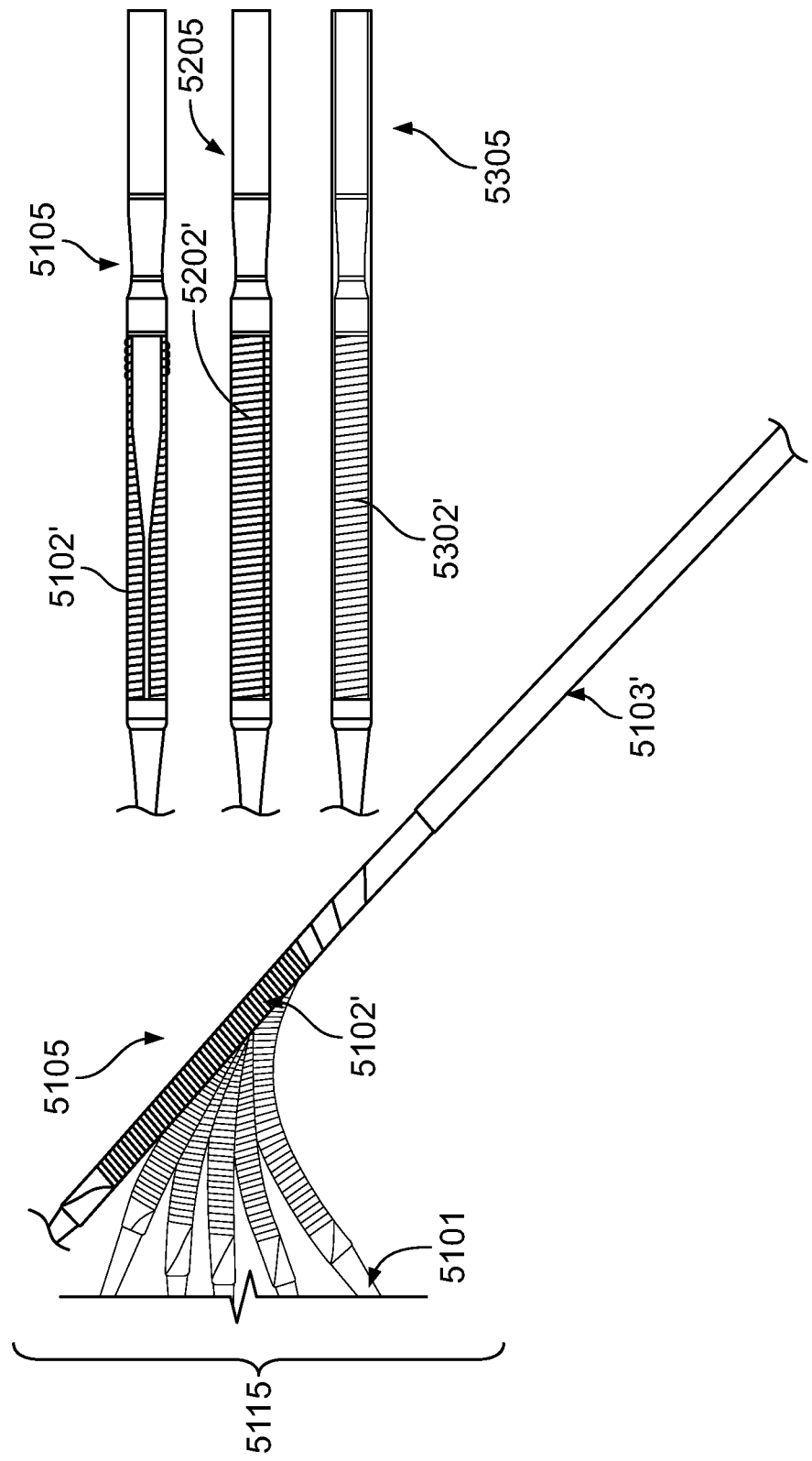
FIG. 5B shows perspective views of a plurality of needles of a needle ablation catheter having variable stiffness along their lengths, in accordance with some embodiments of the present specification.

Referring now to FIG. 4C in addition to FIGS. 5A and 5B, the middle portion 4002', 5002' includes the laser cut portion 4026 that imparts the middle portion 4002', 5002' with the second stiffness thereby enabling the needle 4005, 5005 to bend at the portion 4002', 5002' yet the comparatively higher first and third stiffness allows sufficient rigidity to the tip portion 4001, 5001 and the proximal portion 4003', 5003'. In some embodiments, the middle portion 4002', 5002' is configured to additionally include the tapered portion 4027. The tapered portion 4027 imparts further bendability and pliability to the middle portion 4002', 5002'.

FIG. 5B illustrates various needles 5105, 5205, 5305 of needle ablation catheters having variable stiffness, in accordance with some embodiments of the present specification. Each needle 5105, 5205, 5305 has a different laser cut pattern in the middle portion 5102', 5202', 5302', imparting each needle with a different stiffness in this portion and therefore a different degree of flexibility. For example, in an embodiment, needle 5105 has a middle portion 5102' laser cut such that the tip portion 5101 may be flexed in a range 5115 relative to the proximal portion 5103'. The variable stiffness allows for both bending at the middle portion and pushability along the catheter body.

Figure 5C:
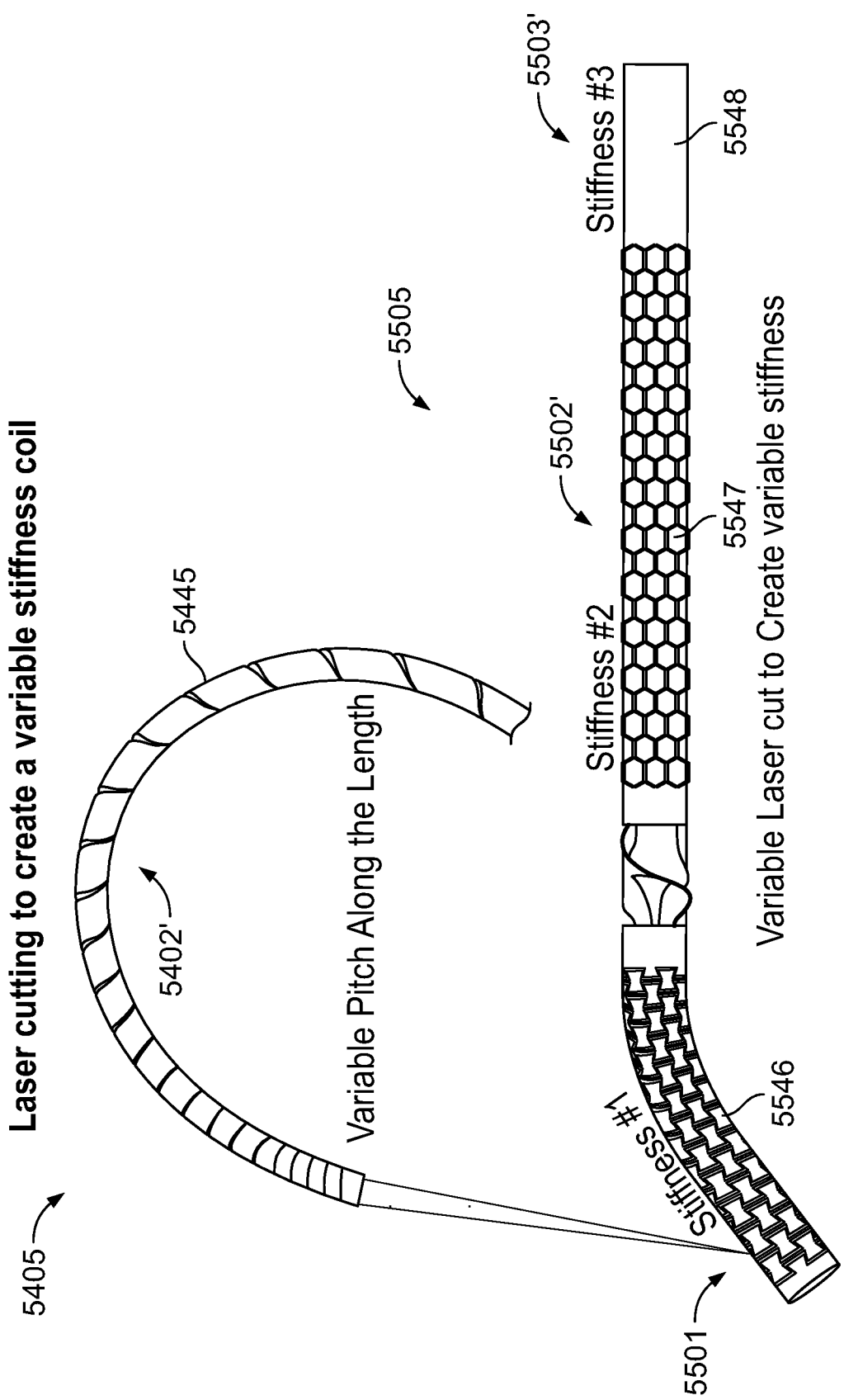
FIG. 5C shows first and second needles of needle ablation catheters having different laser cut portions, in accordance with some embodiments of the present specification.

FIG. 5C illustrates laser cutting patterns or designs to impart variable levels of stiffness to different portions of various needles 5405, 5505, in accordance with some embodiments of the present specification. As shown in FIG. 5C, in one embodiment, the middle portion 5402' of the needle 5405 is configured to have a substantially helical or spiral laser cutting 5445. A pitch of the cutting 2045 varies along the length of the middle portion 5402' to impart a predefined level of stiffness to enable the needle 5405 to bend along the middle portion 5402'. In another embodiment, a tip portion 5501 of a needle 5505 has a first laser cutting design 5546 imparting a first level of stiffness to the region, the middle portion 5502' has a second laser cutting design 5547 imparting a second level of stiffness to the region and the proximal portion 5503' has a third laser cutting design 5548 imparting a third level of stiffness to the region. In one embodiment, the first laser cutting design 5546 is such that less material of the needle 5505 in the tip portion 5501 is removed compared to the second laser cutting design 5547. As a result the second level of stiffness is comparatively less than the first level of stiffness. On the other hand, the third laser cutting design 5548 may involve removal of no or substantially no material in the proximal portion 5503'. Consequently, the third level of stiffness is greater than the first and second level of stiffness.

Figure 5D:
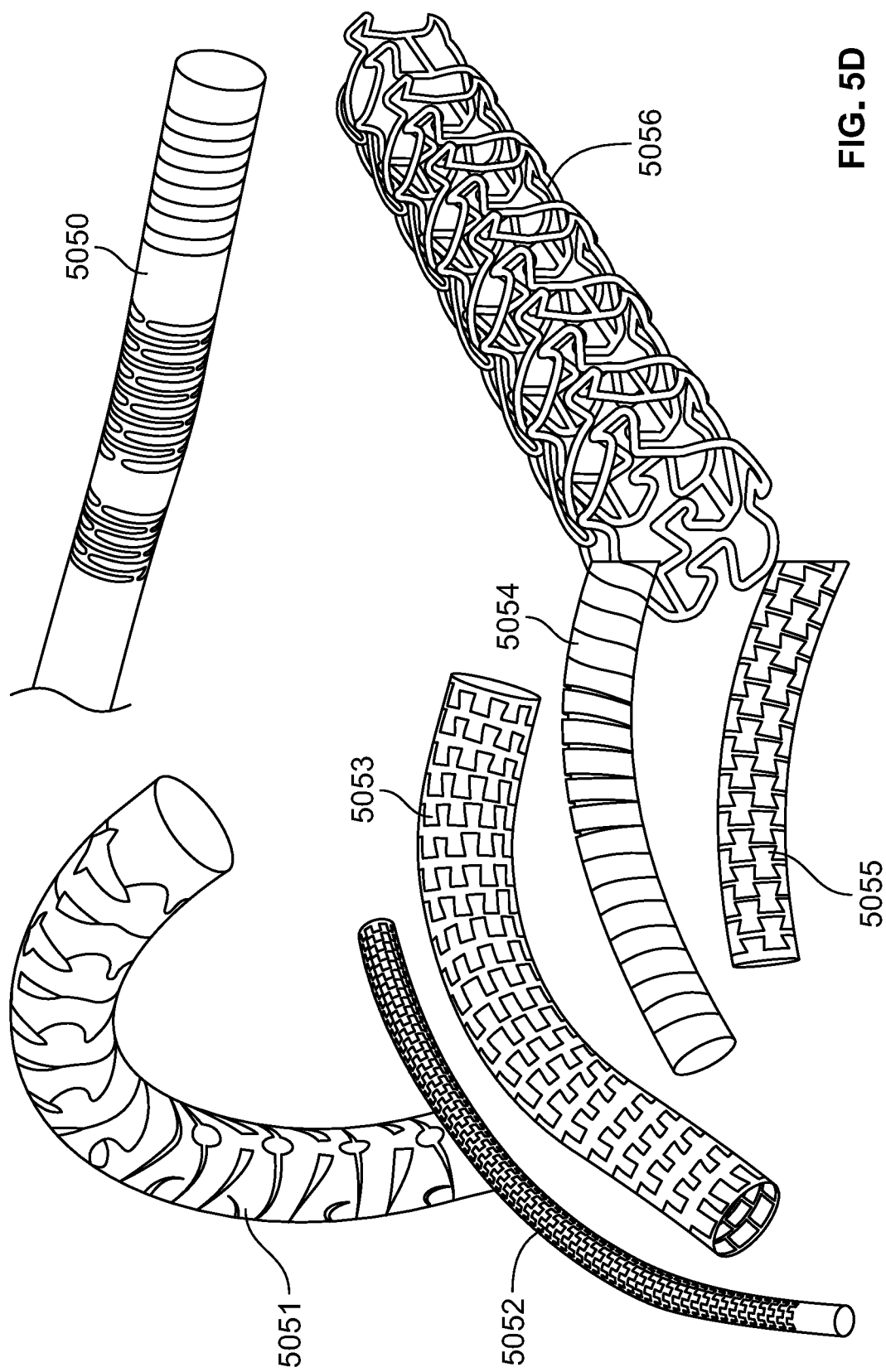
FIG. 5D shows a plurality of laser cutting patterns for a needle of a needle ablation catheter, in accordance with some embodiments of the present specification.

FIG. 5D illustrates additional laser cutting designs to impart variable levels of stiffness to different portions of various needles, in accordance with some embodiments of the present specification. The figure illustrates first, second, third, fourth, fifth, sixth and seventh laser cutting patterns 5050, 5051, 5052, 5053, 5054, 5055, 5056, respectively. For example, the pattern 5056 is sparsest and therefore imparts the least level of stiffness. Patterns 5052, 5054 and 5055 are comparatively dense, in that they involve less removal of the material of the needle, thereby corresponding to higher level of stiffness compared to the pattern 5056.

Figure 6A:
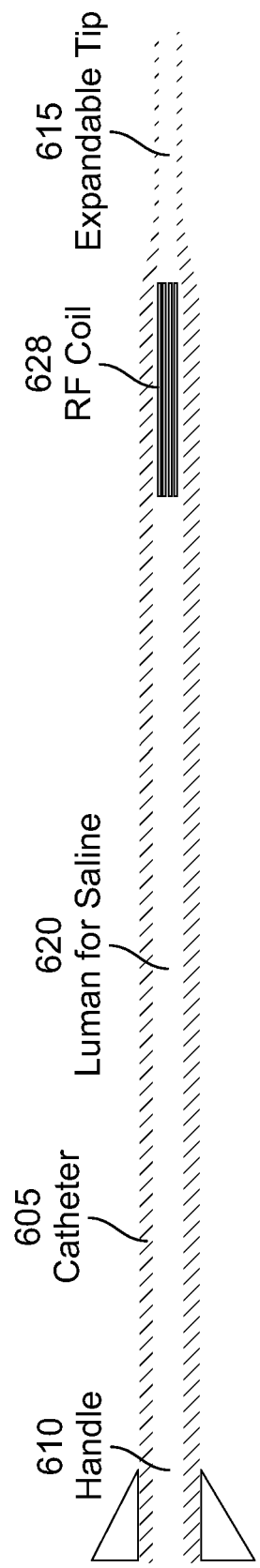
FIG. 6A is a first cross-sectional view of a catheter for insertion into a needle of the needle ablation device of FIG. 2A, in accordance with an embodiment of the present specification.
Figure 6B:
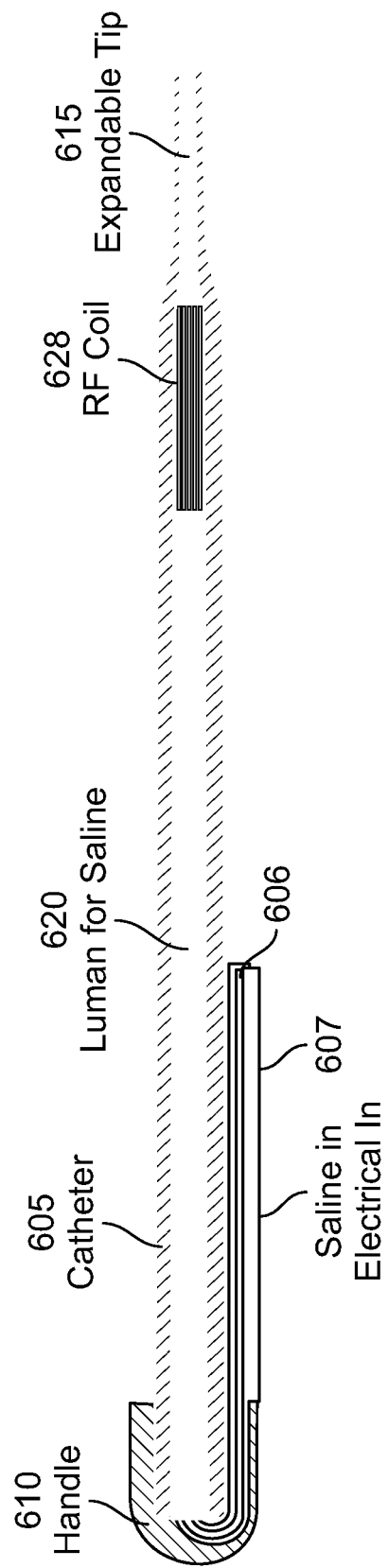
FIG. 6B is a second cross-sectional view of the catheter of FIG. 6A, in accordance with an embodiment of the present specification.

While in some embodiments, the needle 4005 houses the heating chamber 4028—as shown in FIGS. 4C and 4D, in some embodiments the heating chamber is housed in a separate vapor delivery catheter and not in the needle. FIGS. 6A and 6B illustrate longitudinal cross-sectional views of a vapor delivery catheter 605 having a handle 610 at a proximal end, an expandable tip 615 at a distal tip and a lumen 620 extending from the proximal end to the distal end of the catheter 605. As shown in FIG. 6B, in some embodiments, the handle 610 is configured to lock onto an endoscope handle without increasing a length of a resultant lever arm significantly. Saline and electrical connections (for the heating chamber 628) enter the handle 610 from the proximal end.

Referring now to FIGS. 6A and 6B, at least one flexible heating chamber 628 (comprising a plurality of electrodes) is positioned within the lumen 620 proximate a proximal end of the expandable tip 615. In accordance with an embodiment, an outer diameter of the expandable tip 615 is less than an inner diameter of a lumen of an ablation needle, such as the needle 4005 of FIGS. 4C and 4D, so that the tip 615 may slide easily into the lumen of the needle. In some embodiments, the vapor delivery catheter 605 is positioned within the needle, which in turn is positioned within an outer catheter. In some embodiments, the inner diameter of the outer catheter is 3.5 mm, an outer diameter of the needle 2005 is 3.1 mm and an outer diameter of the vapor delivery catheter 605 is 2.1 mm.

During operation saline enters the catheter 605 through the proximal end and is converted into steam/vapor that enters the lumen of the needle through the expandable tip 615. In embodiments, the catheter 605 includes a saline in port 606 for the delivery of saline and a connector 607 for an electrical connector for current delivery for the RF coil/heating chamber 628. The expandable tip 615 gets heated with the flowing vapor and expands radially such that the outer diameter of the tip 615 expands to approximate the inner diameter of the lumen of the needle. This causes blocking of the space between the expanded tip 615 and the needle to form a seal and prevent backflow of vapor between the catheter 605 and the needle.

Figure 6C:
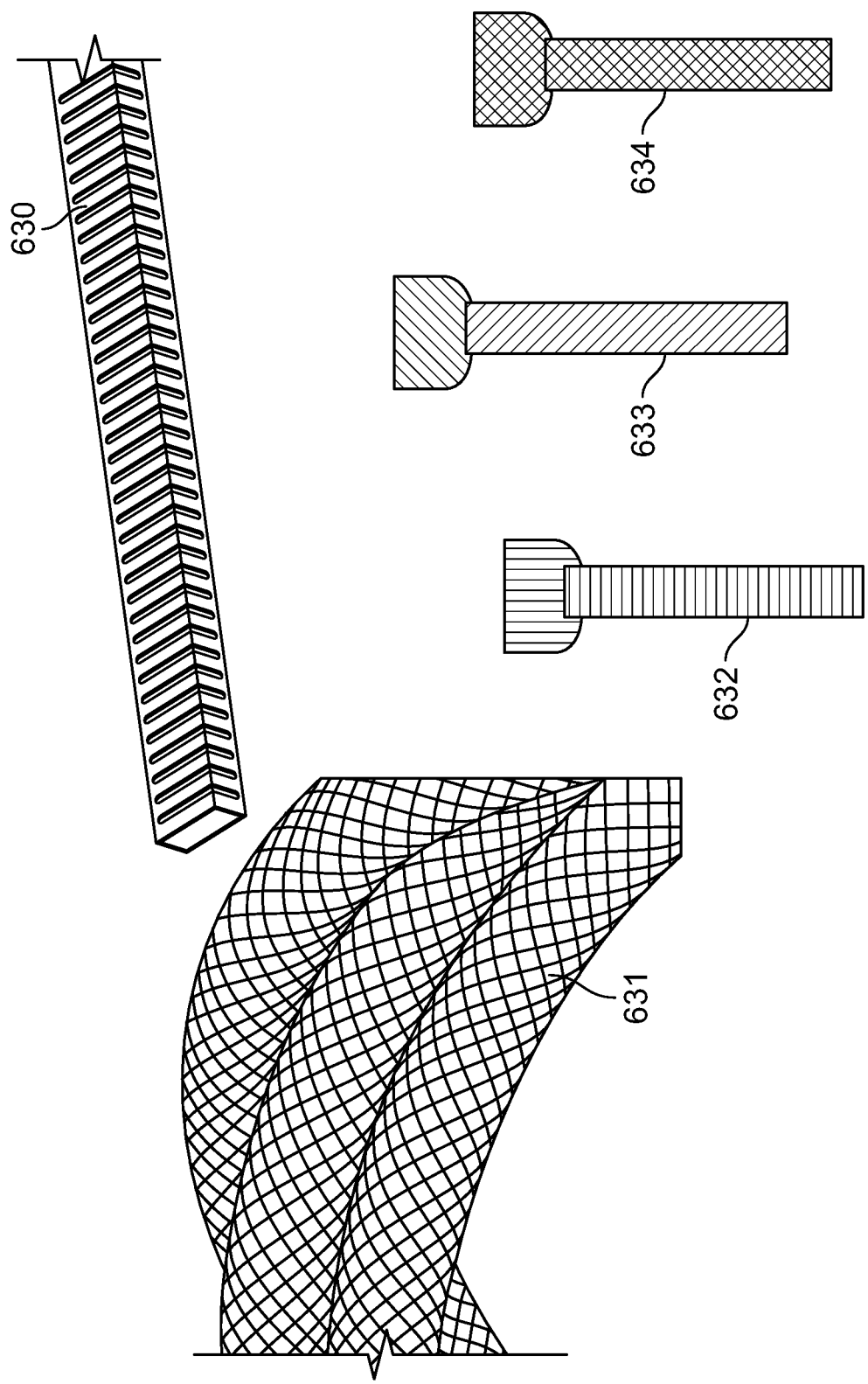
FIG. 6C illustrates a first plurality of configurations of an expandable tip of the catheter of FIG. 6A, in accordance with some embodiments of the present specification.
Figure 6D:
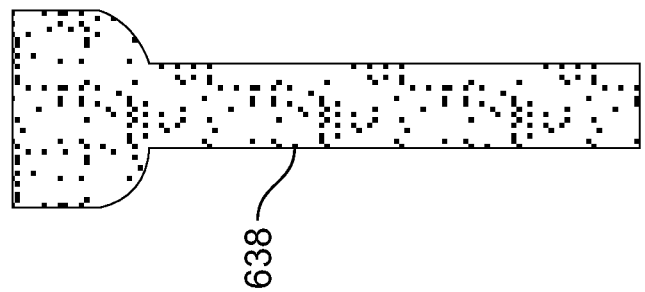
FIG. 6D illustrates a second plurality of configurations of the expandable tip of the catheter of FIG. 6A, in accordance with some embodiments of the present specification.
Figure 6D:
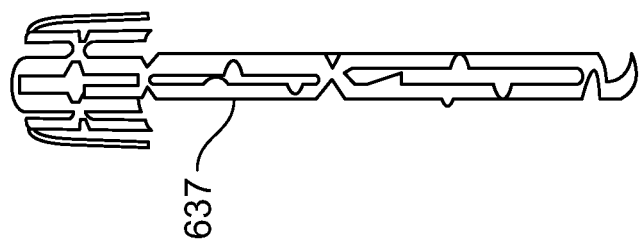
Figure 6D:
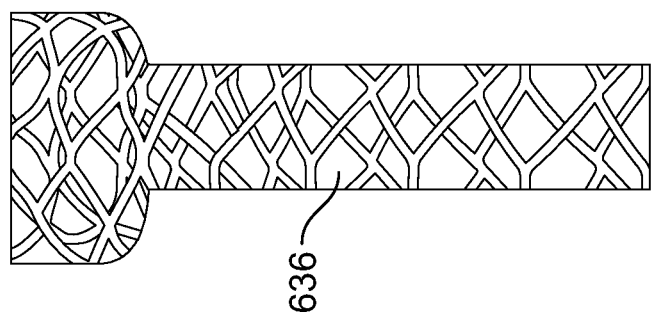
Figure 6D:
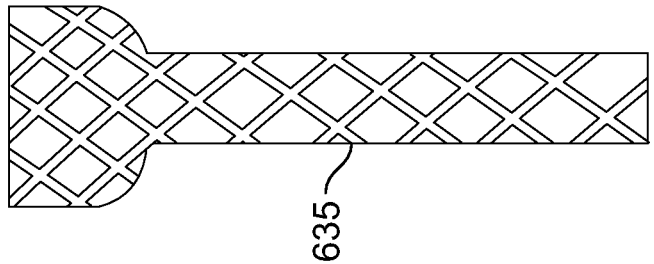

In some embodiments, the expandable tip 615 has an expandable metal coil covered by an insulating thermoplastic such as, but not limited to, PTFE, ePTFE, and silicone. In some embodiments, the metal of the expandable metal coil is a shape memory metal that exhibits radial expansion due to a transformation from a martensite state to an austenite state. In some embodiments, the metal of the expandable metal coil is steel that exhibits radial expansion due to thermal expansion of the steel. FIGS. 6C and 6D illustrate first and second plurality of expandable tip designs, in accordance with various embodiments of the present specification. FIG. 6C shows first, second, third, fourth and fifth web or mesh patters 630, 631, 632, 633, 634 respectively, for the expandable tip 615. FIG. 6D shows sixth, seventh, eighth and ninth web or mesh patterns 635, 636, 637, 638 respectively, for the expandable tip 615.

Positioning Elements

The positioning elements in FIGS. 7A to 7E have been disclosed in the aforementioned related applications. However, in this case, the positioning elements have been modified such that, upon the pressure within a volume enclosed by two or more positioning elements meeting or exceeding a predefined threshold value, such as 5 atm, the positioning element deforms by, for example, have one or more components, such as a plate, disc portion, flap, mesh weaving, bend inward or outward from the planes defining the original deployed shape to increase fluid flow from inside the enclosed volume to an area outside the enclosed volume. The deformation may be accomplished by adding a hinge, crease, groove, more flexible material, or other point of decreased material strength 51 between one or more of the components and the rest of the positioning element.

Figure 7D:
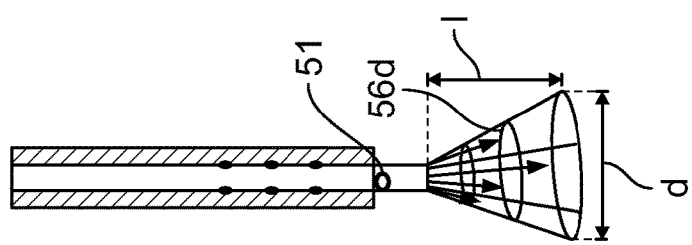
FIG. 7D illustrates the ablation device with a conical positioning element, in accordance with an embodiment of the present specification.
Figure 7C:
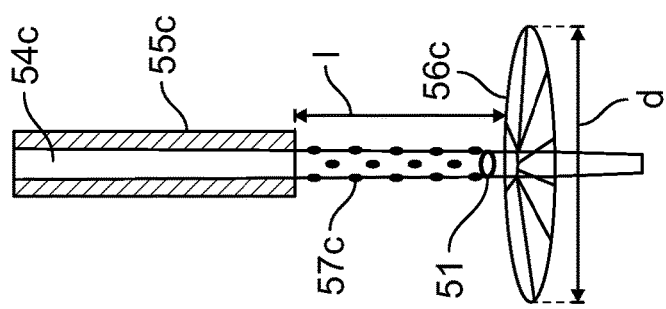
FIG. 7C illustrates a completely deployed positioning device, in accordance with an embodiment of the present specification.
Figure 7E:
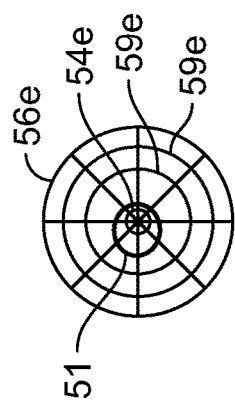
FIG. 7E illustrates the ablation device with a disc shaped positioning element, in accordance with an embodiment of the present specification.
Figure 7B:
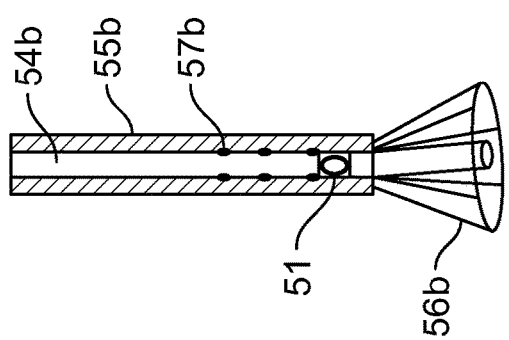
FIG. 7B illustrates a partially deployed positioning device, in accordance with an embodiment of the present specification.
Figure 7A:
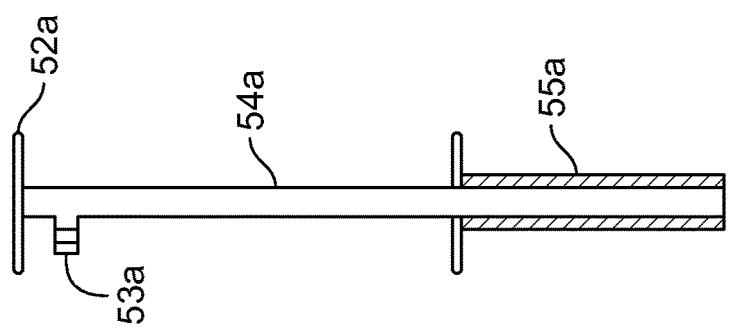
FIG. 7A illustrates the ablation device with a coaxial catheter design, in accordance with an embodiment of the present specification.

FIG. 7A illustrates an ablation device with a coaxial catheter design, in accordance with an embodiment of the present specification. The coaxial design has a handle 52a, an infusion port 53a, an inner sheath 54a and an outer sheath 55a. The outer sheath 55a is used to constrain the positioning device 56a in the closed position and encompasses ports 57a. FIG. 7B shows a partially deployed positioning device 56b, with the ports 57b still within the outer sheath 55b. The positioning device 56b is partially deployed by pushing the catheter 54b out of sheath 55b.

FIG. 7C shows a completely deployed positioning device 56c. The infusion ports 57c are out of the sheath 55c. The length 'l' of the catheter 54c that contains the infusion ports 57c and the diameter 'd' of the positioning element 56c are predetermined/known and are used to calculate the amount of thermal energy needed. FIG. 7D illustrates a conical design of the positioning element. The positioning element 56d is conical with a known length 'l' and diameter 'd' that is used to calculate the amount of thermal energy needed for ablation. FIG. 7E illustrates a disc shaped design of the positioning element 56e comprising circumferential rings 59e. In some embodiments, positioning element 56e has a diameter ranging from 5 mm to 55 mm. Positioning element 56e may be of any round shape, and may not necessarily be a perfect circle. The circumferential rings 59e are provided at a fixed predetermined distance from the catheter 54e and are used to estimate the diameter of a hollow organ or hollow passage in a patient's body.

Hood Vapor Delivery Device

Figure 8A:
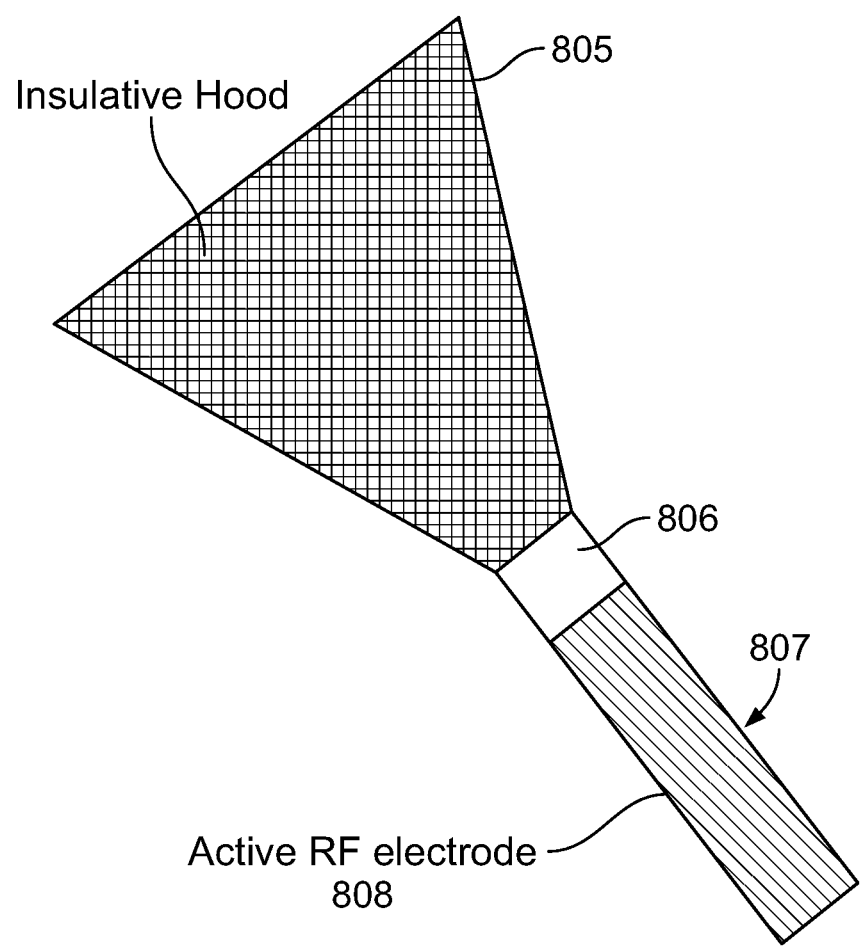
FIG. 8A illustrates a conical hood shaped positioning element, in accordance with an embodiment of the present specification.

FIG. 8A illustrates a positioning element or attachment 805, in accordance with an embodiment of the present specification. The positioning element 805 is configured as a substantially conical insulating hood that is attached proximate to a tip 806 of a catheter 807. In some embodiments, the positioning element has length and breadth of 0.5 cm and 5 cm, respectively. In alternative embodiments, the positioning element 805 is of a different structure, such as including and not limited to square, rectangular, and parallelogram. The catheter 807, in an embodiment, accommodates at least one flexible heating chamber 808 comprising a plurality of RF electrodes to convert saline, entering a proximal end of the catheter 807, into steam/vapor.

Figure 8B:
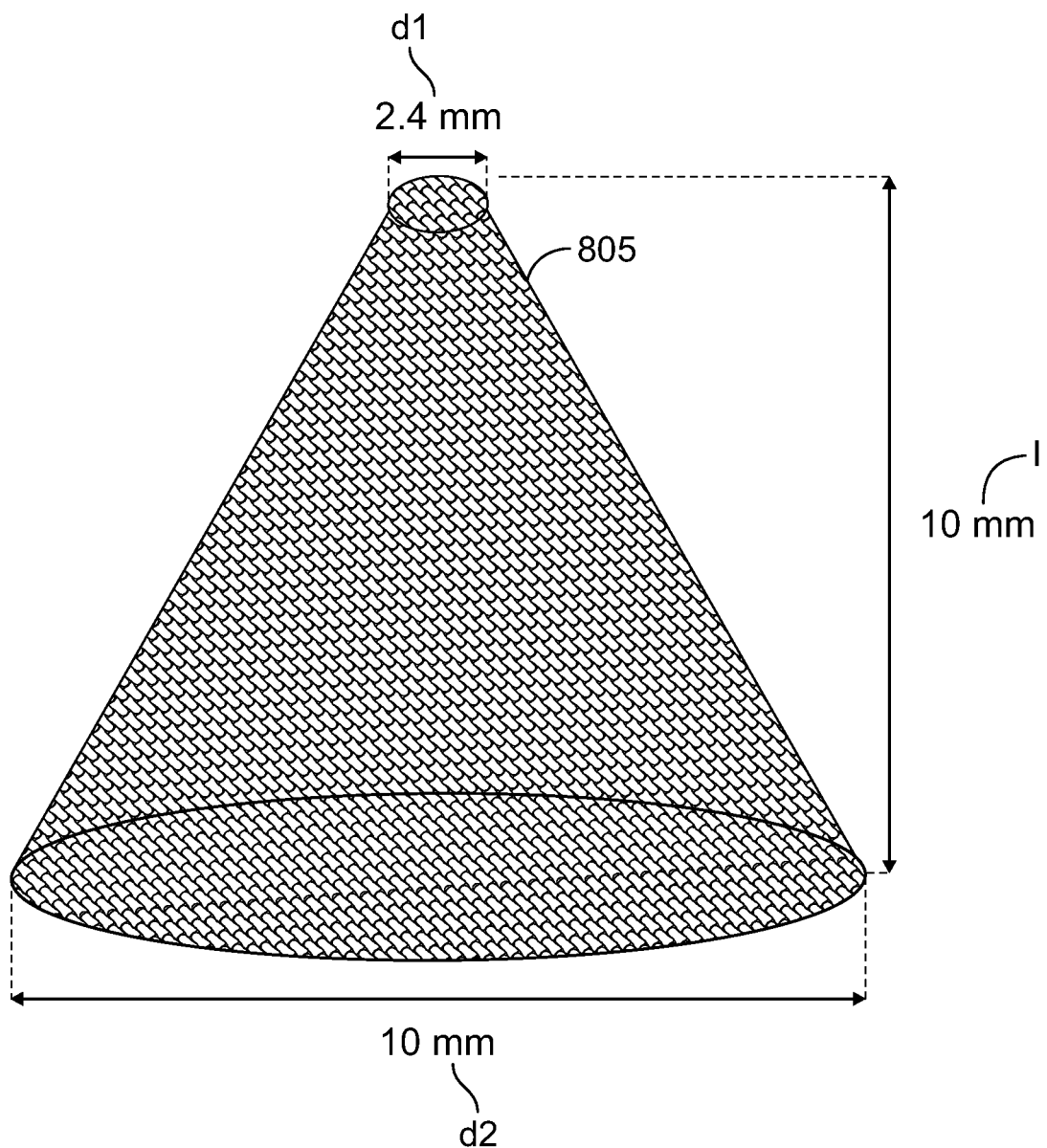
FIG. 8B illustrates a cross-sectional view of the conical hood shaped positioning element, in accordance with an embodiment of the present specification.

FIG. 8B illustrates a first set of exemplary dimensions for the positioning element 805, in accordance with an embodiment of the present specification. The substantially conical shaped hood or positioning element 805 has a proximal diameter $d_1$ of 2.4 mm, a distal diameter $d_2$ of 10 mm and a length '1' of 10 mm. In various embodiments, length '1' ranges from 0.1 mm to 10 cm and the distal diameter $d_2$ ranges from 0.1 mm to 10 cm. In preferred embodiments, the length '1' and the distal diameter $d_2$ range from 5 mm to 5 cm.

Figure 8C:
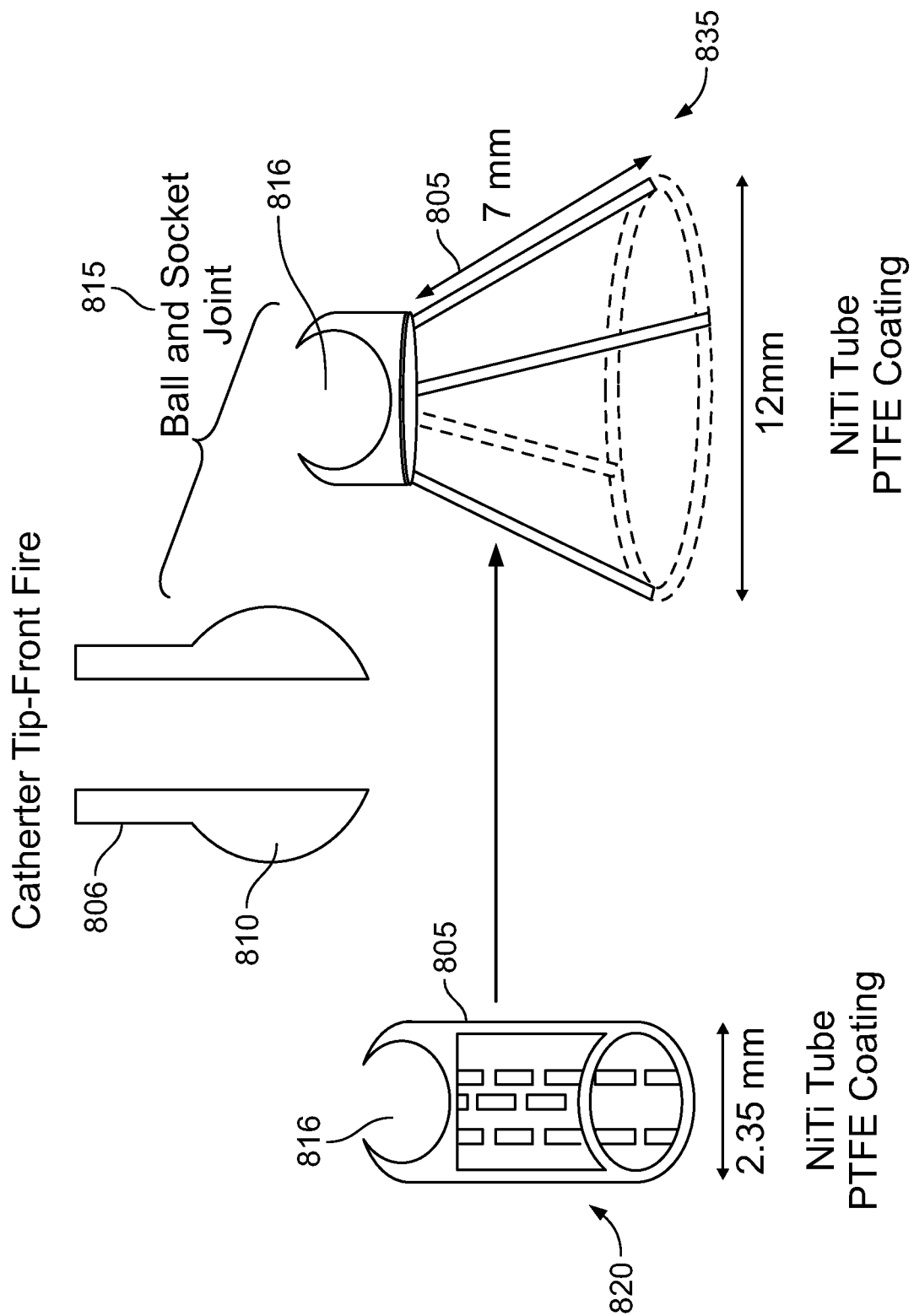
FIG. 8C illustrates a ball and socket attachment of the conical hood shaped positioning element to a catheter tip, in accordance with an embodiment of the present specification.
Figure 8D:
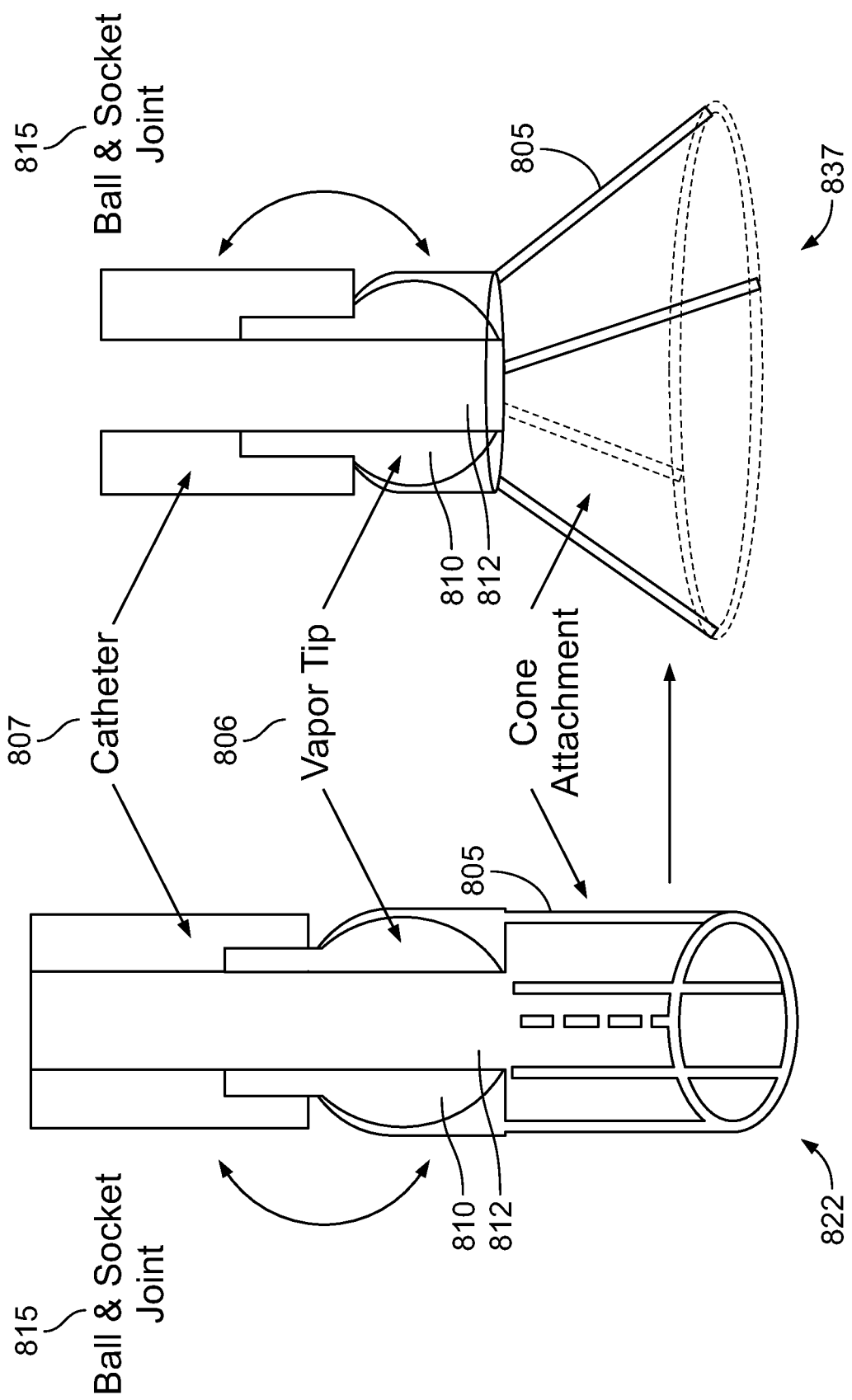
FIG. 8D illustrates cross-sectional views of the conical hood shaped positioning element attached to the catheter tip, in accordance with an embodiment of the present specification.

FIGS. 8C and 8D illustrate a ball and socket attachment 815 to couple the positioning element 805 to the tip 806 of the catheter 807, in accordance with an embodiment of the present specification. The tip 806, at its distal end, has a ball 810 and a front-fire or straight-fire port 812. The positioning element 805 has a socket 816 at its proximal end. As shown in FIG. 8D, when the positioning element 805 is attached to the tip 806, the ball 810 is accommodated within the socket 815 to form the ball and socket attachment 815.

Referring now to FIGS. 8C and 8D, the ball and socket attachment 815 enables ample movement of the positioning element 805 with respect to the tip 806. In some embodiments, a minimum range of movement, of the positioning element 805 with respect to the tip 806, is 90 degrees in any direction. The views 820, 822 illustrate the positioning element 805 in a closed configuration, such as when the positioning element 805 and the tip 806 are positioned within an outer catheter. In some embodiments, the positioning element 805 is in a substantially cylindrical shape of diameter 2.35 mm when in the closed configuration. The views 835, 837 illustrate the positioning element 805 in an open or deployed configuration, such as when the positioning element 805 and the tip 806 are pushed out of the outer catheter. The positioning element 805 acquires a substantially conical shape, in the open or deployed configuration, having a base diameter of 12 mm and a side of 7 mm, in some embodiments. In some embodiments, the positioning element 805 is a NiTi tube, web or mesh coated with PTFE, ePTFE or silicone. In some embodiments, the coating, such as of silicone, covers a portion of or the entirety of the positioning element 805. In some embodiments, the silicone-coated positioning element 805 has one or more pores with diameter of each pore ranging from 10 microns to 1000 microns. The pores may allow for air or steam to vent out from the chamber.

Figure 8E:
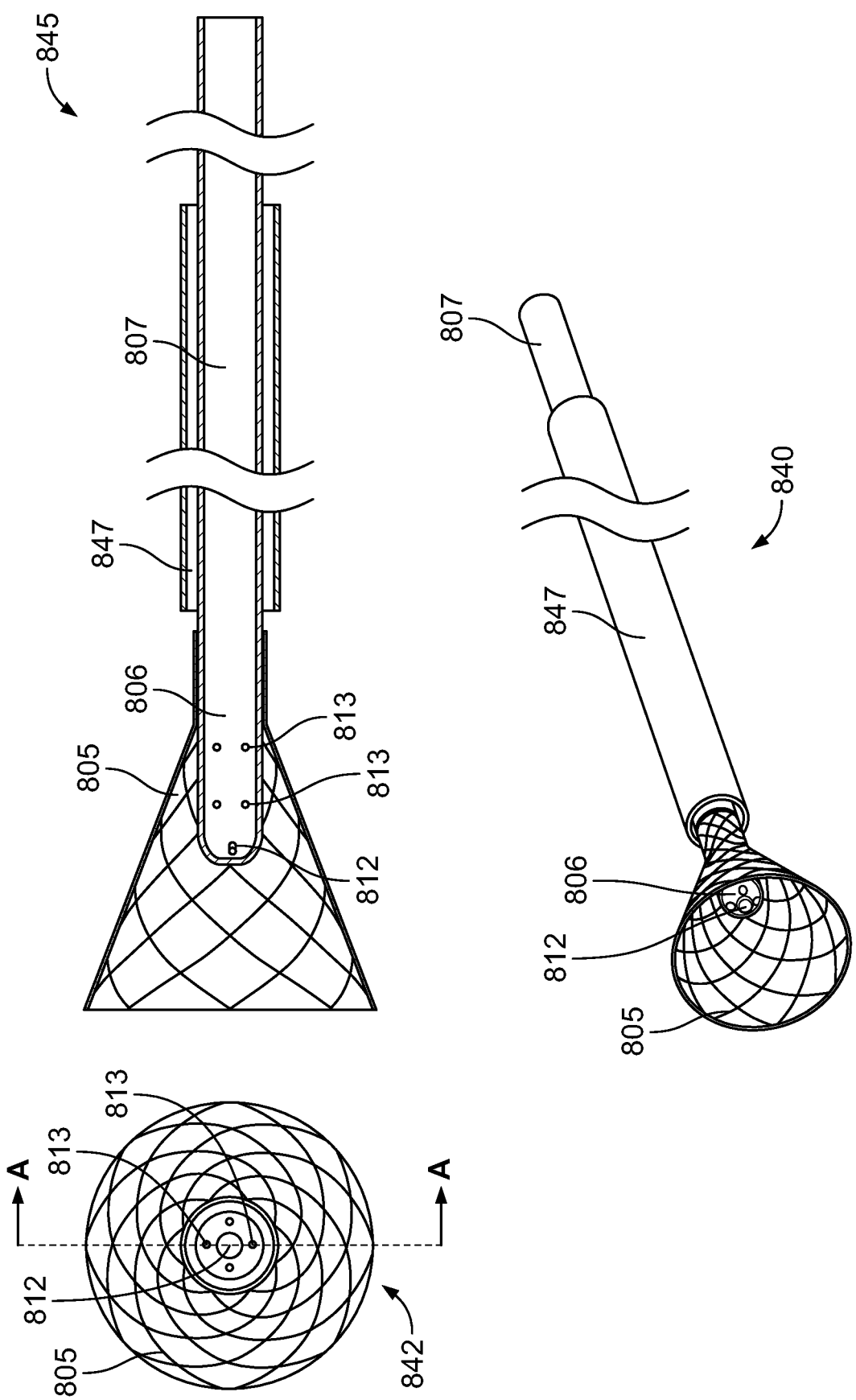
FIG. 8E illustrates perspective views of the conical hood shaped positioning element attached to the catheter tip, in accordance with an embodiment of the present specification.

FIG. 8E shows a first perspective view 840, a second perspective view 842 and a longitudinal cross-sectional view 845 of the positioning element 805 attached to the tip 806 of the catheter 807, in accordance with an embodiment of the present specification. The catheter 807 is shown extending out from an outer catheter 847 such that the positioning element 805 is in the deployed configuration wherein the positioning element 805 acquires a substantially conical configuration. The tip 806 includes the front-fire or straight-fire port 812 at a distal end and/or two pairs of side ports 813 formed diametrically opposed on the sides of the tip 806 and positioned proximate the distal end of the tip 806. In some embodiments, the port 812 has a diameter of 0.9 mm, to allow a guide wire through, while the ports 813 have a diameter of 0.3 mm. In some embodiments, the catheter 807 has a length of 2500 mm from a proximal end of the catheter 807 to a distal end of the positioning element 805. In some embodiments, the outer catheter 847 has a length of 1800 mm (+/−50 mm) from a proximal end to a distal end of the outer catheter 847.

Figure 8F:
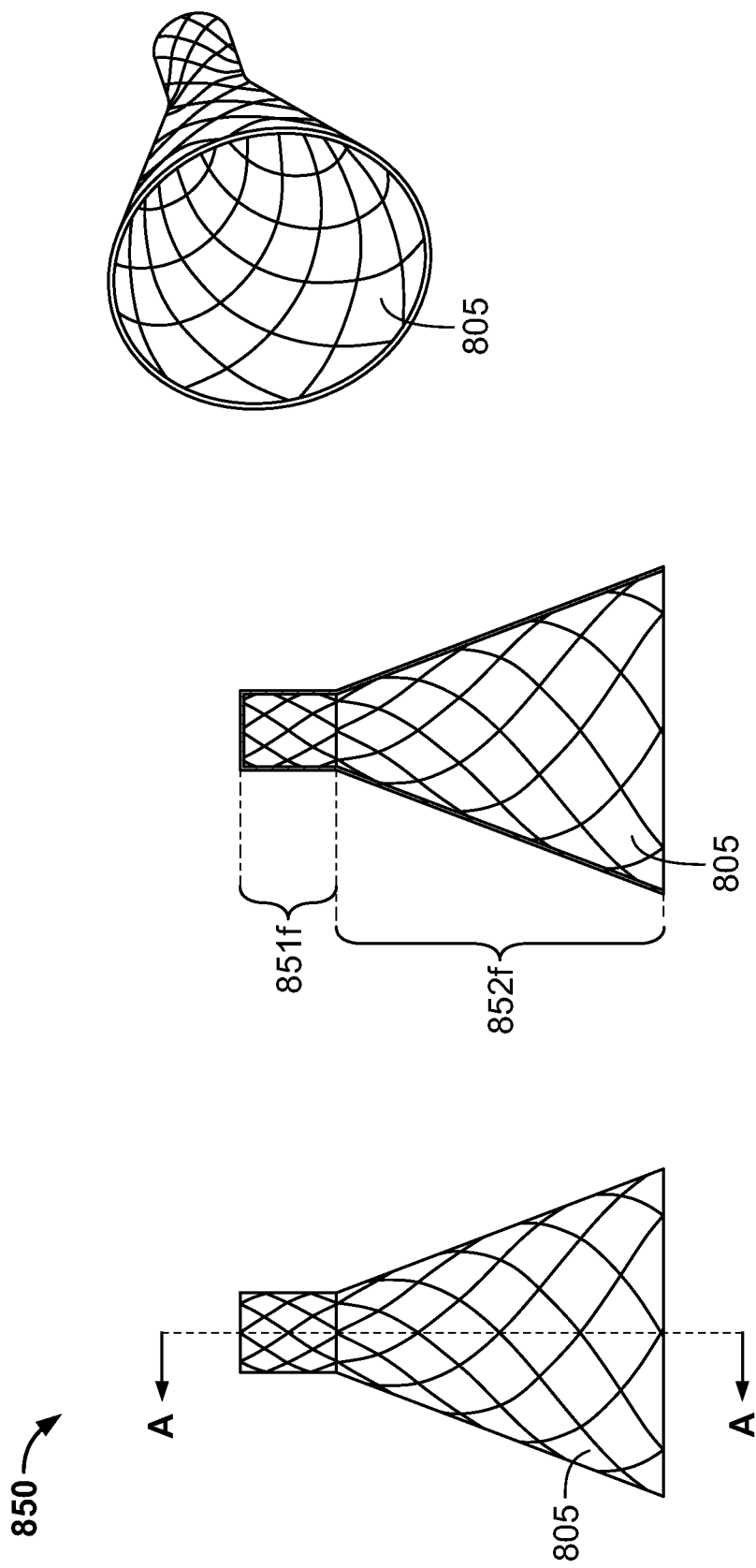
FIG. 8F shows a first configuration of the conical hood shaped positioning element, in accordance with an embodiment of the present specification.

FIG. 8F illustrates perspective and cross-sectional views of a first configuration 850 of the positioning element 805, in accordance with an embodiment of the present specification. The first configuration 850 comprises a substantially cylindrical proximal portion 851f and a substantially conical distal portion 852f. In some embodiments, the substantially cylindrical proximal portion 851f is attached, such as by using glue, to the tip 806 as shown in FIG. 8E. In the first configuration 850, the substantially cylindrical proximal portion 851f has a diameter of 2.4 mm and a length of 3 mm, the substantially conical distal portion 852f has a base diameter of 10 mm (+/−1 mm), a length of 10 mm (+/−1 mm) and a vertex or opening angle of 41.6 degrees. The total length of the proximal and distal portions 851f, 852f is 13 mm.

Figure 8G:
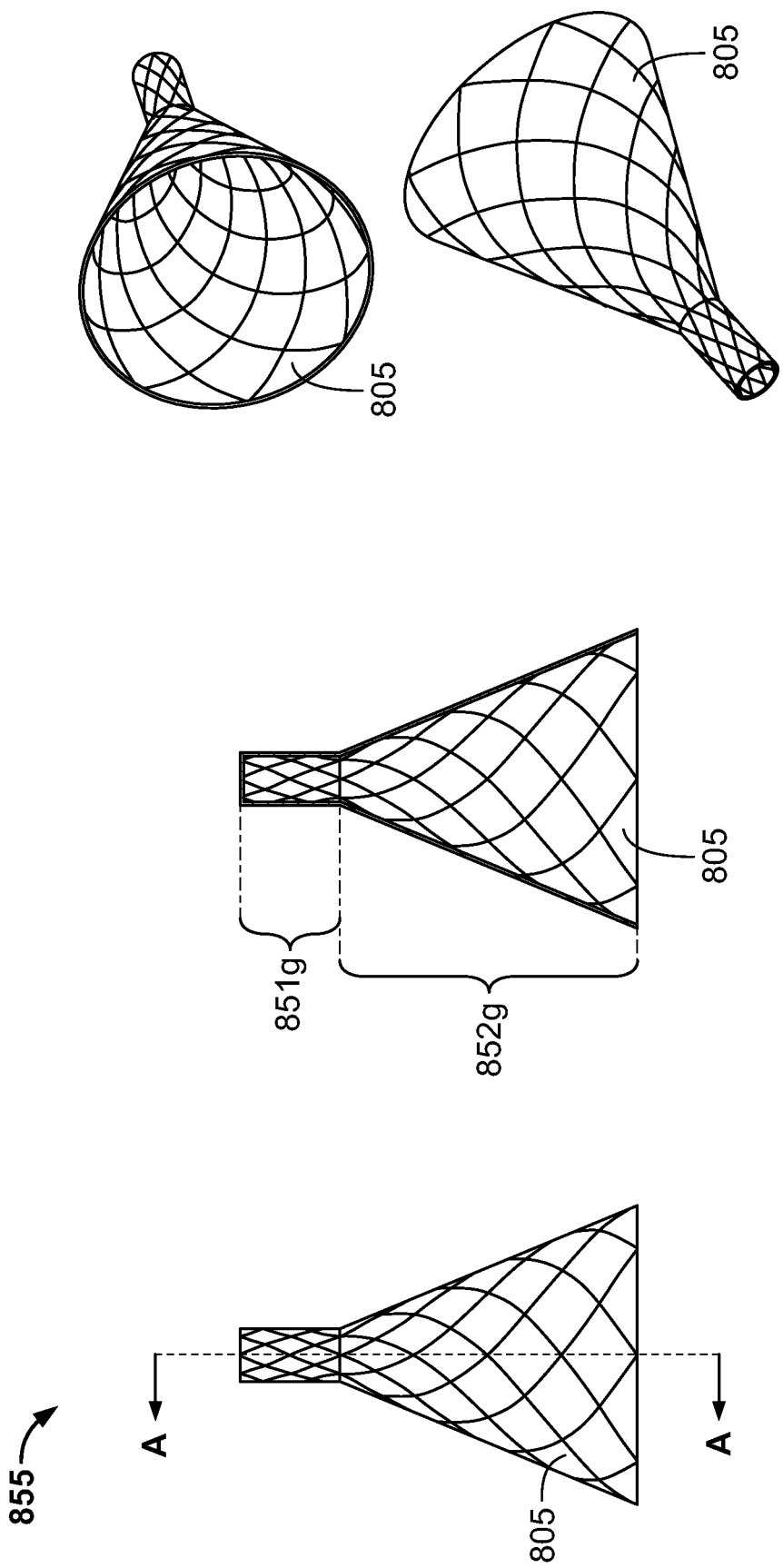
FIG. 8G shows a second configuration of the conical hood shaped positioning element, in accordance with an embodiment of the present specification.

FIG. 8G illustrates perspective and cross-sectional views of a second configuration 855 of the positioning element 805, in accordance with an embodiment of the present specification. The second configuration 855 comprises a substantially cylindrical proximal portion 851g and a substantially conical distal portion 852g. In some embodiments, the substantially cylindrical proximal portion 851g is attached, such as by using glue, to the tip 806 as shown in FIG. 8E. In the second configuration 855, the substantially cylindrical proximal portion 851g has a diameter of 2.4 mm and a length of 5 mm, the substantially conical distal portion 852g has a base diameter of 15 mm (+/−2 mm), a length of 15 mm (+/−1 mm) and a vertex or opening angle of 45.6 degrees. The total length of the proximal and distal portions 851g, 852g is 20 mm.

Figure 8H:
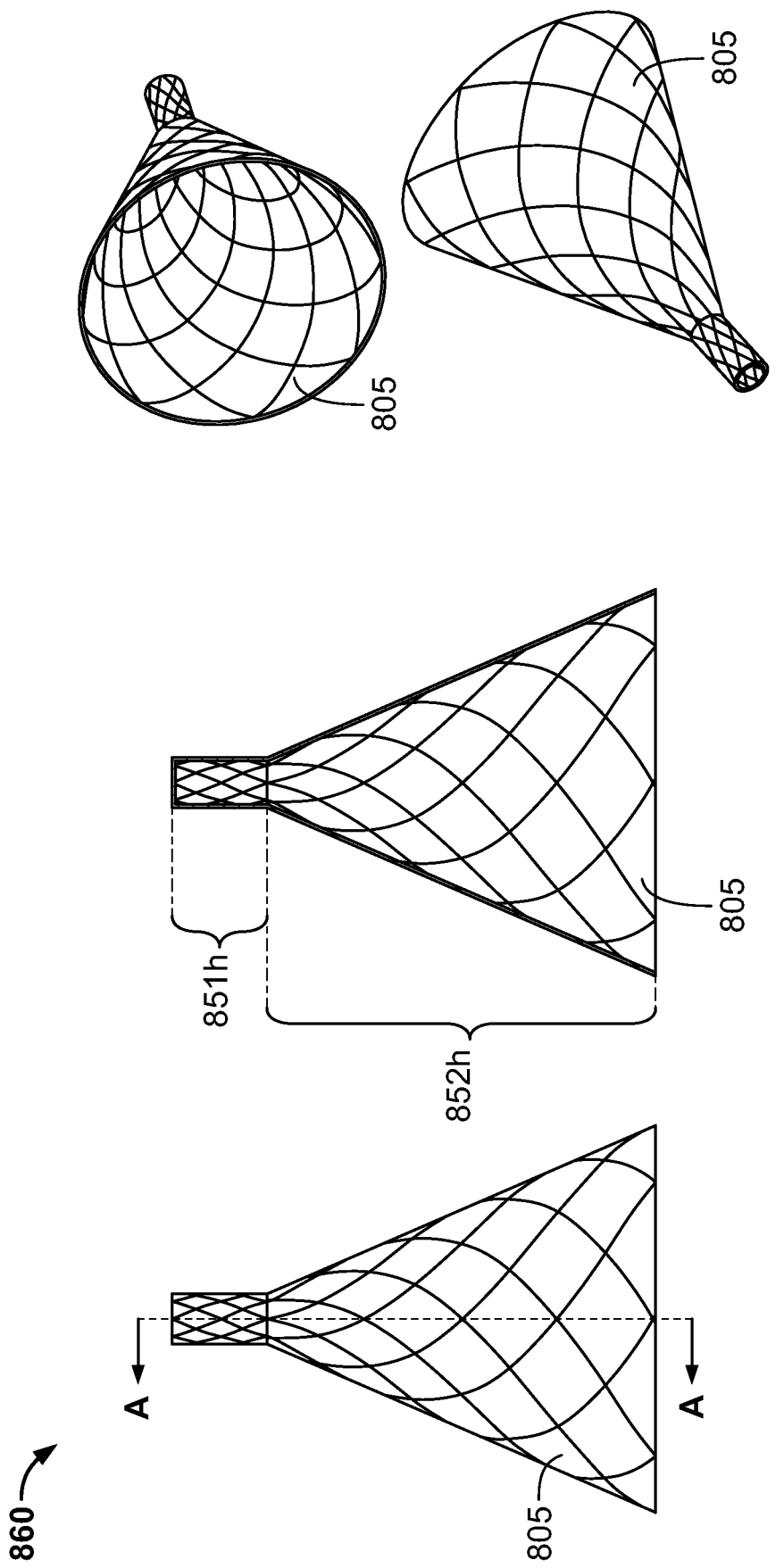
FIG. 8H shows a third configuration of the conical hood shaped positioning element, in accordance with an embodiment of the present specification.

FIG. 8H illustrates perspective and cross-sectional views of a third configuration 860 of the positioning element 805, in accordance with an embodiment of the present specification. The third configuration 860 comprises a substantially cylindrical proximal portion 851h and a substantially conical distal portion 852h. In some embodiments, the substantially cylindrical proximal portion 851h is attached, such as by using glue, to the tip 806 as shown in FIG. 8E. In the third configuration 860, the substantially cylindrical proximal portion 851h has a diameter of 2.4 mm, the substantially conical distal portion 852h has a base diameter of 20 mm (+/−2 mm), a length of 20 mm (+/−2 mm) and a vertex or opening angle of 47.5 degrees. The total length of the proximal and distal portions 851h, 852h is 25 mm.

Figure 8I:
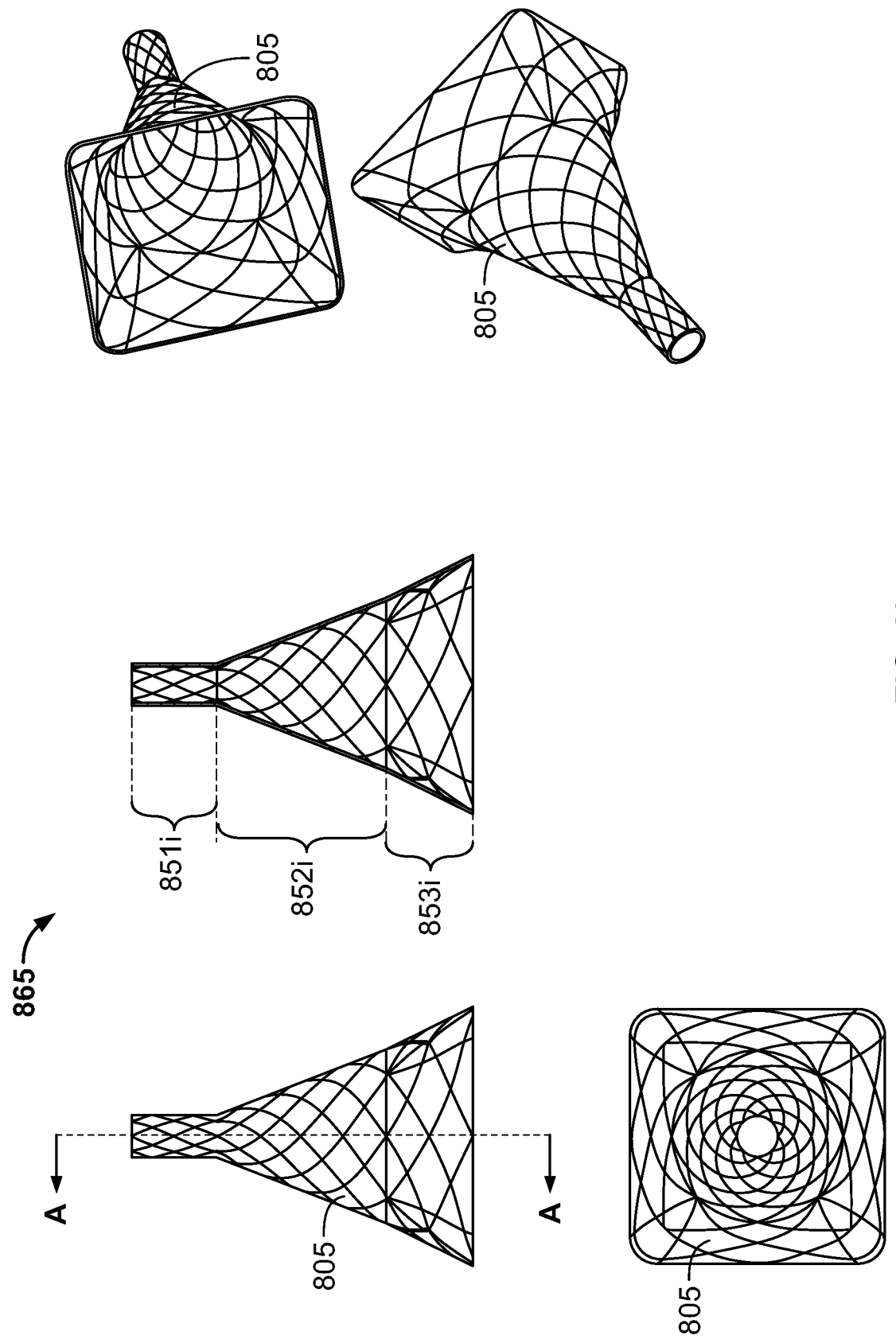
FIG. 8I shows a fourth configuration of the conical hood shaped positioning element having a pyramidal base, in accordance with an embodiment of the present specification.

FIG. 8I illustrates perspective and cross-sectional views of a fourth configuration 865 of the positioning element 805, in accordance with an embodiment of the present specification. The fourth configuration 865 comprises a substantially cylindrical proximal portion 851i, a substantially conical middle portion 852i and a substantially pyramidal distal portion 853i. The substantially pyramidal distal portion 853i is attached as a base to the substantially conical middle portion 852i. In an alternate embodiment, the entire positioning element 805 is substantially pyramidal shape.

In some embodiments, the substantially cylindrical proximal portion 851*i* is attached, such as by using glue, to the tip 806 as shown in FIG. 8E. In the fourth configuration 865, the substantially cylindrical proximal portion 851*i* has a diameter of 2.4 mm and a length of 5 mm, the substantially conical middle portion 852*i* has a length of 10 mm (+/−2 mm) and a vertex or opening angle of 41.6 degrees, while the substantially pyramidal distal portion 853*i* has a square base having each side of 15 mm (+/−2 mm). The total length of the middle and distal portions 852*i*, 853*i* is 15 mm (+/−2 mm). The total length of the proximal, middle and distal portions 851*l*, 852*i*, and 853*i* is 20 mm (+/−2 mm). Though FIGS. 8A through 8I depict positioning elements having conical and pyramidal or rectangular shapes, in other embodiments, the positioning element or attachments may have other three dimensional polygonal or curved shapes.

In various embodiments, the positioning element is mechanically compressed for passage into an endoscope channel or an outer catheter and expands when deployed or protruded.

In some embodiments, positioning element 805 comprises a shape memory alloy, such as Nitinol, thereby allowing it to transform from a compressed configuration for delivery through an endoscope to an expanded configuration for treatment. In some embodiments, the compressed configuration approximates a cylindrical shape, to enable passing through the lumen of an endoscope, attached to the distal end of the catheter, and has a 5 mm diameter and a length in a range of 0.5 cm to 5 cm. On expansion, the positioning element 805 has a surface area (from which the steam exits) in a range of 1 $cm^2$ to 6.25 $cm^2$. In a preferred embodiment, the surface area is square with dimensions of 1.5 cm by 1.5 cm. On expansion, the length shortens somewhat so the expanded configuration would have a shorter length than the compressed configuration. In an embodiment, use of an ablation catheter with positioning element 805 creates a seal forming an ablation area having a radius of 1 cm, a length of 1 cm, a surface area of 6.28 $cm^2$ and a treatment volume of 3.14 $cm^3$.

Referring to the various embodiments of the positioning elements described in context of FIGS. 7A to 7E, and 8A to 8I, in some embodiments, a range of vapor delivery times is between 1 second to 20 seconds for applications of the gastrointestinal (GI) areas. The duration where the mucosal temperature is >60° C. but<110° C. is between 1 second and 10 seconds. Multiple sessions could be repeated after an off time of >1 second and <30 minutes. The duration of each session could be the same or different. In one embodiment, the duration of two or more sessions is the same, and in another embodiment the duration of a first session is less than a duration of a second session. In another embodiment, a duration of a first session is greater than a duration of a second session.

In various embodiments, multiple sessions with variable times/doses are applied. In some embodiments, each session is defined by a therapeutic time (T1) and dose (D1). In an embodiment, a first session is delivered for a time<T1 at dose T1. Then, the physician waits for a time from 1 second to 30 minutes for a certain degree of edema to set in and then delivers a second with a dose in a range of 1×T1 to 5×T1. Negative pressure, in the form of suction or vacuum, is applied to the ablated zone after the steam is turned off to increase blood flow to cool the tissue. This increase blood flow could also increase the edema formation.

Figure 8J:
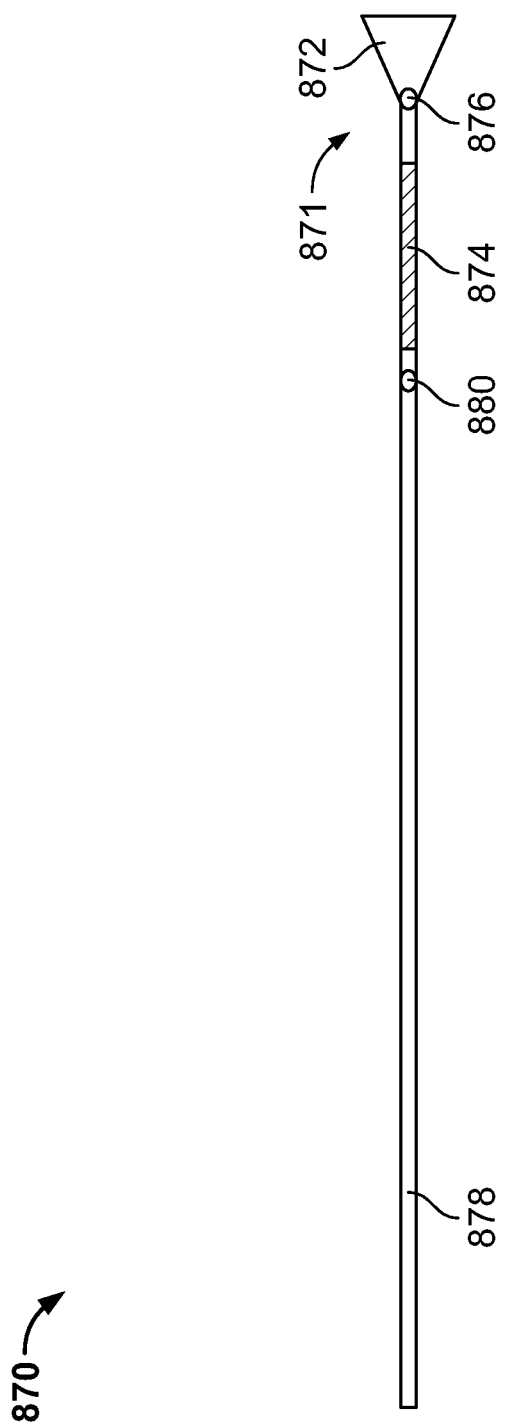
FIG. 8J illustrates an ablation catheter with a conical shaped attachment or positioning element and an electrode heating chamber, in accordance with some embodiments of the present specification.

FIG. 8J illustrates an ablation catheter 870 with at least one conical shaped attachment or positioning element 872 and an electrode heating chamber 874, in accordance with some embodiments of the present specification. In various embodiments, the attachment or positioning element 872 is similar to those described with reference to FIGS. 8A through 8I. The attachment or positioning element 872 is positioned at the distal end of the catheter 870, and at least one port 876 is positioned at the distal end of the catheter such that the port will deliver vapor or steam into a volume enclosed by the attachment or positioning element once the catheter 870 is deployed. In embodiments, distal tip 871 of the catheter 870 comprises the at least one port 876 and the at least one positioning element 872 attached to the distal tip 871 such that, upon being in an operational configuration, the at least one positioning element 872 encircles the at least one port 876 and is configured to direct all vapor exiting from the at least one port 876. In some embodiments, the attachment or positioning element 872 is comprised of a shape memory metal and is transformable from a first, compressed configuration for delivery through a lumen of an endoscope and a second, expanded configuration for treatment. Electrode heating chamber 874 is positioned within a lumen of the catheter body 878 and, in embodiments, is in a range of 1 mm to 50 cm from the delivery port 876. In some embodiments, the catheter 870 includes a filter 880 with micro-pores which provides back pressure to the delivered steam, thereby pressurizing the steam. The predetermined size of micro-pores in the filter determine the back-pressure and hence the temperature of the steam being generated.

Figure 9B:
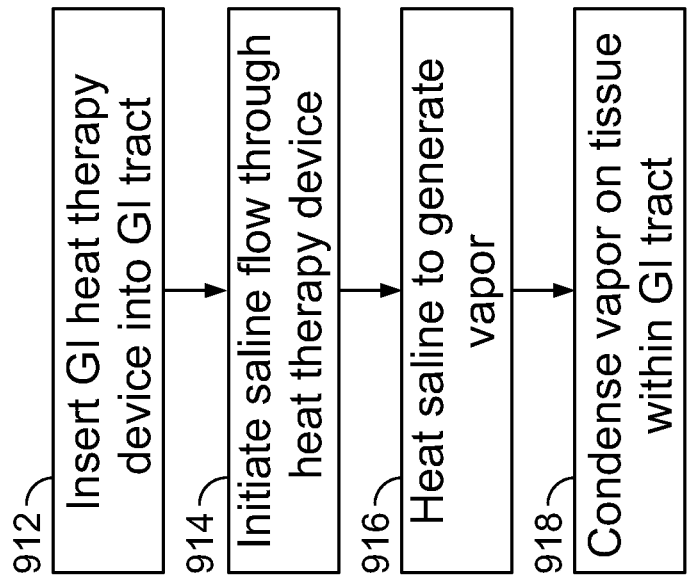
FIG. 9B is a flow chart illustrating a method of ablating a tissue inside a gastrointestinal tract of a patient, in accordance with other embodiments of the present specification.
Figure 9A:
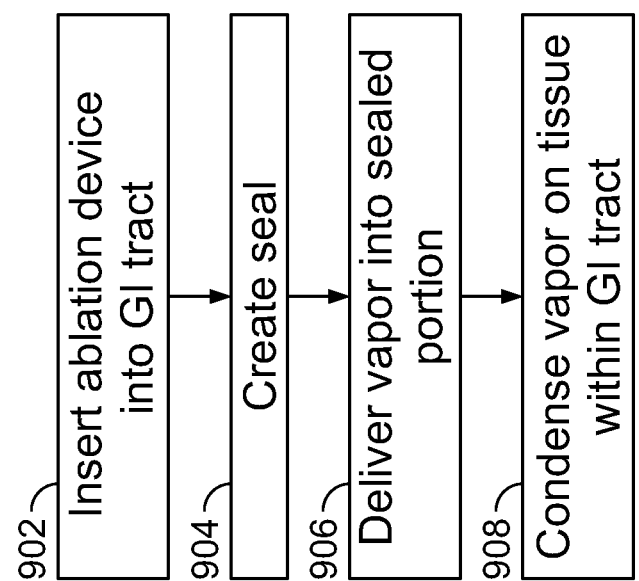
FIG. 9A is a flow chart illustrating a method of ablating a tissue inside a gastrointestinal tract of a patient, in accordance with some embodiments of the present specification.

FIG. 9A is a flow chart illustrating a method of ablating a tissue inside a gastrointestinal tract of a patient, in accordance with other embodiments of the present specification. In embodiments, the method of FIG. 9A illustrates focal ablation that is performed after observing the patient following circumferential focused ablation, to treat any remaining pre-cancerous or cancerous tissue in the esophagus, duodenum, bile duct, and pancreas. In embodiments, ablation catheters disclosed in the present specification, such as ablation catheter 870 of FIG. 8J, are used to perform the ablation method of FIG. 9A. At 902, an ablation catheter configured for the gastrointestinal (GI) tract is inserted into the GI tract of the patient. At 904, a seal is created between an exterior surface of the ablation catheter and an interior wall of the GI tract, forming a treatment volume. The seal is created by the expansion of an attachment or positioning element of the ablation catheter, as explained in the embodiments of the present specification. In some embodiments, the seal is temperature dependent and it breaks when the temperature within the sealed portion or treatment volume exceeds a specific temperature. In one embodiment, the specific temperature is 90° C. In some embodiments, the seal is pressure dependent and it breaks when the pressure within the sealed portion or treatment volume exceeds a specific pressure. In one embodiment, the specific pressure is 5 atm. At 906, vapor is delivered through the ablation catheter into the sealed portion within the GI tract, while the seal is still in place. At 908, the vapor condenses on the tissue under treatment, thereby ablating the tissue.

FIG. 9B is a flow chart illustrating a method of ablating a tissue inside a gastrointestinal tract of a patient, in accordance with other embodiments of the present specification. In embodiments, the method of FIG. 9B illustrates focal ablation that is performed after observing the patient following circumferential focused ablation, to treat any remaining pre-cancerous or cancerous tissue in the esophagus, duodenum, bile duct, and pancreas. In embodiments, ablation catheters disclosed in the present specification, such as ablation catheter 870 of FIG. 8J, are used to perform the ablation method of FIG. 9B. At 912, an ablation catheter configured for the gastrointestinal (GI) tract is inserted into the GI tract of the patient. At 914, saline with a variable flow rate is introduced through the ablation catheter into the GI tract. At 916, the saline is heated using RF energy to generate vapor through the ablation catheter into the GI tract. In embodiments, the rate of flow of the saline during vapor delivery is different from flow of the saline during the phase where no therapy is delivered. In some embodiments, the rate of flow of saline during the therapy is lower than that during no therapy. In some embodiments, the rate of flow of saline during the therapy is lower than that during no therapy. At 918, the vapor condenses on the tissue under treatment, thereby ablating the tissue.

Figure 9C:
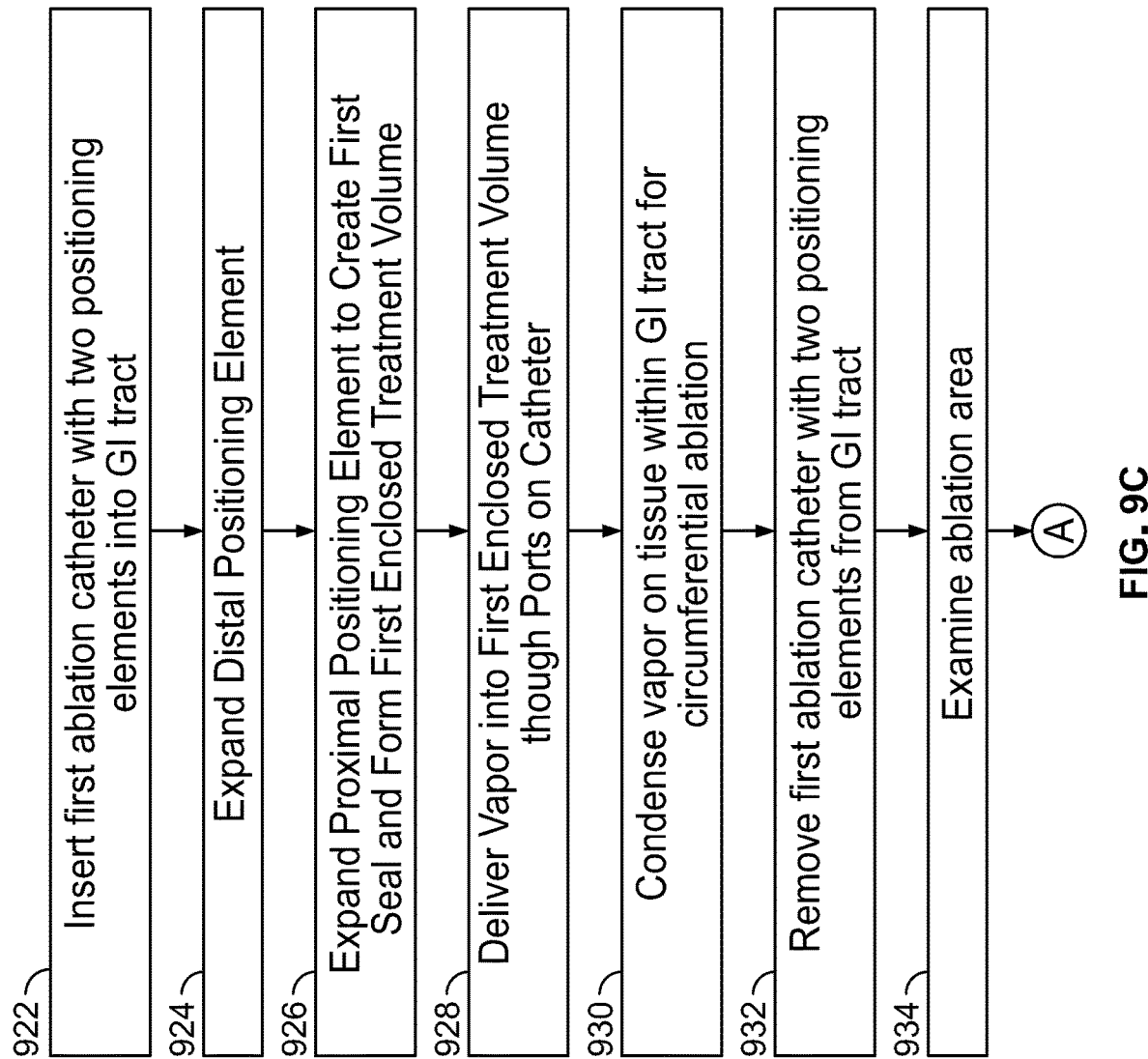
FIG. 9C is a flow chart illustrating a method of using a first ablation catheter to perform circumferential ablation and then a second ablation catheter to perform focal ablation, in accordance with some embodiments of the present specification.
Figure 9C:
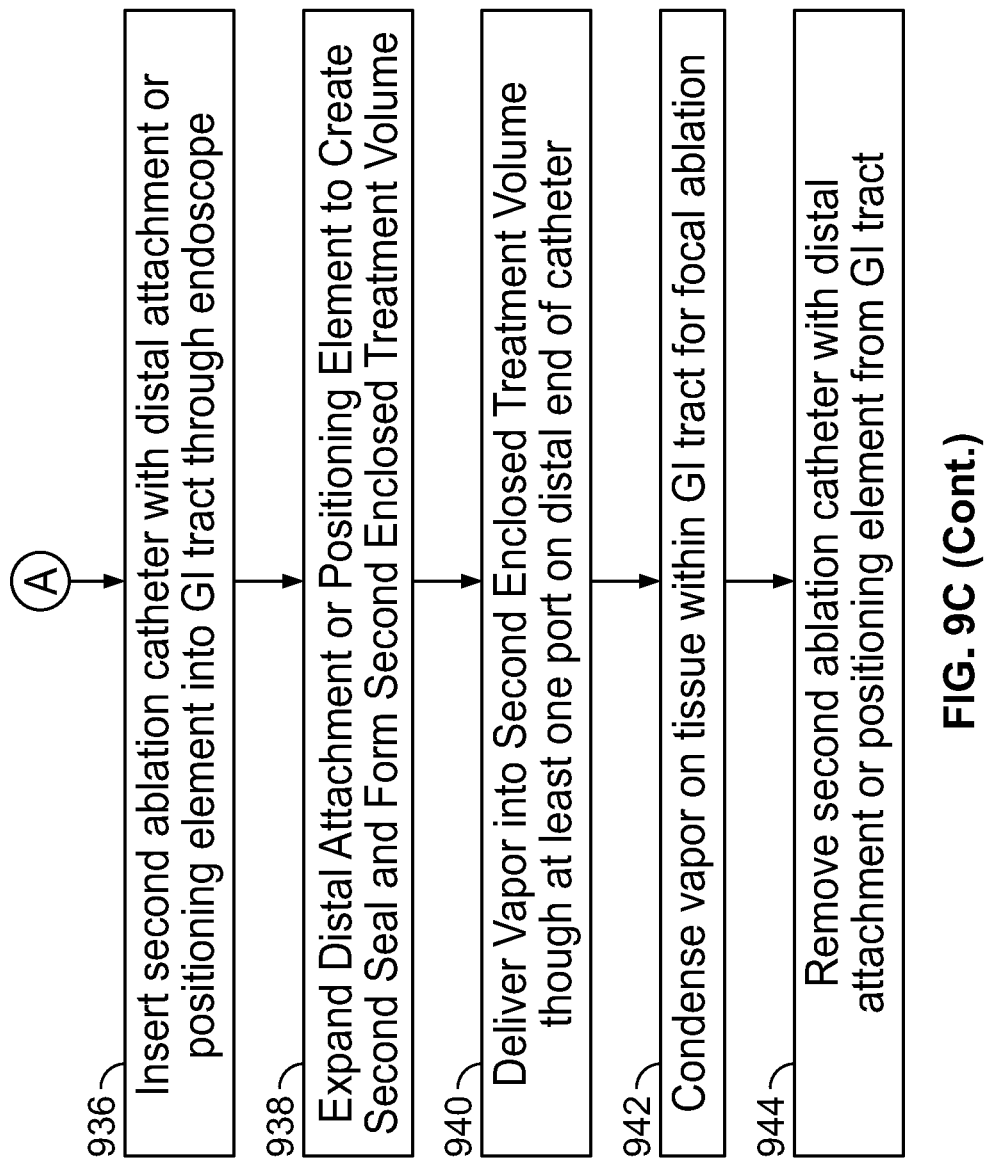

FIG. 9C is a flow chart illustrating a method of using a first ablation catheter to perform circumferential ablation and then a second ablation catheter to perform focal ablation, in accordance with some embodiments of the present specification. It should be noted that, optionally, in other embodiments, a first phase of circumferential ablation using a first ablation catheter is followed by a second phase of circumferential ablation using the same first ablation catheter, either immediately or at a later date, rather than using the second ablation catheter for focal ablation. The method of FIG. 9C includes a two-step, or phase, process to ensure complete or near complete ablation of a target tissue. In some embodiments, in a first phase, a patient is treated with a first ablation catheter having two positioning elements to perform circumferential ablation. In embodiments, the first ablation catheter having two positioning elements used for the first phase is similar to ablation catheter 1991 of FIG. 1K. At step 922, the first ablation catheter is inserted into a patient's GI tract. A distal positioning element is expanded at step 924. A proximal positioning element is then expanded at step 926, creating a first seal between the peripheries of the distal and proximal positioning elements and the GI tract and forming a first enclosed treatment volume between the two positioning elements and the surface of the patient's GI tract. Vapor is delivered via ports, positioned on the first ablation catheter between the positioning elements, into the first enclosed treatment volume at step 928. In some embodiments, the system comprises a foot pedal in data communication with a controller controlling the catheter, a switch on the catheter, or a switch on the controller, for controlling vapor flow and step 928 is achieved using the foot pedal in data communication with the controller, a switch on the catheter, or a switch on the controller. The vapor condenses on the tissue within the first enclosed treatment volume at step 930 to circumferentially ablate the tissue. The first ablation catheter having two positioning elements is then removed from the GI tract at step 932.

After ablation is performed using the first ablation catheter with two positioning elements, the ablation area is examined by the physician at step 934. Upon observing the patient, the physician may identify patches of tissue requiring focused ablation. A second phase is then performed, wherein a second ablation catheter with a needle or cap, hood, or disc attachment or positioning element on the distal end is used for focal ablation. The second phase may be performed immediately after the first phase or at a later date. In embodiments, the second ablation catheter with a needle or cap, hood, or disc attachment or positioning element on the distal end used for the second phase is similar to ablation catheter 870 of FIG. 8J. (Alternatively, in other embodiments, the physician may wait a period of time, ranging from six weeks to two years, measure the efficacy of the first phase, and then perform a second phase using the same first ablation catheter for another round of circumferential ablation.) At step 936, the second ablation catheter with a distal attachment or positioning element is inserted into the patient's GI tract through the lumen of an endoscope. The distal attachment or positioning element is expanded at step 938 to create a second seal between the periphery of the distal attachment or positioning element and the GI tract and form a second enclosed treatment volume between the distal attachment or positioning element and the surface of the patient's GI tract. Vapor is delivered via at least one port, positioned at the distal end of the catheter, into the second enclosed treatment volume at step 940. In some embodiments, the system comprises a foot pedal in data communication with a controller controlling the catheter, a switch on the catheter, or a switch on the controller, for controlling vapor flow and step 940 is achieved using the foot pedal in data communication with the controller, a switch on the catheter, or a switch on the controller. The vapor condenses on the tissue within the second enclosed treatment volume at step 942 to focally ablate the tissue. The second ablation catheter having a distal attachment or positioning element is then removed from the GI tract at step 944.

Figure 9D:
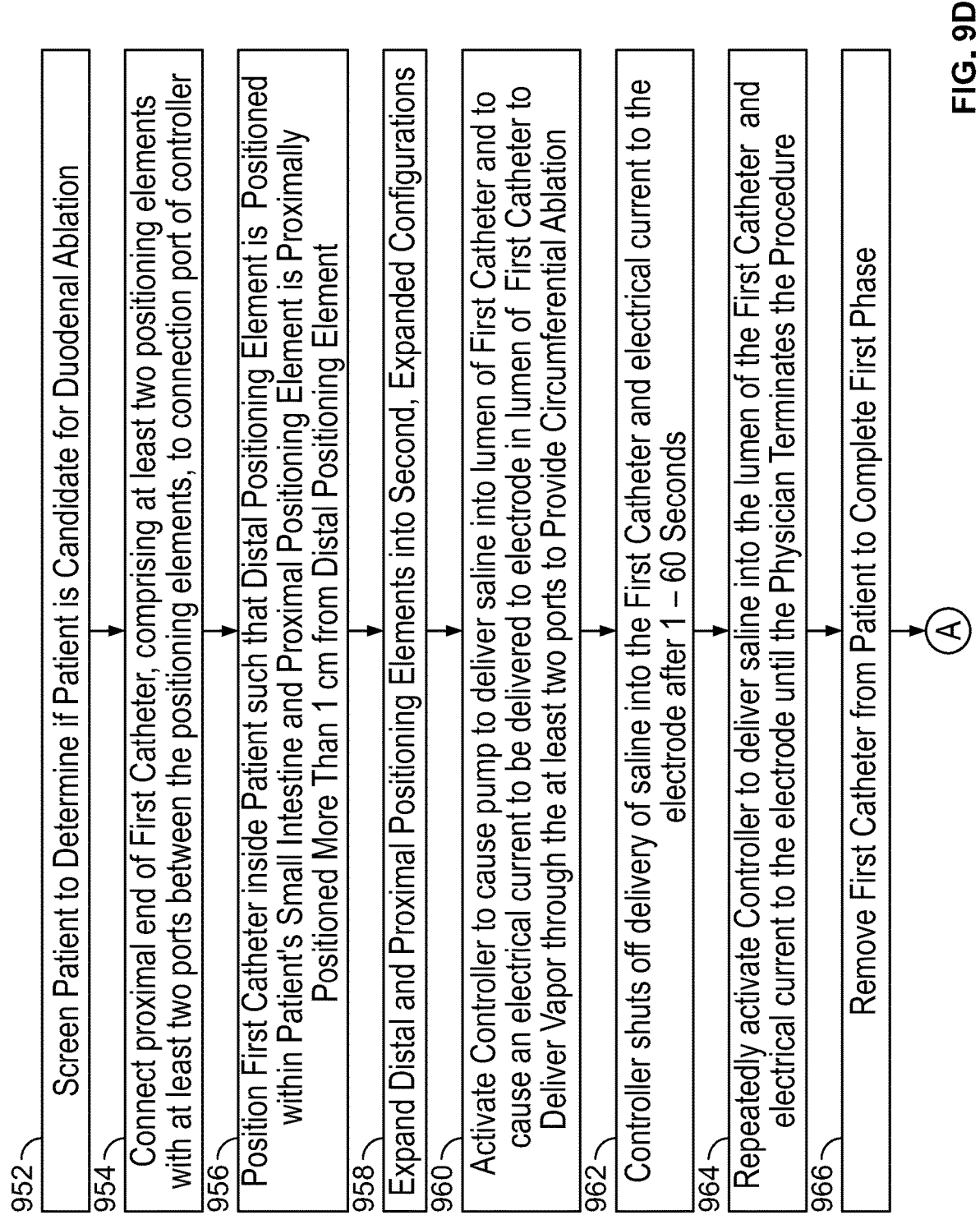
FIG. 9D is a flow chart illustrating a multi-phase method of using a vapor ablation system for duodenal ablation in order to treat obesity, excess weight, eating disorders, metabolic syndrome, diabetes, dyslipidemia, non-alcoholic steatohepatitis (NASH), non-alcoholic fatty liver disease (NAFLD), or a polycystic ovary disease, in accordance with embodiments of the present specification.
Figure 9D:
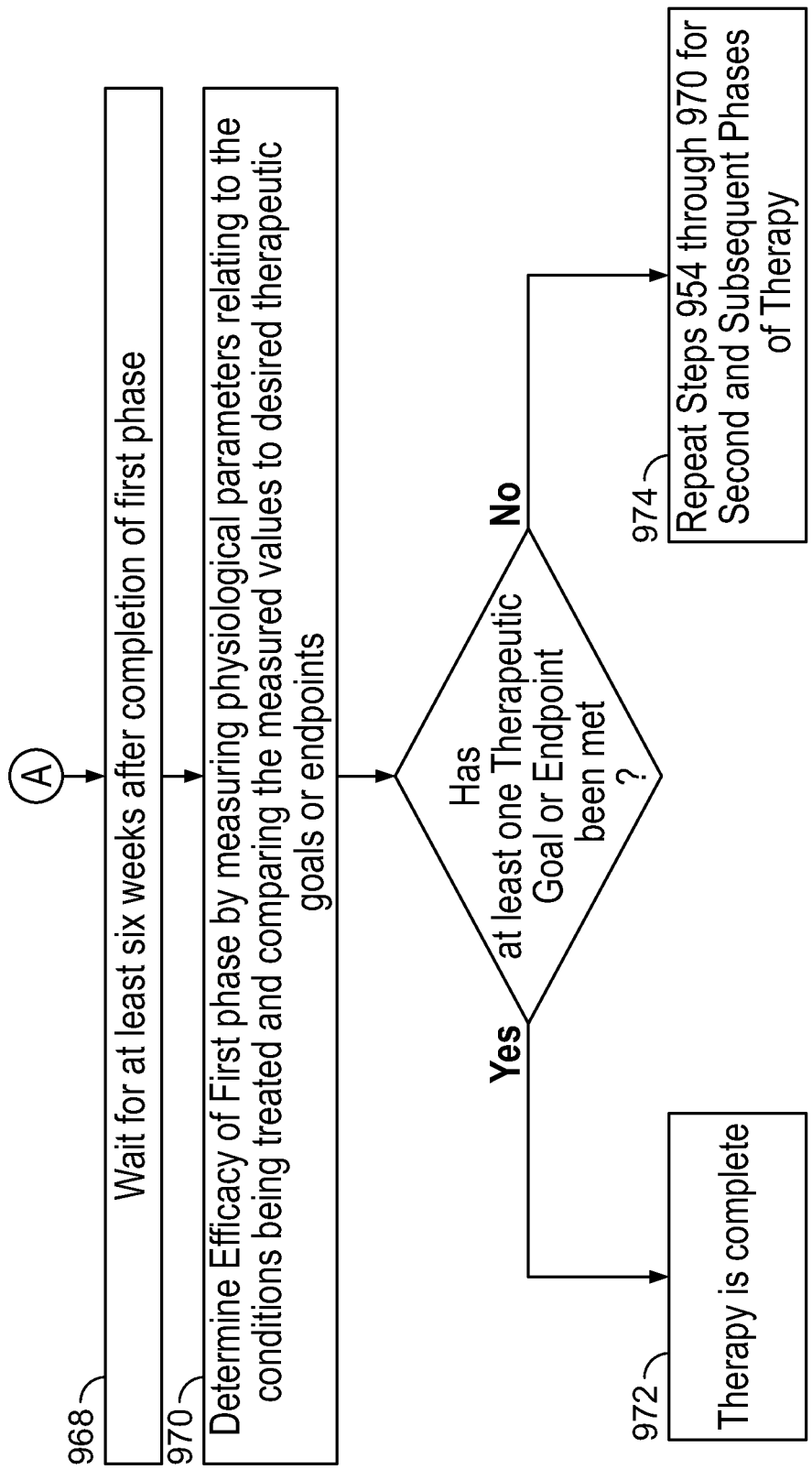

FIG. 9D is a flow chart illustrating a multi-phase method of using a vapor ablation system for duodenal ablation in order to treat obesity, excess weight, eating disorders, metabolic syndrome, diabetes, dyslipidemia, non-alcoholic steatohepatitis (NASH), non-alcoholic fatty liver disease (NAFLD), or a polycystic ovary disease, in accordance with embodiments of the present specification. At step 952, a patient is first screened to determine if the patient is a candidate for duodenal ablation using the ablation systems of the present specification. For diabetes, metabolic syndrome, obesity or excess weight, in various embodiments, the patient must have a BMI (Body Mass Index) of 25 or greater (overweight being 25-30, obese being 30 and above, and morbid obesity being above 35). In accordance with various aspects of the present specification, a patient with diabetes must have HbA1c levels of at least 6.5 gm %, fasting blood glucose levels of at least 126 mg/dL or a random plasma glucose level of at least 200 mg/dL, 2-hour plasma glucose levels of at least 200 mg/dL (11.1 mmol/L) during an oral glucose tolerance test (OGTT), or a fasting insulin concentration of at least 5.7 µU/mL (109 pmol/L). For insulin resistance, in various embodiments, a patient must have a homeostatic model assessment of insulin resistance (HOMA-IR) of at least 1.6. In accordance with various aspects of the present specification, a patient with dyslipidemia must have a serum triglyceride concentration of at least 130 mg/dL (1.47 mmol/L) or a ratio of triglyceride to high-density lipoprotein (HDL) cholesterol concentration of greater than 3.0 (1.8 SI units).

Patients screened at step 952 and determined to be candidates for duodenal ablation then proceed with an ablation procedure using a vapor ablation system in accordance with embodiments of the present specification. The vapor ablation system is configured to deliver circumferential ablation of a patient's duodenum or small intestine to treat any one or more of the conditions listed above. The vapor ablation system comprises a controller having at least one processor in data communication with at least one pump and a catheter connection port in fluid communication with the at least one pump. At step 954 of a first phase of treatment, a proximal end of a first catheter is connected to the catheter connection port to place the first catheter in fluid communication with the at least one pump. The first catheter comprises at least two positioning elements separated along a length of the catheter and at least two ports positioned between the at least two positioning elements, wherein each of the at least two positioning elements has a first configuration and a second configuration, and wherein, in the first configuration, each of the at least two positioning elements is compressed within the catheter and in the second configuration, each of the at least two positioning elements is expanded to be at least partially outside the catheter. At step 956, the first catheter is positioned inside a patient such that, upon being expanded into the second configuration, a distal one of the at least two positioning elements is positioned within in the patient's small intestine and a proximal one of the at least two positioning elements is proximally positioned more than 1 cm from the distal one of the at least two positioning elements. Then, at step 958 each of the at least two positioning elements is expanded into their second configurations. At step 960, the controller is activated, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter. The electrical current causes the electrode to heat and contact of the saline with the heating electrode converts the saline to vapor, or steam, which is delivered via the at least two ports to circumferentially ablate target tissue.

In various embodiments, the vapor is delivered to treat at least 1-15 cm of contiguous or non-contiguous small intestine mucosa. In various embodiments, the vapor is delivered to treat at least 50% of a circumference of small intestine. In various embodiments, the vapor dose is characterized at least one of: having an energy of 5-25 J/cm$^2$, delivered over 1-60 seconds, delivered at an energy rate of 5-2500 cal/sec, delivered such that the total dose is 5-40 calories/gram of tissue to be ablated, delivered to elevate a target tissue temperature above 60° C. but less than 110° C., has a vapor temperature between 99° C. and 110° C., or delivered such that a pressure in a small intestine is less than 5 atm, and preferably less than 1 atm.

At step 962, the controller shuts off the delivery of saline and electrical current after a time period ranging from 1 to 60 seconds. In embodiments, the controller automatically shuts off the delivery of saline and electrical current. The controller is repeatedly activated at step 964 to deliver saline into the lumen and electrical current to the at least one electrode until the physician terminates the procedure. In some embodiments, the system further comprises a foot pedal in data communication with the controller, a switch on the catheter, or a switch on the controller, for controlling vapor flow and step 964 is achieved using the foot pedal in data communication with the controller, a switch on the catheter, or a switch on the controller. The first catheter is removed from the patient at step 966 to complete a first phase of treatment.

At step 968, the physician then waits for at least six weeks after the completion of the first phase to allow the ablation therapy to take effect before evaluating the efficacy of the treatment. After at least six weeks, at step 970, a post-first phase evaluation is performed wherein the efficacy of the first phase of treatment is determined by measuring physiological parameters relating to the conditions being treated and comparing the measured values to desired therapeutic goals or endpoints.

In various embodiments, ablation therapy is provided to achieve the following therapeutic goals or endpoints for patients with obesity, excess weight, eating disorders, dyslipidemia, or diabetes and a first phase of treatment is considered successful for these patients if any one or more of the following therapeutic goals or endpoints is reached: a total body weight of the patient decreases by at least 1% relative to a total body weight of the patient before ablation; an excess body weight of the patient decreases by at least 1% relative to an excess body weight of the patient before ablation; a total body weight of the patient decreases by at least 1% relative to a total body weight of the patient before ablation and a well-being level of the patient does not decrease more than 5% relative to a well-being level of the patient before ablation; an excess body weight of the patient decreases by at least 1% relative to an excess body weight of the patient before ablation and a well-being level of the patient does not decrease more than 5% relative to a well-being level of the patient before ablation; a pre-prandial ghrelin level of the patient decreases by at least 1% relative to a pre-prandial ghrelin level of the patient before ablation; a post-prandial ghrelin level of the patient decreases by at least 1% relative to a post-prandial ghrelin level of the patient before ablation; an exercise output of the patient increases by at least 1% relative to an exercise output of the patient before ablation; a glucagon-like peptide-1 level of the patient increases by at least 1% relative to a glucagon-like peptide-1 level of the patient before ablation; a leptin level of the patient increases by at least 1% relative to a leptin level of the patient before ablation; the patient's appetite decreases, over a predefined period of time, relative to the patient's appetite before ablation; a peptide YY level of the patient increases by at least 1% relative to a peptide YY level of the patient before ablation; a lipopolysaccharide level of the patient decreases by at least 1% relative to a lipopolysaccharide level of the patient before ablation; a motilin-related peptide level of the patient decreases by at least 1% relative to a motilin-related peptide level of the patient before ablation; a cholecystokinin level of the patient increases by at least 1% relative to a cholecystokinin level of the patient before ablation; a resting metabolic rate of the patient increases by at least 1% relative to a resting metabolic rate of the patient before ablation; a plasma-beta endorphin level of the patient increases by at least 1% relative to a plasma-beta endorphin level of the patient before ablation; an HbA1c level of the patient decreases by at least 0.3% relative to an HbA1c level of the patient before ablation; a triglyceride level of the patient decreases by at least 1% relative to a triglyceride level of the patient before ablation; a total blood cholesterol level of the patient decreases by at least 1% relative to a total blood cholesterol level of the patient before ablation; a glycemia level of the patient decreases by at least 1% relative to a glycemia level of the patient before ablation; a composition of the person's gut microbiota modulates from a first state before ablation to a second state after ablation, wherein the first state has a first level of bacteroidetes and a first level of firmicutes, wherein the second state has a second level of bacteroidetes and a second level of firmicutes, wherein the second level of bacteroidetes is greater than the first level of bacteroidetes by at least 3%, and wherein the second level of firmicutes is less than the first level of firmicutes by at least 3%; or, a cumulative daily dose of the patient's antidiabetic medications decreases by at least 10% relative to a cumulative daily dose of the patient's antidiabetic medications before ablation.

In various embodiments, ablation therapy is provided to achieve the following therapeutic goals or endpoints for patients with dyslipidemia and a first phase of treatment is considered successful for these patients if any one or more of the following therapeutic goals or endpoints is reached: a lipid profile of the patient improves by at least 10% relative a lipid profile of the patient before ablation, wherein lipid profile is defined at least by a ratio of LDL cholesterol to HDL cholesterol, and improve is defined as a decrease in the ratio of LDL cholesterol to HDL cholesterol; an LDL-cholesterol level of the patient decreases by at least 10% relative to an LDL-cholesterol level of the patient before ablation; or, a VLDL-cholesterol level of the patient decreases by at least 10% relative to a VLDL-cholesterol level of the patient before ablation.

In various embodiments, ablation therapy is provided to achieve the following therapeutic goals or endpoints for patients with non-alcoholic steatohepatitis (NASH) or non-alcoholic fatty liver disease (NAFLD), and a first phase of treatment is considered successful for these patients if any one or more of the following therapeutic goals or endpoints is reached: at least a 10% decrease in either ALT or AST levels relative to ALT or AST levels before ablation; at least a 10% improvement in serum ferritin level or an absolute serum ferritin level of less than 1.5 ULN (upper limit normal) relative to serum ferritin levels before ablation; at least a 5% improvement in hepatic steatosis (HS) or less than 5% HS relative to HS levels before ablation, as measured on liver biopsy; at least a 5% improvement in HS or less than 5% HS relative to HS levels before ablation, as measured by magnetic resonance (MR) imaging, either by spectroscopy or proton density fat fraction; at least a 5% improvement in an NAFLD Fibrosis Score (NFS) relative to an NFS before ablation; at least a 5% improvement in an NAFLD Activity Score (NAS) relative to an NAS before ablation; at least a 5% improvement in a Steatosis Activity Fibrosis (SAF) score relative to an SAF score before ablation; at least a 5% decrease in a mean annual fibrosis progression rate relative to a mean annual fibrosis progression rate before ablation, as measured by histology, Fibrosis-4 (FIB-4) index, aspartate aminotransferase (AST) to platelet ratio index (APRI), serum biomarkers (Enhanced Liver Fibrosis (ELF) panel, Fibrometer, FibroTest, or Hepascore), or imaging (transient elastography (TE), MR elastography (MRE), acoustic radiation force impulse imaging, or supersonic shear wave elastography); at least a 5% decrease in circulating levels of cytokeratin-18 fragments relative to circulating levels of cytokeratin-18 fragments before ablation; at least a 5% improvement in FIB-4 index, aspartate aminotransferase (AST]) to platelet ratio index (APRI), serum biomarkers (Enhanced Liver Fibrosis (ELF) panel, Fibrometer, FibroTest, or Hepascore), or imaging (transient elastography (TE), MR elastography (MREO, acoustic radiation force impulse imaging, or supersonic shear wave elastography) relative to FIB-4 index, aspartate aminotransferase (AST]) to platelet ratio index (APRI), serum biomarkers (Enhanced Liver Fibrosis (ELF) panel, Fibrometer, FibroTest, or Hepascore), or imaging (transient elastography (TE), MR elastography (MRE), acoustic radiation force impulse imaging, or supersonic shear wave elastography) before ablation; at least a 5% decrease in liver stiffness relative to liver stiffness before ablation, as measured by vibration controlled transient elastography (VCTE/FibroScan); an improvement in NAS by at least 2 points, with at least 1-point improvement in hepatocellular ballooning and at least 1-point improvement in either lobular inflammation or steatosis score, and no increase in the fibrosis score, relative to NAS, hepatocellular ballooning, lobular inflammation, steatosis, and fibrosis scores before ablation; at least a 5% improvement in NFS scores relative to NFS scores before ablation; or, at least a 5% improvement in any of the above listed NAFLD parameters as compared to a sham intervention or a placebo.

If any one of the above therapeutic goals or endpoints is met, therapy is completed at step 972 and no further ablation is performed. If none of the above therapeutic goals or endpoints are met, then the entire ablation procedure and evaluation, less the screening process, and comprising steps 954-970, is repeated for a second therapy phase, and subsequent therapy phases if therapeutic goals or endpoints are still not met, waiting at least six weeks each time between each ablation procedure and each evaluation.

Figure 9E:
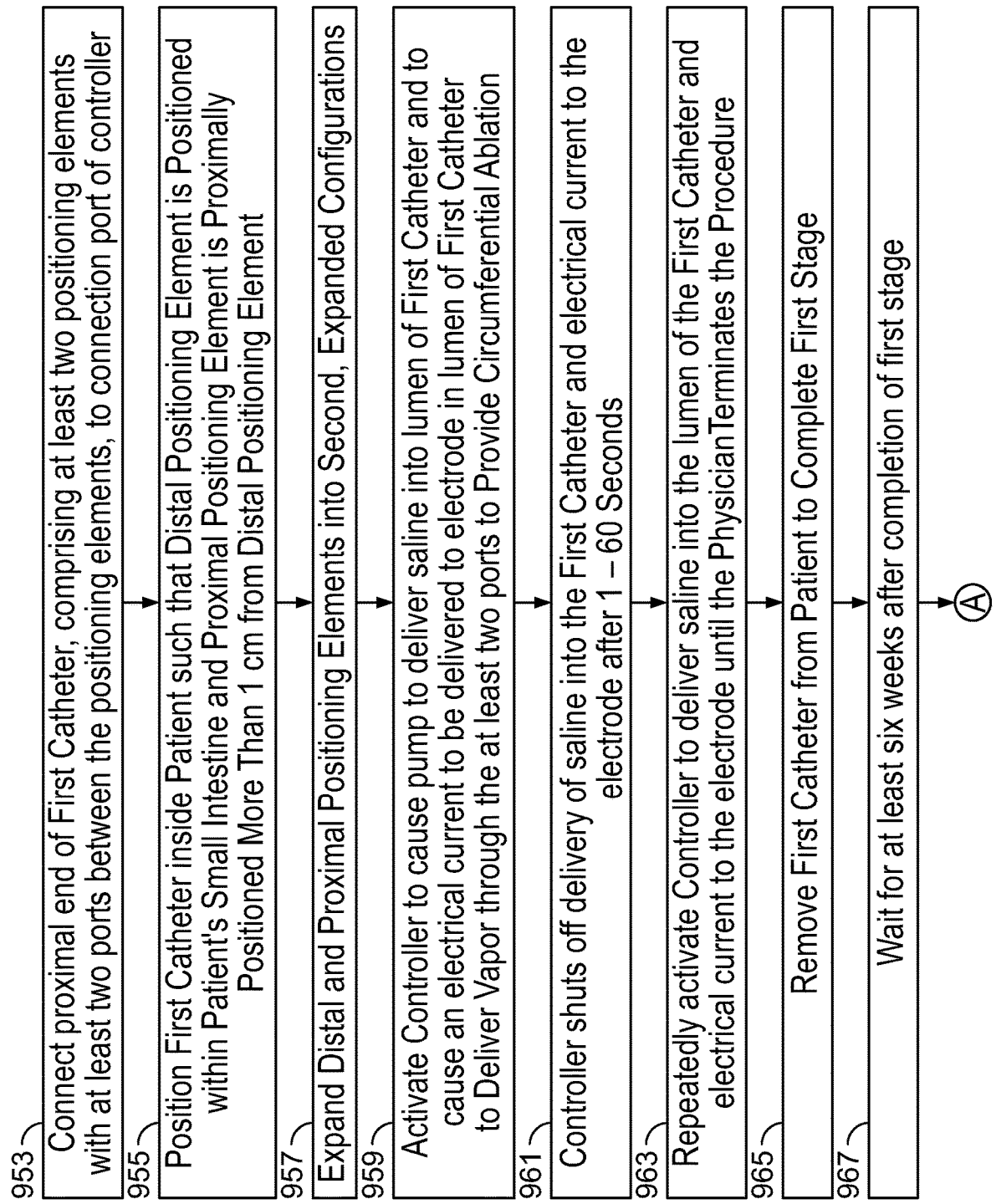
FIG. 9E is a flow chart illustrating a multi-stage method of using a vapor ablation system for treating cancerous or precancerous esophageal tissue, in accordance with various embodiments of the present specification.
Figure 9E:
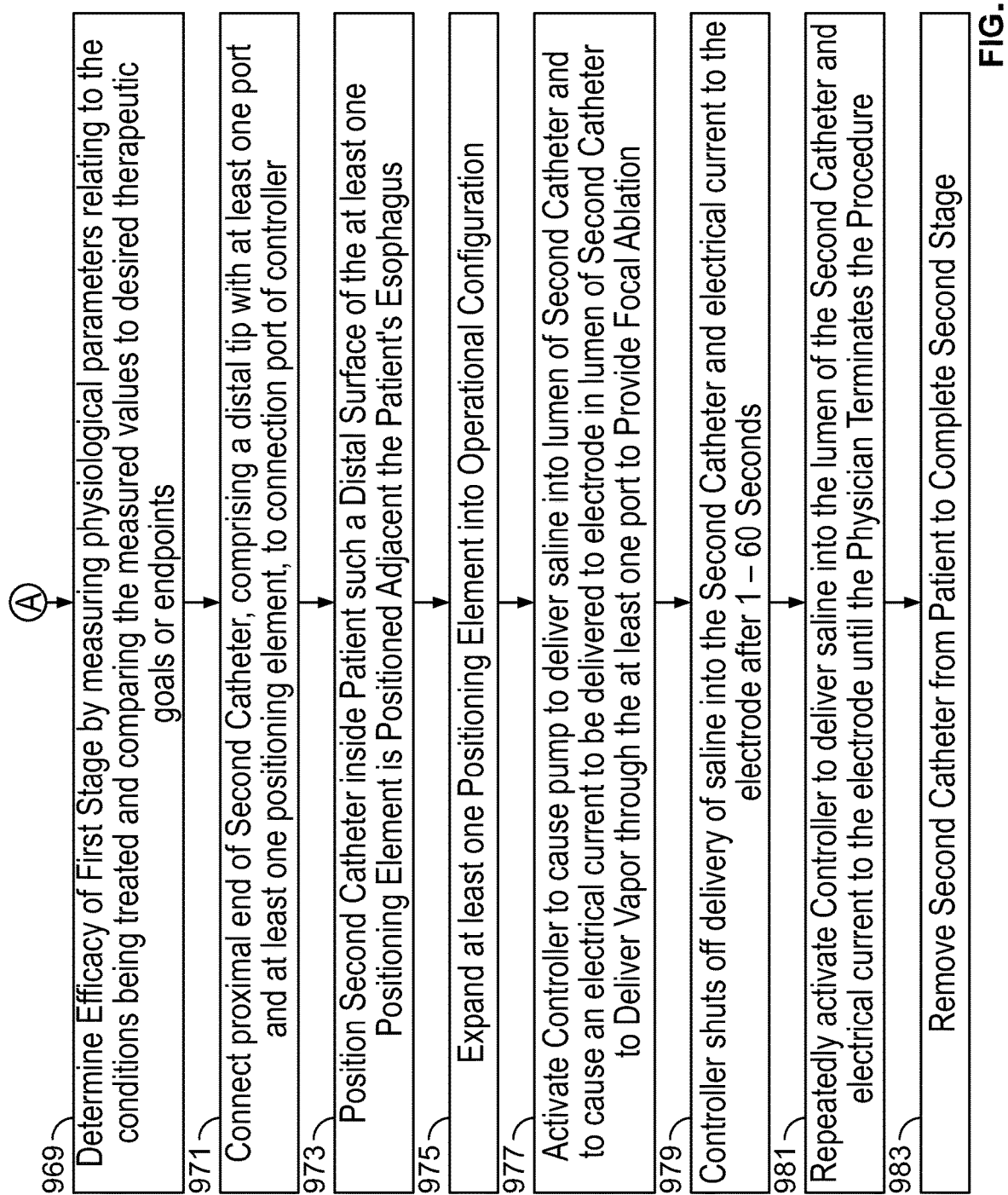

FIG. 9E is a flow chart illustrating a multi-stage method of using a vapor ablation system for treating cancerous or precancerous esophageal tissue, in accordance with various embodiments of the present specification. The vapor ablation system comprises a controller having at least one processor in data communication with at least one pump and a catheter connection port in fluid communication with the at least one pump. At step 953, a proximal end of a first catheter is connected to the catheter connection port to place the first catheter in fluid communication with the at least one pump, wherein the first catheter comprises at least two positioning elements separated along a length of the catheter and at least two ports positioned between the at least two positioning elements, wherein each of the at least two positioning elements has a first configuration and a second configuration, and wherein, in the first configuration, each of the at least two positioning elements is compressed within the catheter and in the second configuration and each of the at least two positioning elements is expanded to be at least partially outside the catheter. At step 955, the first catheter is positioned inside a patient such that, upon being expanded into the second configuration, a distal one of the at least two positioning elements is positioned adjacent the patient's esophagus and a proximal one of the at least two positioning elements is proximally positioned more than 1 cm from the distal one of the at least two positioning elements. At step 957, each of the at least two positioning elements is expanded into their second configurations. At step 959, the controller is activated, wherein, upon activation, the controller is configured to cause the at least one pump to deliver saline into at least one lumen in the first catheter and, wherein, upon activation, the controller is configured to cause an electrical current to be delivered to at least one electrode positioned within the at least one lumen of the first catheter. The electrical current causes the electrode to heat and contact of the saline with the heating electrode converts the saline to vapor, or steam, which is delivered via the at least two ports to circumferentially ablate target tissue. In some embodiments, during the first stage of treatment, the at least two positioning elements, together with the esophageal tissue, define a first enclosed volume wherein at least one of the at least two positioning elements is positioned relative the esophageal tissue to permit a flow of air out of the second enclosed volume when the vapor is delivered.

In various embodiments, the vapor is delivered to treat at least 1-15 cm of contiguous or non-contiguous small intestine mucosa. In various embodiments, the vapor is delivered to treat at least 50% of a circumference of small intestine. In various embodiments, the vapor dose is characterized at least one of: having an energy of 5-25 J/cm$^2$, delivered over 1-60 seconds, delivered at an energy rate of 5-2500 cal/sec, delivered such that the total dose is 5-40 calories/gram of tissue to be ablated, delivered to elevate a target tissue temperature above 60° C. but less than 110° C., has a vapor temperature between 99° C. and 110° C., or delivered such that a pressure in a small intestine is less than 5 atm, and preferably less than 1 atm.

In various embodiments, the vapor is delivered to treat at least 1-15 cm of contiguous or non-contiguous small intestine mucosa. In various embodiments, the vapor is delivered to treat at least 50% of a circumference of small intestine. In various embodiments, the vapor dose is characterized at least one of: having an energy of 5-25 J/cm$^2$, delivered over 1-60 seconds, delivered at an energy rate of 5-2500 cal/sec, delivered such that the total dose is 5-40 calories/gram of tissue to be ablated, delivered to elevate a target tissue temperature above 60° C. but less than 110° C., has a vapor temperature between 99° C. and 110° C., or delivered such that a pressure in a small intestine is less than 5 atm, and preferably less than 1 atm.

At step 961, the controller shuts off the delivery of saline and electrical current. In embodiments, the controller automatically shuts off the delivery of saline and electrical current. Optionally, at step 963, the controller is reactivated to deliver saline into the lumen of the first catheter and electrical current to the electrode until the physician terminates the procedure. The catheter is removed from the patient at step 965 to complete a first stage of treatment.

The physician waits for at least six weeks at step 967 before evaluating the efficacy of the first stage. After at least six weeks, at step 969, a post-first stage evaluation is performed wherein the efficacy of the first stage of treatment is determined by measuring physiological parameters relating to the conditions being treated and comparing the measured values to desired therapeutic goals or endpoints. (Alternatively, in other embodiments, a visible evaluation is performed immediately after completion of the first stage and, if deemed necessary based on the visual observation, a second stage of treatment using a second catheter is performed before waiting at least six weeks.)

If the desired therapeutic goals or endpoints have not been achieved, a second stage of therapy is performed. At step 971, a proximal end of a second catheter is connected to the catheter connection port to place the second catheter in fluid communication with the at least one pump, wherein the second catheter comprises a distal tip having at least one port and at least one positioning element attached to the distal tip such that, upon being in an operational configuration, the at least one positioning element encircles the at least one port and is configured to direct all vapor exiting from the at least one port. At step 973, the second catheter is positioned inside the patient such that a distal surface of the at least one positioning element is positioned adjacent the patient's esophagus. Optionally, the at least one positioning element is expandable from a first, collapsed configuration to an expanded, operational configuration and, at step 975, the at least one positioning element is expanded into the operation configuration. At step 977, the controller is activated, wherein, upon activation, the controller is configured to cause the at least one pump to deliver saline into at least one lumen in the second catheter and, wherein, upon activation, the controller is configured to cause an electrical current to be delivered to at least one electrode positioned within the at least one lumen of the second catheter. The electrical current causes the electrode to heat and contact of the saline with the heating electrode converts the saline to vapor, or steam, which is delivered via the at least one port to focally ablate target tissue. In some embodiments, during the second stage of treatment, the at least one positioning element, together with the esophageal tissue, defines a second enclosed volume wherein the at least one positioning element is positioned relative the esophageal tissue to permit a flow of air out of the second enclosed volume when the vapor is delivered.

In various embodiments, the vapor is delivered to treat at least 1-15 cm of contiguous or non-contiguous small intestine mucosa. In various embodiments, the vapor is delivered to treat at least 50% of a circumference of small intestine. In various embodiments, the vapor dose is characterized at least one of: having an energy of 5-25 J/cm$^2$, delivered over 1-60 seconds, delivered at an energy rate of 5-2500 cal/sec, delivered such that the total dose is 5-40 calories/gram of tissue to be ablated, delivered to elevate a target tissue temperature above 60° C. but less than 110° C., has a vapor temperature between 99° C. and 110° C., or delivered such that a pressure in a small intestine is less than 5 atm, and preferably less than 1 atm.

At step 979, the controller shuts off the delivery of saline and electrical current after a time period ranging from 1 to 60 seconds. In embodiments, the controller automatically shuts off the delivery of saline and electrical current. Optionally, in some embodiments, the controller is repeatedly activated at step 981 to deliver saline into the lumen and electrical current to the at least one electrode until the physician terminates the procedure. In some embodiments, the system further comprises a foot pedal in data communication with the controller, a switch on the catheter, or a switch on the controller, for controlling vapor flow and step 981 is achieved using the foot pedal in data communication with the controller, a switch on the catheter, or a switch on the controller. The second catheter is removed from the patient at step 983 to complete the second stage of treatment. In some embodiments, evaluations are performed at least six weeks to two years after completion of the second stage to determine efficacy of the second stage and, if desired therapeutic goals or endpoints are not achieved, further first and/or second stages, with further evaluations, may be performed as needed.

Therapeutic Pressure Profiles for Ablation Therapy

In various embodiments, the catheters of the present specification measure and monitor pressure of the steam/vapor throughout an ablation therapy and maintain the pressure below a predefined limit, such as 5 atm or 5 psi, in order to limit the amount of thermal energy transferred to the tissues during the therapy.

Figure 10A:
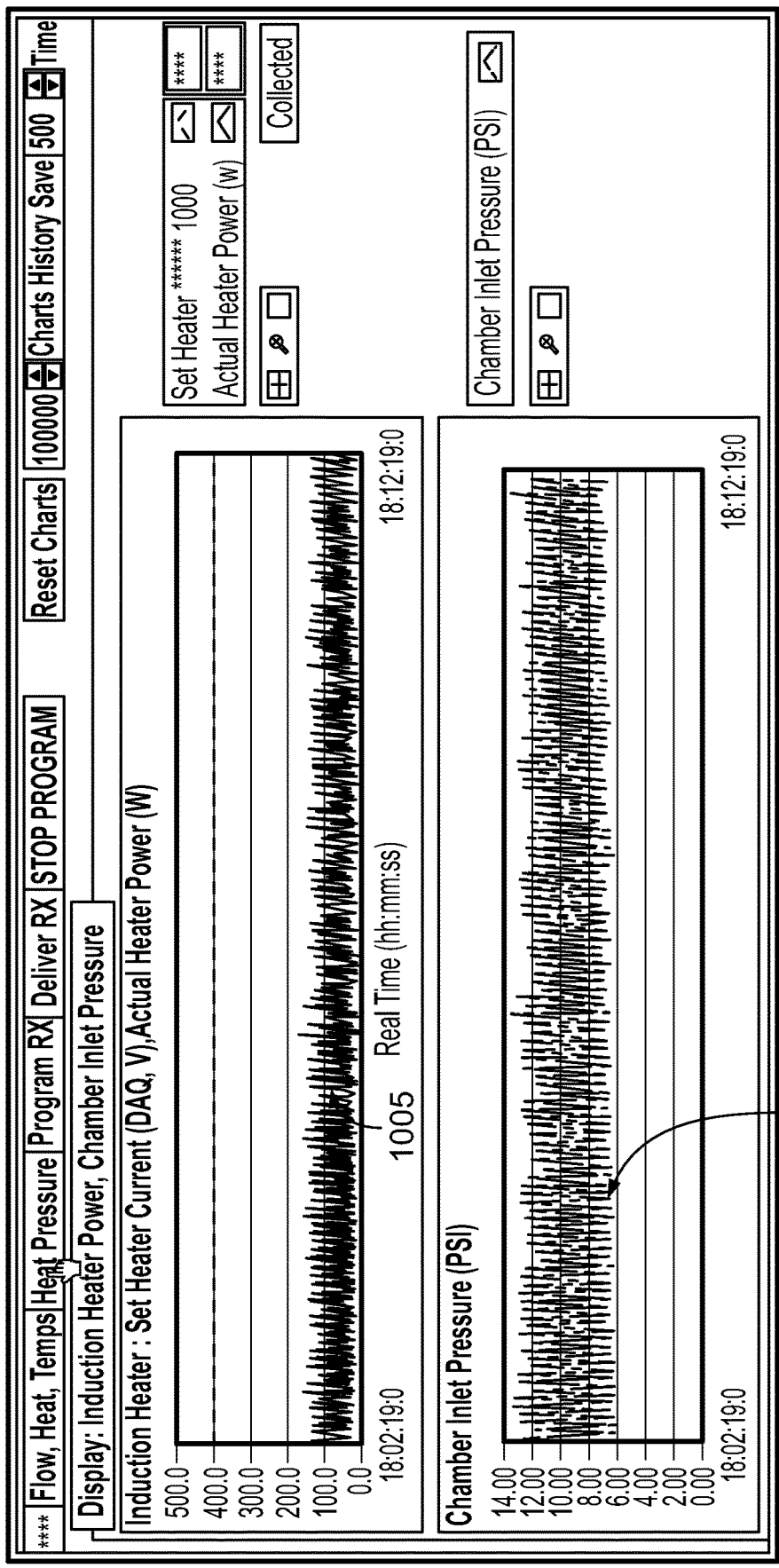
FIG. 10A shows first and second graphs illustrating energy consumption profile by a heating chamber (flexible heating chamber with RF electrodes or inductive coil based heating chamber) and pressure profile of vapor generated during an ablation therapy, in accordance with an embodiment of the present specification.
Figure 10B:
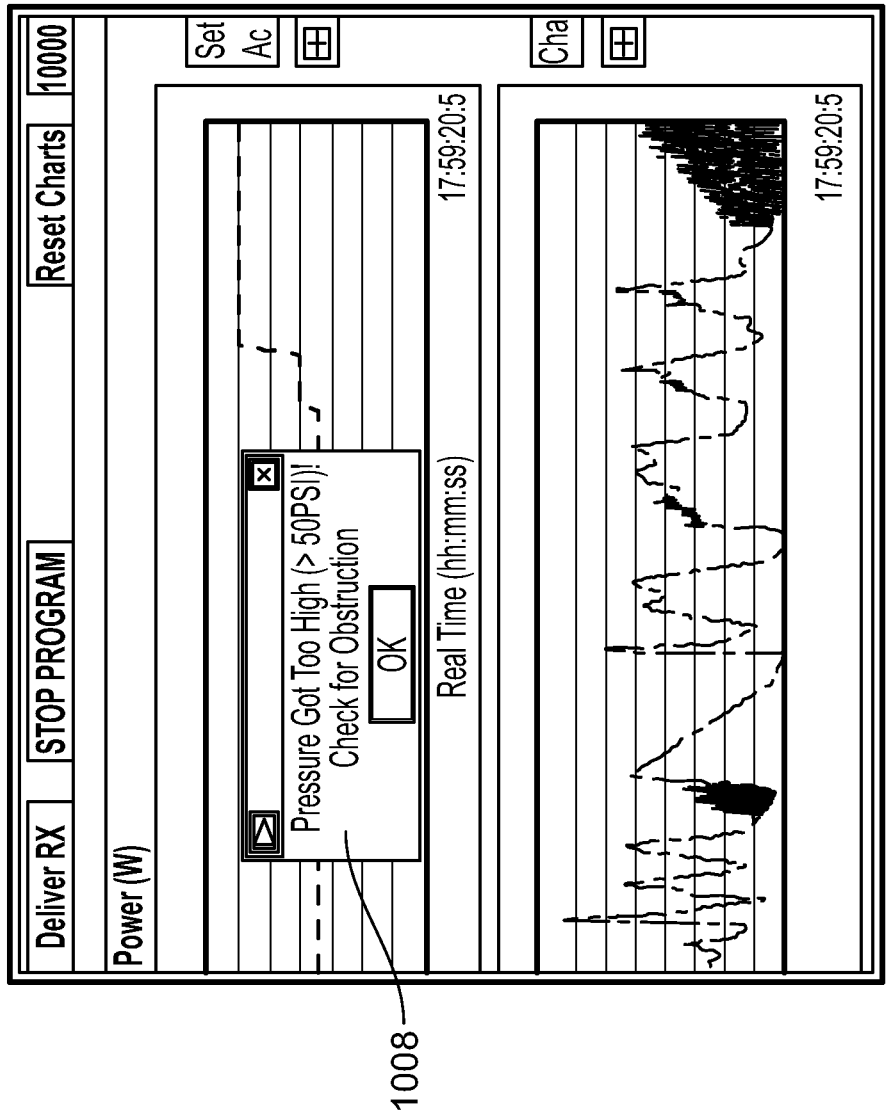
FIG. 10B illustrates an alert being generated when vapor pressure at the heating chamber reaches above a predefined limit, in accordance with an embodiment of the present specification.

In accordance with an aspect of the present specification, the energy consumed by the heating chamber is reflective of vapor pressure generated. FIG. 10A shows first and second graphs illustrating energy consumption profile by a heating chamber (flexible heating chamber with RF electrodes or inductive coil based heating chamber) and pressure profile of vapor generated during an ablation therapy, in accordance with an embodiment of the present specification. The first graph 1005 illustrates the power or energy consumption profile (in Watts) of the heating chamber with respect to time while the second graph 1007 illustrates the vapor pressure profile at an inlet of the heating chamber with respect to time. As shown in FIG. 10B the ablation therapy is stopped when the vapor pressure reaches above the predefined limit, such as 5 psi, and an alert 1008 is generated.

Figure 10C:
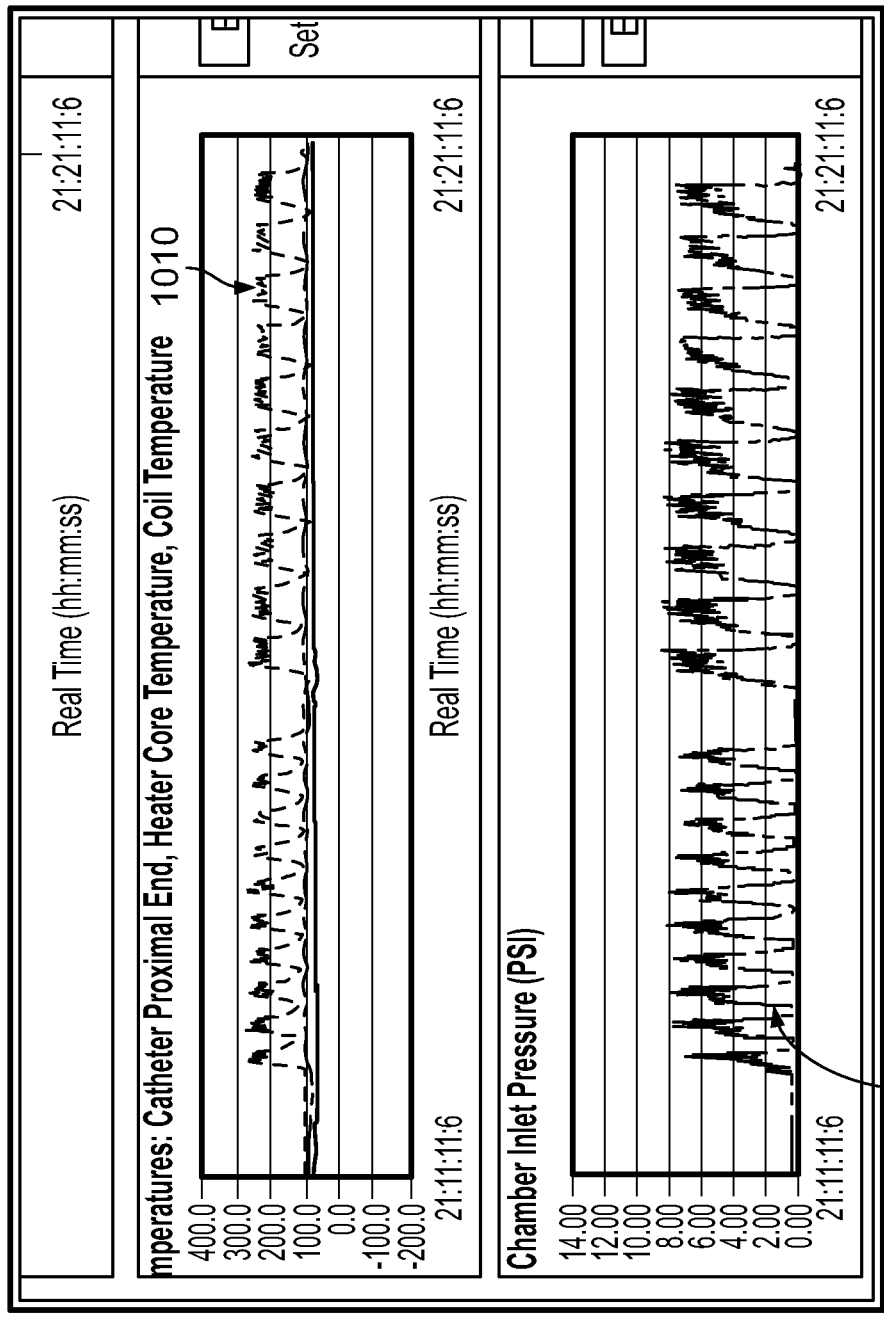
FIG. 10C shows third and fourth graphs illustrating a temperature profile of vapor and a pressure profile of vapor generated during an ablation therapy, in accordance with an embodiment of the present specification.

In accordance with another aspect of the present specification, the temperature of vapor correlates with the vapor pressure measured along the pathway of the vapor. FIG. 10C shows third and fourth graphs illustrating a temperature profile of vapor and a pressure profile of vapor generated during an ablation therapy, in accordance with an embodiment of the present specification. The third graph 1010 illustrates the temperature profile of vapor with respect to time while the fourth graph 1012 illustrates the vapor pressure profile along the vapor pathway with respect to time.

FIGS. 10D through 10P illustrate a plurality of exemplary vapor pressure based therapy profiles during ablation, in accordance with embodiments of the present specification. The pressure therapy profiles in each of the figures are shown as graphs having time (in seconds) on an X-axis and pressure (in atmospheres, atm) on a Y-axis.

Figure 10D:
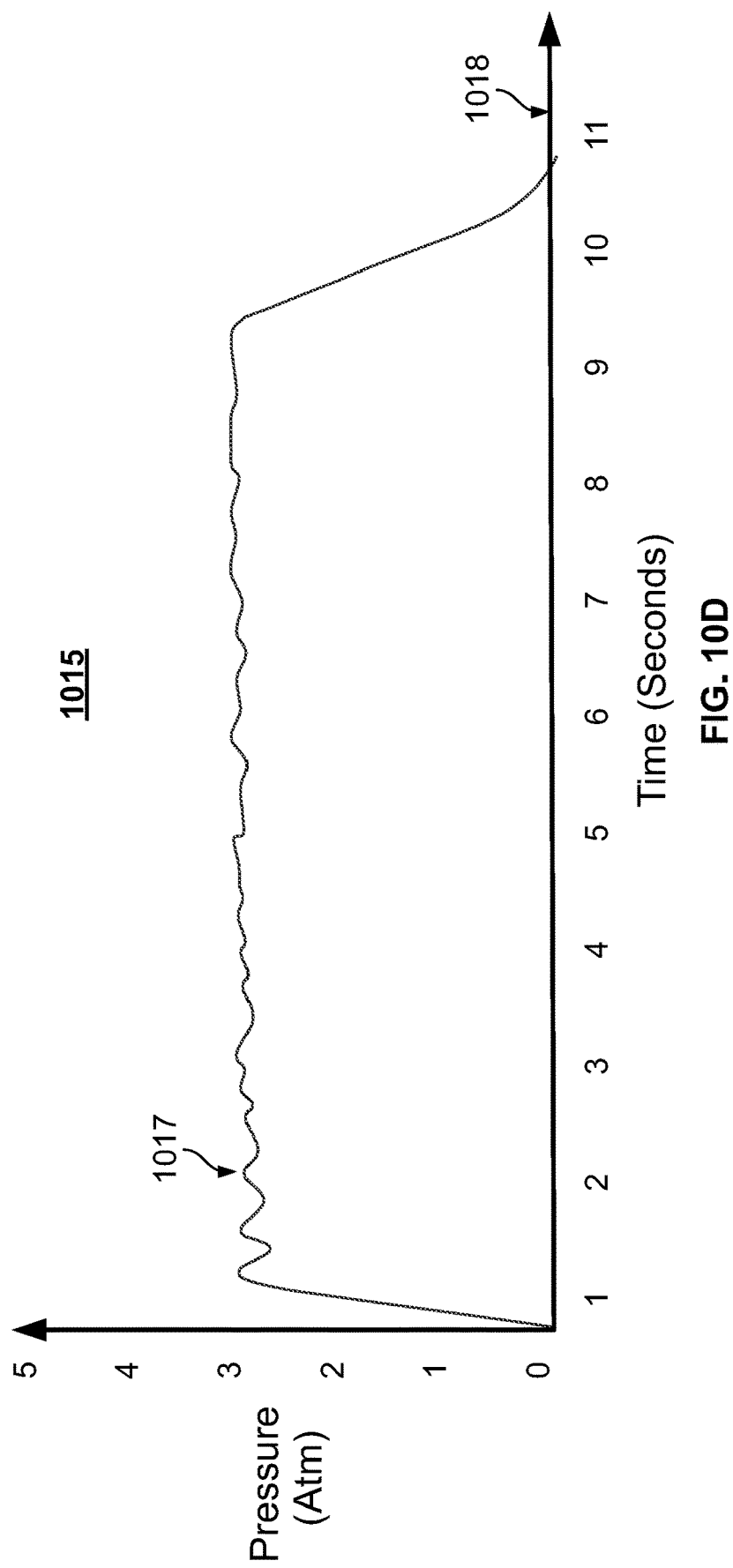
FIG. 10D illustrates a first pressure therapy profile, in accordance with an embodiment of the present specification.

FIG. 10D illustrates a pressure therapy profile 1015 wherein vapor delivery is initiated and pressure is raised to a desired maximum pressure 1017, such as 3 atm. The vapor pressure is maintained at the maximum pressure 1017 for a predefined time, such as 10 seconds, and thereafter the vapor delivery is stopped allowing the pressure to return to baseline 1018.

Figure 10E:
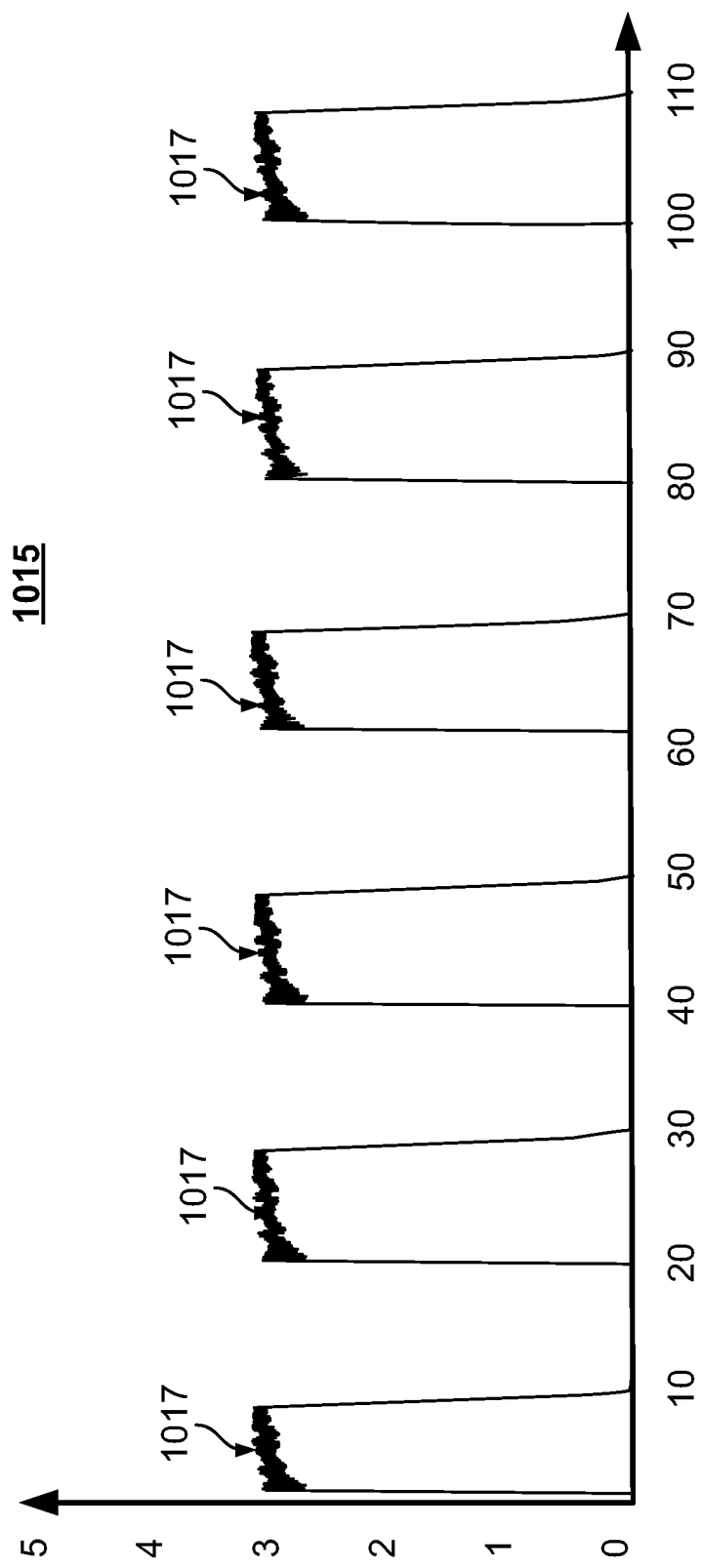
FIG. 10E illustrates a plurality of cycles of the first pressure therapy profile, in accordance with an embodiment of the present specification.
Figure 10F:
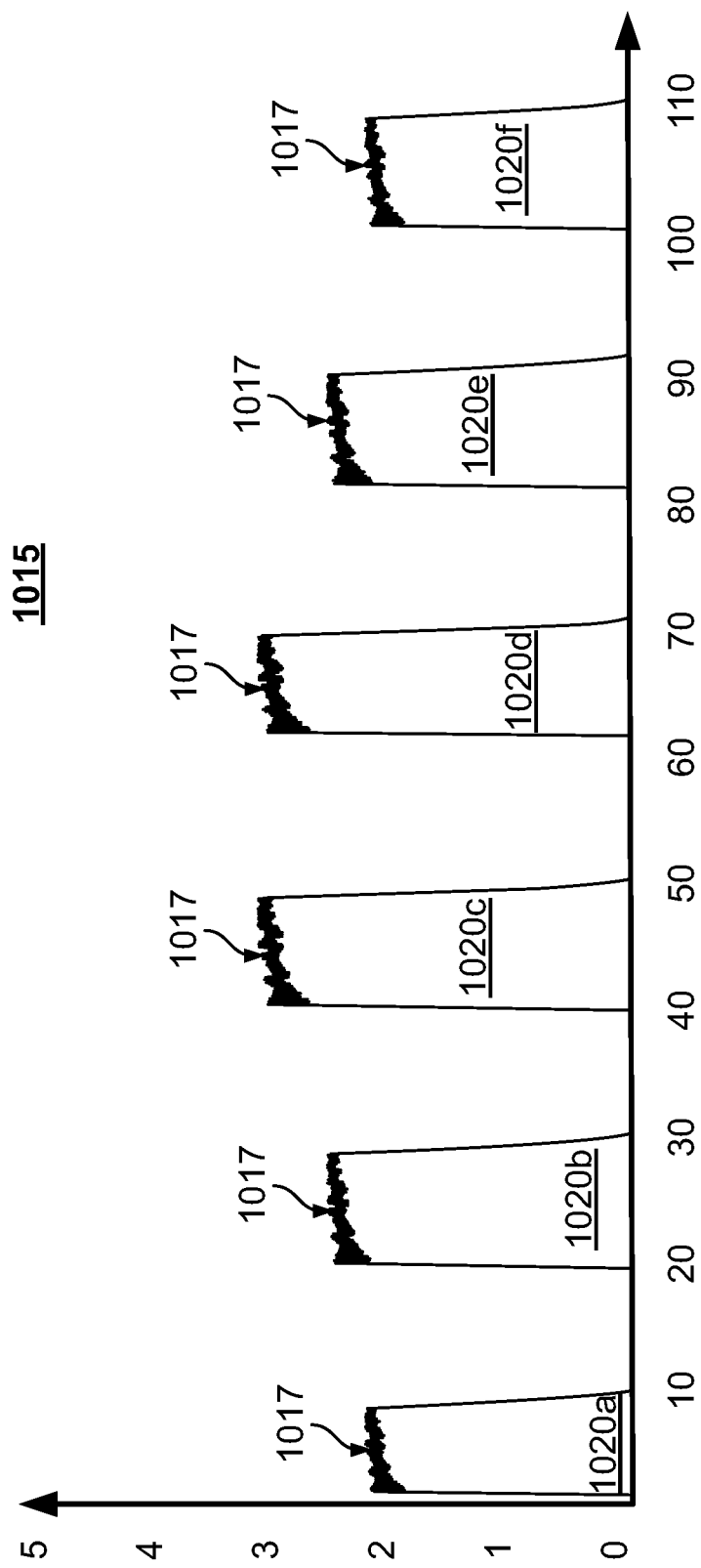
FIG. 10F illustrates a plurality of cycles of the first pressure therapy profile, in accordance with another embodiment of the present specification.

FIG. 10E illustrates the pressure therapy profile 1015 being repeated for a plurality of cycles, wherein the desired maximum pressure 1017 is same for each cycle. FIG. 10F illustrates the pressure therapy profile 1015 being repeated for a plurality of cycles wherein the desired maximum pressure 1017 is customized for each cycle. For example, the desired maximum pressure 1017 is: 2 atm for the first cycle 1020a, 2.5 atm for the second cycle 1020b and 3 atm for the third cycle 1020c. Thereafter, the desired maximum pressure 1017 is: maintained at 3 atm for the fourth cycle 1020d, 2.5 atm for the fifth cycle 1020e and 2 atm for the sixth cycle 1020f. In other words, the desired maximum pressure 1017 is increased and decreased for individual cycles 1020a through 1020f by increasing and decreasing the flow of vapor to create custom treatment profile.

Figure 10G:
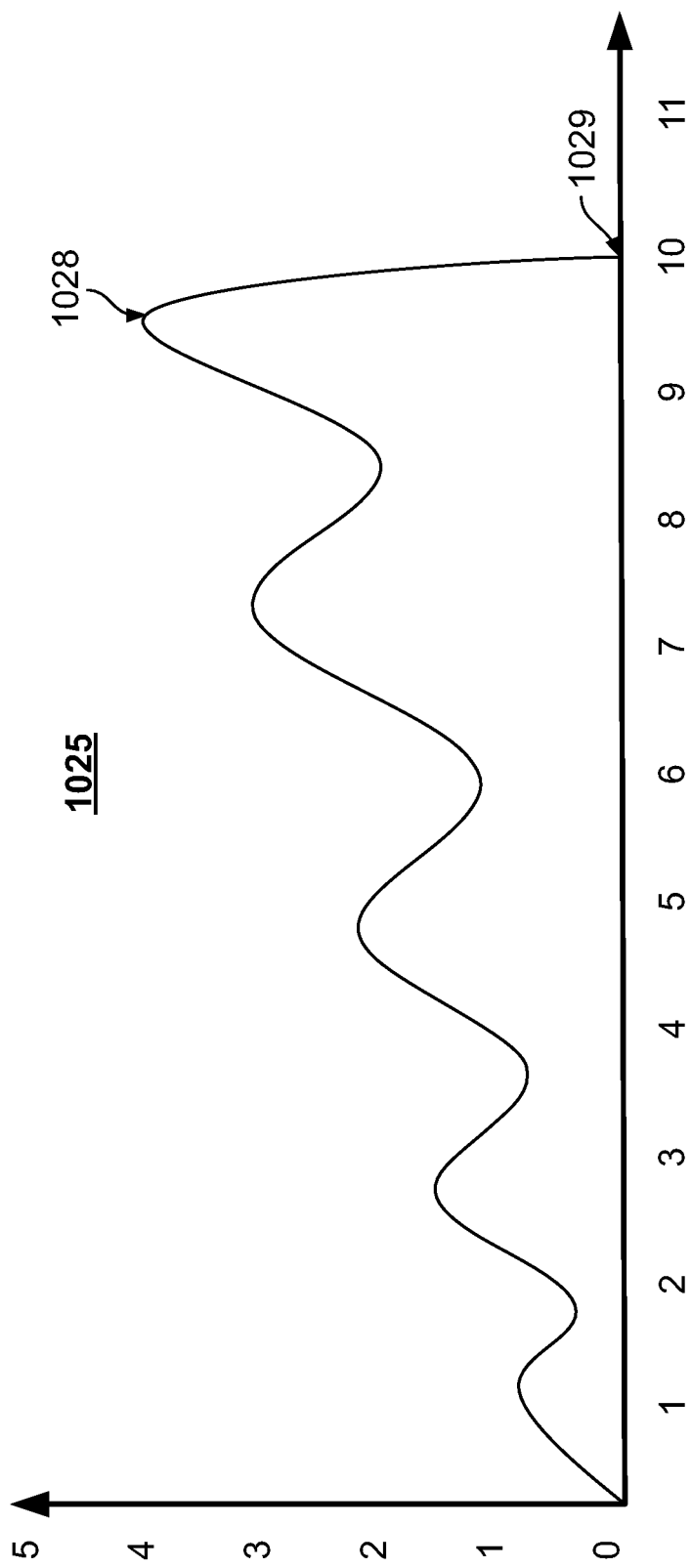
FIG. 10G illustrates a second pressure therapy profile, in accordance with an embodiment of the present specification.
Figure 10H:
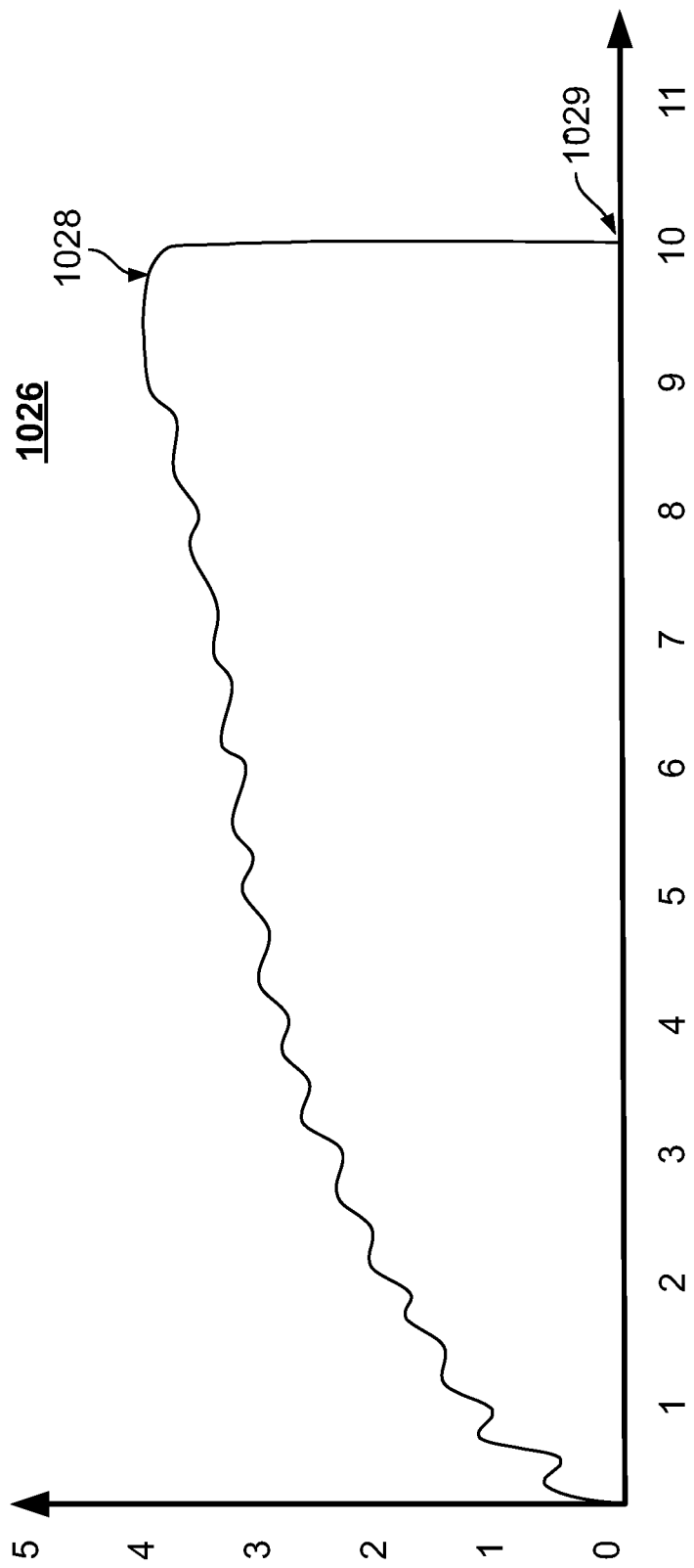
FIG. 10H illustrates the second pressure therapy profile, in accordance with another embodiment of the present specification.
Figure 10I:
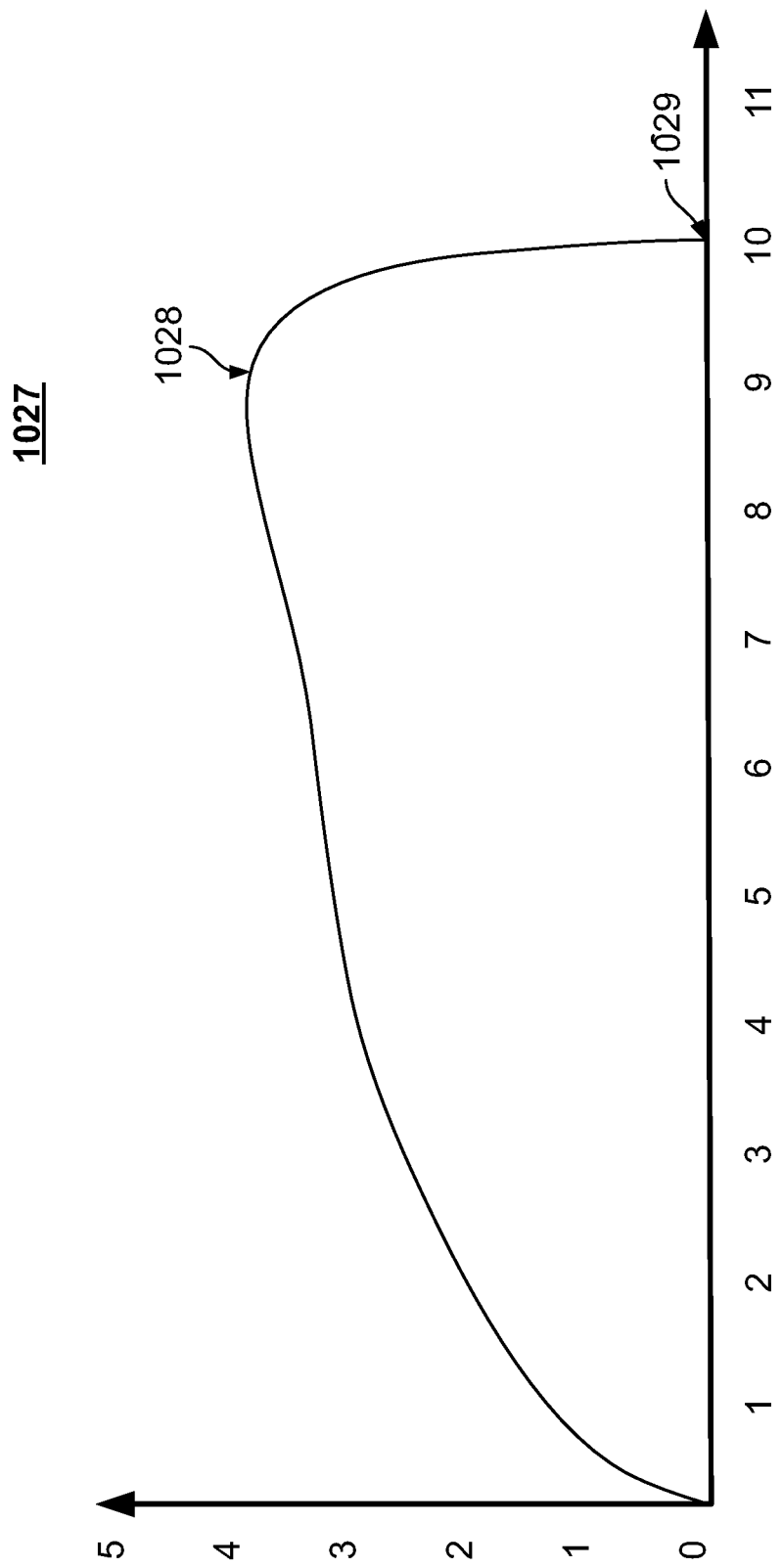
FIG. 10I illustrates the second pressure therapy profile, in accordance with another embodiment of the present specification.
Figure 10J:
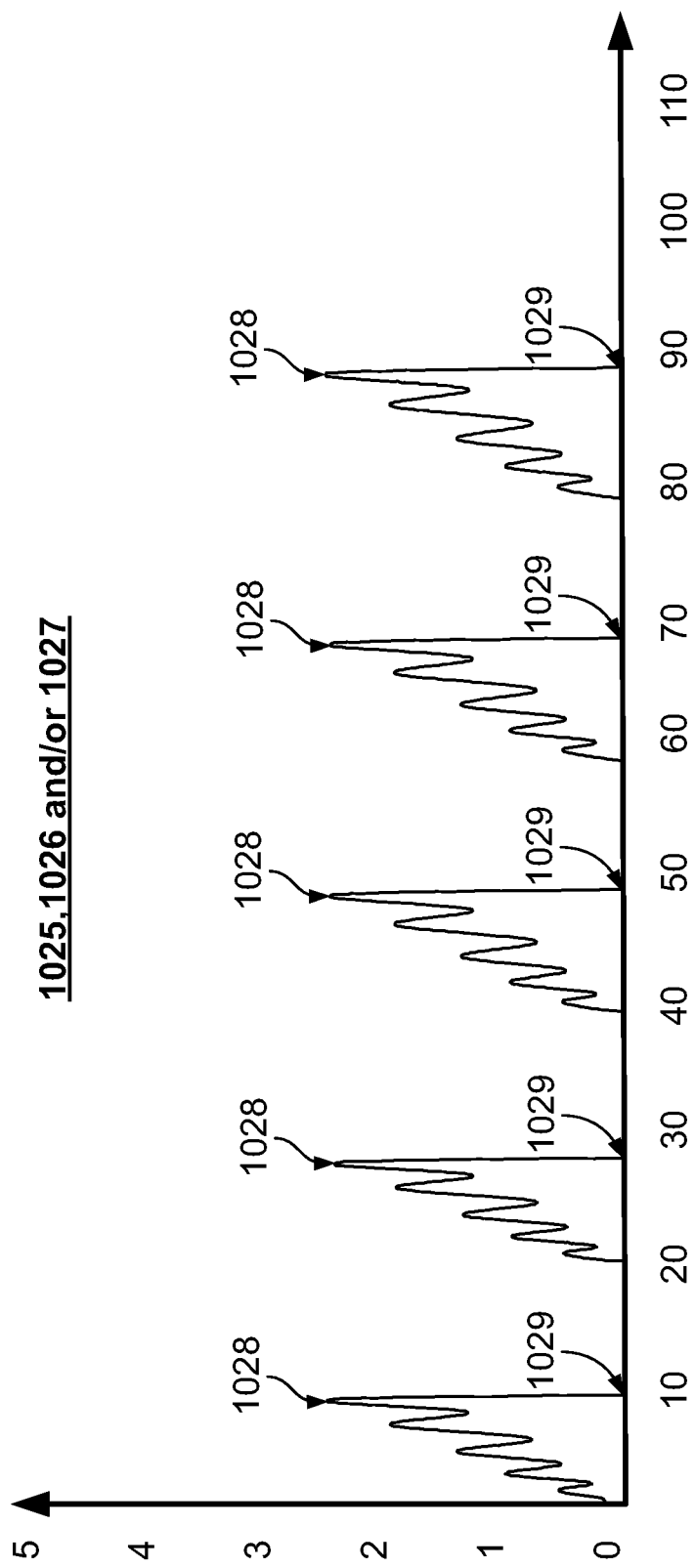
FIG. 10J illustrates a plurality of cycles of the second pressure therapy profile, in accordance with an embodiment of the present specification.

FIGS. 10G, 10H and 10I illustrate pressure therapy profiles 1025, 1026 and 1027, wherein the pressure of vapor delivery is gradually increased to reach a target pressure 1028 at which time, the vapor delivery is aborted allowing the pressure to return to a baseline pressure 1029. FIG. 10J illustrates a plurality of cycles of at least one of the pressure therapy profiles 1025, 1026 and 1027, wherein for each cycle the therapy pressure builds up to the desired target pressure 1028 and then stops to return to the baseline pressure 1029 and recycles.

FIG. 10K illustrates a pressure therapy profile 1030, wherein the pressure of vapor delivery is rapidly increased to reach a target pressure 1032 during a predefined period of time after which, the vapor delivery is gradually decreased allowing the pressure to slowly return to a baseline pressure 1034.

Figure 10L:
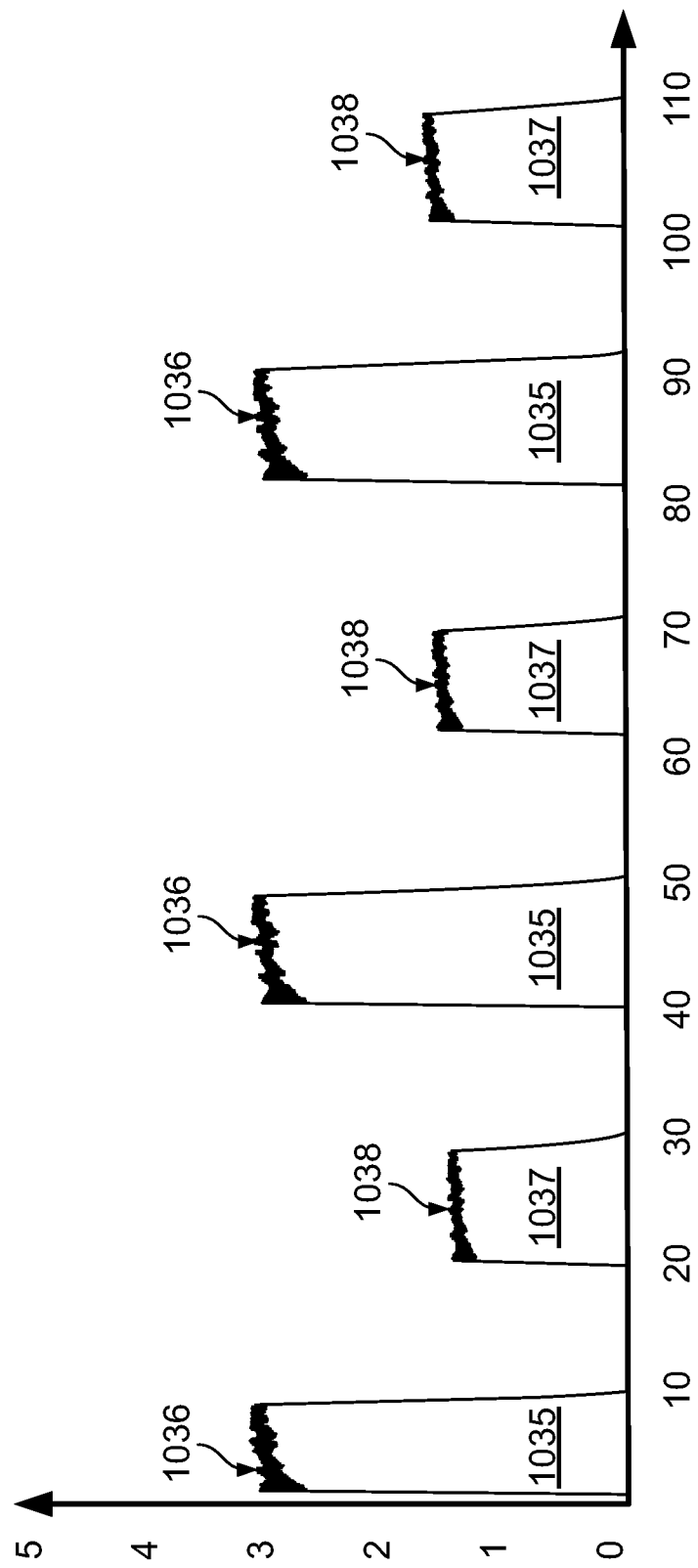
FIG. 10L illustrates a plurality of cycles of a pair of pressure profiles, in accordance with an embodiment of the present specification.

FIG. 10L illustrates a plurality of cycles of a pair of first and second pressure profiles 1035, 1037 wherein the first pressure profile 1035 has a first maximum pressure 1036 and the second pressure profile 1037 has a second maximum pressure 1038. In some embodiments, the first maximum pressure 1036 is higher than the second maximum pressure 1038. Thus, a higher pressure of vapor delivery is cycled with a lower pressure of vapor delivery.

Figure 10M:
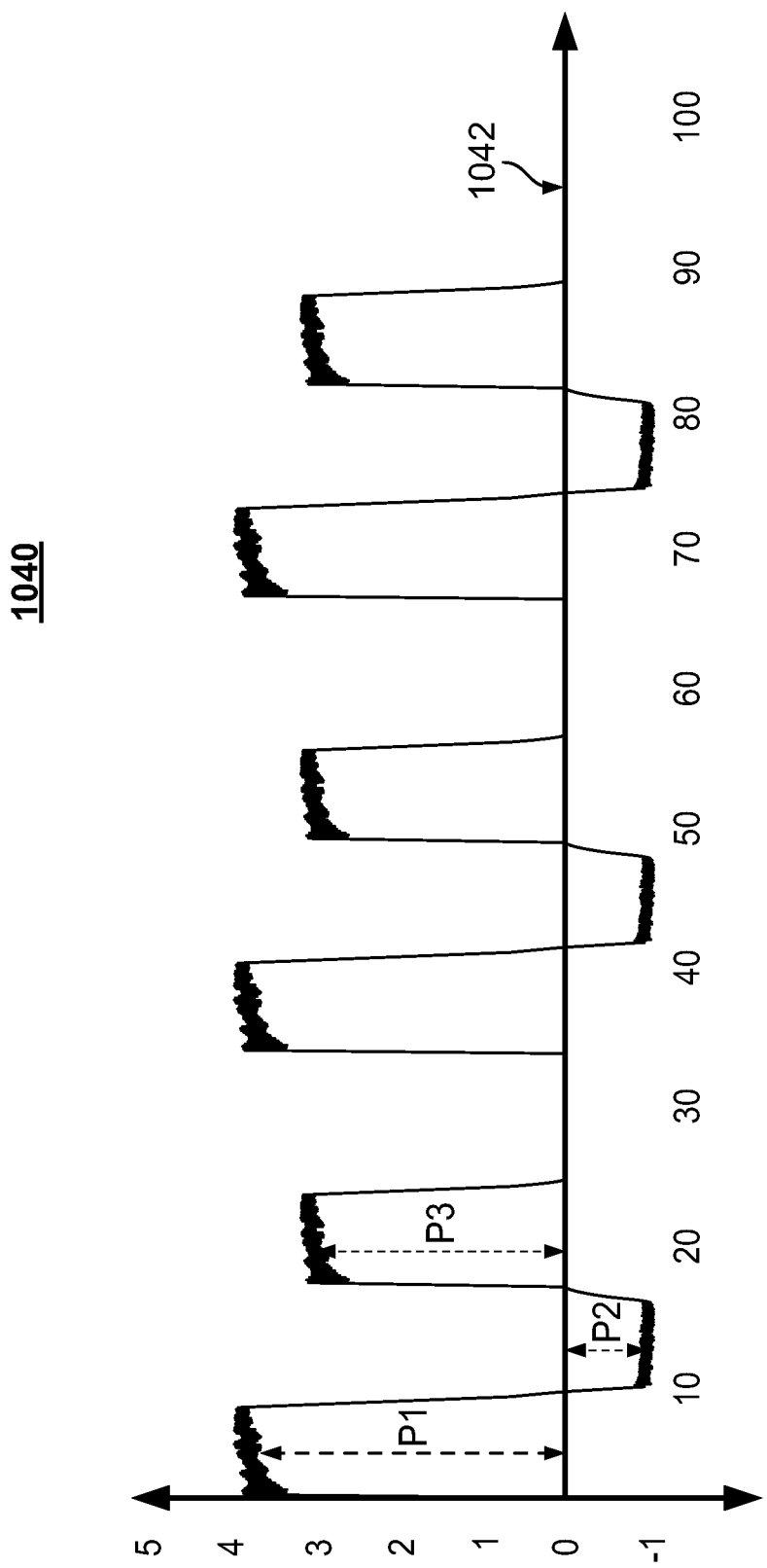
FIG. 10M illustrates a plurality of cycles of a fourth pressure profile, in accordance with an embodiment of the present specification.

FIG. 10M illustrates a plurality of cycles of a pressure profile 1040 wherein for each cycle the vapor is delivered to a pressure $P_1$ for a predetermined duration of time. Next, the vapor delivery is aborted and the pressure is allowed to decrease to a pressure $P_2$, below baseline 1042 for another predetermined duration of time. Thereafter, the vapor delivery is reinitiated and delivered to a pressure $P_3$ for yet another predetermined duration of time. Finally, the vapor delivery is aborted allowing the pressure to return to baseline pressure 1042. In some embodiments, the pressure $P_1$ is comparable to or approximately equal to a sum of $P_2$ and $P_3$.

Figure 10N:
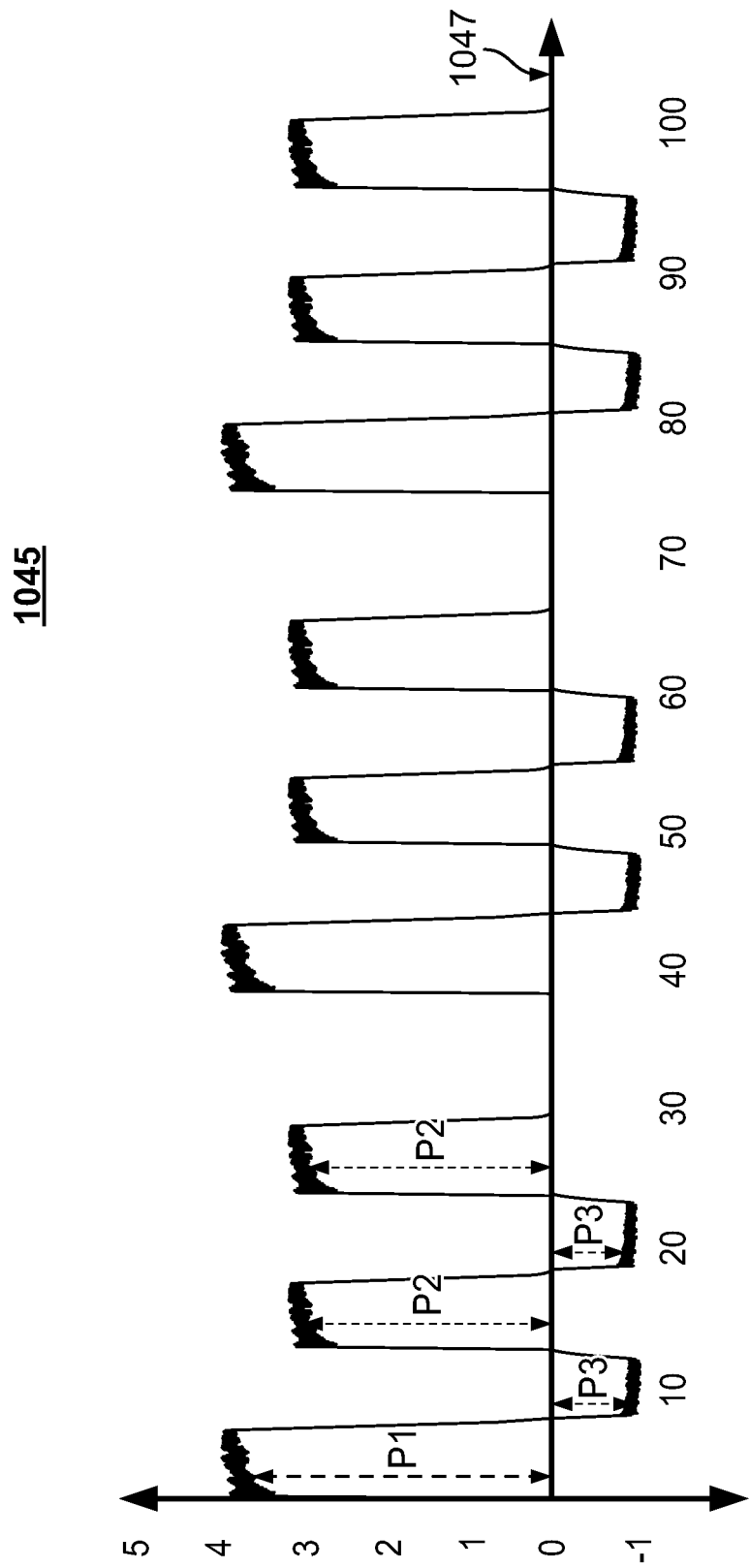
FIG. 10N illustrates a plurality of cycles of a fifth pressure profile, in accordance with an embodiment of the present specification.

FIG. 10N illustrates a plurality of cycles of a pressure profile 1045 wherein for each cycle the vapor is delivered to a pressure $P_1$ for a predetermined duration of time. Next, the vapor delivery is aborted and the pressure is allowed to decrease to a pressure $P_3$, below baseline 1047 for another predetermined duration of time. Now, the vapor delivery is reinitiated and delivered to a pressure $P_2$ for another predetermined duration of time. Next, the vapor delivery is aborted and the pressure is allowed to decrease to the pressure $P_3$, below baseline 1047 for another predetermined duration of time. Thereafter, the vapor delivery is reinitiated and delivered to the pressure $P_2$ for another predetermined duration of time. Finally, the vapor delivery is aborted allowing the pressure to return to the baseline pressure 1047. In some embodiments, the pressure $P_1$ is comparable to or approximately equal to a sum of $P_2$ and $P_3$.

Figure 10O:
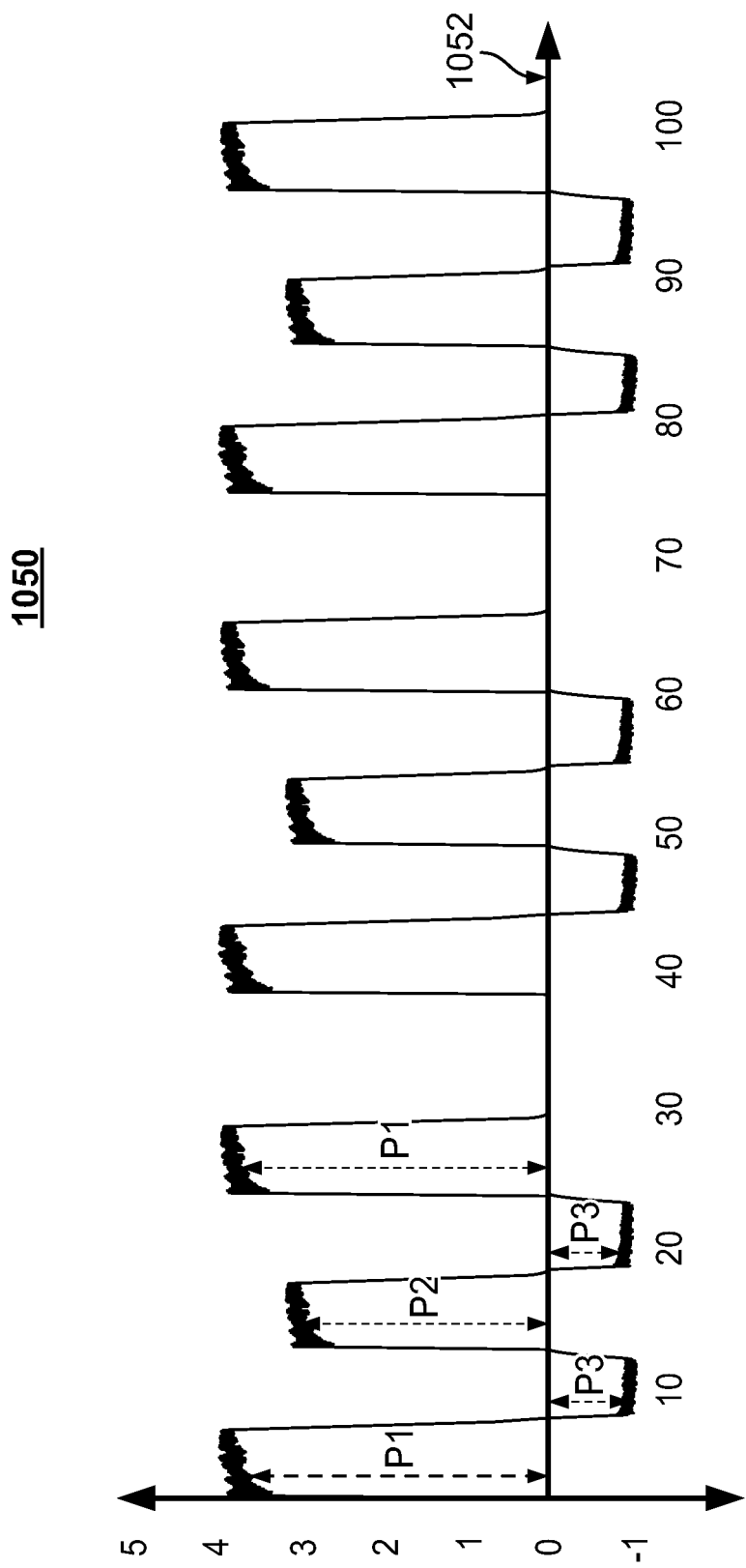
FIG. 10O illustrates a plurality of cycles of a sixth pressure profile, in accordance with an embodiment of the present specification.

FIG. 10O illustrates a plurality of cycles of a pressure profile 1050 wherein for each cycle the vapor is delivered to a pressure $P_1$ for a predetermined duration of time. Next, the vapor delivery is aborted and the pressure is allowed to decrease to a pressure $P_3$, below baseline 1052 for another predetermined duration of time. Now, the vapor delivery is reinitiated and delivered to a pressure $P_2$ for another predetermined duration of time. Next, the vapor delivery is aborted and the pressure is allowed to decrease to the pressure $P_3$, below baseline 1052 for another predetermined duration of time. Thereafter, the vapor delivery is reinitiated and delivered to the pressure $P_1$ for another predetermined duration of time. Finally, the vapor delivery is aborted allowing the pressure to return to the baseline pressure 1052. In some embodiments, the pressure $P_1$ is comparable to or approximately equal to a sum of $P_2$ and $P_3$.

Figure 10P:
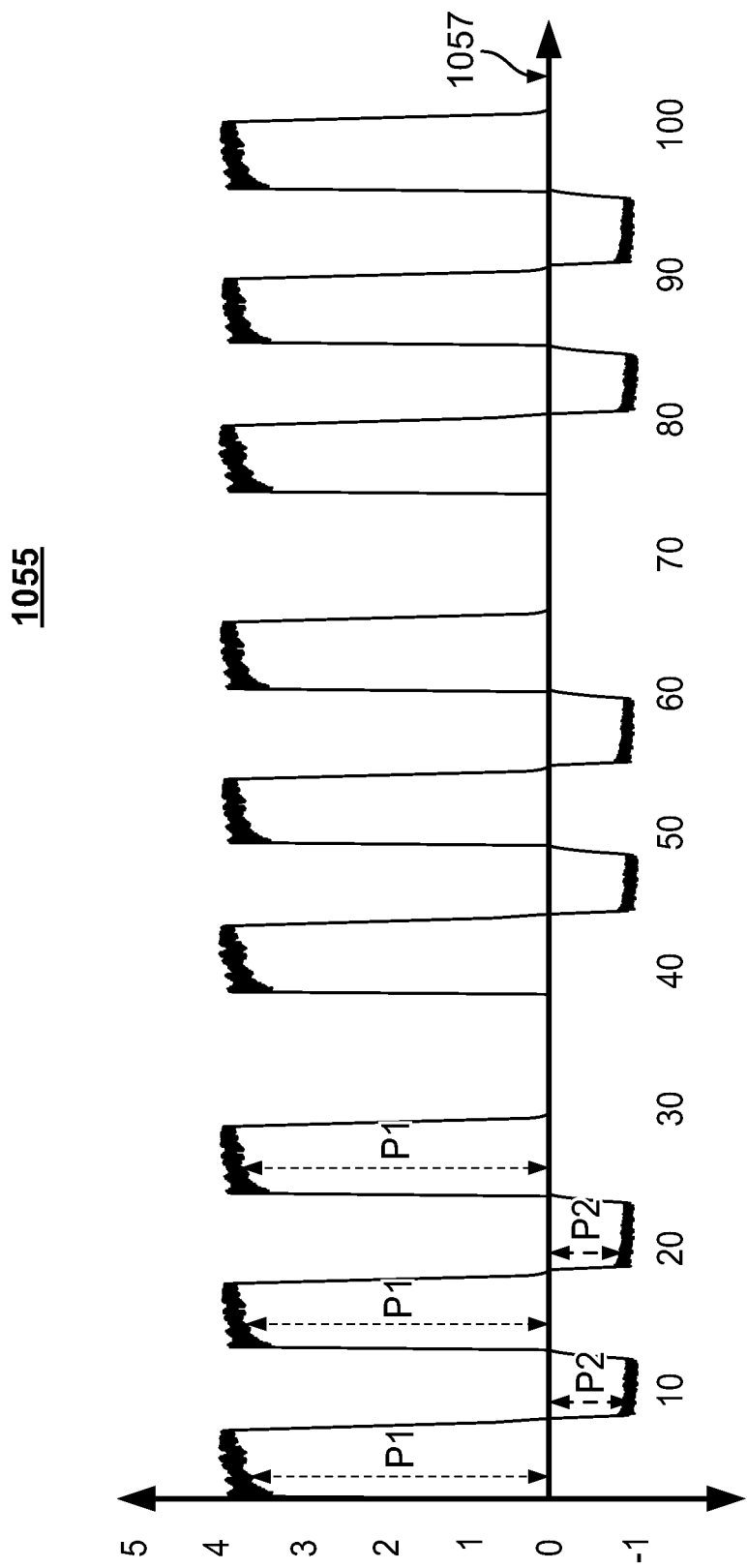
FIG. 10P illustrates a plurality of cycles of a seventh pressure profile, in accordance with an embodiment of the present specification.

FIG. 10P illustrates a plurality of cycles of a pressure profile 1055 wherein for each cycle the vapor is delivered to a pressure $P_1$ for a predetermined duration of time. Next, the vapor delivery is aborted and the pressure is allowed to decrease to a pressure $P_2$, below baseline 1057 for another predetermined duration of time. Now, the vapor delivery is reinitiated and delivered to the pressure $P_1$ for another predetermined duration of time. Next, the vapor delivery is aborted and the pressure is allowed to decrease to the pressure $P_2$, below baseline 1057 for another predetermined duration of time. Thereafter, the vapor delivery is reinitiated and delivered to the pressure $P_1$ for another predetermined duration of time. Finally, the vapor delivery is aborted allowing the pressure to return to the baseline pressure 1057. In some embodiments, the pressure $P_1$ is substantially greater than the pressure $P_2$.

Figure 11A:
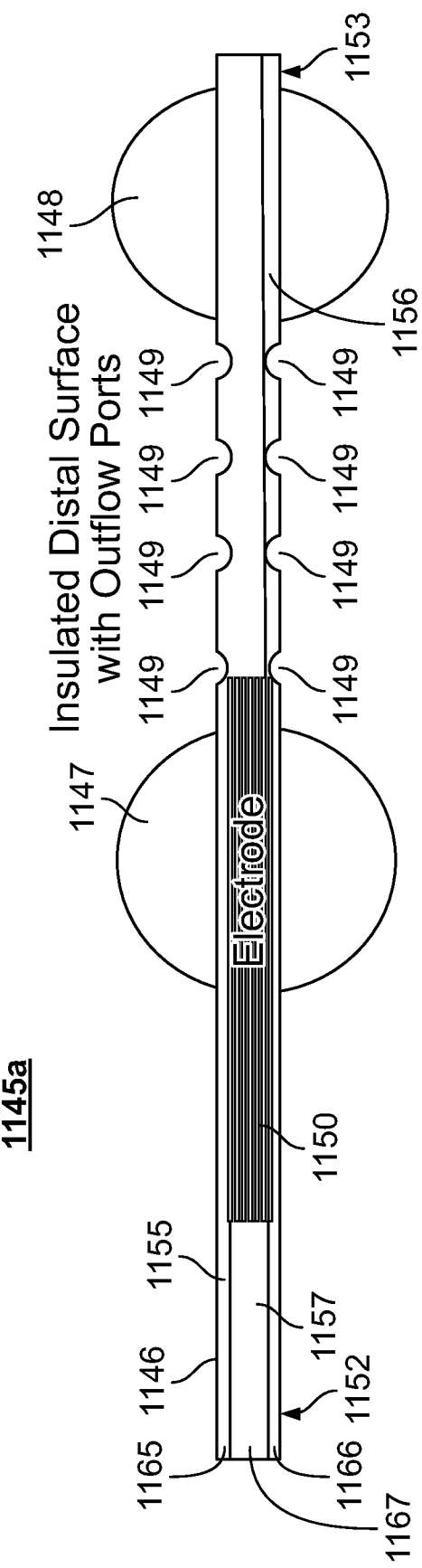
FIG. 11A illustrates a single lumen double balloon catheter comprising an in-line heating element, in accordance with an embodiment of the present specification.
Figure 11B:
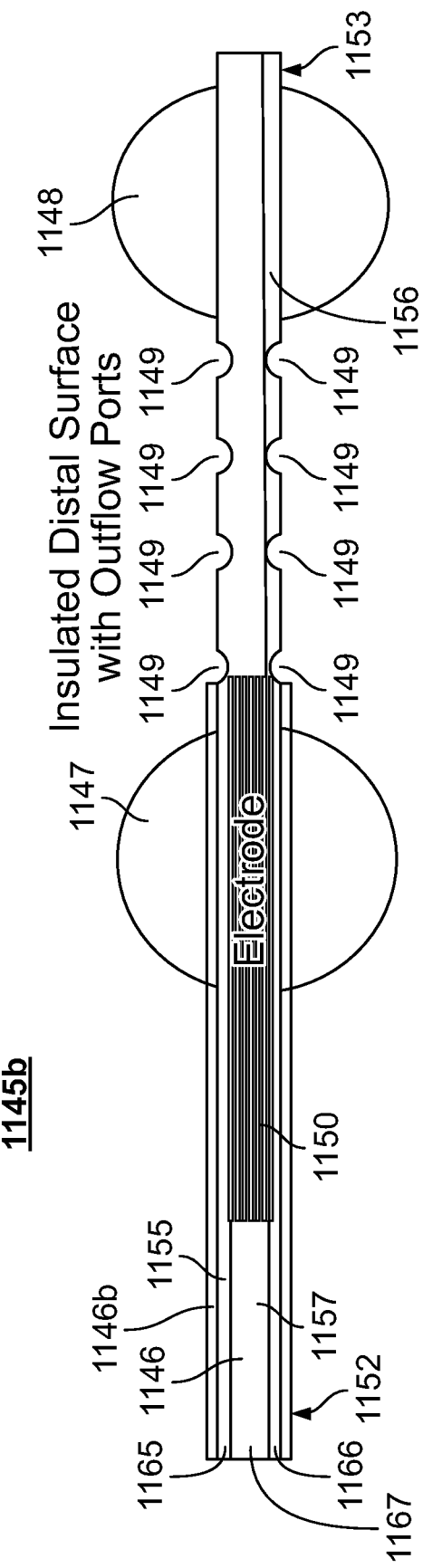
FIG. 11B illustrates a coaxial lumen double balloon catheter comprising an in-line heating element, in accordance with an embodiment of the present specification.

FIGS. 11A and 11B illustrate single and coaxial double balloon catheters 1145a, 1145b in accordance with embodiments of the present specification. The catheters 1145a, 1145b include an elongate body 1146 with a proximal end 11511 and a distal end 1153 and a first lumen 1155, a second lumen 1156, and a third lumen 1157 within. In an embodiment, the elongate body 1146 is insulated. The catheters 1145a, 1145b include at least one positioning element 1148 proximate their distal end 1153. In various embodiments, the positioning element is an inflatable balloon. In some embodiments, the catheters include more than one positioning element. As shown in FIG. 11B, the coaxial catheter 1145b includes an outer catheter 1146b that accommodates the elongate body 1146.

In the embodiments depicted in FIGS. 11A, 11B, the catheters 1145a, 1145b include a proximal first inflatable balloon 1147 and a distal second inflatable balloon 1148 positioned proximate the distal end of the body 1146 with a plurality of infusion ports 1149 located on the body 1146 between the two balloons 1147, 1148. It should be appreciated that, while balloons are preferred, other positioning elements, as previously described, may be used.

The body 1146 includes a first lumen 1155 (extending along a portion of the entire length of the body 1146) in fluid communication with a first input port 1165 at the proximal end 11511 of the catheter body 1146 and with said proximal first balloon 1147 to inflate or deflate the proximal first balloons 1147, 1148 by supplying or suctioning air through the first lumen 1155. In an embodiment, use of a two-balloon catheter as shown in FIGS. 11A and 11B results in the creation of a seal and formation of a treatment area having a radius of 3 cm, a length of 9 cm, a surface area of 169.56 cm2 and a treatment volume of 254.34 cm3. The body 1146 includes a second lumen 1156 (extending along the entire length of the body 1146) in fluid communication with a second input port 1166 at the proximal end 1152 of the catheter body 1146 and with said distal second balloon 1148 to inflate or deflate the distal second balloon 1148 by supplying or suctioning air through the second lumen 1156. In another embodiment, the body includes only a first lumen for in fluid communication with the proximal end of the catheters and the first and second balloons for inflating and deflating said balloons. The body 1146 also includes an in-line heating element 1150 placed within a second third lumen 1157 (extending along the length of the body 1146) in fluid communication with a third input port 1167 at the proximal end 1152 of the catheter body 1146 and with said infusion ports 1149. In one embodiment, the heating element 1150 is positioned within the third lumen 1157, proximate and just proximal to the infusion ports 1149. In an embodiment, the heating element 1150 comprises a plurality of electrodes. In one embodiment, the electrodes of the heating element 1150 are folded back and forth to increase a surface contact area of the electrodes with a liquid supplied to the third lumen 1157. The second third lumen 1157 serves to supply a liquid, such as water/saline, to the heating element 1150.

In various embodiments, a distance of the heating element 1150 from a nearest port 1149 ranges from 1 mm to 50 cm depending upon a type of therapy procedure to be performed.

A fluid pump, an air pump and an RF generator are coupled to the proximate end of the body 1146. The air pump propels air via said first and second inputs 1165, 1166 through the first and second lumens to inflate the balloons 1147, 1148 so that the catheters 1145a, 1145b are held in position for an ablation treatment. The fluid pump pumps a liquid, such as water/saline, via said third input 1167 through the second third lumen 1157 to the heating element 1150. The RF generator supplies power an electrical current to the electrodes of the heating element 1150, thereby causing the electrodes to heat and converting the liquid (flowing through around the heating element 1150) into vapor. The generated vapor exits the ports 1149 for ablative treatment of target tissue. In embodiments, the supply of liquid and electrical current, and therefore delivery of vapor, is controlled by a microprocessor.

Figure 11C:
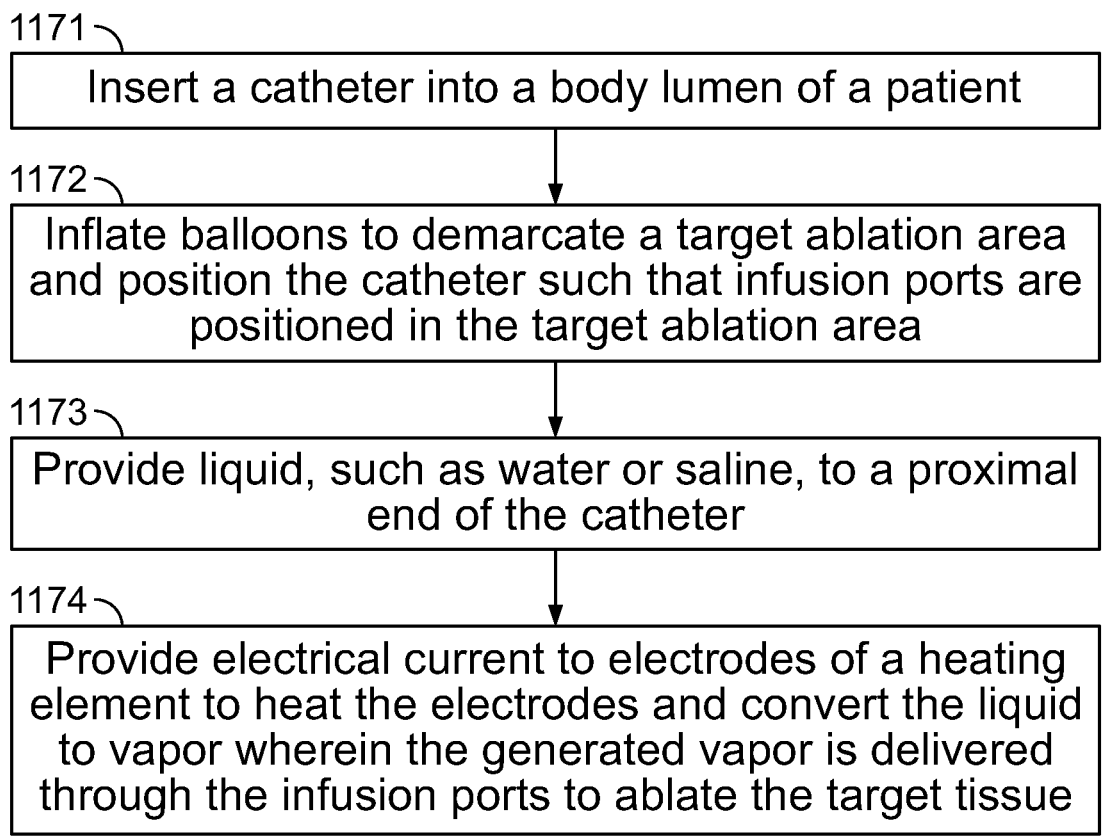
FIG. 11C is a flow chart of a plurality of steps of using the catheter of FIG. 11A to perform ablation in a body lumen, such as Barrett's esophagus of a patient, in accordance with an embodiment of the present specification.

FIG. 11C is a flow chart of a plurality of steps of using the catheters 1145a, 1145b to perform ablation in a body lumen, such as in Barrett's esophagus of a patient, in accordance with an embodiment of the present specification. At step 1171, insert the catheters 1145a, 1145b into a body lumen. In one embodiment, the body lumen is an esophagus of a patient. At step 1172, inflate the balloons 1147, 1148 to demarcate a target ablation area, such as Barrett's esophagus, and position the catheters 1145a, 1145b such that the infusion ports 1149 are positioned in the target ablation area, such as in a portion of Barrett's esophagus. At step 1173, provide liquid, such as water or saline, to a proximal end of the catheters 1145a, 1145b. Finally, at step 1174, provide electrical current to the electrodes of the heating element 1150 to heat the electrodes and convert the liquid to vapor wherein the generated vapor is delivered through the infusion ports 1149 to ablate the target tissue, such as Barrett's esophagus of the patient. In various embodiments, steps 1173 and 1174 are performed simultaneously or step 1174 is performed prior to step 1173.

Figure 12A:
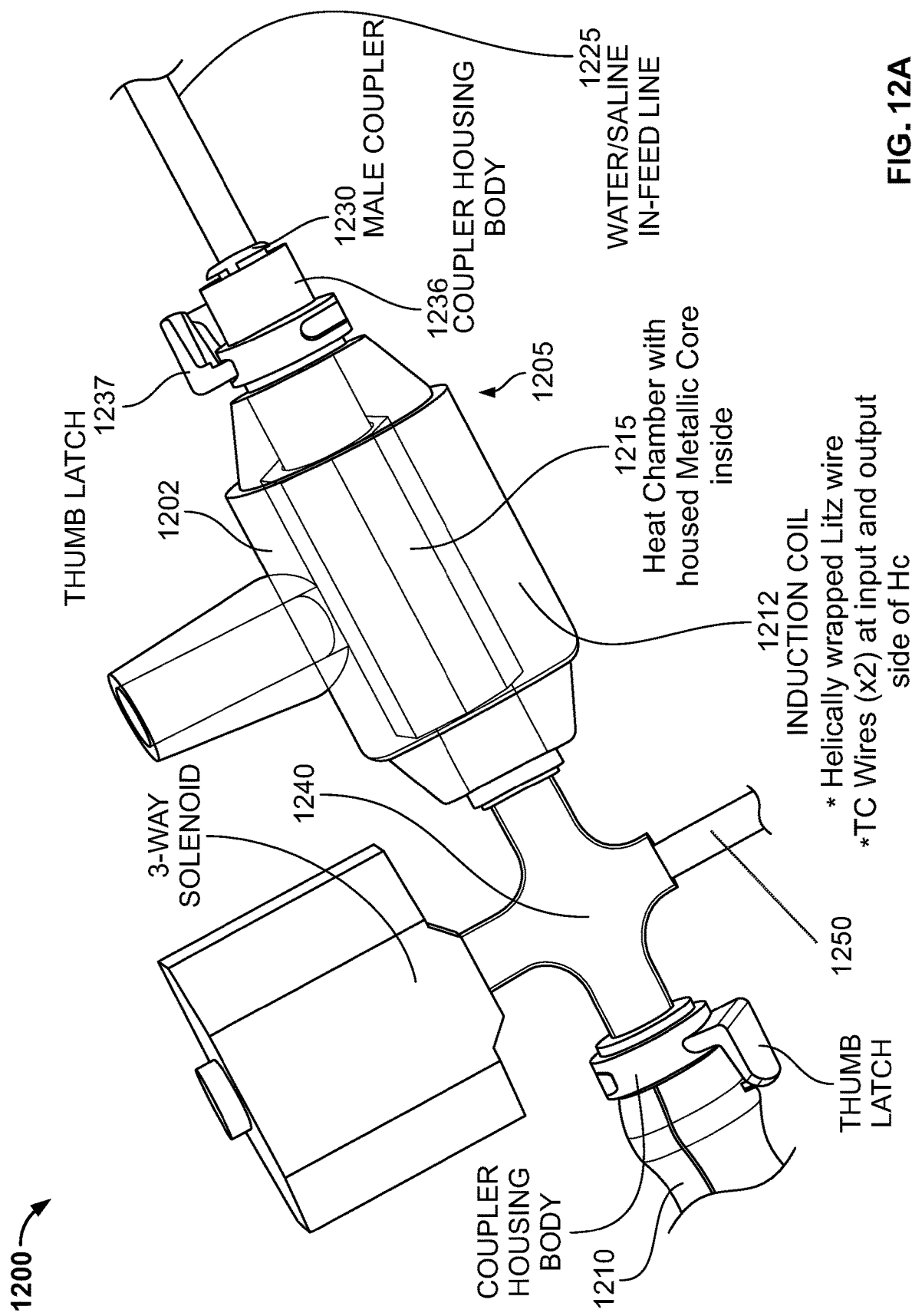
FIG. 12A is an assembled schematic view of a vapor generation system, in accordance with an embodiment of the present specification.
Figure 12B:
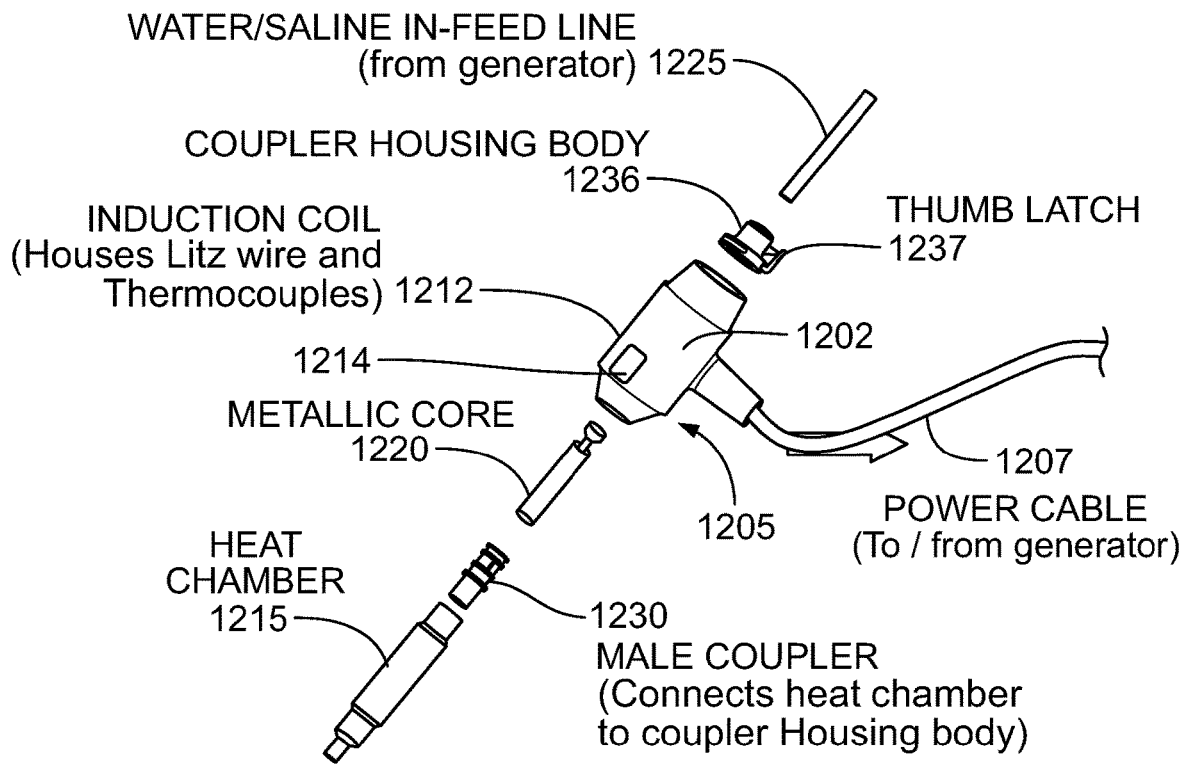
FIG. 12B is an exploded view of components upstream to an induction heating unit of the vapor generation system of FIG. 12A.
Figure 12C:
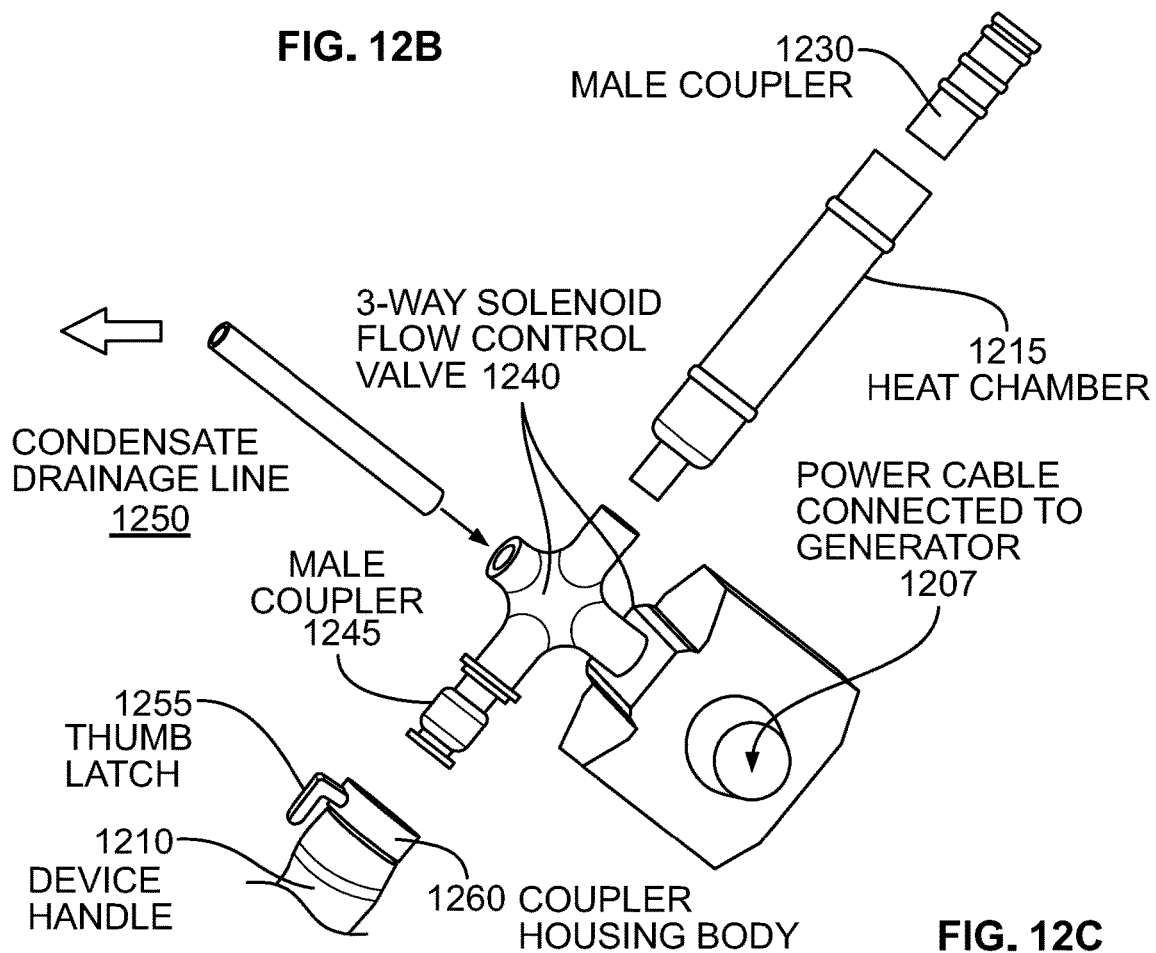
FIG. 12C is an exploded view of components downstream to the induction heating unit of the vapor generation system of FIG. 12A.

FIG. 12A is an assembled schematic view of a vapor generation system 1200 comprising an induction heating unit 1205 coupled or attached fluidically in-series (or in-line) with, and at a proximal end of, a catheter handle 1210, in accordance with an embodiment of the present specification, while FIGS. 12B and 12C are exploded views of components upstream and downstream to the induction heating unit 1205. Referring to FIGS. 12A, 12B and 12C simultaneously, the induction heating unit 1205 includes an induction coil 1212 surrounding a heating chamber 1215 that, in turn, houses a metallic or ferromagnetic core 1220 within. In embodiments, the induction coil 1212 comprises Litz electromagnetic conducing wire wound in a tight helical fashion. A power cable 1207 extends from the induction coil 1212 to a power generator. The induction coil 1212 is positioned in a thermally insulated external "soft skin" housing 1202. In embodiments, the housing 1202 is a thermally stable, over molded component consisting of low to medium durometer thermoplastic elastomer material such as Kraton®. Optionally, the induction heating unit 1205 further comprises at least one thermocouple 1214 to measure input and output temperature at the heating chamber 1215.

In embodiments, the heating chamber 1215 is manufactured from high temperature resistant materials such as, but not limited to, PEEK (polyetheretherketone) or polysulfone. The core 1220 may be fabricated from conductive metals or alloys such as, but not limited to, carbon steel, stainless steel or other ferro-magnetic materials such as Mu-metal (soft magnetic alloy with high Nickel/Iron content for high permeability and efficient electromagnetic conductance). Composition of an exemplary Mu metal may approximately be 77% nickel, 16% iron, 5% copper and 2% chromium or molybdenum.

The induction heating unit 1205 is reusable and securely locks onto the heating chamber 1215. In some embodiments, the induction heating unit 1205 snap fits over the heating chamber 1215. In some embodiments, the heating chamber 1215 incorporates male détentes on its outer surface which lock onto female détentes on an internal surface of the housing 1202. In this way, the induction heating unit 1205 positively locks over the heating chamber 1215, insulating the operator from the heat affected zone during ablation. In accordance with aspects of the present specification, once loaded over the heating chamber 1215, the induction heating unit 1205 can be rotated, about its longitudinal axis, based on operator preference, to ensure that the workspace around a catheter, associated with the catheter handle 1210, is clutter-free.

The core 1220 located inside the heating chamber 1215 serves as a heating element to convert saline/water, received through a saline/water in-feed tube 1225 at a proximal end of the induction heating unit 1205, to steam once electricity is passed through the induction coil 1212. The saline/water in-feed tube 1225 tracks from a disposable pump head and incorporates a first thumb latch 1237 operated first female coupler housing body 1236 at its distal end. The first female coupler housing body 1236 is configured to lock onto a first male coupler end cap 1230 extending from a proximal portion of the heating chamber 1215.

In embodiments, the core 1220 is solid or tubular. Optionally, the core 1220 may have fenestrations or a helical screw thread on its outer diameter to assist with water to steam conversion. The core 1220 is locked/held inside the heating chamber 1215 via the first male coupler end cap 1230. The first male coupler end cap 1230 connects the heating chamber 1215 to the first female coupler housing body 1236. Once the first male coupler 1230 has been inserted into the first female coupler housing body 1236, a water tight seal is created which prevents water/vapor leakage from the assembly. To de-couple the first male and female coupler parts, the first thumb latch 1237 is depressed and the parts are axially separated. The first male coupler end cap 1230 is water/steam contacting and is fabricated from a high temp resistant material such as PEEK or polysulfone, for example.

Figure 13A:
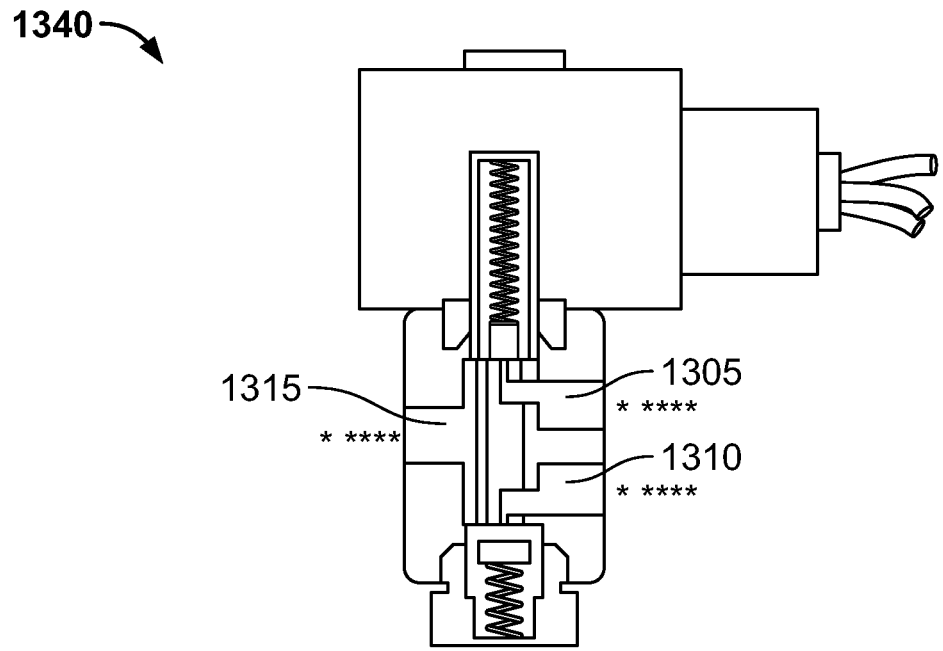
FIG. 13A illustrates a de-energized state of a 3-way flow control solenoid valve.
Figure 13B:
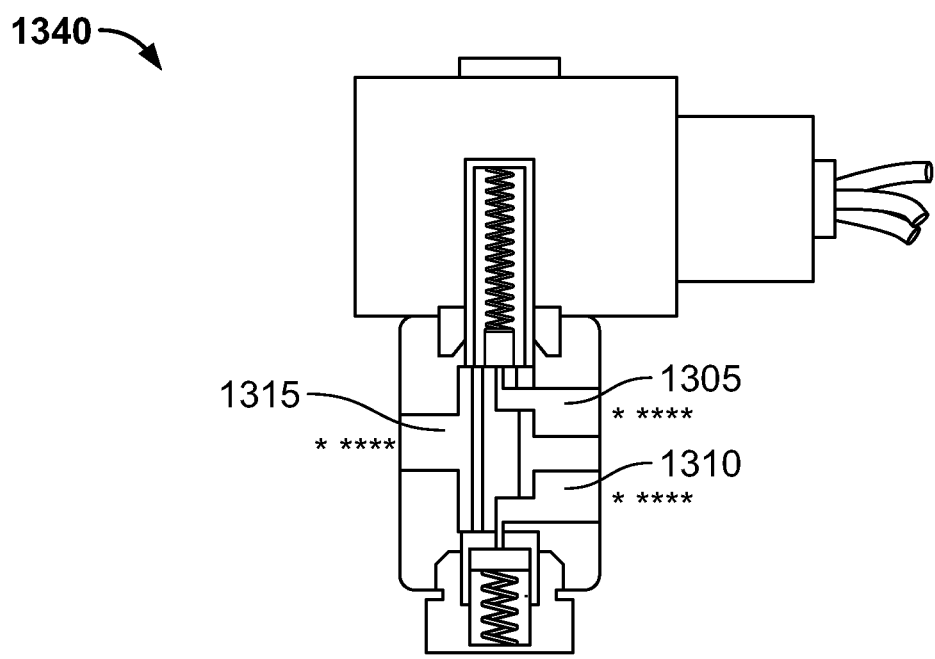
FIG. 13B illustrates an energized state of the 3-way flow control solenoid valve.

As shown in FIGS. 12A and 12C, a 3-way flow control valve 1240, such as a solenoid valve in an embodiment, is located downstream of the induction heating unit 1205 between the heating chamber 1215 and a second male coupler 1245 that connects the induction heating unit 1205 to the catheter handle 1210. FIGS. 13A and 13B respectively illustrate de-energized and energized states of a 3-way flow control solenoid valve 1340 (similar to the valve 740). The valve 1340 enables the following types of flow operations: a) normally closed flow operation—as shown in FIG. 13A, when the valve 1340 is de-energized, a pressure port 1305 is closed and an exhaust port 1310 is connected to a cylinder port 1315. When the valve 1340 is energized, the exhaust port 1310 is closed and the pressure port 1305 is connected to the cylinder port 1315; b) normally open flow operation—as shown in FIG. 13B, when the valve 1340 is de-energized, the pressure port 1305 is connected to the cylinder port 1315 and the exhaust port 1310 is closed. When the valve 1340 is energized, the pressure port 1305 is closed and the cylinder port 1315 is connected to the exhaust port 1310.

Referring back to FIGS. 12A through 12C, at the start of an ablation procedure, as the ablation system 1200 is being set up and "primed" there will be a residual reservoir of water already in the system 1200. This water (or condensate) must be drained from the system 1200 and an amount of high temperature vapor injected to a target ablation site, maximized. To prime the system 1200, the power generator is switched on and a duty cycle activated. Condensate flow is diverted to a condensate drainage line or tube 1250 until such time as only vapor exits this line. Once this occurs, a generator controller will energize the solenoid valve 1240 to an open position (FIG. 13B). In this way, the system 1200 is primed with vapor and drained of condensate, such that only vapor is delivered from the heating chamber 1215 to the catheter.

As shown in FIG. 12C, the second male coupler 1245 connects the valve 1240 to a second thumb latch 1255 operated second female coupler housing body 1260 positioned at a proximal end of the catheter handle 1210. In accordance with aspects of the present specification, the entire induction heating unit 1205 assembly is rotatable around a longitudinal axis of the catheter to ensure that associated power cables and tubing lines can be positioned as desired by the operator.

Figure 14B:
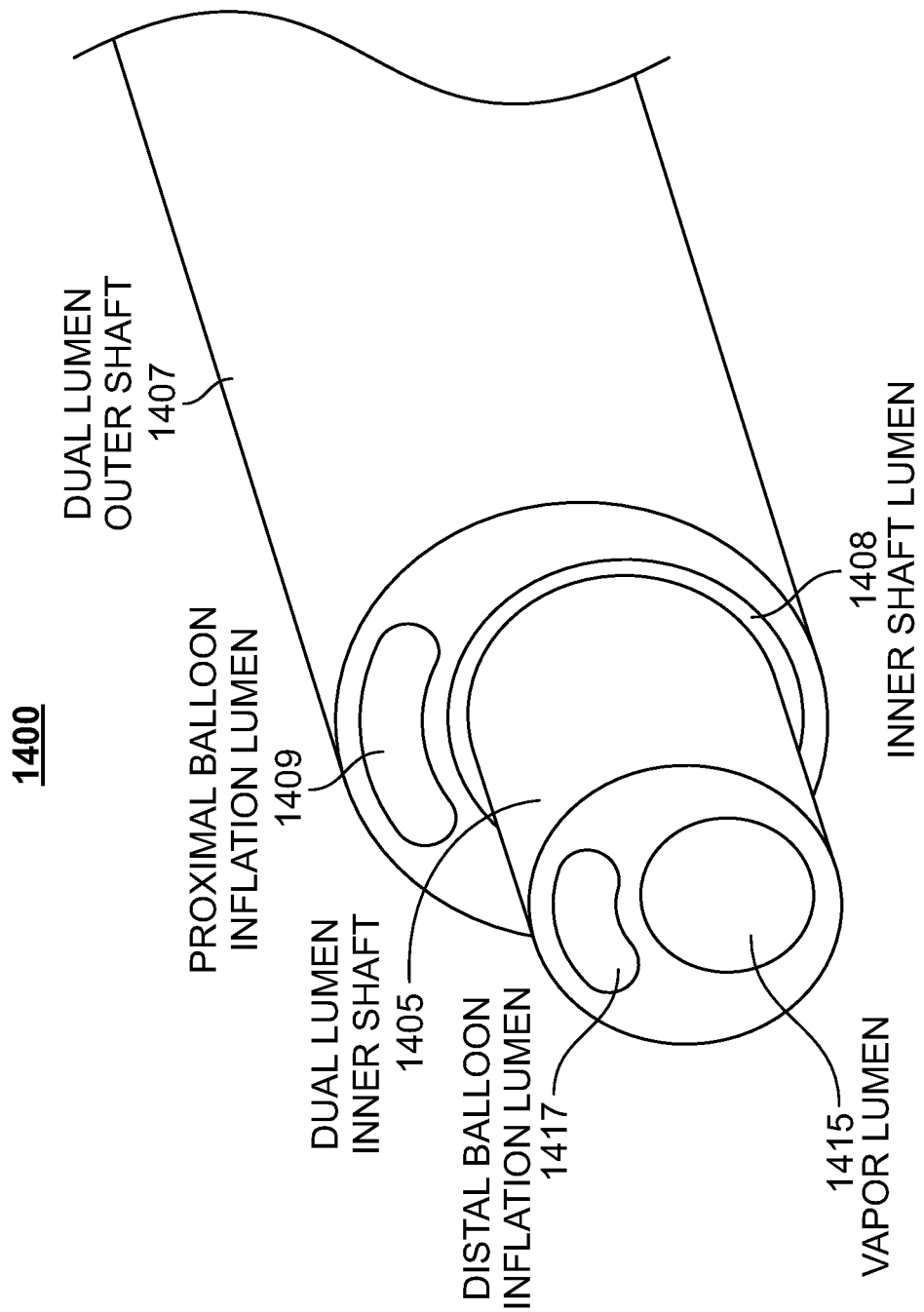
FIG. 14B shows two elongate catheter shafts, in accordance with embodiments of the present specification.

FIG. 14A shows a dual-balloon, dual shaft, multi-lumen catheter system 1400 while FIG. 14B shows two elongate catheter shafts 1405, 1407 for the catheter system 1400, in accordance with embodiments of the present specification. Referring to FIGS. 14A and 14B simultaneously, the catheter system 1400 comprises distal and proximal inflatable anchoring balloons 1410, 1412 that, in one embodiment, are respectively coupled with two different catheter shafts 1405, 1407. The catheter shafts 1405, 1407 are of a multi-lumen construction and are manufactured from polymer material which is capable of maintaining performance under continuous exposure to vapor/steam and temperatures ranging from 110° C. to 120° C., such as PEEK or polysulfone.

The outer shaft 1407 is connected to the proximal balloon 1412 while the inner shaft 1405 is connected to the distal balloon 1410. The outer shaft 1407 has a first lumen 1408 to accommodate the inner shaft 1405 and a second lumen 1409 to allow inflation fluid (such as air) to flow into the proximal balloon 1412 for inflation or be suctioned for deflation. The inner shaft 1405 telescopes axially within the first lumen 1408. The inner shaft 1405 has a first (vapor) lumen 1415 to enable ablation fluid, such as vapor, to flow through the catheter system 1400 and be released from a plurality of exit ports 1440 located between the distal and proximal balloons 1410, 1412 and a second lumen 1417 to allow inflation fluid (such as air) to flow into the distal balloon 1410 for inflation or be suctioned for deflation. Accordingly, both catheter shafts 1405, 1407 are capable of axial movement independently of each other. In this way, a distance between the distal and proximal balloons 1410, 1412 may be adjusted before or during an ablation procedure, thereby adjusting a length of a coagulation/ablation zone 1420. In some embodiments, the length of the zone 1420 ranges from 4 cm to 6 cm. In some embodiments, the lumens 1409 and 1417 have a "smiley" shaped cross-section. However, in alternate embodiments, the cross-section can be of other shapes such as, but not limited to, circular, square or rectangular.

Once positioned at an appropriate ablation treatment location, the distal and proximal balloons 1410, 1412 are inflated and anchored—such as, for example, against a wall of an esophagus—both distally and proximally. This ensures that a defined, controlled coagulation zone 1420 is achieved prior to the creation and delivery of vapor to the treatment site. In some embodiments, the diameters of both proximal and distal balloons 1410, 1412 are capable of being inflated to cover a range of desired esophageal diameters (ranging between 18 mm to 32 mm) to be treated. Once the balloons have been inflated in position, vapor is generated via the induction heating unit 1205 (FIG. 12A) at a proximal end of the catheter handle 1210 (FIG. 12A) outside a patient and injected through the vapor lumen 1415 of the inner shaft 1405.

Figure 14C:
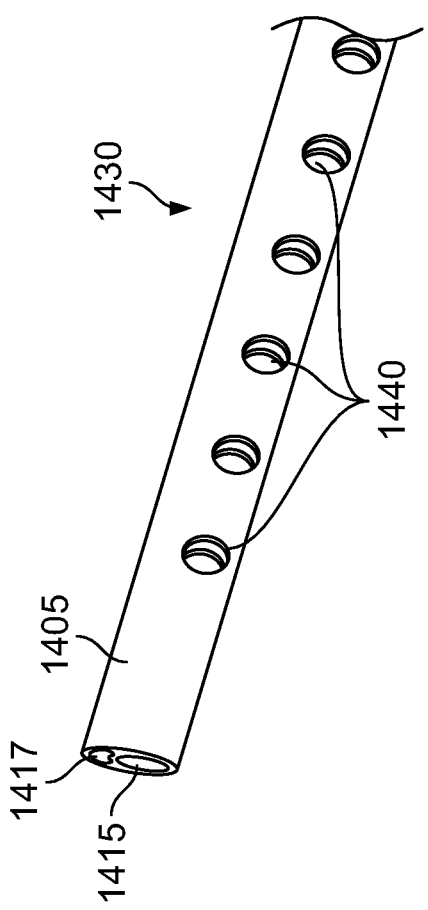
FIG. 14C illustrates a first eyehole pattern, in accordance with embodiments of the present specification.
Figure 14D:
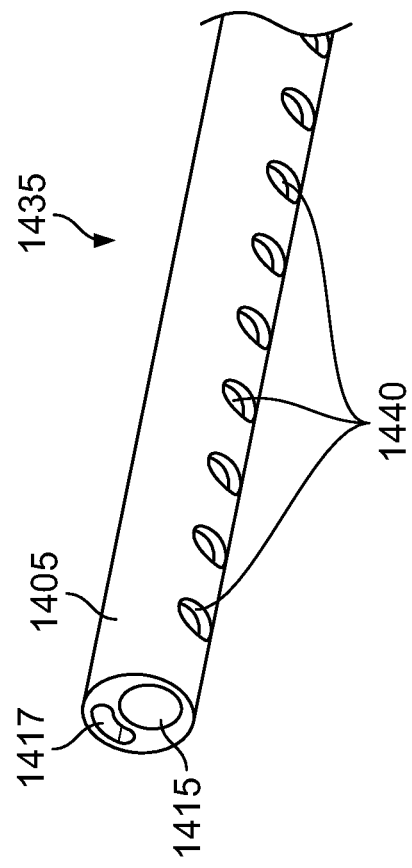
FIG. 14D illustrates a second eyehole pattern, in accordance with embodiments of the present specification.

A portion of the catheter shaft system 1400 between the balloons 1410, 1412 contains a number of eyeholes, configured around the circumference of the shafts 1405, 1407. These eyeholes serve as vapor exit ports 1440. FIGS. 14C and 14D respectively illustrate first and second eyehole patterns 1430, 1435, in accordance with embodiments of the present specification. The first eyeholes pattern 1430 has a plurality of exit ports 1440 formed on both sides of the inner shaft 1405 into the first (vapor) lumen 1415, positioned approximately 90 degrees about a circular axis on either side of the distal balloon inflation lumen 1417, while the second eyeholes pattern 1435 has a plurality of exit ports 1440 on a single side, opposite the distal balloon inflation lumen 1417, of the inner shaft 1405 into the first (vapor) lumen 1415. Vapor is delivered from these ports 1440, contacting and treating diseased tissue encapsulated in the coagulation/ablation zone 1420 demarcated by both balloons 1410, 1412.

Figure 14E:
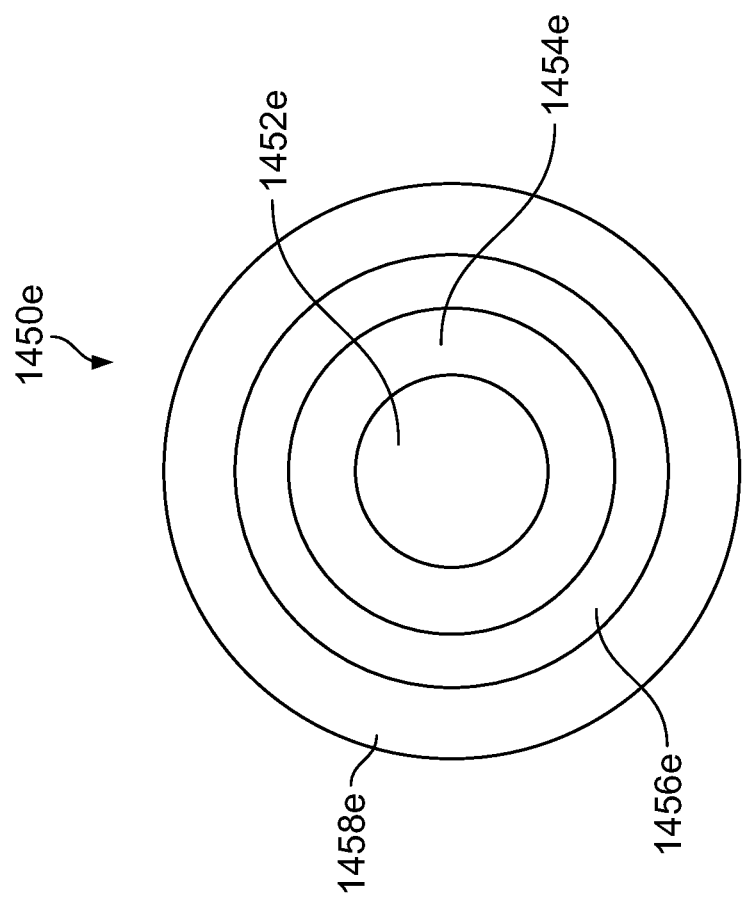
FIG. 14E illustrates a transverse cross-sectional view of a multi-lumen shaft of the catheter system of FIG. 14A, in accordance with an embodiment of the present specification.

FIG. 14E illustrates a transverse cross-sectional view of a multi-lumen shaft 1450e of the catheter system 1400 of FIG. 14A, in accordance with an embodiment of the present specification. The shaft 1450e comprises a first inner most lumen 1452e that allows water/saline to flow therein and also accommodates a heating element, such as the flexible heating chamber (comprising a plurality of electrodes) or an induction heating chamber (comprising an induction coil), a second lumen 1454e provides a pathway for inflation of the distal balloon 1410 or control of a distal positioning element, a third lumen 1456e that is configured as an inner sheath and a fourth lumen 1458e provides a pathway for inflation of the proximal balloon 1412 or control of a proximal positioning element. In embodiments the heating element is positioned substantially close to the plurality of vapor exit ports 1440. In various embodiments, the heating element is positioned not more than 6 inches back from a distal end of the proximal balloon 1412.

Figure 15A:
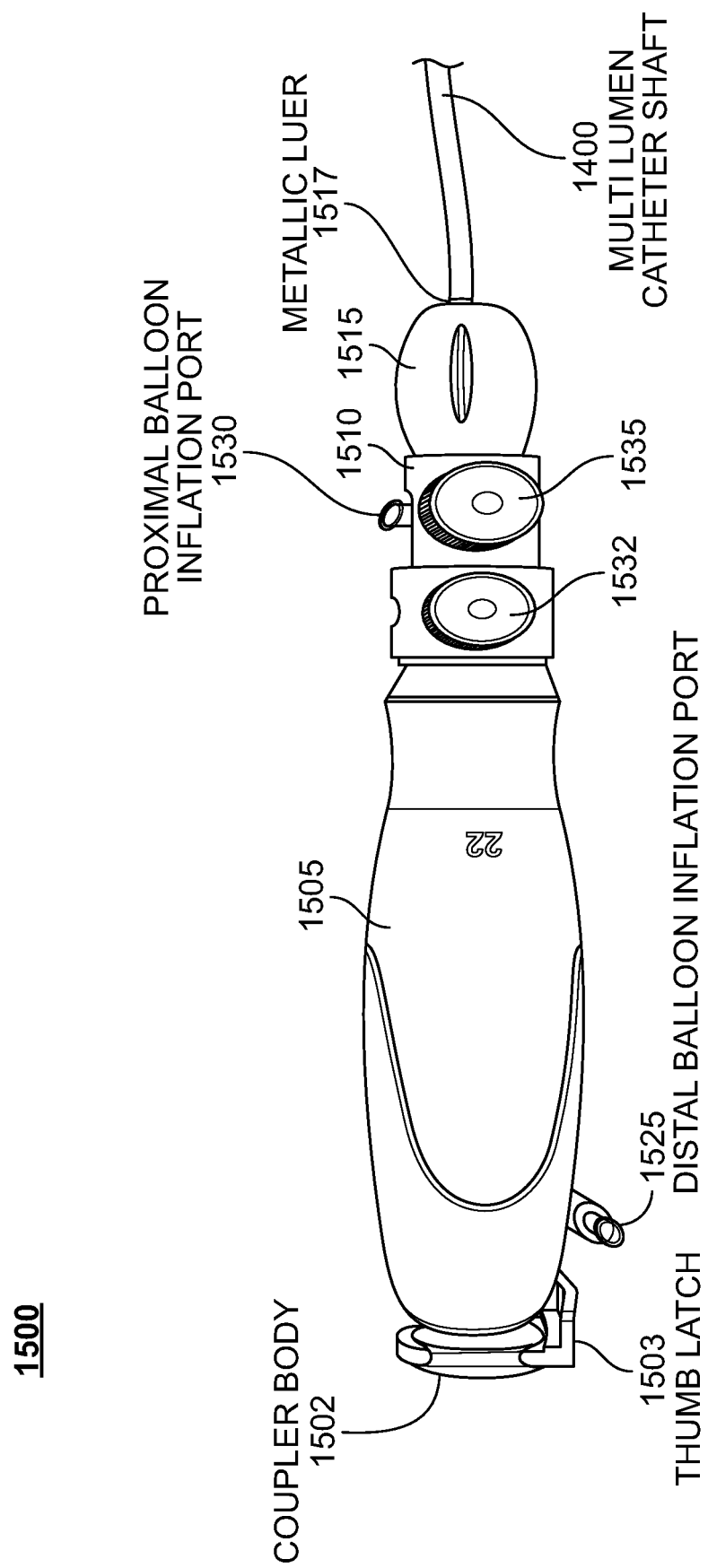
FIG. 15A shows a telescoping catheter handle with a first handle component in a first position relative to a second handle component, in accordance with embodiments of the present specification.
Figure 15B:
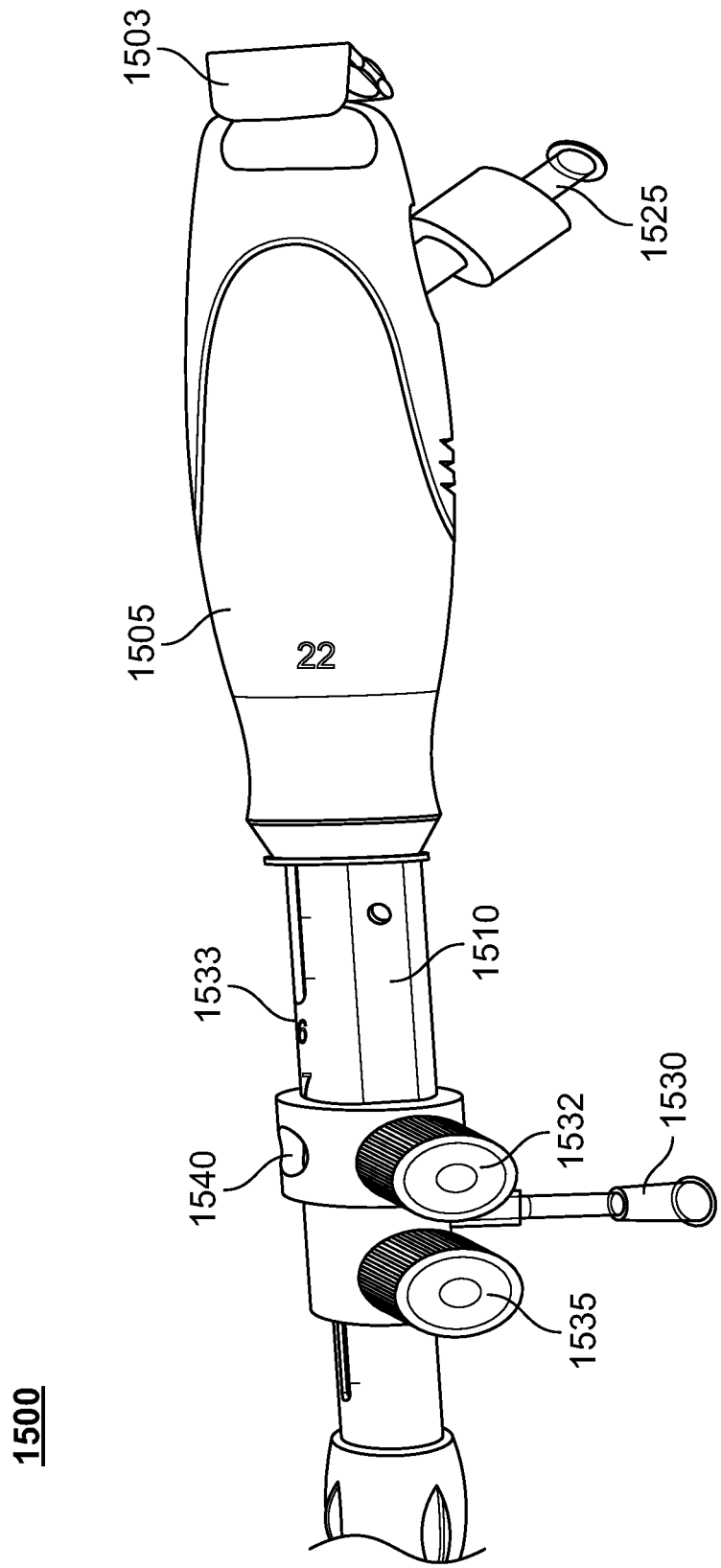
FIG. 15B shows the telescoping catheter handle with the first handle component in a second position relative to the second handle component, in accordance with embodiments of the present specification.

FIGS. 15A and 15B illustrate a telescoping catheter handle 1500 for use with the dual-balloon, dual shaft, multi-lumen catheter system 1400 of FIG. 14A, in accordance with embodiments of the present specification. Referring now to FIGS. 14A, 14B, 15A and 15B simultaneously, the handle 1500 comprises a first handle component 1505 in a first position relative to a second handle component 1510, in accordance with one embodiment of the present specification. In one embodiment, the first handle component 1505 has an elongate body with a proximal end and distal end and comprises a thumb latch 1503 operated female coupler 1502 at the proximal end. In one embodiment, the second handle component 1510 has an elongate body with a proximal end and a distal end. The second handle component 1510 telescopes in and out of the distal end of the first handle component 1505 thereby adjusting the distance between the distal and proximal balloons 1410, 1412. A connector 1515 is included at the distal end of the second handle component 1510 and includes a luer component 1517 (at a distal end of the connector 1515) for attaching the catheter handle 1500 to a working channel port of an endoscope handle. The shaft of the dual-balloon, multi-lumen catheter system 1400 extends beyond the distal end of the second handle component 1510.

A first inlet port 1525 is located at the first handle component 1505 and attached to the inner shaft 1405 to inflate/deflate the distal balloon 1410. A second inlet port 1530 is located at the second handle component 1510 and attached to the outer shaft 1407 to inflate/deflate the proximal balloon 1412. The first handle component 1505 includes a first thumbscrew 1532 to extend the catheter system 1400 beyond the endoscope and the second handle component 1510 includes a second thumbscrew 1535 to adjust a length of the coagulation/ablation zone 1420.

In the first position depicted in FIG. 15A, the first handle component 1505 is positioned most proximally relative to the second handle component 1510. Referring to FIG. 15B, the second handle component 1510 includes a plurality of markings 1533 along its body. In one embodiment, the markings 1533 are numbers. The first handle component 1505 includes a window 1540 proximate its distal end which aligns with one of said markings as the first handle component 1505 is moved longitudinally relative to the second handle component 1510. The marking 1533 in the window 1540 indicates the length of the catheter system 1400 extended beyond a distal end of the working channel of the endoscope and into a body lumen of a patient. FIG. 15B illustrates the catheter handle 1500 with the first handle component 1505 in a second position relative to the second handle component 1510. The marking 1533 in window 1540 indicates to an operator that the first handle component 1505 is in its most distal position relative to the second handle component 1510 and that the catheter system 900 is fully extended within the body lumen of the patient.

Figure 15C:
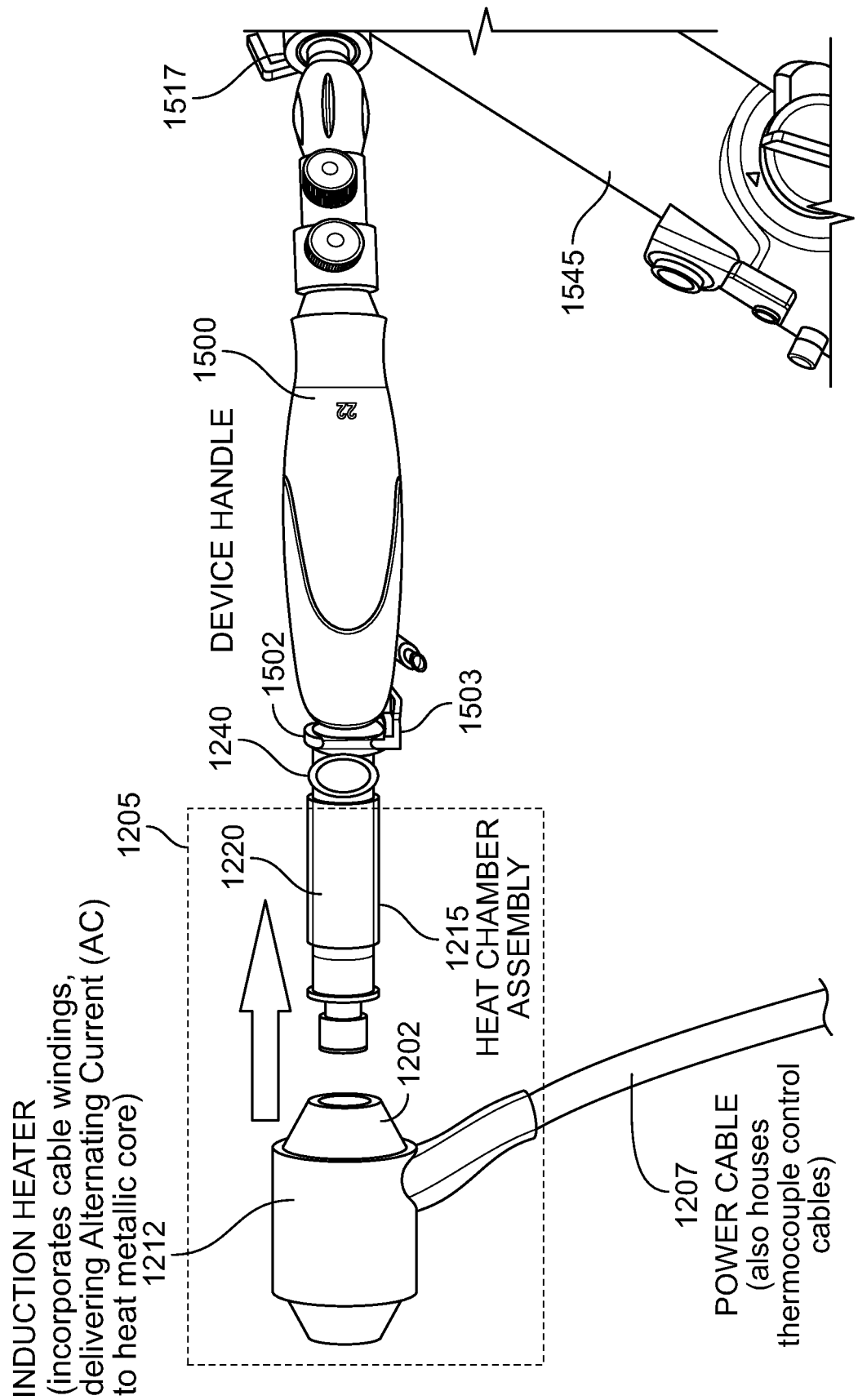
FIG. 15C illustrates an induction heating unit attached in-series with a proximal end of the catheter handle, in accordance with embodiments of the present specification.

Referring now to FIG. 15C along with FIGS. 12A, 12B, 12C, the catheter handle 1500 at its distal end is attached to a working channel port of the endoscope 1545 by means of the luer component 1517 or a latch-type locking mechanism in various embodiments. At its proximal end the catheter handle 1500 is connected to the induction heating unit 1205 through the thumb latch 1503 operated female coupler 1502. FIG. 15C shows a disassembled view of the inducting heating unit 1205 illustrating an assembly of the heating chamber 1215 and the core 1220 over which the housing 1202, comprising the induction coil 1212, is slidably attached. The power cable 1207 extends from the induction coil 1212 to a power generator. The 3-way flow control valve 1240 is also shown positioned between the catheter handle 1500 and the induction heating unit 1205. The thumb latch 1503 operated female coupler 1502 provides the operator with a mechanism to attach/detach the valve 1240 and the assembly of the heating chamber 1215 and the core 1220 from the catheter handle 1500.

Figure 15D:
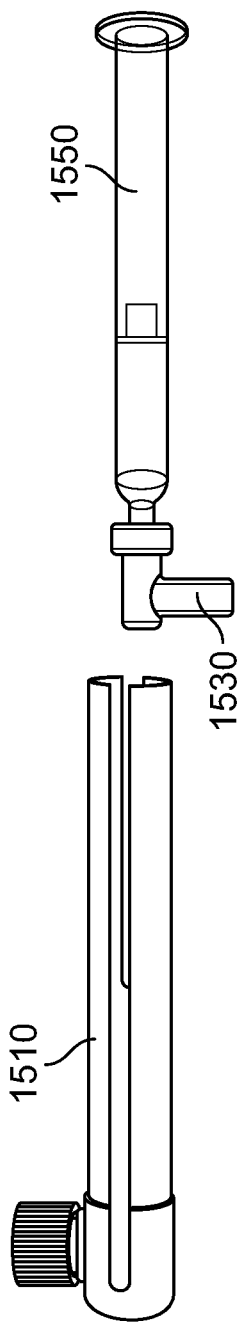
FIG. 15D shows a disassembled view of the second handle component of the catheter handle, in accordance with embodiments of the present specification.
Figure 15F:
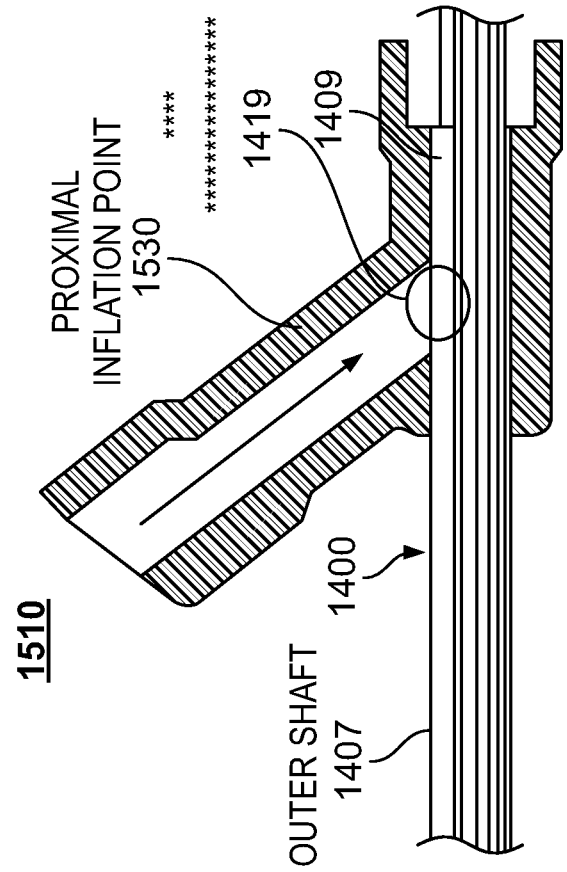
FIG. 15F shows a cross-sectional view of the second handle component of the catheter handle, in accordance with embodiments of the present specification.
Figure 15E:
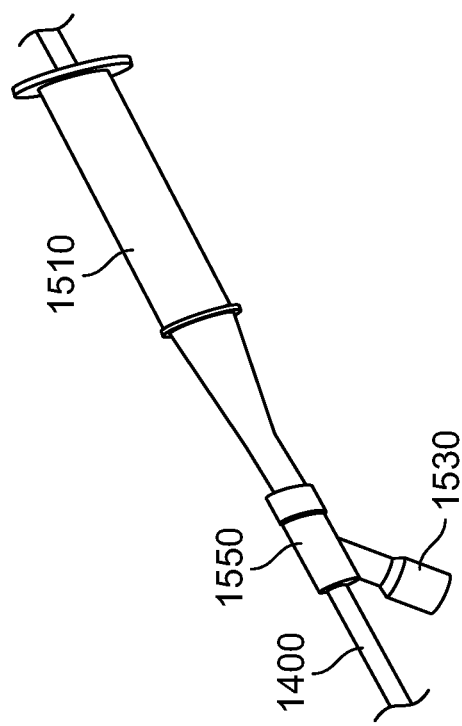
FIG. 15E shows a perspective view of the second handle component separated out from the first handle component of the catheter handle, in accordance with embodiments of the present specification.

FIG. 15D is a disassembled view of the second handle component 1510, FIG. 15E is a perspective view of the second handle component 1510 separated out from the first handle component 1505, while FIG. 15F is a cross-sectional view of the second handle component 1510. Referring now to FIGS. 15D, 15E, 15F along with FIGS. 14A and 14B, the second handle component 1510 houses a tube 1550 that, at its proximal end, is connected to the second inlet port 1530. The catheter system 1400 passes along the second handle component 1510 as shown in FIG. 15E, 15F. The second inlet port 1530 is in fluid communication via a skive 1419 into the second lumen 1409 of the outer shaft 1407 to enable inflation/deflation of the proximal balloon 1412.

Figure 15G:
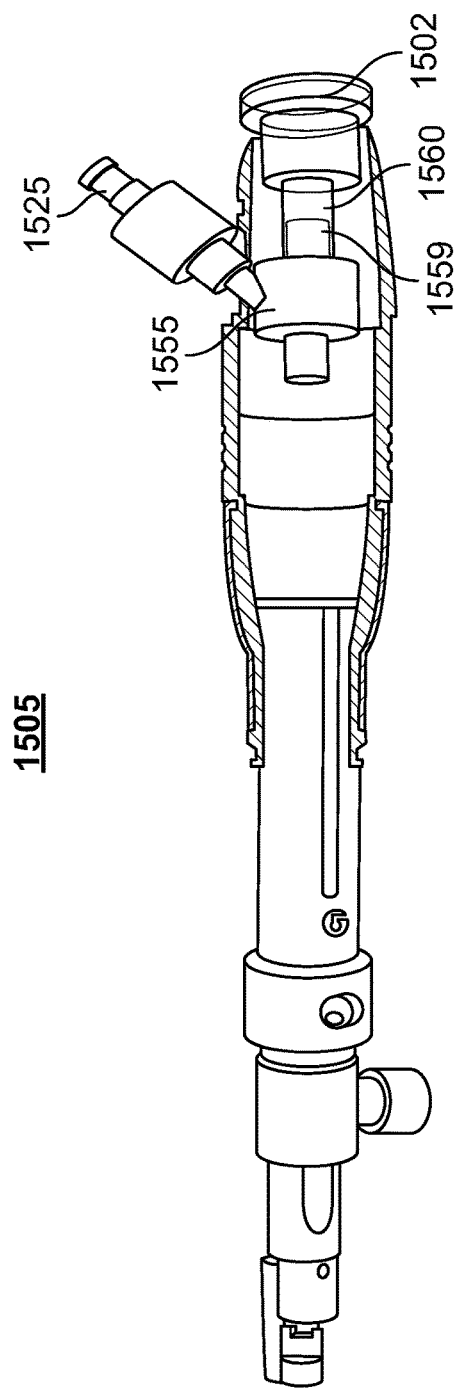
FIG. 15G shows a break-away view of the first handle component of the catheter handle, in accordance with embodiments of the present specification.
Figure 15H:
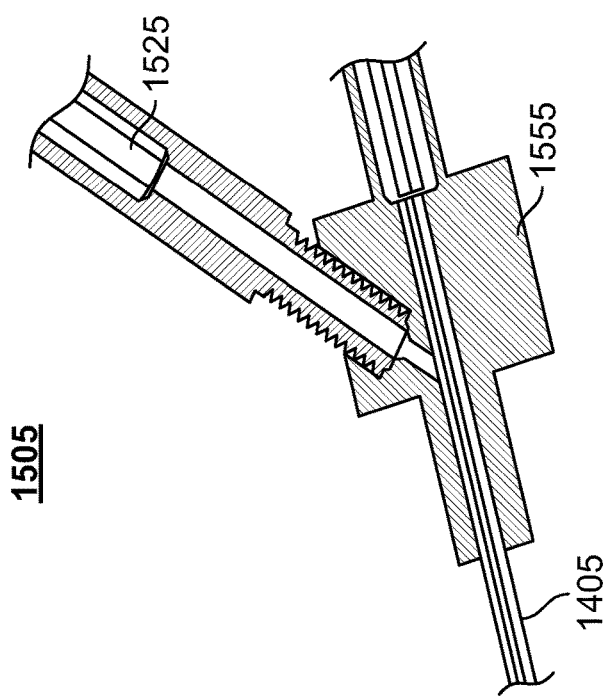
FIG. 15H is a cross-sectional view of the first handle component of the catheter handle, in accordance with embodiments of the present specification.

FIG. 15G is a break-away view of the first handle component 1505 while FIG. 15H is a cross-sectional view of the first handle component 1505. Referring now to FIGS. 15G, 15H along with FIGS. 14A, 14B, the first inlet port 1525 is attached (threaded, in an embodiment) into a manifold 1555 and is in fluid connection with the second lumen 1417 of the inner shaft 1405 to enable inflation/deflation of the distal balloon 1410. The housing 1560 of the female coupler 1502 attaches to a male luer 1559 of the manifold 1555.

Figure 16A:
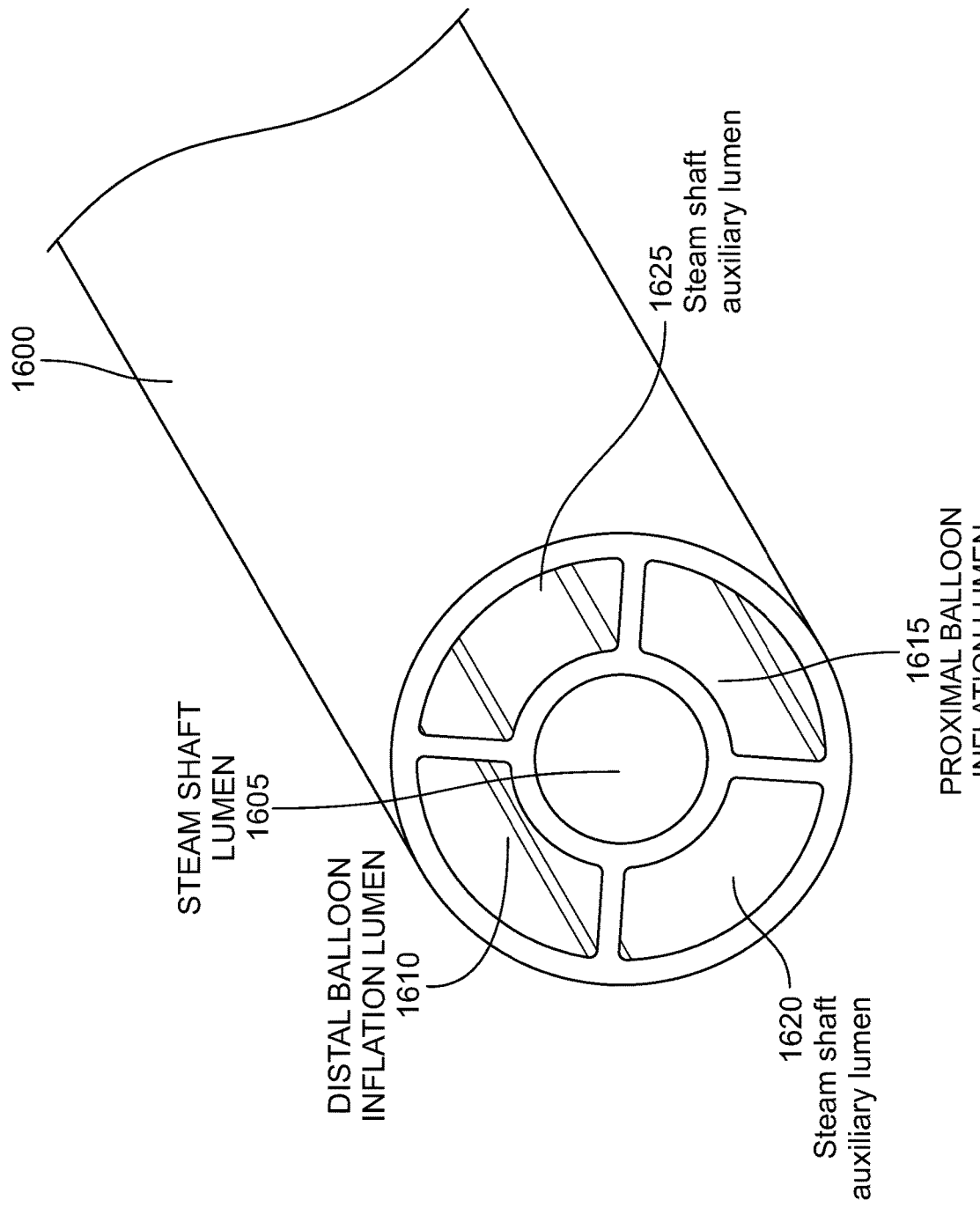
FIG. 16A shows a single multi-lumen shaft, in accordance with embodiments of the present specification.

FIG. 16A shows a single multi-lumen shaft 1600 for the dual-balloon, multi-lumen catheter system 1400 of FIG. 14A, in accordance with embodiments of the present specification. Referring now to FIGS. 16A and 14A simultaneously, the distal and proximal balloons 1410, 1412 are coupled with the single multi-lumen shaft 1600. As a result, a distance between the balloons 1410, 1412 is fixed and thus, a length of the coagulation/ablation zone 1420 is also fixed. A distal portion of the shaft 1600 between the balloons 1410, 1412 contains a number of eyeholes that serve as vapor exit ports 1440.

In accordance with an embodiment, the shaft 1600 includes five lumens and is manufactured from polymer material which is capable of maintaining performance under continuous exposure to vapor/steam and temperatures ranging from 110° C. to 120° C., such as PEEK or polysulfone. A first lumen 1605 allows ablation fluid, such as steam/vapor, to flow therethrough and exit from the vapor exit ports 1440. A second lumen 1610 is in fluid communication with the distal balloon 1410 to enable an inflation fluid, such as air, to flow or be suctioned therethrough for inflation/deflation of the balloon 1410. A third lumen 1615 is in fluid communication with the proximal balloon 1412 to enable the inflation fluid, such as air, to flow or be suctioned therethrough for inflation/deflation of the balloon 1412. Fourth and fifth lumens 1620, 1625 serve as auxiliary lumens for the first (steam) lumen 1605. The fourth and fifth lumens 1620, 1625 are in fluid communication with the first lumen 1605 at a distal portion of the shaft 1600 to allow flow of vapor from the first lumen 1605 through fourth and fifth lumens 1620, 1625 and out exit ports 1440 to ablate target tissue.

FIG. 16B illustrates a pattern of vapor exit ports 1440 at the distal portion of the shaft 1600 in accordance with an embodiment of the present specification. As shown, the vapor exit ports 1440 are arranged on first and second sides 1630, 1635 along a longitudinal axis of the shaft 1600 such that the two sides 1630, 1635 are 180° opposed. As shown in FIGS. 16C, 16D, the steam or vapor lumen 1605 is located in the center of the shaft 1600. To inject vapor from the central steam lumen 1605, the ports 1440 are drilled/laser cut through the outer wall 1640 of the shaft 1600, through the auxiliary lumens 1620, 1625 and through the inner wall 1645 of the steam lumen 1605.

Figure 16E:
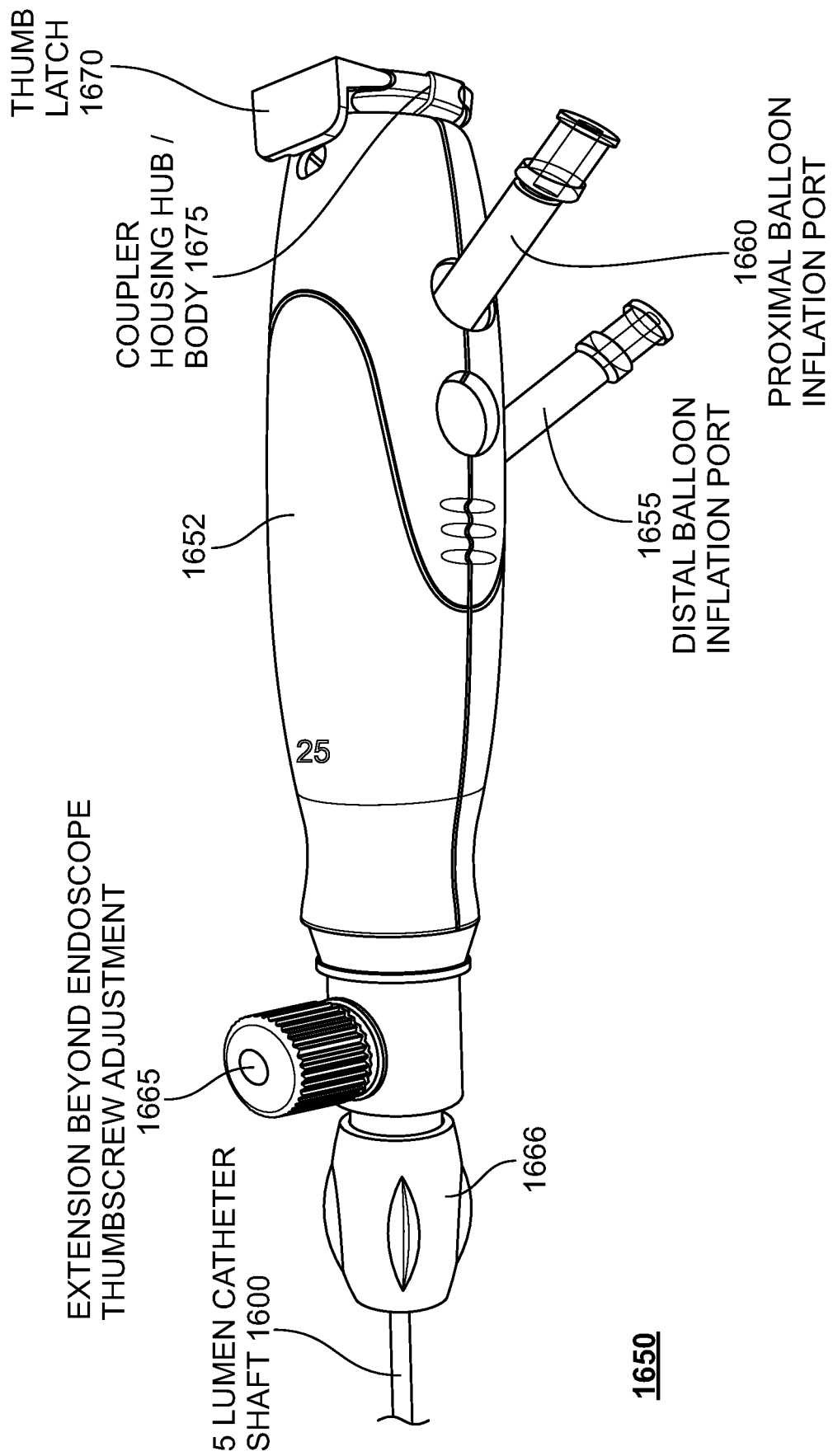
FIG. 16E is a perspective view of a non-telescoping catheter handle, in accordance with embodiments of the present specification.
Figure 16F:
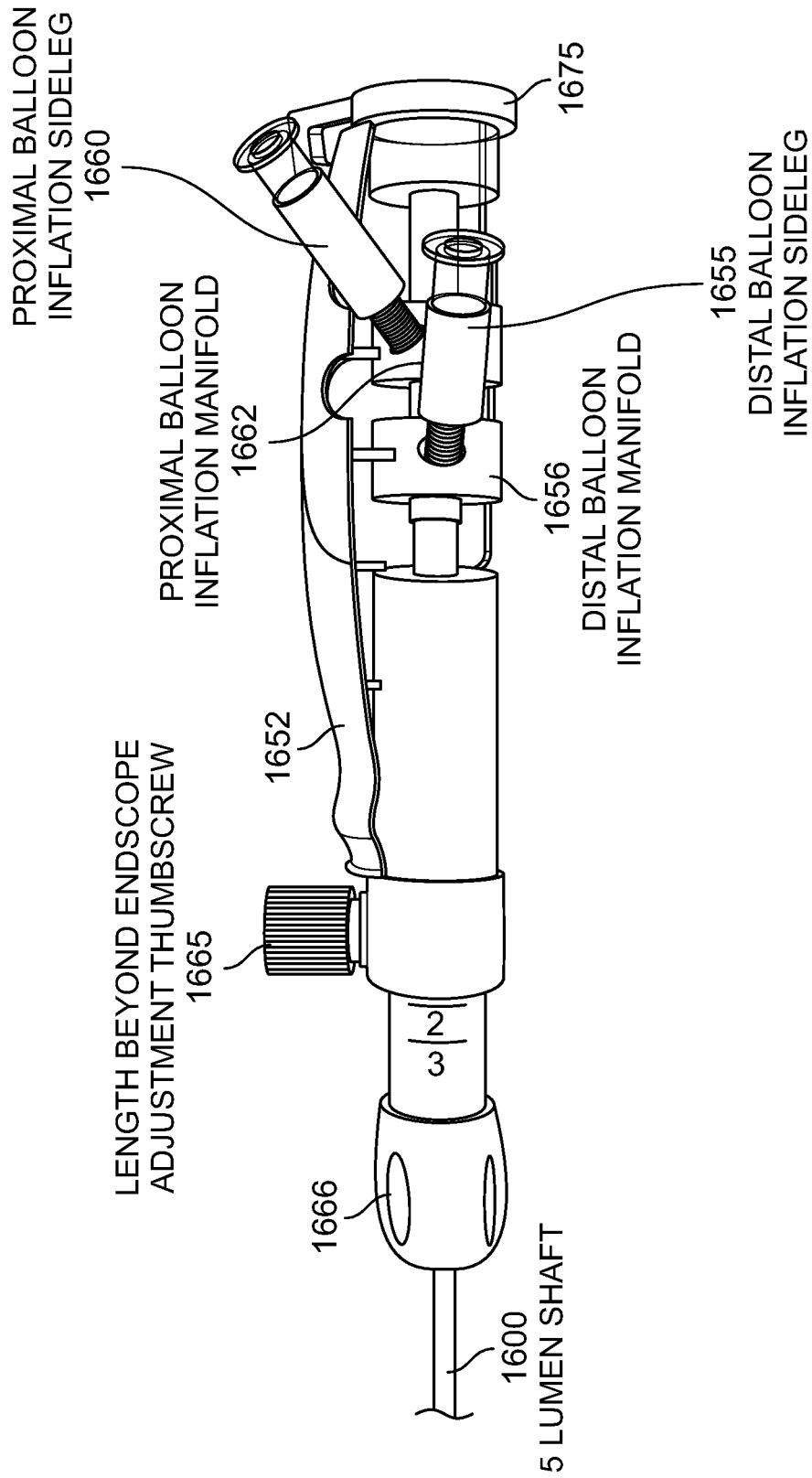
FIG. 16F is a partial break-away view of the non-telescoping catheter handle, in accordance with embodiments of the present specification.

FIGS. 16E and 16F illustrate, respectively, perspective and break-away views of a non-telescopic catheter handle 1650 for use with the single multi-lumen shaft 1600, in accordance with embodiments of the present specification. Referring to FIGS. 16E and 16F along with FIG. 14A, the catheter handle 1650 has an elongate body 1652 comprising: a first inlet port 1655 attached to a first manifold 1656 that holds the port 1655 in fluid communication with the second lumen 1610 to enable inflation/deflation of the distal balloon 1410; and a second inlet port 1660 attached to a second manifold 1662 that holds the port 1660 in fluid communication with the third lumen 1615 to enable inflation/deflation of the proximal balloon 1412. In some embodiments, the first and second manifolds 1656, 1662 are configured to be coupled to the shaft 1600 and fabricated from PEEK/polysulfone. First and second tubing lines (not shown) are respectively connected to the first and second ports 1655, 1660. Proximal ends of both tubing lines are connected to two independent inflation pumps which are housed in a generator. Inflation and deflation (if desired) of both balloons 1410, 1412 is controlled via both lines. In embodiments, both tubing lines are flexible polymer extrusions and are disposable.

A connector 1666 is positioned at a distal end of the body 1652 and a luer component is attached at a distal end of the connector 1666 to enable the handle 1650 to be attached to a working channel port of an endoscope. The catheter shaft 1600 extends beyond the distal end of the connector.

A thumbscrew 1665 is positioned proximate a distal end of the handle 1650 to enable adjustment of the shaft 1600 beyond the endoscope when the handle 1600 is attached to a working channel of the endoscope. A thumb latch 1670 operated female coupler 1675 is positioned at a proximal end of the handle 1650 to enable an induction heating unit (such as the unit 1205) to be attached in-series or in-line to the handle 1650 (similar to as illustrated in FIG. 15C). The second manifold 1662 is fluidically connected to the housing body of the female coupler 1675.

In accordance with aspects of the present specification, it is preferred that the thumbscrew 1665 and the thumb latch 1670 be facing in the same direction so that orientation is towards the operator when the handle 1650 is locked onto the endoscope. It is also preferred that both ports 1655, 1660 are positioned or oriented approximately 90 degrees opposed to the thumb latch 1670 so that they provide favorable ergonomics for the operator and do not interfere with handle 1650 manipulation during an ablation procedure.

Figure 17C:
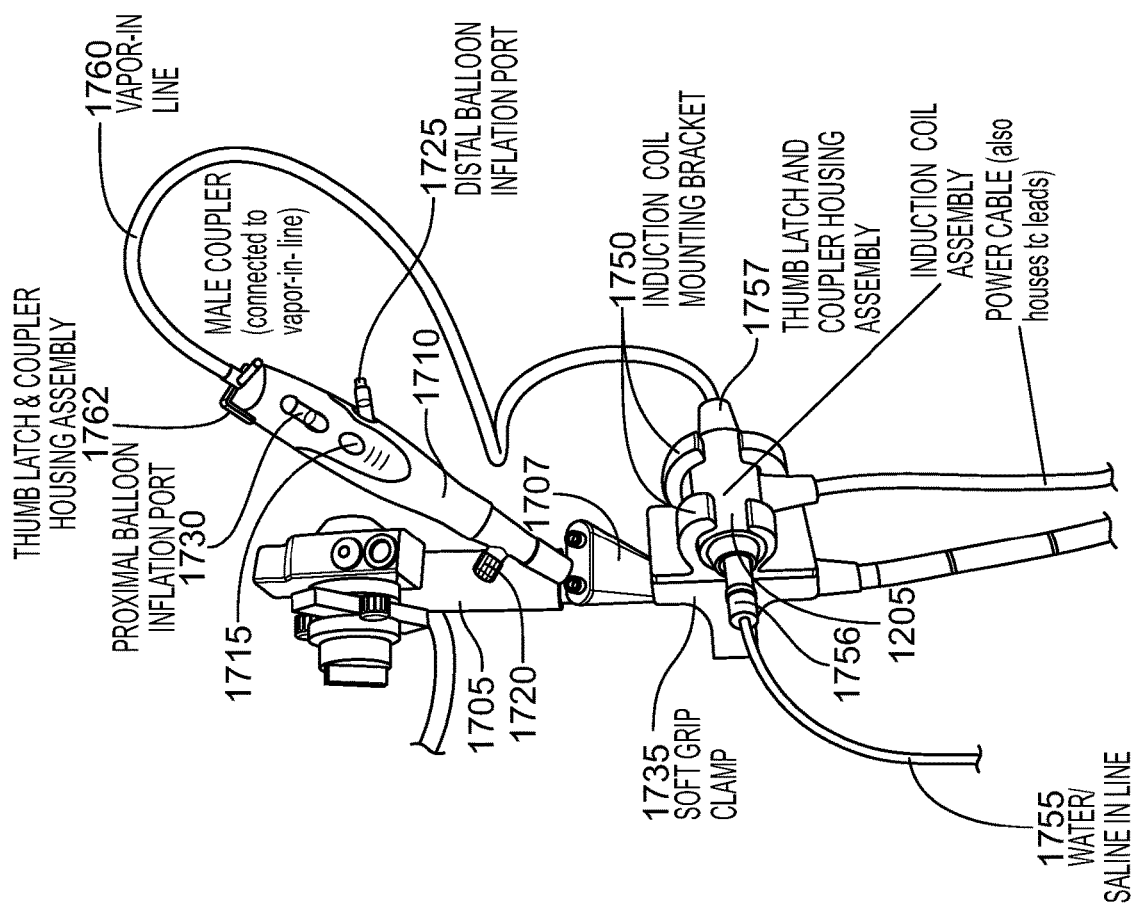
FIG. 17C shows an induction heating unit mounted on an endoscope separately from a catheter handle (also mounted on the endoscope), in accordance with embodiments of the present specification.
Figure 17A:
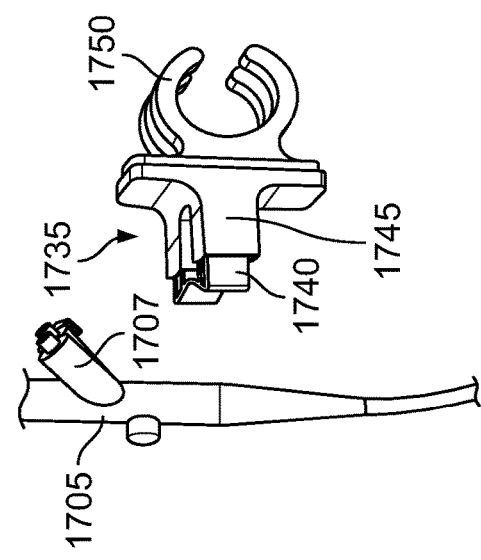
FIG. 17A shows a clamp in accordance with embodiments of the present specification.
Figure 17B:
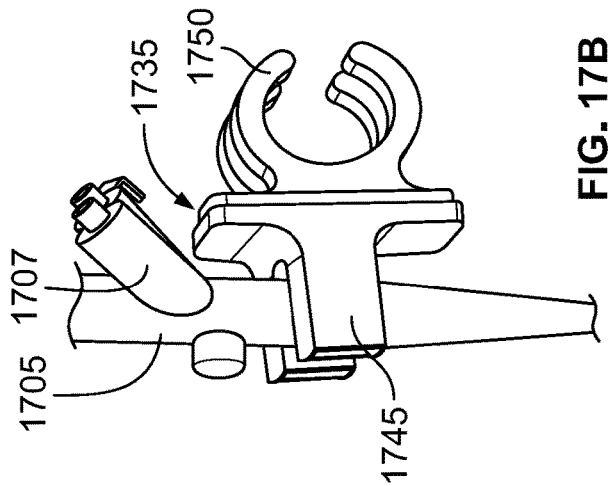
FIG. 17B shows the clamp removably attached to a shaft of an endoscope, in accordance with embodiments of the present specification.

In accordance with an aspect of the present specification, FIG. 17C shows an induction heating unit being removably mounted onto an endoscope, while FIGS. 17A and 17B illustrate perspective views of a clamp in accordance with embodiments of the present specification. Referring now to FIGS. 17A, 17B and 17C along with FIG. 12A, the induction heating unit 1205, comprising an assembly of the heating chamber 1215 (with the core 1220) and the induction coil 1212, is mounted on a body of an endoscope 1705, below a biopsy port bifurcation 1707 on the endoscope 1705. Mounting the induction heating unit 1205 to this location reduces the moment arm and weight on a catheter handle 1710 and moves a number of components away from the immediate handle working space around the thumbscrews 1715, 1720 as well as distal and proximal balloon inflation ports 1725, 1730 for inflation/deflation of distal and proximal balloons of a dual-balloon multi-lumen catheter (such as catheter system 1400 of FIG. 14A). In some embodiments, the catheter handle 1710 is a telescopic handle (such as the handle 1500 of FIG. 15A) while in other embodiments the catheter handle 1710 is a non-telescopic handle (such as the handle 1650 of FIG. 16E).

Figure 17D:
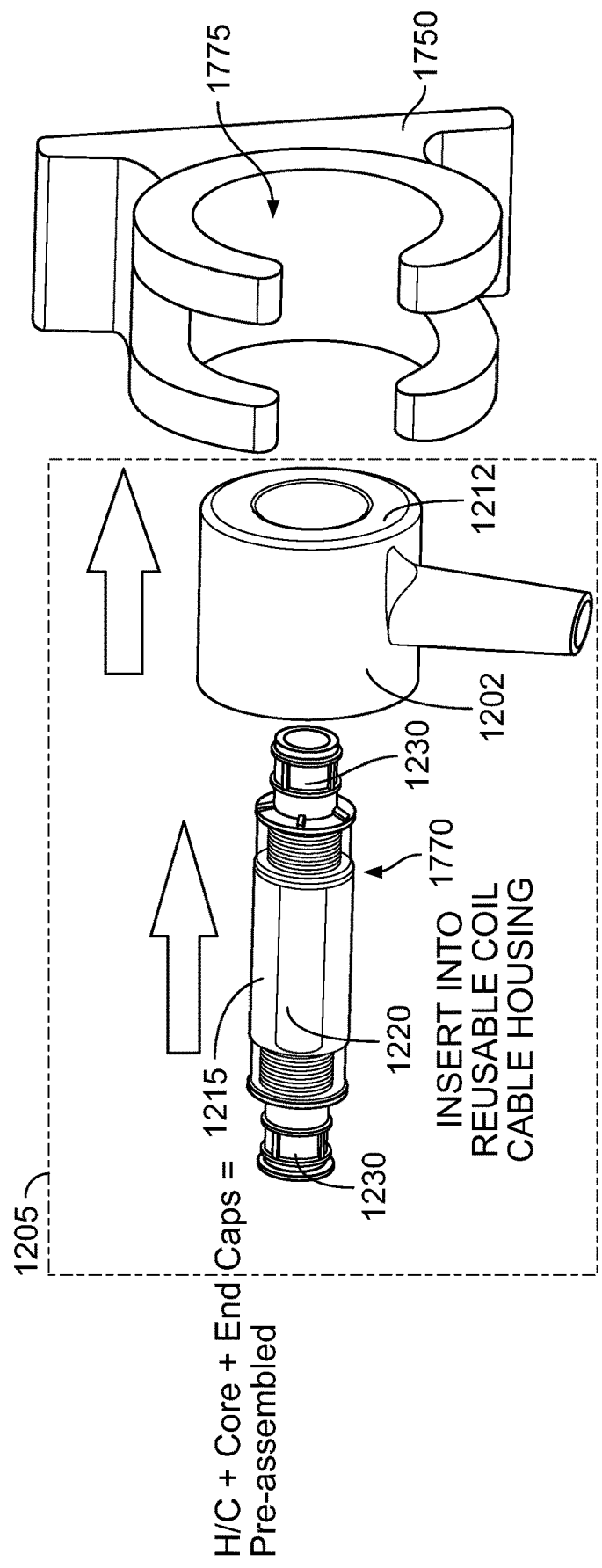
FIG. 17D illustrates an assembly of the induction heating unit being slidably mounted to the clamp of FIG. 17A, in accordance with an embodiment of the present specification

The induction heating unit 1205 is removably attached to a main shaft of the endoscope 1705 using a soft grip clamp 1735. In an embodiment, the clamp 1735 consists of a soft, deformable, rubber grip 1740 attached to a rigid polymeric frame 1745 which incorporates a bracket 1750 to mount the induction heating unit 1205. In an embodiment, the bracket 1750 is configured as a C-clamp. As shown in FIG. 17D, the heating chamber 1215, the core 1220 and the two male coupler end caps 1230 are pre-assembled as a module 1770, in accordance with an embodiment. Next, the module 1770 is slidably inserted into the housing 1202, comprising the induction coil 1212, thereby forming the induction heating unit 1205. Subsequently, the induction heating unit 1205 is slid into an approximately C-shaped space 1775 of the bracket 1750.

Referring back to FIGS. 17A, 17B and 17C, once the induction heating unit 1205 is slidably mounted into the C-clamp the assembly is loaded on to the shaft of the endoscope 1705, below the biopsy port. The deformable nature of the rubber grip 1740 provides a secure attachment to the endoscope 1705. This orientation of the clamp 1735 can be easily adjusted to suit preferred orientation of the induction heating unit 1205 during an ablation procedure. The clamp 1735 may be removed by simply pulling outward on the bracket assembly.

A disposable water/saline tube line 1755 connects to a thumb latch operated female coupler 1756 at a proximal end of the induction heating unit 1205 while a disposable vapor delivery tube line 1760 is connected to the unit 1205 via a thumb latch operate female coupler 1757 at a distal end of the unit 1205 and to the handle 1710 via another thumb latch operated female coupler 1762 at a proximal end of the handle 1710. In various embodiments, the vapor delivery tube line 1760 is made of PEEK, polysulfone, high temperature Nylon, polycarbonate or polyimide material. In some embodiments, this tube may also be braided reinforced to make the tubing more resistant to kinking during the procedure. It should be appreciated that, although not shown in FIG. 17C, a 3-way flow control valve, such as valve 1240, is positioned between the unit 1205 and the handle 1710.

Figure 18:
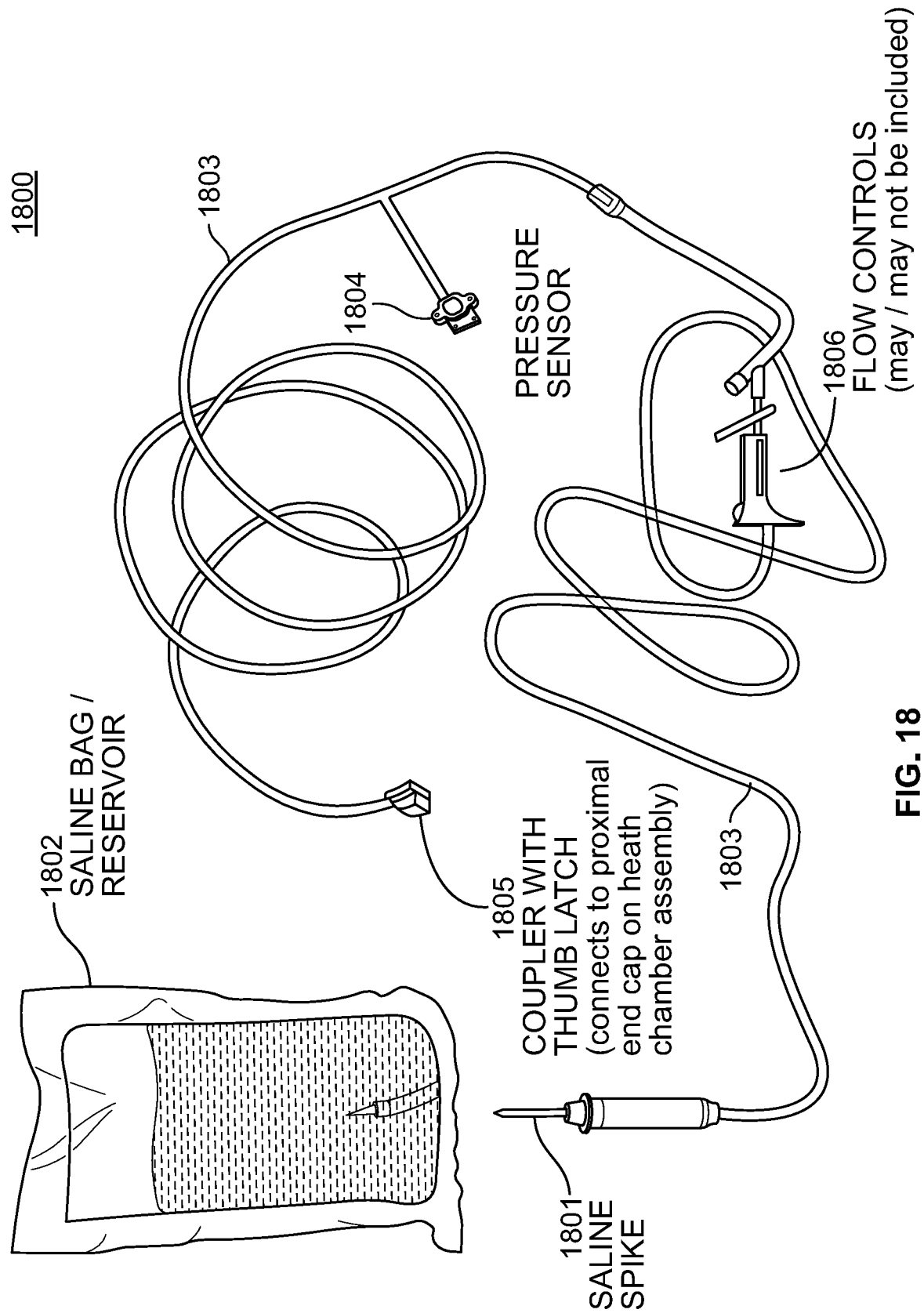
FIG. 18 is an illustration of an embodiment of a disposable tubing set to be used with the ablation systems of the present specification.

FIG. 18 is an illustration of an embodiment of a disposable tubing set 1800 to be used with the ablation systems of the present specification. In an embodiment, the tubing set 1800 includes a rigid plastic spike 1801 to puncture a saline bag or reservoir 1802, flexible polymeric tubing 1803, a pressure sensor 1804, and a coupler with thumb latch 1805. The pressure sensor 1804 connects to a microcontroller on the vapor generator and is used to monitor and control pressure in the system once vapor generation and delivery has been initiated. The coupler with thumb latch 1805 is configured to securely lock the tubing 1803 to the proximal end of the induction heating unit. Alternatively, in an embodiment, the coupler with thumb latch 1805 is replaced with a male coupler to connect with the female coupler 1756 at the proximal end of the inducting heating unit 1205 depicted in FIG. 17C. In an embodiment, the tubing set 1800 also includes a flow control component with thumb dial 1806 for controlling a rate flow from the saline bag or reservoir 1802.

The tubing set 1800 also includes first and second disposable inflation line tubes that are flexible polymer extrusions. Distal ends of the first and second inflation line tubes respectively connect to distal and proximal balloon inflation ports of a catheter handle. Proximal ends of the first and second inflation line tubes are connected to two independent inflation pumps. Inflation and deflation (if desired) of both distal and proximal balloons is controlled via the first and second inflation line tubes.

Figure 19:
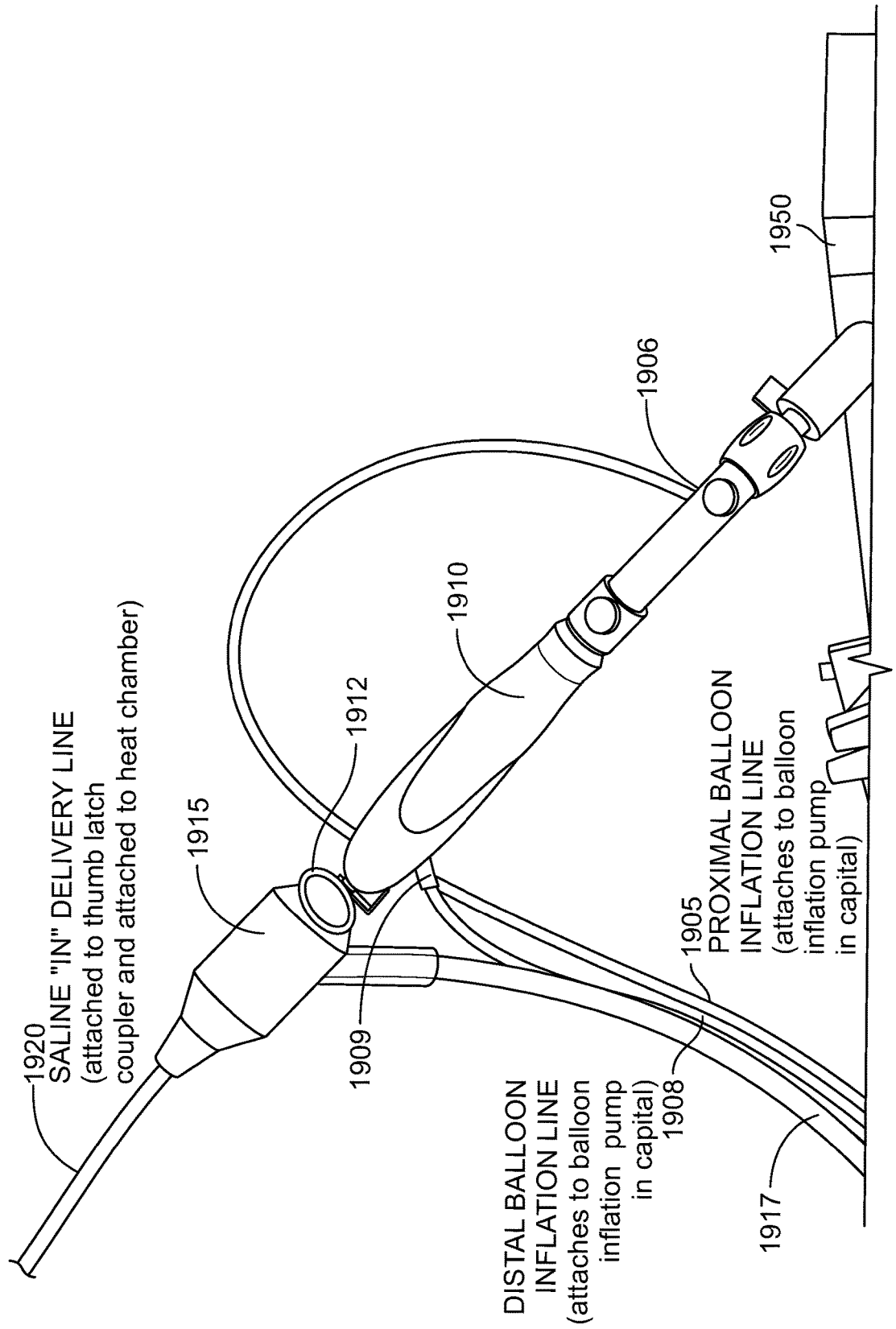
FIG. 19 is an illustration of a telescoping catheter handle attached to an endoscope, in accordance with an embodiment of the present specification.

FIG. 19 is an illustration of a telescoping catheter handle 1910 attached to an endoscope 1950, in accordance with an embodiment of the present specification. A proximal balloon inflation line 1905 is connected to a proximal balloon inflation port 1906 for inflation of a proximal balloon and a distal balloon inflation line 1908 is attached to a distal balloon inflation port 1909 for inflation of a distal balloon. An induction heating unit 1915 is attached to the proximal end of the catheter handle 1910 and includes a power line 1917 for providing electrical current to the wire of the induction coil. A saline delivery line 1920 is connected to the proximal end of the induction heating unit 1915. A three-way valve 1912 is included between the catheter 1910 and induction heating unit 1915 for priming the system to remove residual water before vapor generation.

Figure 20A:
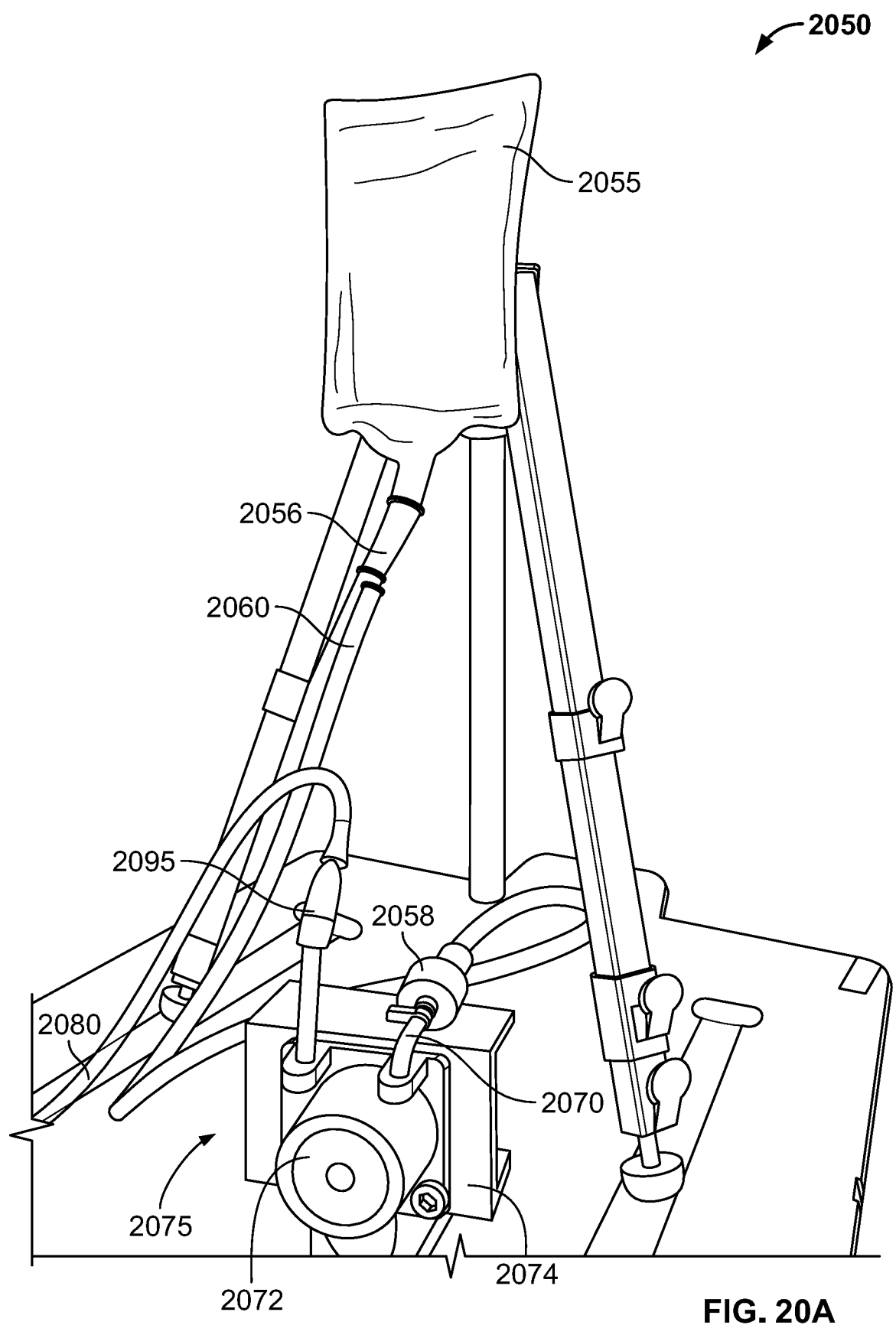
FIG. 20A is an assembled view of a vapor generator, in accordance with embodiments of the present specification.
Figure 20B:
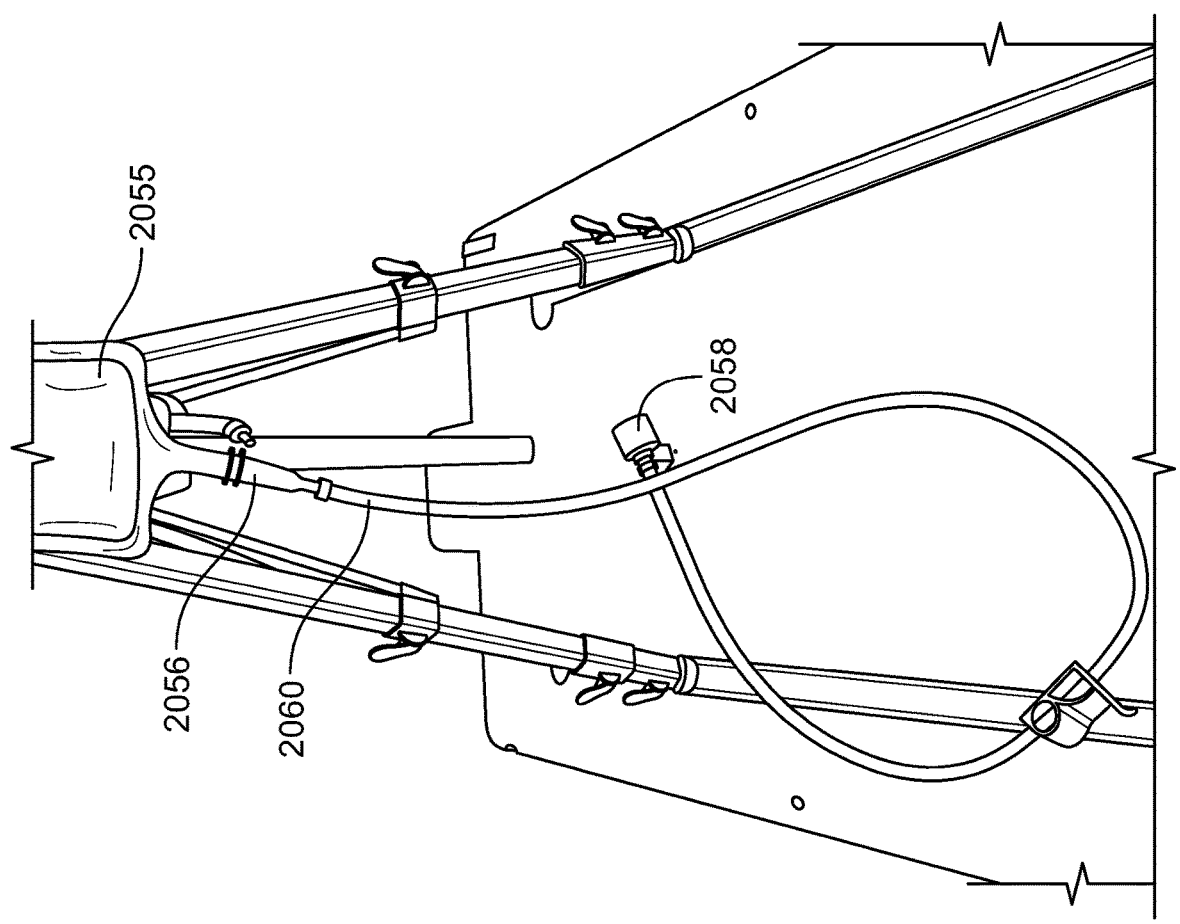
FIG. 20B is a partial disassembled view of the vapor generator, in accordance with embodiments of the present specification.
Figure 20E:
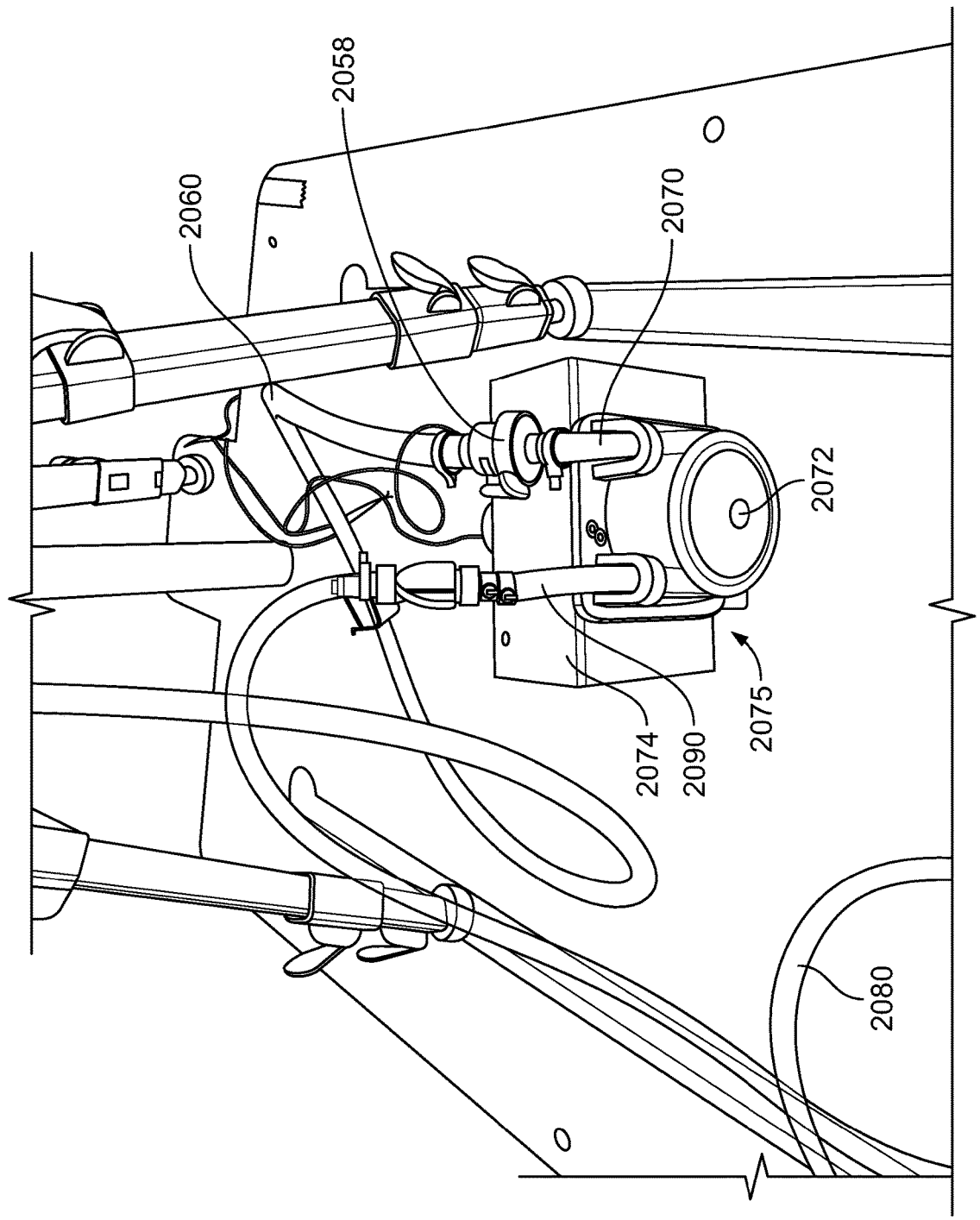
FIG. 20E shows the disposable pump fluidically connected to other components of the vapor generator, in accordance with embodiments of the present specification.

FIG. 20A is an assembled view of a vapor generator 2050, FIG. 20B is a partial disassembled view of the vapor generator 2050, FIG. 20C is a disassembled view of a disposable pump of the vapor generator 2050, FIG. 20D is an assembled view of the disposable pump and FIG. 20E shows the disposable pump fluidically connected to other components of the vapor generator 2050, in accordance with an embodiment of the present specification. Referring to FIGS. 20A through 20E, simultaneously, the vapor generator 2050 comprises a water/saline bag or reservoir 2055 fluidically attached to a first tube 2060. At one end, the first tube 2060 has a rigid plastic spike 2056 to puncture the reservoir 2055 while at another end the first tube 2050 has a first latch operated female connector 2058 for quick connection to a first male coupler end cap 2065 of an in-feed tube portion 2070 of a disposable pump 2075.

The disposable pump 2025 comprises a pump head 2072 that attaches to a pump motor housing 2074. The first tube 2060 feeds water/saline from the reservoir 2055 to the pump 2075. Pressurized water/saline, output by the pump 2075, is carried forward by a second tube 2080 that attaches to a second male coupler end cap 2085, of a tube portion 2090 of the pump 2075, by means of a second female coupler 2095. The second tube 2080 supplies pressurized water/saline to a heating chamber of an induction heating unit.

Gastrointestinal Ablation

Figure 21:
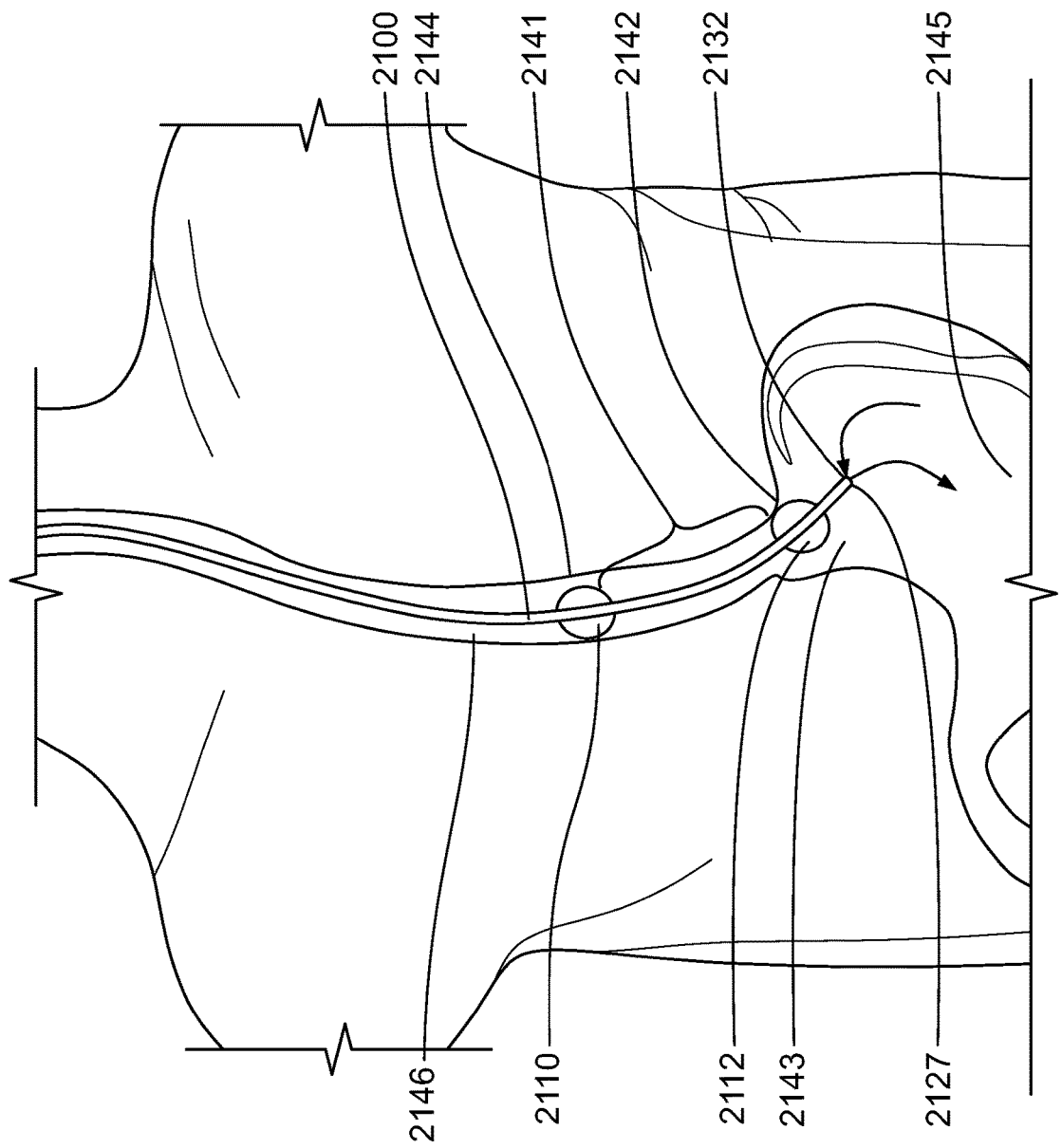
FIG. 21 illustrates an ablation catheter placed in an upper gastrointestinal tract with Barrett's esophagus to selectively ablate the Barrett's tissue, in accordance with an embodiment of the present specification.

FIG. 21 illustrates an ablation catheter placed in an upper gastrointestinal tract with Barrett's esophagus to selectively ablate the Barrett's tissue, in accordance with an embodiment of the present specification. Referring to FIG. 21, the upper gastrointestinal tract comprises Barrett's esophagus 2141, gastric cardia 2142, gastroesophageal junction 2143 and displaced squamo-columnar junction 2144. The area between the gastroesophageal junction 2143 and the displaced squamo-columnar junction 2144 is Barrett's esophagus 2141, which is targeted for ablation. Distal to the cardia 2142 is the stomach 2145 and proximal to the cardia 2142 is the esophagus 2146. The ablation device is passed into the esophagus 2146 and the balloons 2110, 2112 are positioned such that the balloon 2112 is placed in the gastric cardia 2142 abutting the gastroesophageal junction 2143. This affixes the ablation catheter and its infusion ports (shown in FIG. 4A) in the center of the esophagus 2146 and allows for uniform delivery of the ablative agent to the Barrett's esophagus 2141. It should be appreciated that the fluid delivery port 2127 and the suction port 2132 are positioned at a site away from the tissue being ablated so that a) the delivery of fluid does not significantly interfere with delivery of the ablative agent and b) the suction process does not result in suction of the ablative agent.

Figure 22:
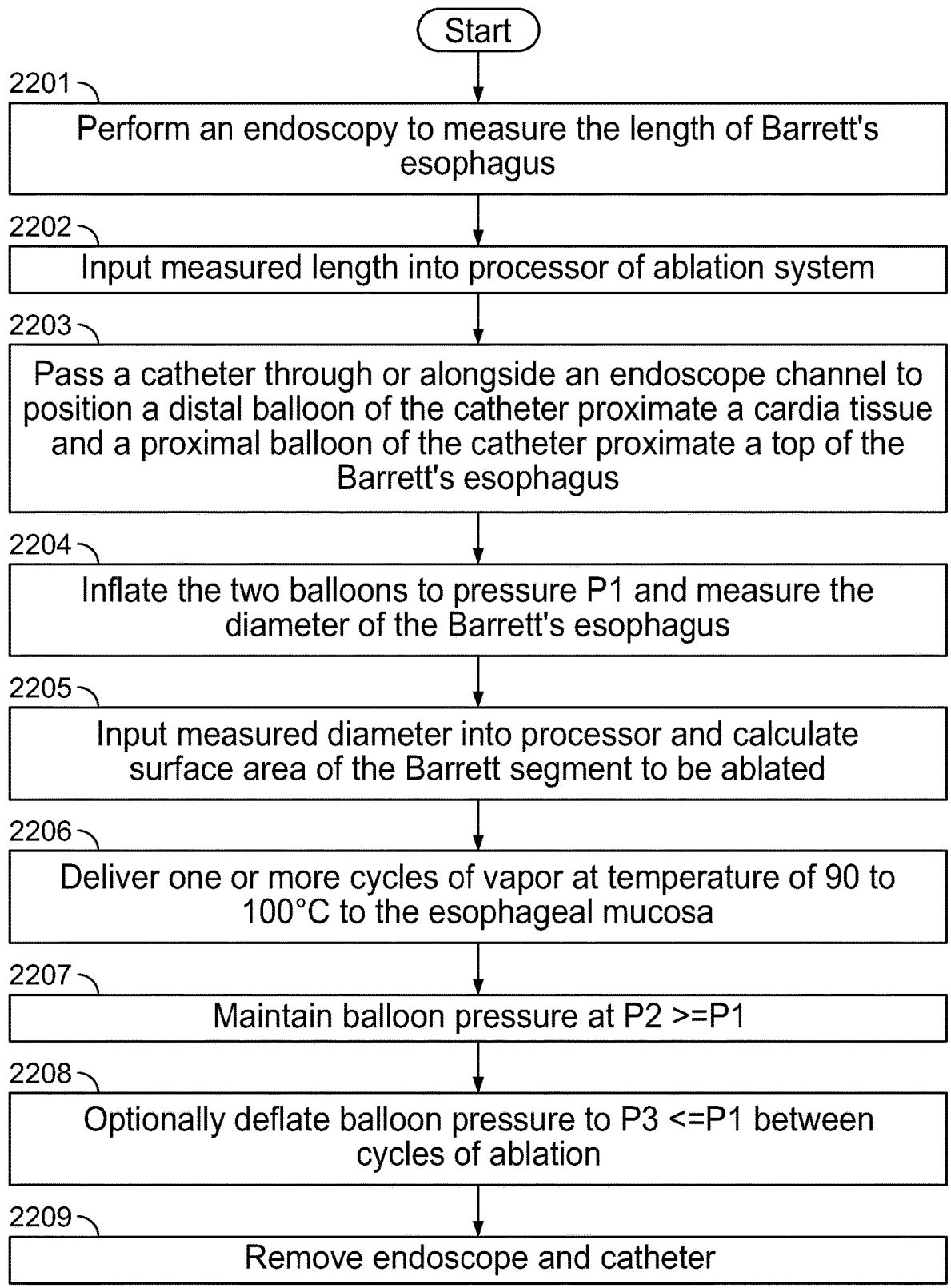
FIG. 22 is a flowchart illustrating a method of ablation of Barrett's esophagus in accordance with one embodiment of the present specification.

FIG. 22 is a flowchart illustrating a method of ablation of Barrett's esophagus in accordance with one embodiment of the present specification. Referring to FIG. 22, in the first step 2201, an endoscopy is performed on the patient to measure the length of Barrett's esophagus in the patient. Thereafter in step 2202, the measured length is input into a processor of an ablation system used to calculate the amount of ablative energy needed to ablate the Barrett's esophagus. In another embodiment, the measured length is used as a reference to select a catheter of appropriate ablation segment length to approximate the length of Barrett's esophagus. Next, in step 2203, a catheter having a first positioning balloon at its distal end and a second positioning balloon at its proximal end is passed through the endoscope channel or alongside the endoscope channel such that the distal balloon is positioned proximate a cardia tissue of a patient and the proximal balloon is positioned proximate the top of the Barrett's esophagus.

In the next step 2204, the two balloons are inflated to a set pressure (P1) and the diameter of the Barrett's esophagus is measured using the proximal balloon. This diameter is manually or automatically input into the processor and a surface area of the Barrett's segment to be ablated is calculated, as shown in step 2205.

Next, in step 2206, one or more cycles of vapor is delivered to the esophageal mucosa through one or more vapor delivery ports on the catheter at a temperature in a range of 90 to 100° C. to ablate the Barrett's esophagus. In step 2207, the balloon pressures during the delivery of ablative agent are maintained at a pressure P2 which is greater than or equal to pressure P1. Optionally, in step 2208, the balloons are deflated to a pressure P3 which is less than or equal to pressure P1 between the cycles of ablation. Finally, the endoscope and the catheter are removed after the ablation is complete in step 2209.

It should be appreciated that any ablation catheter or system of the present specification, used to ablate tissue in an organ, may be used with a controller, wherein the controller is configured to limit a pressure generated by ablation fluid, such as steam/vapor, within the organ to less than 5 atm or 100 psi.

FIG. 23A illustrates deflated 2340d, lateral inflated 23401, and frontal inflated 2340f views of an ablation catheter 2340 having an insulating membrane 2349 for duodenal ablation, in accordance with one embodiment of the present specification. In some embodiments, the catheter 2340 comprises a water-cooled catheter having a proximal inflatable balloon 2342 and a distal inflatable balloon 2344 with an insulating membrane 2349 which extends from a proximal end of the proximal balloon 2342 to a distal end of the distal balloon 2344. A plurality of vapor delivery ports 2343 are positioned on the catheter 2340 between the proximal balloon 2342 and distal balloon 2344. Once the balloons 2342, 2344 are inflated, as depicted in lateral view 23401, the stretching of the insulating membrane 2349 between the balloons 2342, 2344 causes the catheter 2340 to bow, helping to position the insulating membrane over the ampulla of vater, thereby providing a protective shield over the ampulla during vapor ablation therapy.

Figure 23B:
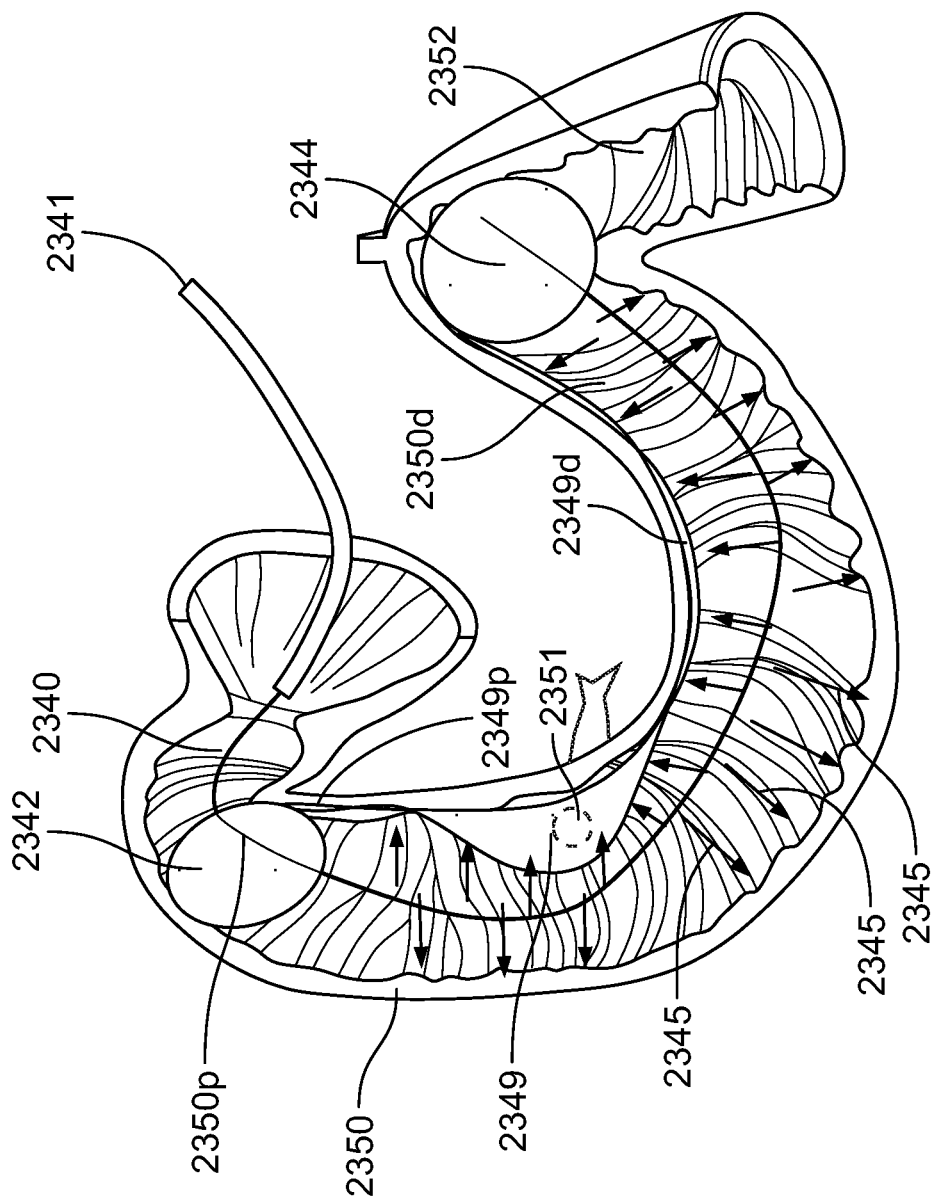
FIG. 23B illustrates the ablation catheter of FIG. 44C deployed in a duodenum of a patient, in accordance with one embodiment of the present specification.

FIG. 23B illustrates the ablation catheter 2340 of FIG. 23A deployed in a duodenum 2350 of a patient, in accordance with one embodiment of the present specification. The catheter 2340 has been deployed through a working channel of an endoscope 2341 such that the distal inflatable balloon 2344 is positioned in the distal duodenum 2350d, proximal to the jejunum 2352, and the proximal inflatable balloon 2342 is positioned in the proximal duodenum 2350p. The insulating membrane 2349 is positioned over the ampulla of Vater 2351 to prevent ablative agent 2345 delivered to the duodenum 2350 from damaging said ampulla 2351. Proximal portions 2349p and distal portions 2349d of the insulating membrane 2349 are attached to the proximal inflatable balloon 2342 and distal inflatable balloon 2344 respectively, such that the insulating membrane 2349 becomes stretched to conform to the shape of the duodenum 2350 once the catheter 2340 is deployed.

In various embodiments, ablation therapy provided by the vapor ablation systems of the present specification is delivered to treat a variety of conditions and efficacy of treatment is determined by measuring certain physiological parameters, as further described below, in a range of time from at least six weeks to two years after treatment. If the therapeutic endpoints are not achieved after a period of at least six weeks, ablation therapy is repeated. Physiological parameters are then measured after at least another six weeks, and ablation therapy may be repeated and evaluated in a similar six week cycle, until the desired therapeutic endpoint is achieved.

In various embodiments, ablation therapy, particularly duodenal ablation, provided by the vapor ablation systems of the present specification is delivered to treat at least one of fatty liver, non-alcoholic fatty liver disease (NAFLD), non-alcoholic steatohepatitis, type II diabetes, metabolic syndrome, overweight patients, and obesity. In various embodiments, ablation therapy, particularly duodenal ablation, provided by the vapor ablation systems of the present specification is delivered to achieve the following therapeutic endpoints: treat type II diabetes by achieving at least a 10% reduction in HbA1c or fasting blood glucose level when measured at least six weeks after treatment; treat metabolic syndrome; or treat hyperlipidemia by achieving at least a 5% reduction in either total cholesterol or LDL or triglyceride or at least a 5% improvement in the HDK cholesterol, as measured at least six weeks after treatment.

In case of the treatment for fatty liver or Non-Alcoholic Fatty Liver Disease (NAFLD)/Non-Alcoholic Steatohepatitis, ablation therapy, particularly duodenal ablation, provided by embodiments of the vapor ablation systems of the present specification is delivered to achieve the following therapeutic endpoints, as measured at least six weeks after treatment: at least a 10% decrease in either ALT or AST levels; a relative improvement of 10% in serum Ferritin level or an absolute level of no more than 1.5 ULN (upper limit normal); at least a 5% relative improvement in hepatic steatosis (HS), or no more than 5% HS as measured on liver biopsy; at least a 5% relative improvement in HS as measured by magnetic resonance (MR) imaging, either by spectroscopy or proton density fat fraction; at least a 5% relative improvement in NAFLD Fibrosis Score (NFS); at least a 5% relative improvement in NAFLD Activity Score (NAS); at least a 5% relative improvement in Steatosis Activity Fibrosis (SAF) score; at least 10% of patients showing a decrease in the mean annual fibrosis progression rate as measured by histology, Fibrosis-4 (FIB-4) index, aspartate aminotransferase (AST) to platelet ratio index (APRI)), serum biomarkers (Enhanced Liver Fibrosis (ELF) panel, Fibrometer, FibroTest, and Hepascore), or imaging (Transient Elastography (TE), MR Elastography (MRE), acoustic radiation force impulse imaging, and supersonic shear wave elastography); at least a 5% relative improvement in circulating levels of cytokeratin-18 fragments; at least a 5% relative improvement in FIB-4 index, aspartate aminotransferase (AST) to platelet ratio index (APRI), serum biomarkers (Enhanced Liver Fibrosis (ELF) panel, Fibrometer, FibroTest, and Hepascore), or imaging (TE, MRE, acoustic radiation force impulse imaging, and supersonic shear wave elastography); at least a 5% relative improvement in liver stiffness measured by vibration controlled transient elastography (VCTE (FibroScan)); at least 10% of patients showing an improvement in NAS by 2 points with at least 1-point improvement in hepatocellular ballooning and 1-point improvement in either the lobular inflammation or steatosis score, and no increase in the fibrosis score; at least 10% of patients showing an improvement in the NFS scores; and at least 5% of patients showing an improvement in any of the above listed NAFLD parameter as compared to a sham intervention or a placebo. In various embodiments, the relative therapeutic goals and endpoints are provided relative to one or more pre-treatment levels of the correspondingly stated physiological indicators.

In various embodiments, ablation therapy, particularly duodenal ablation, provided by the vapor ablation systems of the present specification is delivered to treat obesity in a person by achieving one of the following therapeutic endpoints, as measured at least six weeks after treatment: a total body weight of the person reduces by at least 1% relative to a total body weight of the person before ablation; an excess body weight of the person reduces by at least 1% relative to an excess body weight of the person before ablation; a total body weight of the person reduces by at least 1% relative to a total body weight of the person before ablation and a well-being level of the person does not reduce more than 5% relative to a well-being level of the person before ablation; an excess body weight of the person reduces by at least 1% relative to an excess body weight of the person before ablation and a well-being level of the person does not reduce more than 5% relative to a well-being level of the person before ablation; after at least one ablation, a pre-prandial ghrelin level of the person reduces by at least 1% relative to a pre-prandial ghrelin level of the person before ablation; after at least one ablation, a post-prandial ghrelin level of the person reduces by at least 1% relative to a post-prandial ghrelin level of the person before ablation; after at least one ablation session, exercise output of the patient increases by at least 1% relative to the exercise output of the patient before ablation; after at least one ablation, a glucagon-like peptide-1 level of the person increases by at least 1% relative to a glucagon-like peptide-1 level of the person before ablation; after at least one ablation, a leptin level of the person increases by at least 1% relative to a leptin level of the person before ablation; after at least one ablation, the patient's appetite decreases, over a predefined period of time, relative to the patient's appetite before ablation; after at least one ablation, a peptide YY level of the person increases by at least 1% relative to a peptide YY level of the person before ablation; after at least one ablation, a lipopolysaccharide level of the person reduces by at least 1% relative to a lipopolysaccharide level of the person before ablation; after at least one ablation, a motilin-related peptide level of the person reduces by at least 1% relative to a motilin-related peptide level of the person before ablation; after at least one ablation, a cholecystokinin level of the person increases by at least 1% relative to a cholecystokinin level of the person before ablation; after at least one ablation, a resting metabolic rate of the person increases by at least 1% relative to a resting metabolic rate of the person before ablation; after at least one ablation, a plasma-beta endorphin level of the person increases by at least 1% relative to a plasma-beta endorphin level of the person before ablation; after at least one ablation, the person's level of hemoglobin A1c decreases by an amount equal to at least 0.3%; after at least one ablation, a triglyceride level of the person decreases by at least 1% relative to a triglyceride level of the person before ablation; after at least one ablation, a total blood cholesterol level of the person decreases by at least 1% relative to a total blood cholesterol level of the person before ablation; after at least one ablation, a glycemia level of the person decreases by at least 1% relative to a glycemia level of the person before ablation; after at least one ablation, a composition of the person's gut microbiota modulates from a first state to a second state, wherein the first state has a first level of bacteroidetes and a first level of firmicutes, wherein the second state has a second level of bacteroidetes and a second level of firmicutes, wherein the second level of bacteroidetes is greater than the first level of bacteroidetes by at least 3%, and wherein the second level of firmicutes is less than the first level of firmicutes by at least 3%; after at least one ablation, the cumulative daily dose of a patient's antidiabetic medications decrease by at least 10%; after at least one ablation, a patient's lipid profile improves by at least 10%; after at least one ablation, a patient's LDL-cholesterol decreases by at least 10%; and, after at least one ablation, a patient's VLDL-cholesterol decreases by at least 10%. In various embodiments, the relative therapeutic goals and endpoints are provided relative to one or more pre-treatment levels of the correspondingly stated physiological indicators.

The ablation systems and methods of the present specification, particularly duodenal ablation, may be used to treat a condition including any one of obesity, excess weight, eating disorders, metabolic syndrome and diabetes, NASH/NAFLD or a polycystic ovary disease. In accordance with various aspects of the present specification, the ablation systems and methods, particularly duodenal ablation, enable treating people with a BMI (Body Mass Index) of 25 or greater (overweight being 25-30, obese being 30 and above, and morbid obesity being above 35). In accordance with various aspects of the present specification, the ablation systems and methods, particularly duodenal ablation, also enable treating people with HbA1c levels of at least 6.5 gm %, fasting blood glucose levels of at least 126 mg/dL or a random plasma glucose level of at least 200 mg/dL, a 2-hour plasma glucose level of at least 200 mg/dL (11.1 mmol/L) during an oral glucose tolerance test (OGTT). The ablation systems and methods, particularly duodenal ablation, can also be used to treat nondiabetic, normotensive overweight individuals, with a serum triglyceride concentration of at least 130 mg/dL (1.47 mmol/L), a ratio of triglyceride to high-density lipoprotein (HDL) cholesterol concentration of at least 3.0 (1.8 SI units), and fasting insulin concentration of at least 5.7 µU/mL (109 pmol/L). The ablation systems and methods, particularly duodenal ablation, can also be used to treat patients with insulin resistance defined as homeostatic model assessment of insulin resistance (HOMA-IR) of at least 1.6, or associated disorders. The ablation systems and methods, particularly duodenal ablation, can also be used to treat patients with dyslipidemia.

Figure 24:
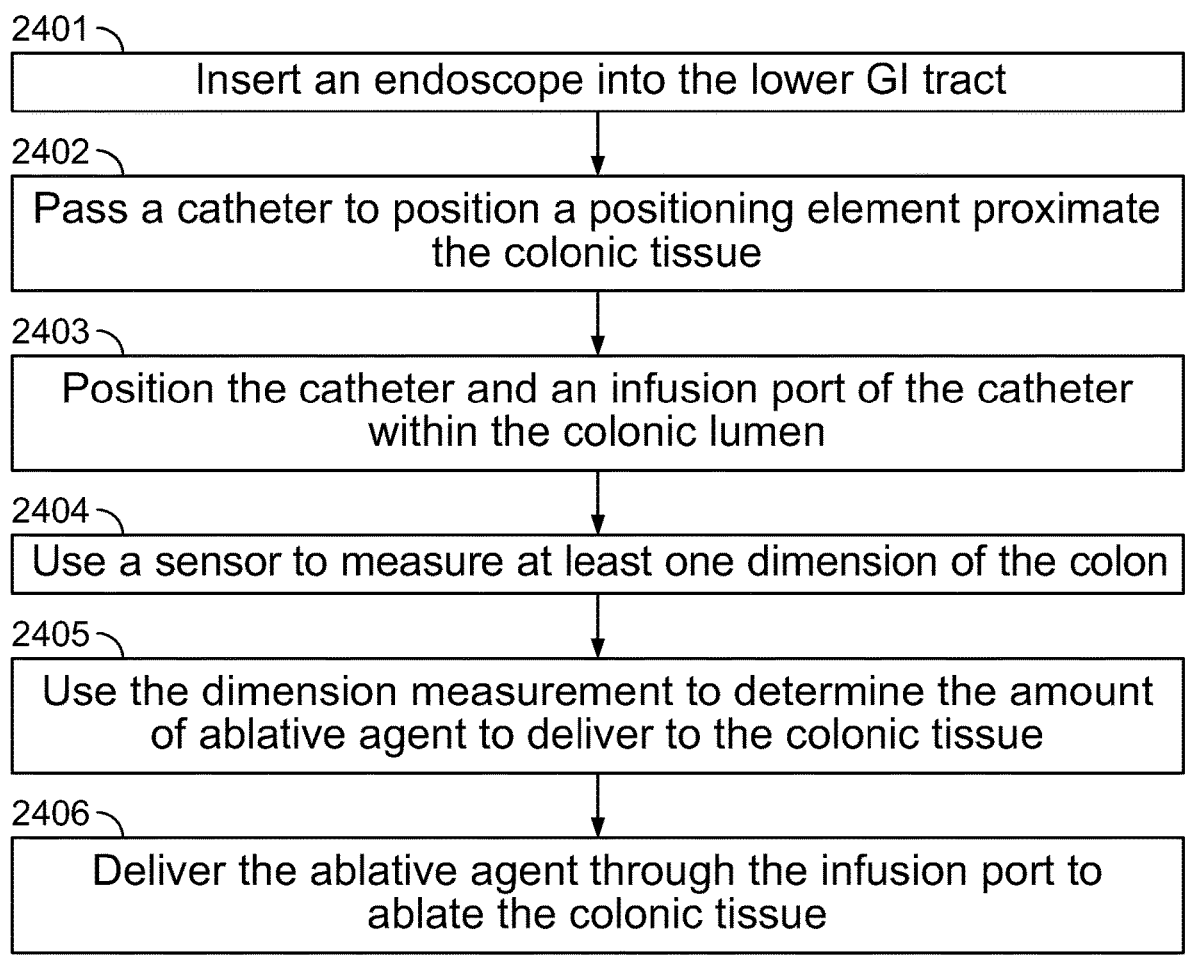
FIG. 24 is a flowchart illustrating a method of ablation of a colon in accordance with one embodiment of the present specification.

FIG. 24 is a flowchart illustrating a method of ablation of a colon in accordance with one embodiment of the present specification. Referring to FIG. 24, the first step 2401 includes inserting an endoscope into the lower gastrointestinal tract of a patient. Next, in step 2402, a catheter of an ablation device is passed through the endoscope, wherein the catheter includes a hollow shaft through which an ablative agent can travel, at least one positioning element, at least one input port for receiving an ablative agent, and at least one infusion port for delivering the ablative agent. The catheter is passed through the endoscope such that the positioning element is positioned proximate to the colonic tissue to be ablated. In an embodiment, the ablation device includes a controller comprising a microprocessor for controlling the delivery of the ablative agent. The positioning element is deployed in the colonic lumen of the patient such that the positioning element contacts a portion of the colon of the patient and the catheter and infusion port are positioned within the colonic lumen in step 2403. In one embodiment, the positioning element is positioned over and encompasses the colonic tissue. Finally, in step 2406, an ablative agent is delivered through the infusion port to ablate the colonic tissue.

Optionally, a sensor is used to measure at least one dimension of the colon in step 2404 and the measurement is used to determine the amount of ablative agent to be delivered in step 2405.

In various embodiments, ablation therapy provided by the vapor ablation systems of the present specification is delivered to achieve the following therapeutic endpoints for duodenal ablation: maintain a tissue temperature at 100° C. or less; ablate at least 50% of a surface area of a duodenal mucosa; ablate a duodenal mucosa without significant ablation of an ampullary mucosa; reduce fasting blood glucose by at least 5% relative to pre-treatment fasting blood glucose; reduce HbA1c by at least 5% relative to pre-treatment HbA1c; reduce total body weight by at least 1% relative to pre-treatment body weight; reduce excess body weight by at least 3% relative to pre-treatment excess body weight; reduce mean blood pressure by at least 3% relative to pre-treatment mean blood pressure; and reduce total cholesterol by at least 3% relative to pre-treatment total cholesterol.

Figure 25:
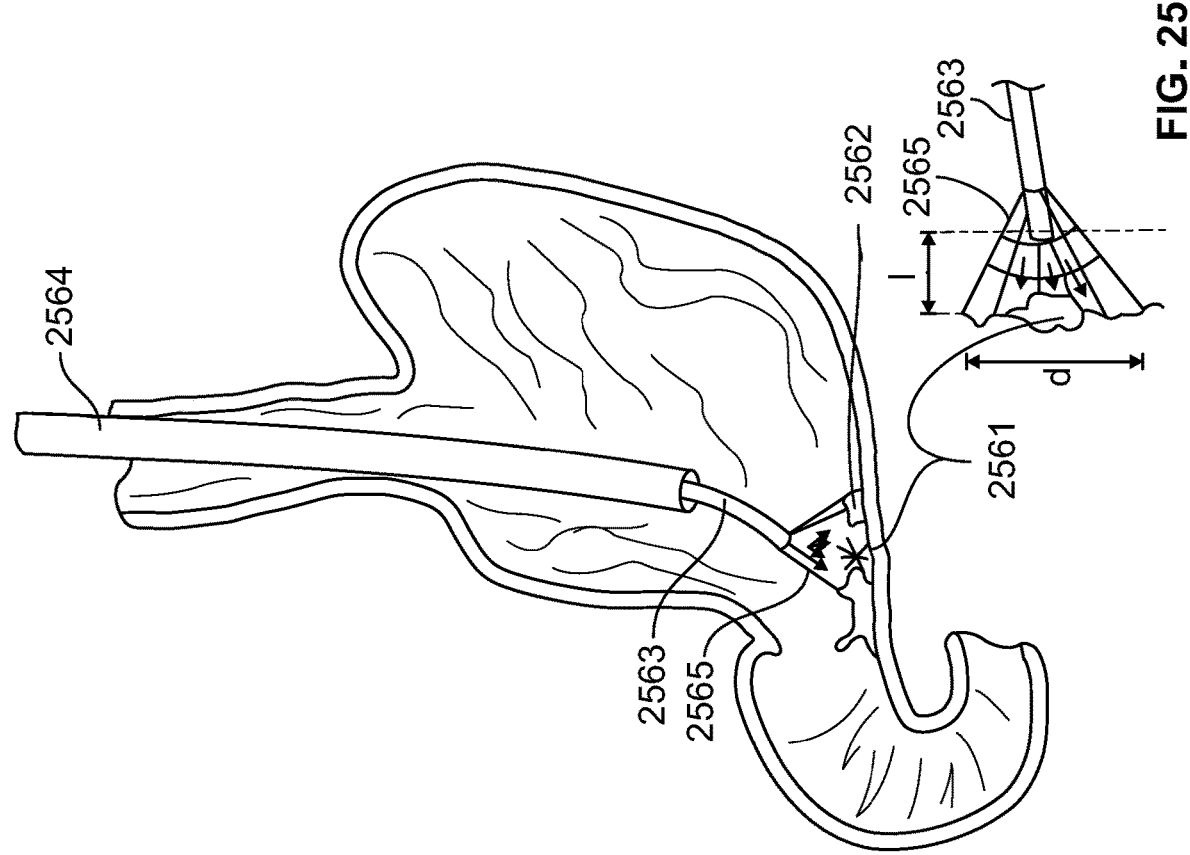
FIG. 25 illustrates an upper gastrointestinal tract with a bleeding vascular lesion being treated by the ablation device, in accordance with an embodiment of the present specification.

FIG. 25 illustrates an upper gastrointestinal tract with a bleeding vascular lesion being treated by an ablation device, in accordance with an embodiment of the present specification. The vascular lesion is a visible vessel 2561 in the base of an ulcer 2562. The ablation catheter 2563 is passed through the channel of an endoscope 2564. The conical positioning element 2565 is placed over the visible vessel 2561. The conical positioning element 2565 has a known length 'l' and diameter 'd', which are used to calculate the amount of thermal energy needed for coagulation of the visible vessel to achieve hemostasis. The conical positioning element has an optional insulated membrane that prevents escape of thermal energy or vapor away from the disease site.

In one embodiment, the positioning attachment must be separated from the ablation region by a distance of greater than 0.1 mm, preferably 1 mm and more preferably 1 cm. In one embodiment, the length 'l' is greater than 0.1 mm, preferably between 5 and 10 mm. In one embodiment, diameter 'd' depends on the size of the lesion and can be between 1 mm and 10 cm, preferably 1 to 5 cm.

Figure 26:
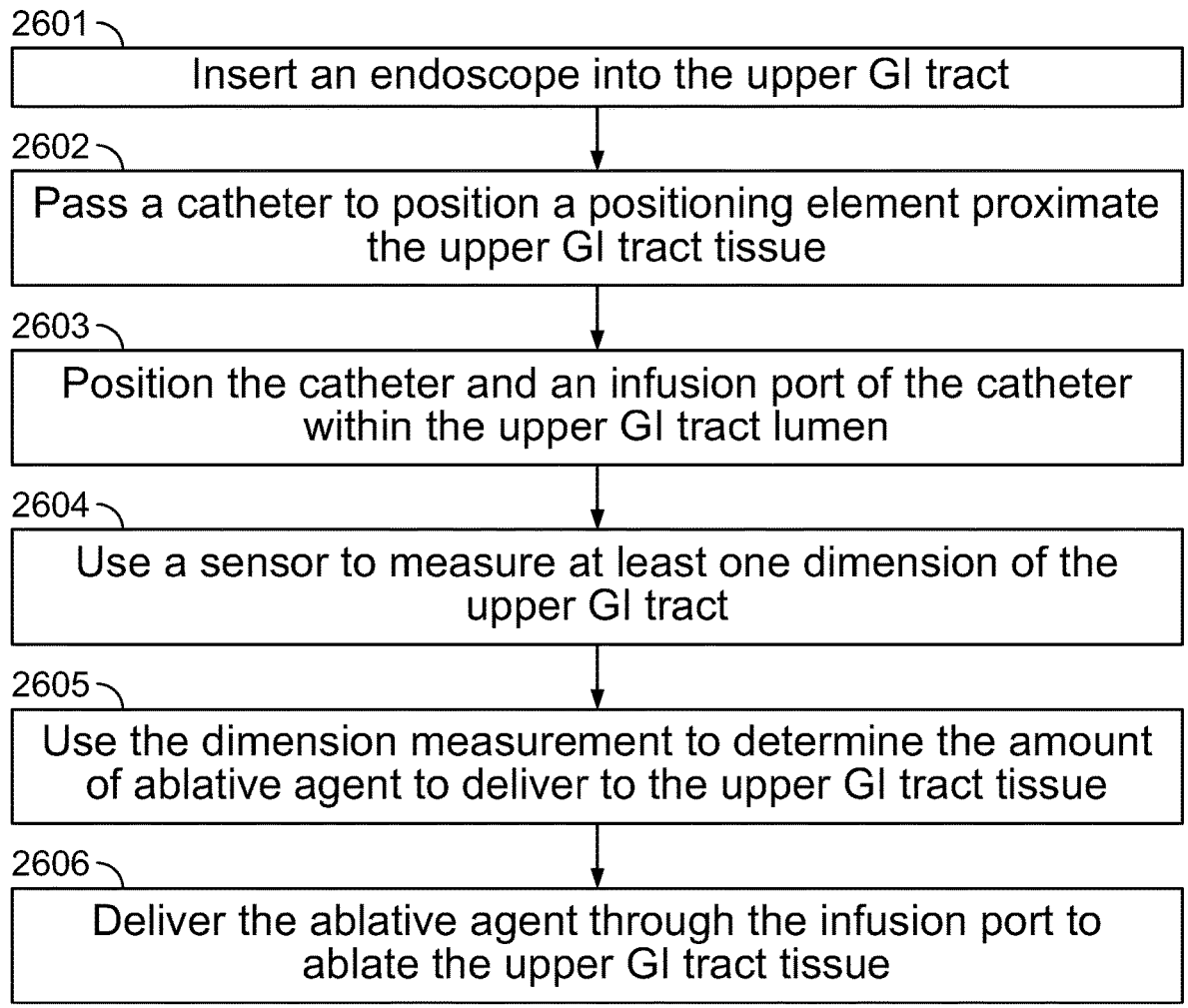
FIG. 26 is a flowchart illustrating a method of ablation of an upper GI tract in accordance with one embodiment of the present specification.

FIG. 26 is a flowchart illustrating a method of ablation of an upper GI tract in accordance with one embodiment of the present specification. Referring to FIG. 26, the first step 2601 includes inserting an endoscope into the upper gastrointestinal tract of a patient. Next, in step 2602, a catheter of an ablation device is passed through the endoscope, wherein the catheter includes a hollow shaft through which an ablative agent can travel, at least one positioning element, at least one input port for receiving an ablative agent, and at least one infusion port for delivering the ablative agent. The catheter is passed through the endoscope such that the positioning element is positioned proximate to the upper GI tract tissue to be ablated. In an embodiment, the ablation device includes a controller comprising a microprocessor for controlling the delivery of the ablative agent. The positioning element is deployed in the upper GI tract lumen of the patient such that the positioning element contacts a portion of the upper GI tract of the patient and the catheter and infusion port are positioned within the upper GI tract lumen in step 2603. In one embodiment, the positioning element is positioned over and encompasses the upper GI tract tissue. Finally, in step 2606, an ablative agent is delivered through the infusion port to ablate the upper GI tract tissue.

Optionally, a sensor is used to measure at least one dimension of the upper GI tract in step 2604 and the measurement is used to determine the amount of ablative agent to be delivered in step 2605.

Figure 27A:
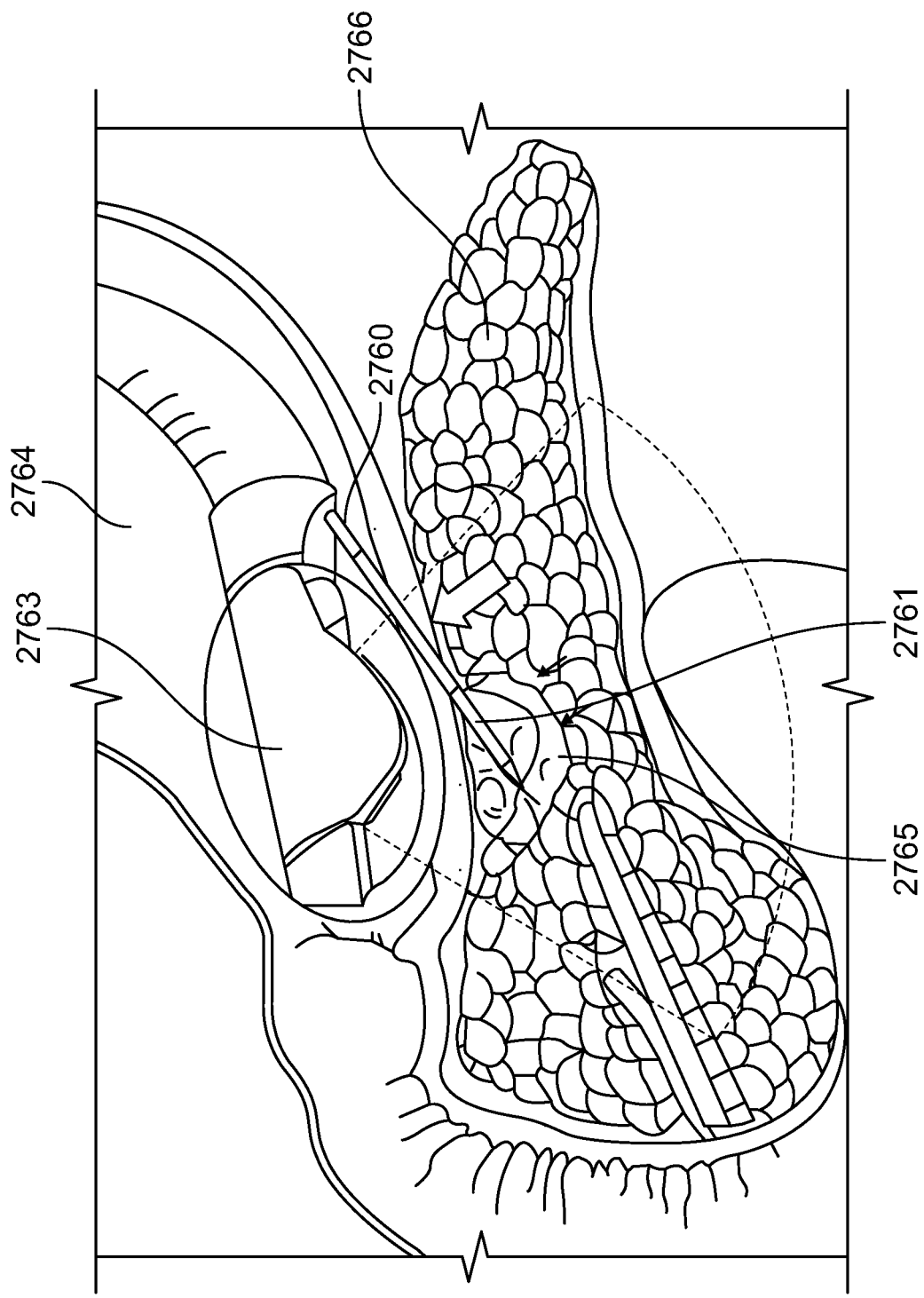
FIG. 27A is an illustration of pancreatic ablation being performed on a pancreatic tumor in accordance with one embodiment of the present specification.

FIG. 27A is an illustration of pancreatic ablation being performed on a pancreatic tumor 2765 in accordance with one embodiment of the present specification. The ablation device 2760 includes a needle 2761 configured to be inserted into a lesion to deliver vapor for ablation. The ablation device 2760 is passed through a channel of an echoendoscope 2763 which has been inserted into a gastrointestinal tract 2764 of a patient to view the patient's pancreas 2766. Vapor is delivered through the needle 2761 of the ablation device 2760 to ablate the pancreatic tumor 2765.

Figure 27B:
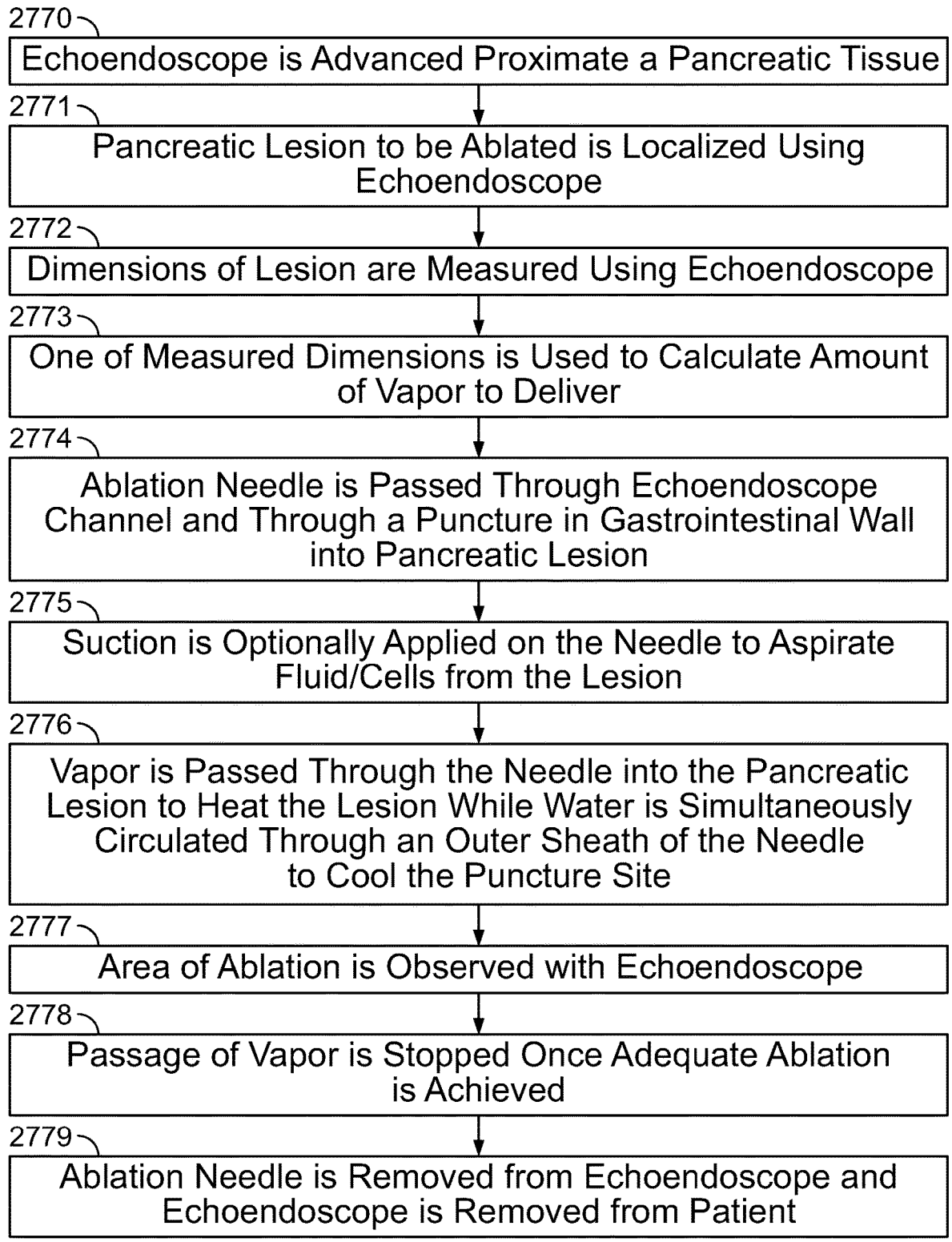
FIG. 27B is a flowchart listing the steps involved in one embodiment of a method of pancreatic ablation.

FIG. 27B is a flowchart listing the steps involved in one embodiment of a method of pancreatic ablation. At step 2770, an echoendoscope is advanced proximate a pancreatic tissue. A pancreatic lesion to be ablated is localized using the echoendoscope at step 2771. At step 2772, dimensions of the lesion are measured using the echoendoscope. One of the measured dimensions is used to calculate an amount of vapor to deliver at step 2773. The ablation needle is passed through a channel in the echoendoscope and through a puncture in the gastrointestinal wall into the pancreatic lesion at step 2774. At step 2775, suction is optionally applied on the needle to aspirate fluid/cells from the lesion. Vapor is passed through the needle into the pancreatic lesion to heat the lesion while water is simultaneously circulated through an outer sheath of the needle to cool the puncture site at step 2776. The area of ablation is observed with the echoendoscope at step 2777. The passage of vapor is stopped once adequate ablation is achieved at step 2778. At step 2779, the ablation needle is removed from the echoendoscope and the echoendoscope is removed from the patient.

Figure 27C:
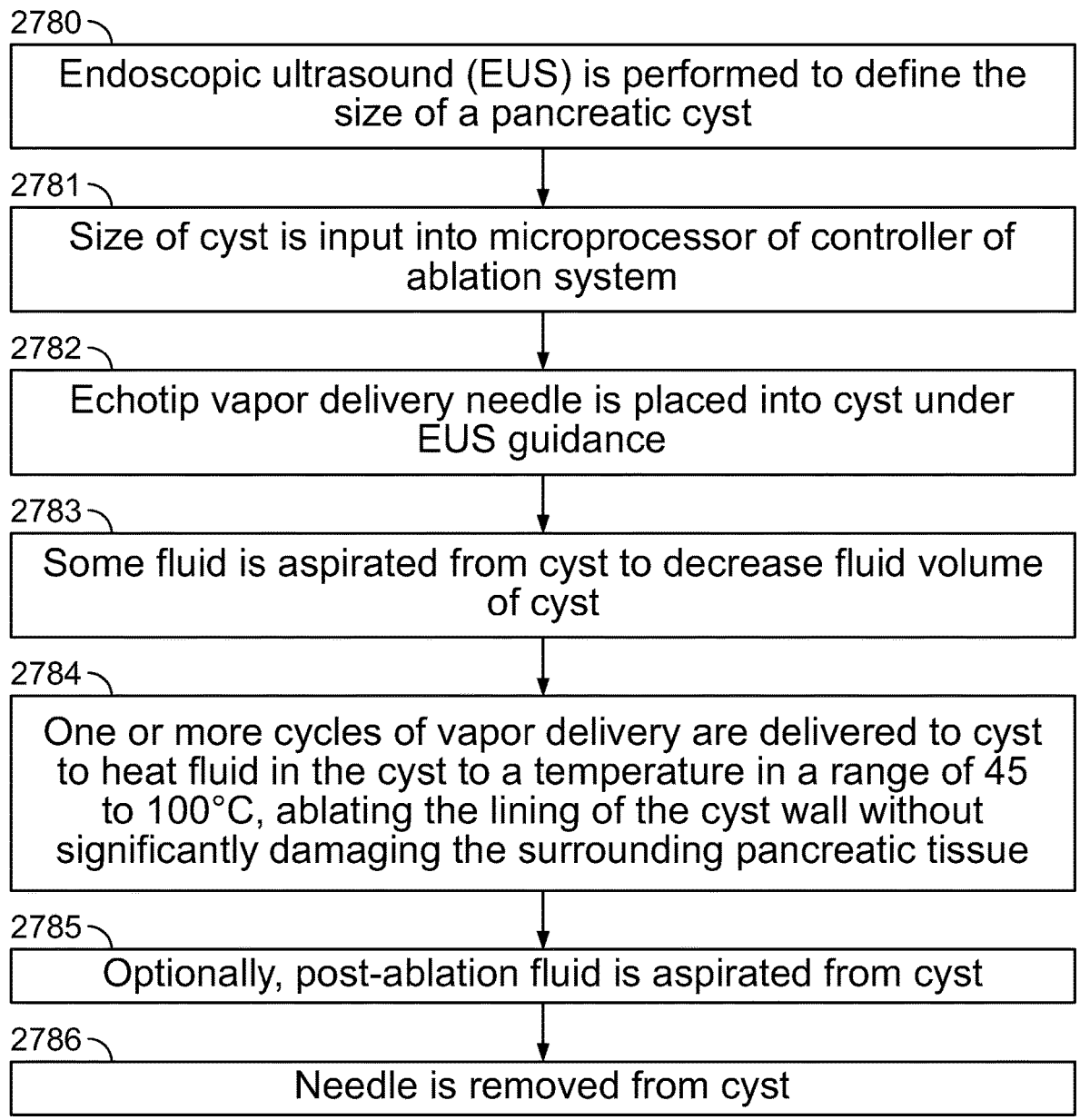
FIG. 27C is a flowchart listing the steps involved in one embodiment of a method of ablation of a pancreatic cyst.

FIG. 27C is a flowchart listing the steps involved in one embodiment of a method of ablation of a pancreatic cyst. In step 2780, an endoscopic ultrasound (EUS) is performed to define the size of the cyst. The size of the cyst is input into a microprocessor of a controller of an ablation system in step 2781 to calculate the amount of ablative therapy to be provided. An echotip vapor delivery needle is placed into the cyst under EUS guidance in step 2782. In step 2783, some fluid is aspirated from the cyst to decrease fluid volume of the cyst. One or more cycles of vapor delivery are delivered to the cyst in step 2784 to heat fluid in the cyst to a temperature in a range of 45 to 100° C., ablating the lining of the cyst wall without significantly damaging the surrounding pancreatic tissue. Optionally, post-ablation fluid is aspirated from the cyst in step 2785. The needle is removed from the cyst in step 2786.

In various embodiments, ablation therapy provided by the vapor ablation systems of the present specification is delivered to achieve the following therapeutic endpoints for a tumor in or proximate the bile duct: maintain a tissue temperature of 100° C. or less; ablate at least 50% of the surface area of a targeted cancer mucosa to a sufficient depth such that after ablation a cross-sectional area improves by at least 10% relative to a pre-treatment cross-sectional area; biliary flow improves by at least 10% relative to pre-treatment biliary flow; tumor volume decreases by at least 10% relative to a pre-treatment tumor volume.

Figure 28:
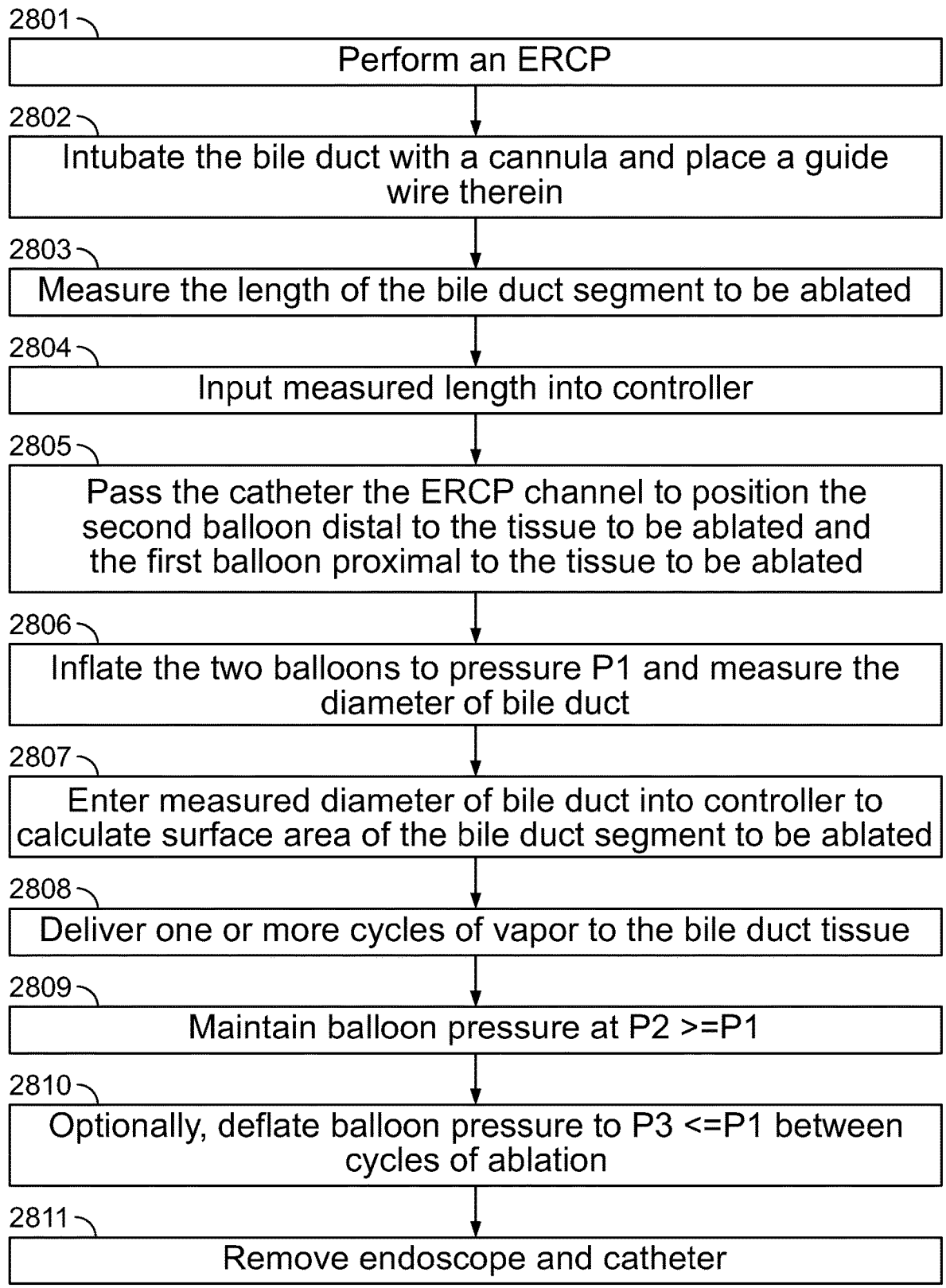
FIG. 28 is a flowchart listing the steps involved in one embodiment of a method of tissue ablation in a bile duct.

FIG. 28 is a flowchart listing the steps involved in one embodiment of a method of tissue ablation in a bile duct. At step 2801, an endoscopic retrograde cholangiopancreatography (ERCP) is performed. Next in step 2802, the bile duct is intubated with a cannula and a guide wire is placed therein. In step 2803, the length of the bile duct segment to be ablated is measured. The length is then input into a controller of an ablation system to determine an amount of ablative therapy to provide in step 2804. In another embodiment, the length is used to select a catheter of appropriate ablation segment length. A catheter of the ablation system is then passed through the ERCP channel over the guide-wire. The catheter includes a first positioning element, a second positioning element distal to the first positioning element, and a plurality of delivery ports positioned on the catheter between the first and second positioning elements. The catheter is passed through the ERCP channel such that the second first positioning element (balloon) is placed distal to the bile duct to be ablated and the first positioning element (balloon) is placed proximal to the bile duct to be ablated in step 2805. In step 2806, the two balloons are inflated to a set pressure P1 and the diameter of the bile duct is measured using a diameter of either of the two balloons or an average of the diameters of the two balloons. The measured bile duct diameter is entered into the controller, either manually or automatically, and used to calculate the surface area of the bile duct to be ablated in 2807. Thereafter, one or more cycles of vapor is delivered to the bile duct through one or more of the vapor delivery ports at a temperature in a range of 90 to 100° C. to ablate the bile duct tissue in 2808. In one embodiment, the balloon pressure is maintained during the delivery of ablative agent at a pressure P2 which is greater than or equal to pressure P1 in 2809. Optionally, the balloons are deflated to a pressure P3 which is less than or equal to P1 between the cycles of ablation in 2810. The endoscope and the catheter are removed after the ablation is complete in step 2811.

Bronchial Ablation

Regarding pulmonary function, there are four lung volumes and four lung capacities. A lung capacity consists of two or more lung volumes. The lung volumes are tidal volume (VT), inspiratory reserve volume (IRV), expiratory reserve volume (ERV), and residual volume (RV). The four lung capacities are total lung capacity (TLC), inspiratory capacity (IC), functional residual capacity (FRC), and vital capacity (VC). Measurement of the single-breath diffusing capacity for carbon monoxide (DLCO) is a fast and safe tool in the evaluation of both restrictive and obstructive lung disease. Arterial blood gases (ABGs) are a helpful measurement in pulmonary function testing in selected patients. The primary role of measuring ABGs in individuals that are healthy and stable is to confirm hypoventilation when it is suspected on the basis of medical history, such as respiratory muscle weakness or advanced COPD. Spirometry includes tests of pulmonary mechanics such as measurements of forced vital capacity (FVC), forced expiratory volume at the end of the first second of forced expiration ($FEV_1$), forced expiratory flow (FEF) values, forced inspiratory flow rates (FIFs), and maximum voluntary ventilation (MVV). Measuring pulmonary mechanics assesses the ability of the lungs to move large volumes of air quickly through the airways to identify airway obstruction.

In various embodiments, ablation therapy provided by the vapor ablation systems of the present specification is delivered to achieve the following therapeutic endpoints for pulmonary ablation: maintain a tissue temperature at 100° C. or less; reduce TLC, defined as the volume in the lungs at maximal inflation, by at least 5% relative to pre-treatment TLC; increase VT, defined as the volume of air moved into or out of the lungs during quiet breathing, by at least 5% relative to pre-treatment VT; decrease RV, defined as the volume of air remaining in the lungs after a maximal exhalation, by 5% relative to pre-treatment RV; increase ERV, defined as the maximal volume of air that can be exhaled from the end-expiratory position, by 5% relative to pre-treatment ERV; increase IRV, defined as the maximal volume that can be inhaled from the end-inspiratory level, by at least 5% relative to pre-treatment IRV; increase IC by at least 5% relative to pre-treatment IC; increase inspiratory vital capacity (IVC), defined as the maximum volume of air inhaled from the point of maximum expiration, by at least 5% relative to pre-treatment IVC; increase VC, defined as the volume of air breathed out after the deepest inhalation, by at least 5% relative to pre-treatment VC; decrease FRC, defined as the volume in the lungs at the end expiratory position, by at least 5% relative to pre-treatment FRC; decrease RV by at least 5% relative to pre-treatment RV; decrease alveolar gas volume ($V^A$) by at least 5% relative to pre-treatment $V^A$; no change in actual lung volume including the volume of the conducting airway ($V^L$) relative to pre-treatment $V^L$; increase DLCO by at least 5% relative to pre-treatment DLCO; increase partial pressure of oxygen dissolved in plasma ($PaO_2$) by at least 2% and/or decrease partial pressure of carbon dioxide dissolved in plasma ($PaCO_2$) by at least 1% relative to pre-treatment $PaO_2$ and $PaCO_2$ levels; increase any spirometry results by at least 5% relative to pre-treatment spirometry results; increase FVC, defined as the vital capacity from a maximally forced expiratory effort, by at least 5% relative to pre-treatment FVC; increase forced expiratory volume over time ($FEV^t$), defined as the volume of air exhaled under forced conditions in the first t seconds, by at least 5% relative to pre-treatment $FEV^t$; increase $FEV_1$ by at least 5% relative to pre-treatment $FEV_1$; increase FEF by at least 5% relative to pre-treatment FEF; increase $FEF^{max}$, defined as the maximum instantaneous flow achieved during a FVC maneuver, by at least 5% relative to pre-treatment $FEF^{max}$; increase FIF by at least 5% relative to pre-treatment FIF; increase peak expiratory flow (PEF), defined as the highest forced expiratory flow measured with a peak flow meter, by at least 5% relative to pre-treatment PEF; increase MVV, defined as the volume of air expired in a specified period during repetitive maximal effort, by at least 5% relative to pre-treatment MVV.

Figure 29A:
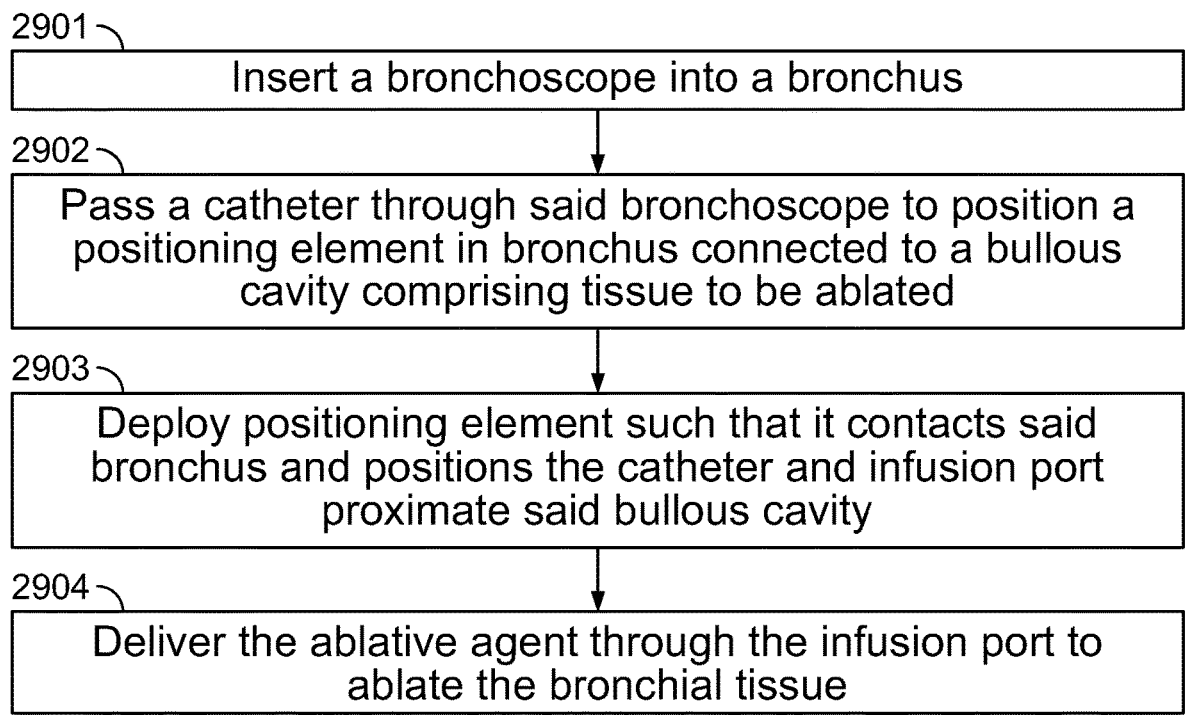
FIG. 29A is a flowchart illustrating a method of ablation of bronchoalveolar tissue in accordance with an embodiment of the present specification.

FIG. 29A is a flowchart illustrating a method of ablation of bronchoalveolar tissue in accordance with an embodiment of the present specification. Referring to FIG. 29A, the first step 2901 includes inserting a bronchoscope into the bronchus of a patient. Next, in step 2902, a catheter of an ablation device is passed through the bronchoscope, wherein the catheter includes a hollow shaft through which an ablative agent can travel, at least one positioning element, and at least one infusion port for delivering the ablative agent. In an embodiment, the ablation device includes a controller comprising a microprocessor for controlling the delivery of the ablative agent. The catheter is inserted into the bronchoscope such that the positioning element is positioned in a bronchus connected to a bullous cavity comprising bronchial tissue to be ablated. The positioning element is deployed such that it contacts a portion of the bronchus and the catheter and infusion port are positioned proximate the bullous cavity in step 2903. In one embodiment, the bronchoscope is used as a fixation point to assist in positioning the catheter and the infusion port within the bullous cavity. Finally, in step 2904, an ablative agent is delivered through the infusion port to ablate the bronchial tissue.

Figure 29B:
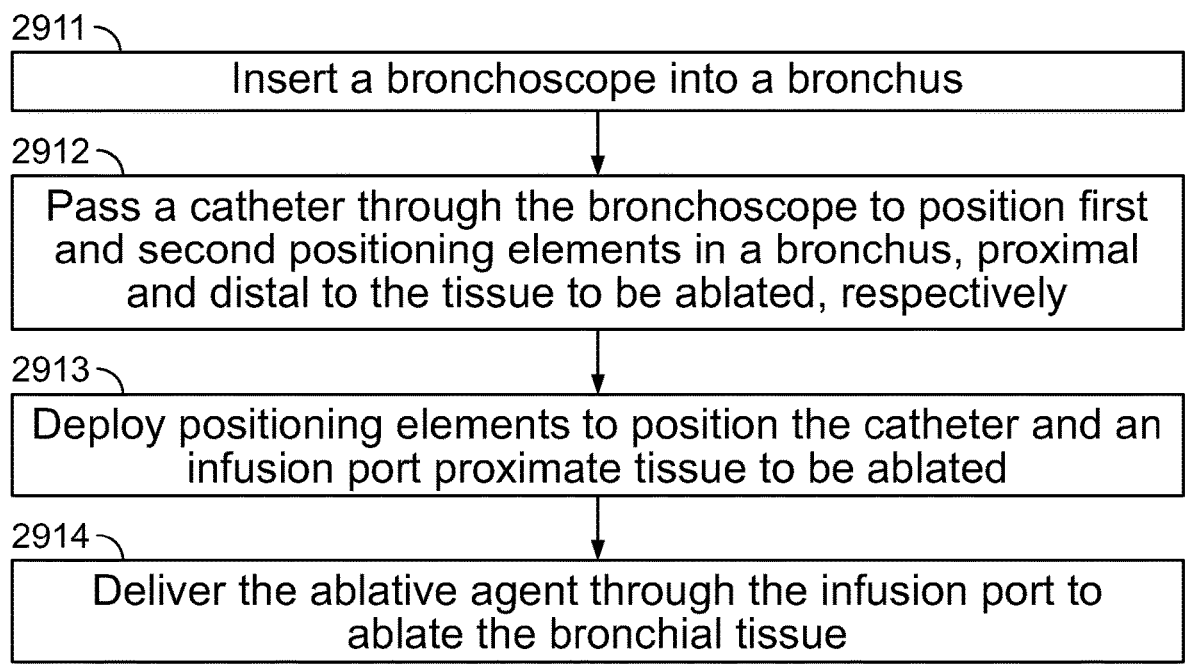

FIG. 29B is a flowchart illustrating a method of ablation of bronchial tissue in accordance with another embodiment of the present specification. Referring to FIG. 29B, the first step 2911 includes inserting a bronchoscope into the bronchus of a patient. Next, in step 2912, a catheter of an ablation device is passed through the bronchoscope, wherein the catheter includes a hollow shaft through which an ablative agent can travel, at least one first positioning element, at least one second positioning element positioned distal to said at least one first positioning element, and at least one infusion port for delivering the ablative agent. In an embodiment, the ablation device includes a controller comprising a microprocessor for controlling the delivery of the ablative agent. The catheter is inserted into the bronchoscope such that the first positioning element is positioned in a bronchus proximal to a bronchial tissue to be ablated and said second positioning element is positioned distal to said bronchial tissue to be ablated. The positioning elements are deployed to contact the bronchus proximal and distal to the tissue to be ablated and the catheter and infusion port are positioned proximate the tissue to be ablated in step 2913. Finally, in step 2914, an ablative agent is delivered through the infusion port to ablate the bronchial tissue.

Bronchial Thermoplasty

Figure 30A:
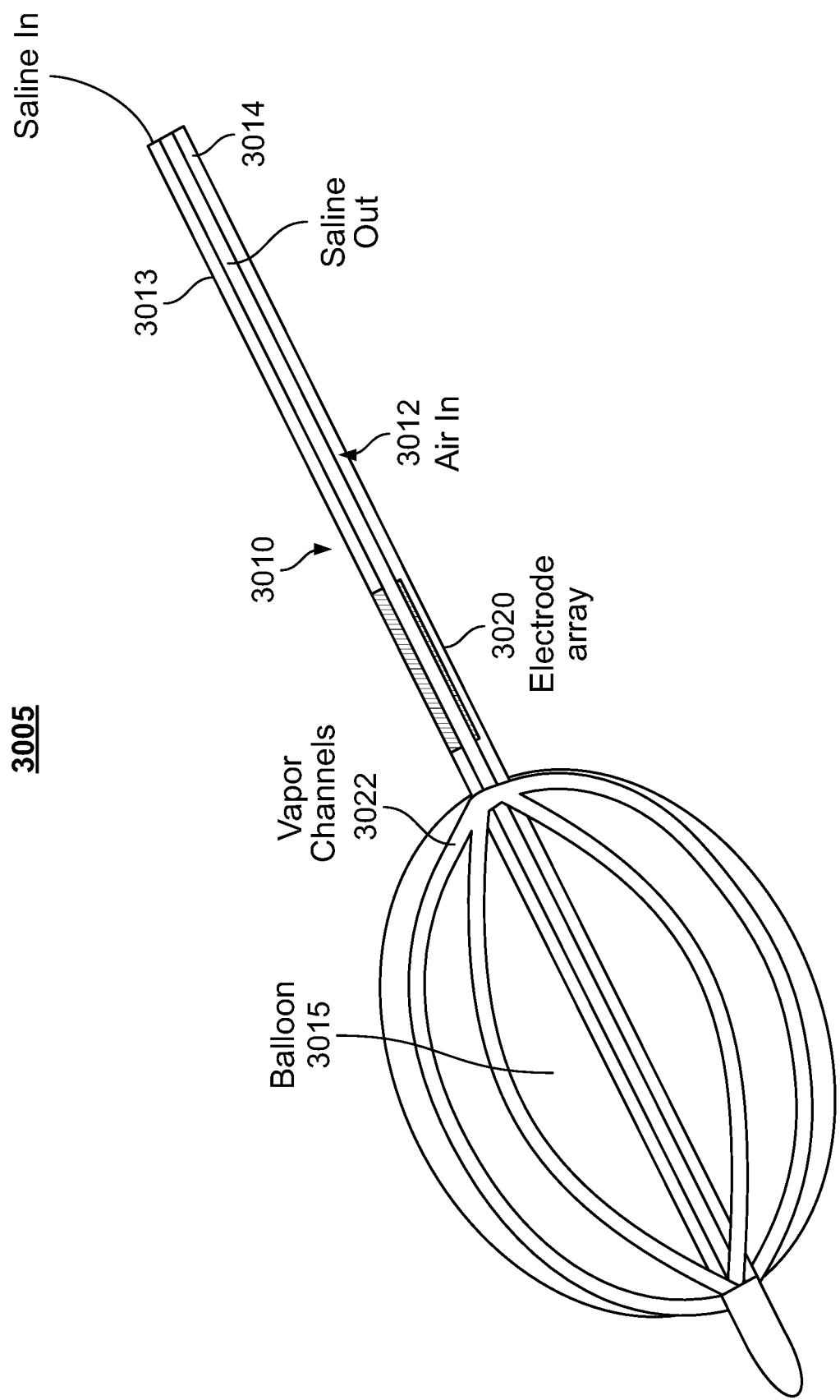

FIG. 30A illustrates a cross-sectional view of a catheter 3005 for performing bronchial thermoplasty, in accordance with an embodiment of the present specification. The catheter 3005 includes an elongate body 3010 having a proximal end and a distal end, and an inflatable multilayer balloon 3015 at the distal end. In some embodiments, the elongate body 3010 has first, second and third lumens 3012, 3013, 3014.

The first lumen 3012 allows air to be pumped, from the proximal end, into the balloon 3015 for inflation. The second lumen 3013 accommodates a heating element 3020 that may be a flexible heating chamber with a plurality of RF electrodes. Saline/water is allowed to be pumped, from the proximal end, into the second lumen 3013 to enter the heating element 3020 for conversion into steam/vapor. The third lumen 3014 allows saline/water to flow out from the proximal end.

The multilayer balloon 3015 comprises of outer and inner balloon layers fused together. A plurality of fluid channels or paths 3022 are defined and sandwiched between the outer and inner layers. The channels 3022 are in fluid communication with the second and third lumens 3013, 3014 such that steam/vapor generated in the second lumen 3013 circulates through the channels 3022 and flows out of the catheter through the third lumen 3014. During operation, the balloon 3015 is inflated to contact target tissue and steam/vapor is allowed to circulate through the channels 3022 to create a deep burn in the target tissue without scarring. This results in steam non-contiguously spreading over the tissue area in a manner that is controlled and can be circulated.

In various embodiments, the channels 3022 are configured into a plurality of patterns (such as, but not limited to, a wave, series of lines, sine wave, square wave) such that the circulating steam/vapor creates ablation proximate the area of the channels 3022 without any ablation in the remaining area (that is, area devoid of the channels 3022) of the balloon 3015. In embodiments, the balloon 3022 is actively air-cooled to control a volume of tissue ablated. In various embodiments, the catheter 3005 has a plurality of applications in nerve or muscle ablation in hollow organs where circumferential ablation is not needed—such as, for example, in PV (Pulmonary Vein) ablation (heart), Renal Denervation (Hypertension) and Hepatic Vein Ablation (Diabetes). In an exemplary application of PV ablation, the channels 3022 create a pattern of ablation in a PV sufficient to block conduction of electrical activity from a PV to a Left Atrium (LA) without causing a significant stricture in the PV, wherein a length of the circumferential pattern of ablation is greater than the circumference of the PV proximate the ablation. In some embodiments, a distance between two adjacent circumferential ablation patterns is greater than two times the thickness of the PV.

Figure 30B:
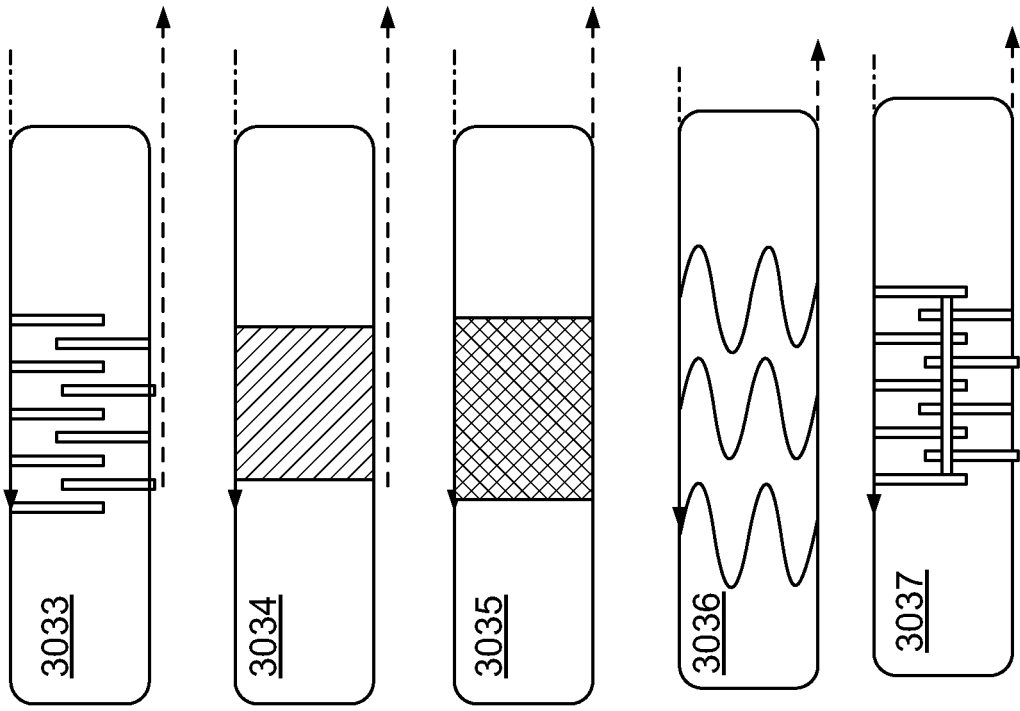
Figure 30B:
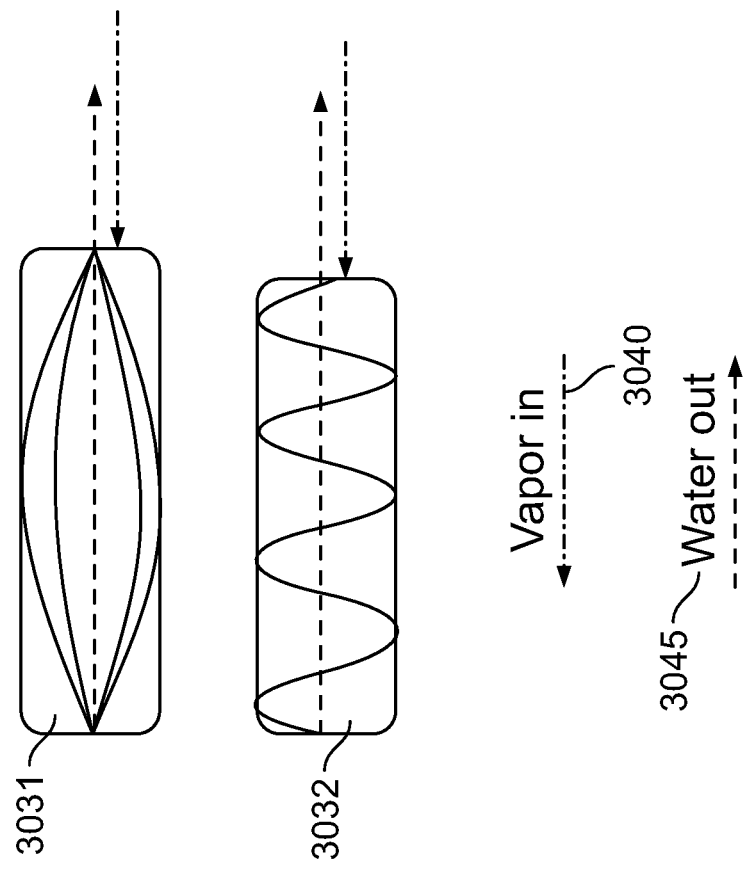

FIG. 30B illustrates a plurality of patterns of the channels 3022, in accordance with various embodiments of the present specification. The figure shows first, second, third, fourth, fifth, sixth and seventh exemplary patterns 3031, 3032, 3033, 3034, 3035, 3036, 3037. For each of the patterns, a first path 3040 shows a direction of flow of steam/vapor while a second path 3045 shows a direction of flow of water/saline out. The patterns of the channels 3022 determine the ablation pattern.

Figure 30C:
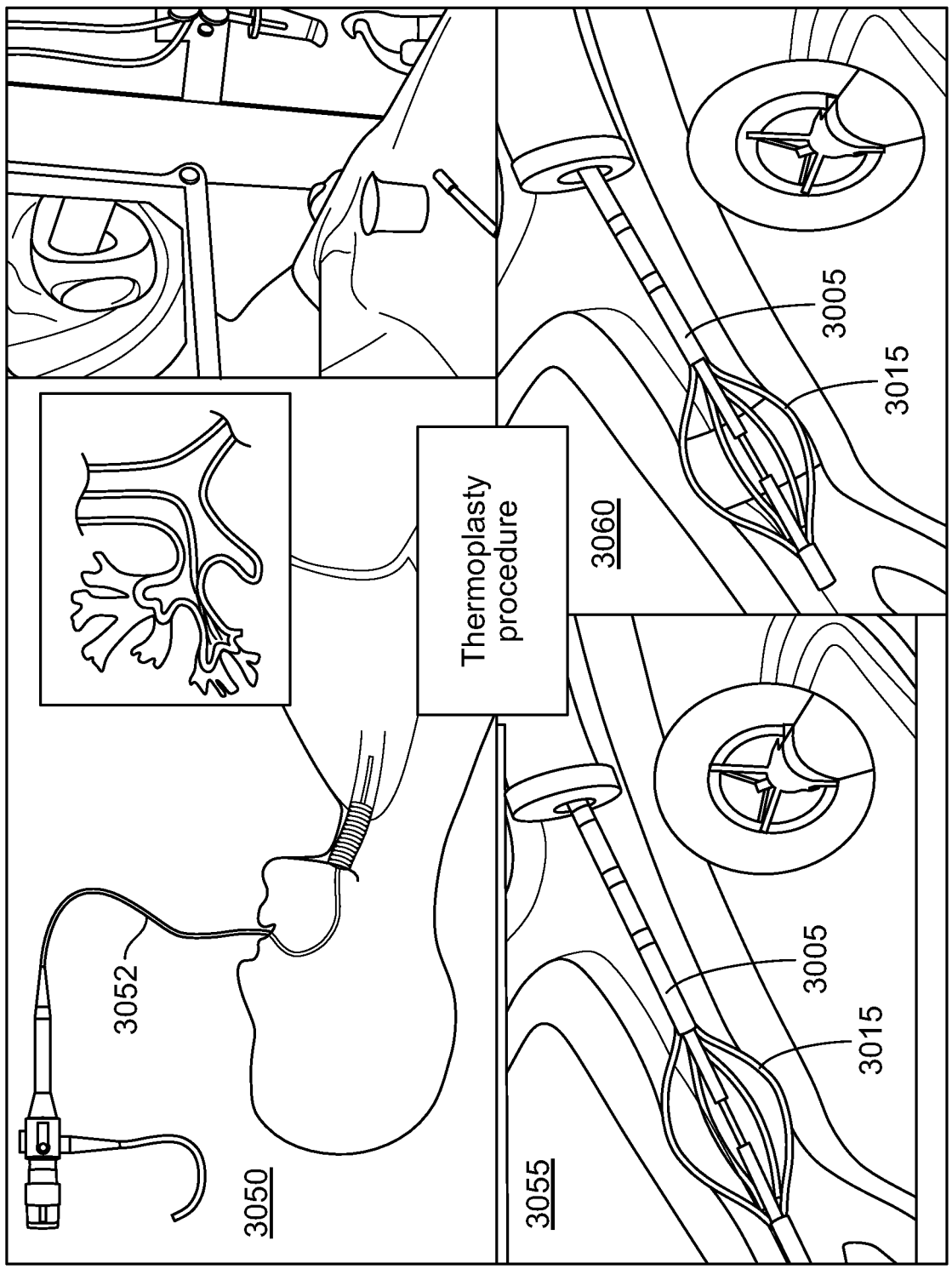

FIG. 30C illustrates a workflow for performing a bronchial thermoplasty procedure using the catheter 3005, in accordance with an embodiment of the present specification. At step 3050 an endoscope tube 3052 is inserted into a patient's lung to position proximate a target tissue area for ablation. At step 3055, the catheter 3005 is inserted through a working channel of the endoscope 3052 such that the balloon 3015 is positioned at the target tissue area. Thereafter, at step 3060, the balloon 3015 is inflated with air such that the balloon 3015 contacts the target tissue area. Steam/vapor is now circulated through the patterned channels 3022 of the balloon to ablate the target tissue area.

Lung Volume Reduction

FIG. 31A illustrates a lung volume reduction (LVR) catheter 3105 while FIG. 31B illustrates the LVR catheter 3105 deployed through an endoscope/bronchoscope 3110, in accordance with embodiments of the present specification. Referring now to FIGS. 31A, 31B, the catheter 3105 includes an elongate shaft 3115 having a proximal end and a distal end. The distal end has at least one vapor delivery port 3120 and a plurality of suction ports 3125. A positioning element 3122 is located proximate the at least one vapor delivery port 3120. In some embodiments, the positioning element 3122 is an inflatable balloon.

In some embodiments, the elongate shaft 3115 has first and second lumens 3130, 3132 extending from the proximal end to the distal end. The first lumen 3130 accommodates a heating element 3135 such as a flexible heating chamber comprising a plurality of RF electrodes of the present specification. Saline/water enters the proximal end to reach the heating element 3135 where it is converted to steam/vapor for delivery through the at least one vapor delivery port 3120. The second lumen 3132 is in fluid communication with the plurality of suction ports 3125. During operation, vapor is delivered through the at least one vapor delivery port 3120 and air is suctioned in through the plurality of suction ports 3125 thereby producing circulation of thermal energy between the vapor delivery port 3120 and the suction ports 3125. In an embodiment, a third lumen (not shown) allows air to be pumped into the balloon 3122 for inflation. FIG. 31B shows the catheter 3105 deployed through a working channel of the endoscope 3110.

In some embodiments, the at least one vapor delivery port 3120 is at least 1 cm apart from a closest of the plurality of suction ports 3125.

Figure 31C:
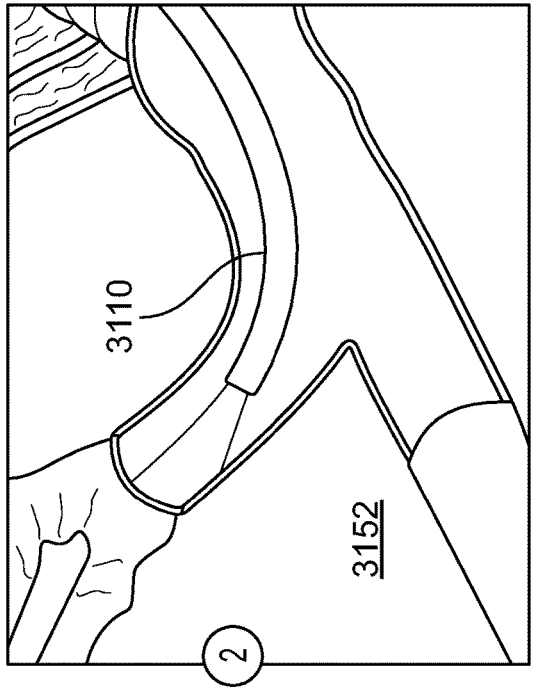
Figure 31C:
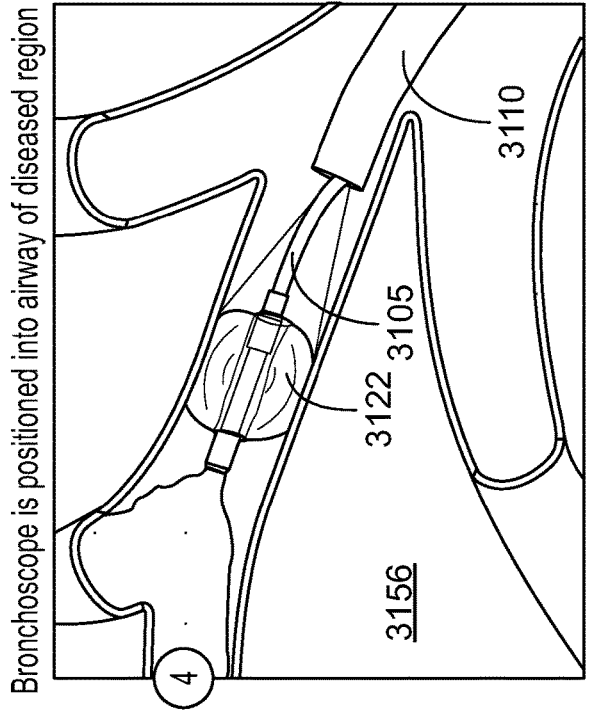
Figure 31C:
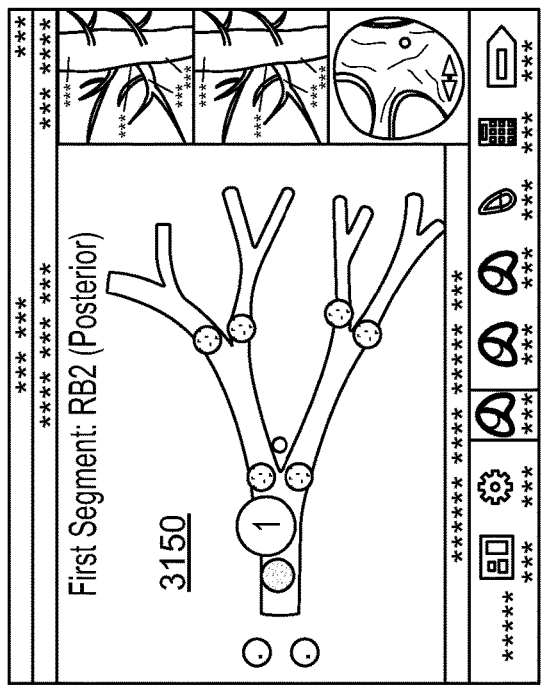
Figure 31C:
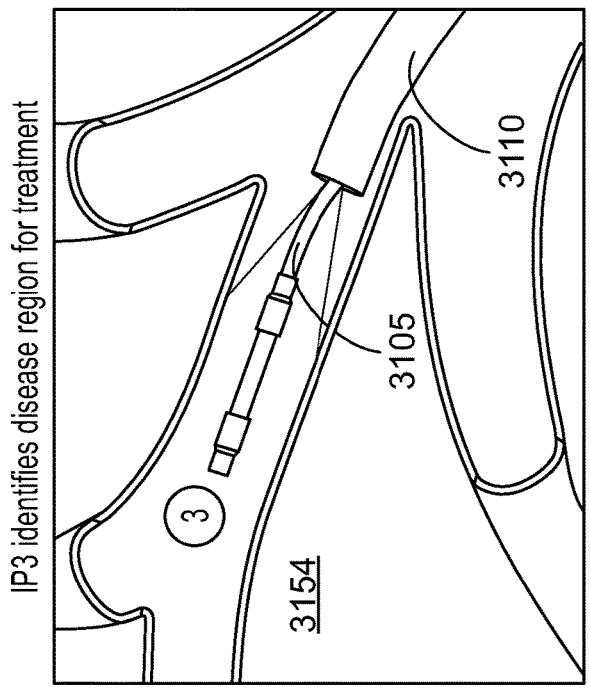

FIG. 31C is a workflow for performing lung volume reduction using the catheter 3105, in accordance with an embodiment of the present specification. At step 3150, diseased region is identified for ablation therapy. At step 3152, the bronchoscope 3110 is positioned into the airway of the diseased region. At step 3154, the catheter 3105 is deployed through a working channel of the bronchoscope 3110 such that the catheter 3105 is positioned proximate the diseased region. At step 3156, the balloon 3122 is inflated, steam/vapor is delivered to the diseased region (through the vapor delivery port 3120) for a predefined period of time, such as 3 to 10 seconds (depending upon the mass of the diseased region), while air is suctioned in through the suction ports 3125.

Figure 32A:
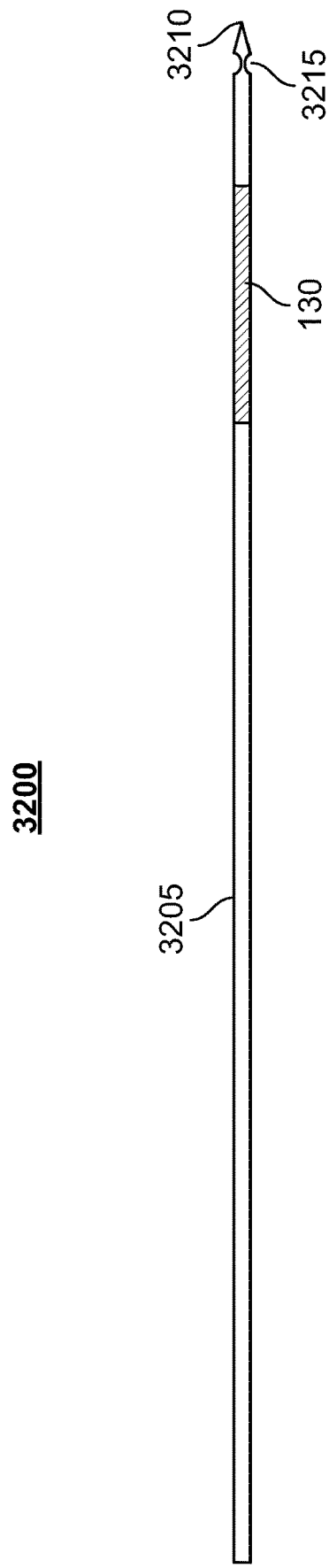
Figure 32B:
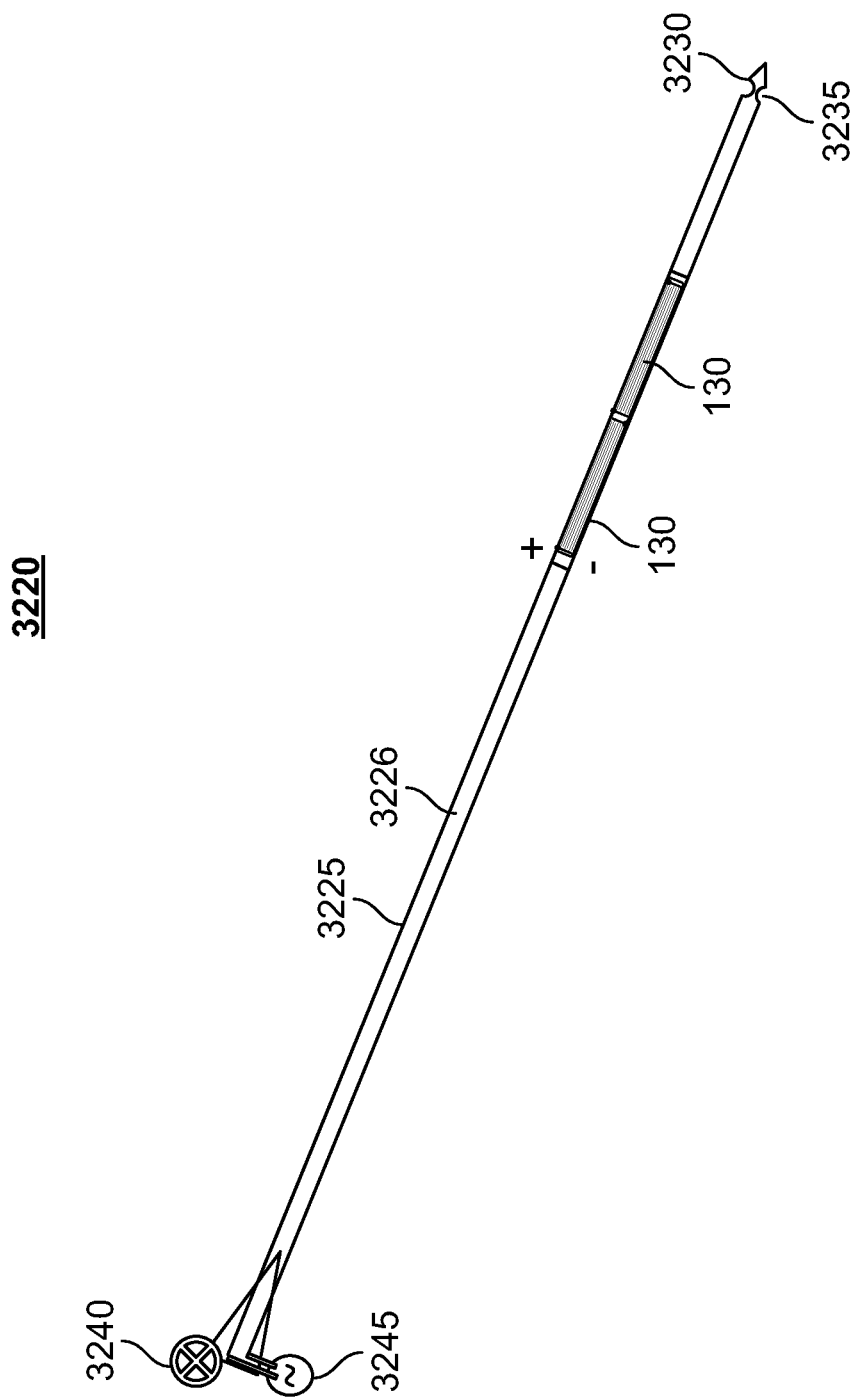

FIG. 32A illustrates a needle catheter 3200 incorporating one flexible heating chamber 130 of FIGS. 1A through 1D, in accordance with an embodiment. FIG. 32B illustrates a needle catheter 3220 incorporating two flexible heating chambers 130, in accordance with an embodiment. Referring now to FIGS. 32A and 32B, the catheters 3200, 3220 each comprise an elongate body 3205, 3225 having a proximal end and a distal end. The bodies 3205, 3225 each have a lumen along their length and at least one needle 3210, 3230 at their distal ends. In some embodiments, the needle is retractable. In an embodiment, at least one infusion port 3215, 3235 is positioned proximate a proximal end of the needle 3210, 3230, or on the needle 3210, 3230, which may be hollow. In various embodiments, the at least one infusion port 3215, 3235 is positioned in a range of 1 mm to 50 cm from the heating chamber(s) 130. In various embodiments, the needle catheters 3200, 3220 comprise any of the needle embodiments discussed in the present specification. At least one heating chamber 130 is incorporated in the catheters 3200, 3220 proximate the distal end of the bodies 3205, 3225. The embodiment of FIG. 32A illustrates one heating chamber 130 while the embodiment of FIG. 32B illustrates two heating chambers 130 arranged in series. Referring to FIG. 32B, a water pump 3240, coupled to the proximal end of the body 3225, supplies water/saline to a proximal end of the heating chambers 130 through a lumen 3226 in the catheter body 3225. An RF generator 3245 provides electrical current to a plurality of electrodes (such as, electrodes 136, 138) included in the heating chambers 130, which causes said electrodes to generate heat, wherein said heat is transferred to said water/saline to convert the water/saline to vapor, which is then delivered via infusion port 3235 to ablate a target tissue.

In some embodiments, the catheters 3200, 3220 may optionally include at least one positioning element, such as an inflatable balloon, at the distal end of the bodies 3205, 3225.

During use, the pump 3240 delivers water/saline to the proximal end of the heating chambers 130 while the RF generator 3245 causes the electrodes to heat up and vaporize the water/saline flowing through the heating chambers 130. The generated vapor exits through the at least one port 3235. The flexible heating chambers 130 impart improved flexibility and maneuverability to the catheters 3200, 3220, allowing a physician to better position the catheters 3200, 3220 when performing needle ablation procedures.

Figure 32C:
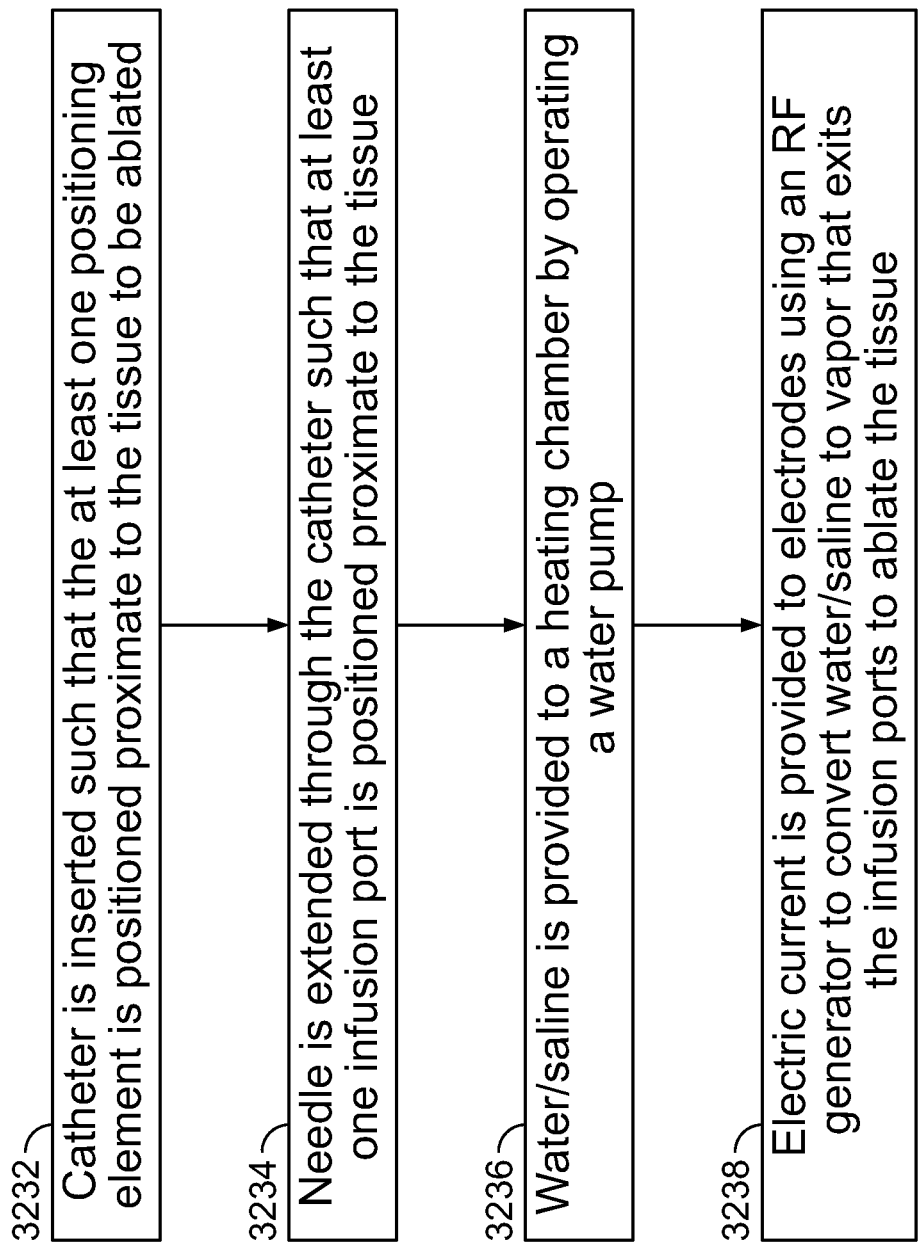

FIG. 32C is a flowchart illustrating one embodiment of a method of ablation of a tissue using the needle catheters 3200, 3220 of FIGS. 32A and 32B. In the first step 3232, the catheter is inserted such that the at least one positioning element is positioned proximate to the tissue to be ablated. The next step 3234 involves extending the needle through the catheter such that the at least one infusion port is positioned proximate to the tissue. At step 3236, water/saline is provided to the heating chamber (to more than one heating chambers, in some embodiments) by operating the water pump. At step 3238, electric current is provided to electrodes of the heating chamber, using the RF generator, to convert water/saline to vapor that exits the infusion ports to ablate the tissue. In another embodiment, the device does not include a positioning element and the method does not include a step of positioning the positioning element proximate the tissue to be ablated.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. An ablation system configured to treat a patient having at least one of excess weight, obesity, eating disorders, metabolic syndrome, dyslipidemia, diabetes, polycystic ovarian disease, fatty liver disease, non-alcoholic fatty liver disease, or non-alcoholic steatohepatitis disease by ablating duodenal tissue, comprising:
   a control unit comprising at least one processor, at least one pump in data communication with the at least one processor, and a catheter connection port in fluid communication with the at least one pump;
   a catheter configured to couple to the catheter connection port and adapted to be positioned within the patient's small intestine, wherein the catheter comprises:
      at least one lumen in fluid communication with the catheter connection port and configured to receive a fluid;
      at least one electrode coupled to the at least one lumen and configured to receive an electrical current from the control unit, wherein, upon the at least one electrode receiving the electrical current and the at least one lumen receiving the fluid, a vapor, having a first flow rate, is generated;
      a first positioning element coupled to a surface of the catheter and adapted to expand from a compressed configuration to an expanded configuration;
      a second positioning element coupled to the surface of the catheter and adapted to expand from a compressed configuration to an expanded configuration, wherein, upon the catheter being positioned in the patient's small intestine and the first positioning element and the second positioning element adopting their expanded configurations, a treatment volume is formed and wherein the treatment volume is bounded by a first surface of the expanded first positioning element, said first surface having a first plurality of spaces, and a second surface of the expanded second positioning element, said second surface having a second plurality of spaces; and
      at least two ports positioned between the first positioning element and the second positioning element, wherein the at least two ports are adapted to release the vapor into the treatment volume, wherein the first plurality of spaces is adapted to permit a portion of the vapor to be released outside the treatment volume, and wherein the second plurality of spaces is adapted to permit a portion of the vapor to be released outside the treatment volume.

2. The ablation system of claim 1, wherein the portion of the vapor to be released outside the treatment volume through the first plurality of spaces has a flow rate in a range of 1% to 80% of the first flow rate.

3. The ablation system of claim 1, wherein the portion of the vapor to be released outside the treatment volume through the second plurality of spaces has a flow rate in a range of 1% to 80% of the first flow rate.

4. The ablation system of claim 1, wherein the first plurality of spaces is positioned between a periphery of the first positioning element and a surface of the patient's small intestine.

5. The ablation system of claim 1, wherein the second plurality of spaces is positioned between a periphery of the second positioning element and a surface of the patient's small intestine.

6. The ablation system of claim 1, wherein the first plurality of spaces and the second plurality of spaces permit a sufficient amount of vapor to flow out of the treatment volume such that a pressure level within the treatment volume remains less than 5 atm.

7. The ablation system of claim 6, wherein the control unit is not configured to regulate an amount of vapor formed to control the pressure level.

8. The ablation system of claim 1, wherein, upon the first positioning element and the second positioning element being expanded in the patient's small intestine, the treatment volume ranges from 3 cubic centimeters to 450 cubic centimeters.

9. The ablation system of claim 1, wherein at least one of the first positioning element or second positioning element is configured to physically modify when a pressure in the treatment volume increases above 10% of a baseline pressure.

10. The ablation system of claim 1, wherein at least one of the first positioning element or second positioning element is configured to physically modify as the vapor is introduced into the treatment volume.

11. The ablation system of claim 1, wherein at least one of the first positioning element or second positioning element is configured to physically modify over time, thereby increasing an amount of the vapor flow out of the treatment volume.

12. The ablation system of claim 1, wherein at least one of the first positioning element and the second positioning element comprises wire mesh.

13. The ablation system of claim 1, wherein at least one of the first positioning element and the second positioning element has a conical shape.

14. The ablation system of claim 1, further comprising at least one of a foot pedal in data communication with the control unit, a switch on the control unit, or a switch on the catheter in data communication with the control unit.

15. The ablation system of claim 14, wherein the control unit is configured to be repeatedly activated to deliver fluid into the lumen of the catheter and to deliver electrical current to the at least one electrode using at least one of the foot pedal, the switch on the control unit, or the switch on the catheter.

16. The ablation system of claim 1, wherein the control unit is configured to automatically shut off a flow of the fluid after a predetermined period of time.

17. The ablation system of claim 16, wherein the predetermined period of time is 60 seconds.

18. The ablation system of claim 1, wherein the control unit is configured to automatically shut off the electrical current after a predetermined period of time.

* * * * *